US012338474B2

(12) United States Patent
Dudkin et al.

(10) Patent No.: US 12,338,474 B2
(45) Date of Patent: Jun. 24, 2025

(54) COMPOSITIONS AND METHODS FOR PRODUCING CIRCULAR POLYRIBONUCLEOTIDES

(71) Applicant: Flagship Pioneering Innovations VI, LLC, Cambridge, MA (US)

(72) Inventors: Vadim Dudkin, Wellesley, MA (US); Ki Young Paek, Brighton, MA (US); Alexandra Sophie De Boer, Somerville, MA (US); Jennifer A. Nelson, Brookline, MA (US)

(73) Assignee: Flagship Pioneering Innovations VI, LLC, Cambridge, MA (US)

( * ) Notice: Subject to any disclaimer, the term of this patent is extended or adjusted under 35 U.S.C. 154(b) by 0 days.

(21) Appl. No.: 18/168,357

(22) Filed: Feb. 13, 2023

(65) Prior Publication Data

US 2023/0212629 A1 Jul. 6, 2023

Related U.S. Application Data

(63) Continuation of application No. PCT/US2022/043808, filed on Sep. 16, 2022.

(60) Provisional application No. 63/245,354, filed on Sep. 17, 2021.

(51) Int. Cl.
*C12P 19/34* (2006.01)
*C12N 7/00* (2006.01)
*C12N 9/02* (2006.01)

(52) U.S. Cl.
CPC ............... *C12P 19/34* (2013.01); *C12N 7/00* (2013.01); *C12N 9/0069* (2013.01); *C12Y 113/12005* (2013.01); *C12N 2770/20022* (2013.01); *C12N 2770/20051* (2013.01)

(58) Field of Classification Search
CPC ......... C12P 19/34; C12N 7/00; C12N 9/0069; C12N 2770/20022; C12N 2770/20051
See application file for complete search history.

(56) References Cited

U.S. PATENT DOCUMENTS

| | | | |
|---|---|---|---|
| 5,766,903 A | 6/1998 | Sarnow et al. | |
| 9,822,378 B2 | 11/2017 | Kruse | |
| 10,407,683 B2 | 9/2019 | Nelson et al. | |
| 10,953,033 B2 | 3/2021 | Stewart et al. | |
| 11,058,706 B2 | 7/2021 | Stewart et al. | |
| 11,160,822 B2 | 11/2021 | De Boer et al. | |
| 11,203,767 B2 | 12/2021 | Anderson et al. | |
| 11,352,640 B2 | 6/2022 | Anderson et al. | |
| 11,352,641 B2 | 6/2022 | Anderson et al. | |
| 11,447,796 B2 | 9/2022 | Anderson et al. | |
| 11,458,156 B2 | 10/2022 | De Boer et al. | |
| 11,845,950 B2 | 12/2023 | Anderson et al. | |
| 2016/0194368 A1 | 7/2016 | Hoge et al. | |
| 2020/0080106 A1 | 3/2020 | Anderson et al. | |
| 2020/0306286 A1 | 10/2020 | Stewart et al. | |
| 2021/0292761 A1 | 9/2021 | Kahvejian et al. | |
| 2021/0371494 A1 | 12/2021 | Wesselhoeft et al. | |
| 2022/0088049 A1 | 3/2022 | Kahvejian et al. | |
| 2022/0142896 A1 | 5/2022 | Kahvejian et al. | |
| 2022/0143062 A1 | 5/2022 | Kahvejian et al. | |
| 2022/0177540 A1 | 6/2022 | Wesselhoeft et al. | |
| 2022/0257794 A1 | 8/2022 | de Boer et al. | |
| 2022/0296729 A1 | 9/2022 | Kahvejian et al. | |
| 2022/0305128 A1 | 9/2022 | Kahvejian et al. | |
| 2023/0061936 A1 | 3/2023 | Kahvejian et al. | |
| 2023/0070937 A1 | 3/2023 | Kahvejian et al. | |
| 2023/0072532 A1 | 3/2023 | Kahvejian et al. | |

FOREIGN PATENT DOCUMENTS

| | | | |
|---|---|---|---|
| WO | WO-1997/007825 A1 | 3/1997 | |
| WO | WO-2010/084371 A1 | 7/2010 | |
| WO | WO-2014186334 A1 * | 11/2014 | ........... C12N 15/115 |
| WO | WO-2015/034925 A1 | 3/2015 | |
| WO | WO-2016/011222 A2 | 1/2016 | |
| WO | WO-2016/197121 A1 | 12/2016 | |
| WO | WO-2019/118919 A1 | 6/2019 | |
| WO | WO-2019236673 A1 * | 12/2019 | ......... A61K 31/7105 |
| WO | WO-2020/181013 A1 | 9/2020 | |
| WO | WO-2020/186991 A1 | 9/2020 | |
| WO | WO-2020/198403 A2 | 10/2020 | |
| WO | WO-2020237227 A1 * | 11/2020 | ............. A61K 35/17 |
| WO | WO-2020/257727 A1 | 12/2020 | |
| WO | WO-2021/041541 A1 | 3/2021 | |
| WO | WO-2021/159129 A2 | 8/2021 | |
| WO | WO-2021/236855 A1 | 11/2021 | |
| WO | WO-2021/236930 A1 | 11/2021 | |
| WO | WO-2021/236980 A1 | 11/2021 | |
| WO | WO-2022/037692 A1 | 2/2022 | |
| WO | WO-2022/051629 A1 | 3/2022 | |
| WO | WO-2022/245901 A1 | 11/2022 | |
| WO | WO-2022/245942 A1 | 11/2022 | |
| WO | WO-2022/247943 A1 | 12/2022 | |
| WO | WO-2022/261490 A2 | 12/2022 | |
| WO | WO-2023/009568 A1 | 2/2023 | |

OTHER PUBLICATIONS

U.S. Appl. No. 17/465,953, De Boer et al.
U.S. Appl. No. 17/560,444, De Boer et al.
U.S. Appl. No. 17/795,915, Kahvejian et al.
U.S. Appl. No. 17/795,939, Kahvejian et al.
U.S. Appl. No. 17/795,943, Kahvejian et al.
U.S. Appl. No. 17/925,920, Kahvejian et al.
U.S. Appl. No. 17/925,966, Kahvejian et al.
U.S. Appl. No. 17/926,254, de Boer et al.
U.S. Appl. No. 17/988,007, Kahvejian et al.
U.S. Appl. No. 18/024,542, Kahvejian et al.
Carmona, Ellese, Dissertation: "Circular RNA: Design Criteria for Optimal Therapeutic Utility," PhD, Division of Medical Sciences, Harvard University, 2019. Retrieved from <http://nrs.harvard.edu/urn-3:HUL.InstRepos:41121328>, (135 pages) (Aug. 2019).

(Continued)

*Primary Examiner* — Kimberly Chong
*Assistant Examiner* — Douglas Charles Ryan
(74) *Attorney, Agent, or Firm* — Clark & Elbing LLP

(57) ABSTRACT

The present disclosure relates, generally, to compositions and methods for producing, purifying, and using circular RNA.

23 Claims, 22 Drawing Sheets

Specification includes a Sequence Listing.

(56) References Cited

OTHER PUBLICATIONS

Costello et al., "Reinventing the Wheel: Synthetic Circular RNAs for Mammalian Cell Engineering," Trends Biotechnol. 38(2):217-30 (Feb. 2020) (15 pages).
Wesselhoeft et al., "Engineering circular RNA for potent and stable translation in eukaryotic cells," Nat Commun. 9(1):2629 (2018) (10 pages).
Wesselhoeft et al., "RNA Circularization Diminishes Immunogenicity and Can Extend Translation Duration In Vivo," Mol Cell. 74(3):508-520 (May 2019) (18 pages).
Petkovic et al., "RNA circularization strategies in vivo and in vitro," Nucleic Acids Res. 43(4):2454-65 (2015).
Puttaraju et al., "Group I permuted intron-exon (PIE) sequences self-splice to produce circular exons," Nucleic Acids Res. 20(20):5357-64 (1992).
International Search Report and Written Opinion for PCT/US2022/043808, mailed Jan. 27, 2023 (10 pages).
Holdt et al., "Molecular roles and function of circular RNAs in eukaryotic cells," Cell Mol Life Sci. 75(6):1071-98 (Mar. 2018).
Chen, "The expanding regulatory mechanisms and cellular functions of circular RNAs," Nat Rev Mol Cell Biol. 21(8):475-90 (Aug. 2020).
Ford et al., "Synthesis of circular RNA in bacteria and yeast using RNA cyclase ribozymes derived from a group I intron of phage T4," Proc Natl Acad Sci U S A. 91(8):3117-21 (Apr. 1994).
Lupták et al., "Distinct sites of phosphorothioate substitution interfere with folding and splicing of the Anabaena group I intron," Nucleic Acids Res. 32(7):2272-2280 (Apr. 2004).

\* cited by examiner

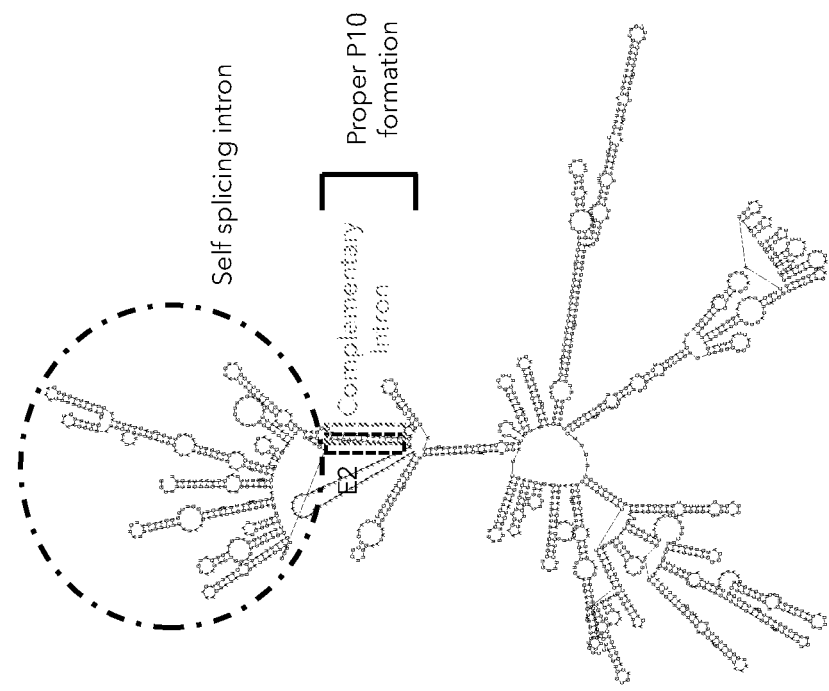
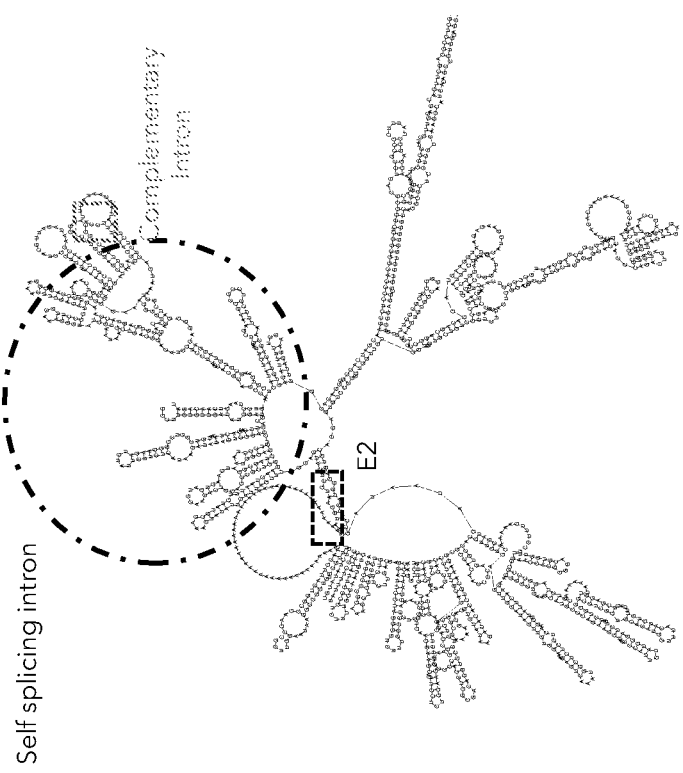
Fig. 10B
Fig. 10A

FIG. 19

| Organism | Modification | Original | Extended |
|---|---|---|---|
| Synechococcus elongatus | Synechococcus 1 TCCGCTGACTGTAAAGG (SEQ ID NO: 92)<br>Synechococcus 2 TCCGCTGC*GT*C*TACCGT* (SEQ ID NO: 93) | 7nts | 17nts |
| Anabaena azollae | Anabaena azollae 1 TCCGTTGACTGTAAAAA (SEQ ID NO: 94)<br>Anabaena azollae 2 TCCGTA*GCGT*C*TACCAT* (SEQ ID NO: 95) | 5nts | 17nts |
| Anabaena cylindrica | Anabaena cylindrica 1 TCCGTTGACCTTAAACG (SEQ ID NO: 96)<br>Anabaena cylindrica 2 TCCGTA*GCGT*C*TACCAT* (SEQ ID NO: 97) | 5nts | 17nts |
| Scytonema hofmanni | Scytonema 1 CCCGAAGGTCAGTGGTT (SEQ ID NO: 98)<br>Scytonema 2 CCCGAC*GAGCTACCAGG* (SEQ ID NO: 99) | 5nts | 17nts |

(SEQ ID NO: 100)

1. Extend stem of P6b (Anabaena 4)

(SEQ ID NO: 101)

2. Change bulge of P6b to stem (Anabaena 5)

(SEQ ID NO: 102)

COMPOSITIONS AND METHODS FOR PRODUCING CIRCULAR POLYRIBONUCLEOTIDES

SEQUENCE LISTING

This application contains a Sequence Listing which has been filed electronically in XML format and is hereby incorporated by reference in its entirety. Said XML copy, created on Aug. 28, 2023, is named 51509-031003_Sequence_Listing_8_28_23.XML and is 83,155 bytes in size.

BACKGROUND

There is a need for methods of producing, purifying, and using circular polyribonucleotides.

SUMMARY OF THE INVENTION

The disclosure provides compositions and methods for producing, purifying, and using circular RNA.

In one aspect, the invention features a linear polyribonucleotide having the formula 5'-(A)-(B)-(C)-(D)-(E)-(F)-(G)-3'. The linear polyribonucleotide includes, from 5' to 3', (A) a 3' half of Group I catalytic intron fragment; (B) a 3' splice site; (C) a 3' exon fragment; (D) a polyribonucleotide cargo; (E) a 5' exon fragment; (F) a 5' splice site; and (G) a 5' half of Group I catalytic intron fragment. The polyribonucleotide includes a first annealing region that has from 2 to 50, e.g., 5 to 50, e.g., 6 to 50, e.g., 7 to 50, e.g., 8 to 50 (e.g., from 10 to 30, 10 to 20, or 10 to 15, e.g., at least 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50) ribonucleotides and is present within (A) the 3' half of Group I catalytic intron fragment; (B) the 3' splice site; or (C) the 3' exon fragment. The polyribonucleotide also includes a second annealing region that has from 2 to 50, e.g., 5 to 50, e.g., 6 to 50, e.g., 7 to 50, e.g., 8 to 50 (e.g., from 10 to 30, 10 to 20, or 10 to 15, e.g., at least 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50) ribonucleotides and is present within (E) the 5' exon fragment; (F) the 5' splice site; or (G) the 5' half of Group I catalytic intron fragment. The first annealing region has from 80% to 100% (e.g., 85% to 100%, e.g., 90% to 100%, e.g., 80%, 85%, 90%, 95%, 97%, 99%, or 100%) complementarity with the second annealing region or has from zero to 10 (e.g., 0, 1, 2, 3, 4, 5, 6, 7, 8, 9, or 10), mismatched base pairs.

In another aspect, the invention features a linear polyribonucleotide having the formula 5'-(A)-(B)-(C)-(D)-(E)-(F)-(G)-3'. The linear polyribonucleotide includes, from 5' to 3', (A) a 3' half of Group I catalytic intron fragment; (B) a 3' splice site; (C) a 3' exon fragment; (D) a polyribonucleotide cargo; (E) a 5' exon fragment; (F) a 5' splice site; and (G) a 5' half of Group I catalytic intron fragment, wherein the 3' half of Group I catalytic intron fragment of (A) and the 5' half of Group I catalytic intron fragment of (G) are from a Cyanobacterium *Anabaena* pre-tRNA-Leu gene. The polyribonucleotide includes a first annealing region that has from 5 to 50, e.g., 6 to 50 (e.g., from 10 to 30, 10 to 20, or 10 to 15, e.g., at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50) ribonucleotides and is present within (A) the 3' half of Group I catalytic intron fragment; (B) the 3' splice site; or (C) the 3' exon fragment. The polyribonucleotide also includes a second annealing region that has from 5 to 50, e.g., 6 to 50 (e.g., from 10 to 30, 10 to 20, or 10 to 15, e.g., at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50) ribonucleotides and is present within (E) the 5' exon fragment; (F) the 5' splice site; or (G) the 5' half of Group I catalytic intron fragment. The first annealing region has from 80% to 100% (e.g., 85% to 100%, e.g., 90% to 100%, e.g., 80%, 85%, 90%, 95%, 97%, 99%, or 100%) complementarity with the second annealing region or has from zero to 10 e.g., (0, 1, 2, 3, 4, 5, 6, 7, 8, 9, or 10) mismatched base pairs.

In another aspect, the invention features a linear polyribonucleotide having the formula 5'-(A)-(B)-(C)-(D)-(E)-(F)-(G)-3'. The linear polyribonucleotide includes, from 5' to 3', (A) a 3' half of Group I catalytic intron fragment; (B) a 3' splice site; (C) a 3' exon fragment; (D) a polyribonucleotide cargo; (E) a 5' exon fragment; (F) a 5' splice site; and (G) a 5' half of Group I catalytic intron fragment, wherein the 3' half of Group I catalytic intron fragment of (A) and the 5' half of Group I catalytic intron fragment of (G) are from a Tetrahymena pre-rRNA. The polyribonucleotide includes a first annealing region that has from 6 to 50, e.g., 7 to 50 (e.g., from 10 to 30, 10 to 20, or 10 to 15, e.g., at least 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50) ribonucleotides and is present within (A) the 3' half of Group I catalytic intron fragment; (B) the 3' splice site; or (C) the 3' exon fragment. The polyribonucleotide also includes a second annealing region that has from 6 to 50, e.g., 7 to 50 (e.g., from 10 to 30, 10 to 20, or 10 to 15, e.g., at least 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50) ribonucleotides and is present within (E) the 5' exon fragment; (F) the 5' splice site; or (G) the 5' half of Group I catalytic intron fragment. The first annealing region has from 80% to 100% (e.g., 85% to 100%, e.g., 90% to 100%, e.g., 80%, 85%, 90%, 95%, 97%, 99%, or 100%) complementarity with the second annealing region or has from zero to 10 e.g., (0, 1, 2, 3, 4, 5, 6, 7, 8, 9, or 10) mismatched base pairs.

In some embodiments, (A) or (C) includes the first annealing region and (E) or (G) includes the second annealing region.

In some embodiments, the 3' exon fragment of (C) includes the first annealing region and the 5' exon fragment of (E) includes the second annealing region.

In some embodiments, the 3' exon fragment of (C) includes the first annealing region and the 5' half of Group I catalytic intron fragment of (G) includes the second annealing region.

In some embodiments, the 3' half of Group I catalytic intron fragment of (A) includes the first annealing region and the 5' exon fragment of (E) includes the second annealing region.

In some embodiments, first annealing region and the second annealing region include zero or one mismatched base pair.

In some embodiments, the first annealing region and the second annealing region are 100% complementary.

In some embodiments, the 3' half of Group I catalytic intron fragment of (A) and the 5' half of Group I catalytic intron fragment of (G) are from a cyanobacterium *Anabaena* pre-tRNA-Leu gene, a Tetrahymena pre-rRNA, or a T4 phage td gene.

In some embodiments, the 3' half of Group I catalytic intron fragment of (A) and the 5' half of Group I catalytic intron fragment of (G) are from a Cyanobacterium *Anabaena* pre-tRNA-Leu gene, and the 3' exon fragment of (C) includes the first annealing region and the 5' exon fragment of (E) includes the second annealing region. The first annealing region may include, e.g., from 5 to 50, e.g., from 10 to 15 (e.g., 10, 11, 12, 13, 14, or 15) ribonucleotides and the second annealing region may include, e.g., from 5 to 50, e.g., from 10 to 15 (e.g., 10, 11, 12, 13, 14, or 15) ribonucleotides.

In some embodiments, the 3' half of Group I catalytic intron fragment of (A) and the 5' half of Group I catalytic intron fragment of (G) are from a Tetrahymena pre-rRNA, and the 3' half of Group I catalytic intron fragment of (A) includes the first annealing region and the 5' exon fragment of (E) includes the second annealing region. In some embodiments, the 3' exon fragment of (C) includes the first annealing region and the 5' half of Group I catalytic intron fragment of (G) includes the second annealing region. The first annealing region may include, e.g., from 6 to 50, e.g., from 10 to 16 (e.g., 10, 11, 12, 13, 14, 15, or 16) ribonucleotides, and the second annealing region may include, e.g., from 6 to 50, e.g., from 10 to 16 (e.g., 10, 11, 12, 13, 14, 15, or 16) ribonucleotides.

In some embodiments, the 3' half of Group I catalytic intron fragment of (A) and the 5' Group I catalytic intron fragment of (G) are from a T4 phage td gene. The 3' exon fragment of (C) may include the first annealing region and the 5' half of Group I catalytic intron fragment of (G) may include the second annealing region. The first annealing region may include, e.g., from 2 to 16, e.g., 10 to 16 (e.g., 2, 3, 4, 5, 6, 7, 8, 9, 10, 11, 12, 13, 14, 15, or 16) ribonucleotides, and the second annealing region may include, e.g., from 2 to 16, e.g., 10 to 16 (e.g., 2, 3, 4, 5, 6, 7, 8, 9, 10, 11, 12, 13, 14, 15, or 16) ribonucleotides.

In some embodiments, the 3' half of Group I catalytic intron fragment of (A) is the 5' terminus of the linear polynucleotide.

In some embodiments, the 5' half of Group I catalytic intron fragment of (G) is the 3' terminus of the linear polyribonucleotide.

In some embodiments, the linear polyribonucleotide does not include a further annealing region.

In some embodiments, the linear polyribonucleotide does not include an annealing region 3' to (A) that includes partial or complete nucleic acid complementarity with an annealing region 5' to (G).

In some embodiments, the polyribonucleotide cargo of (D) includes an expression sequence, a non-coding sequence, or an expression sequence and a non-coding sequence.

In some embodiments, the polyribonucleotide cargo of (D) includes an expression sequence encoding a polypeptide.

In some embodiments, the polyribonucleotide cargo of (D) includes an IRES operably linked to an expression sequence encoding a polypeptide.

In some embodiments, the IRES is located upstream of the expression sequence. In some embodiments, the IRES is located downstream of the expression sequence.

In some embodiments, the polyribonucleotide cargo of (D) includes an expression sequence that encodes a polypeptide that has a biological effect on a subject.

In some embodiments, the linear polyribonucleotide further includes a first spacer region between the 3' exon fragment of (C) and the polyribonucleotide cargo of (D). The first spacer region may be, e.g., at least 5 (e.g., at least 10, at least 15, at least 20) ribonucleotides in length. In some embodiments, the linear polyribonucleotide further includes a second spacer region between the polyribonucleotide cargo of (D) and the 5' exon fragment of (E). The second spacer region may be, e.g., at least 5 (e.g., at least 10, at least 15, at least 20) ribonucleotides in length. In some embodiments, each spacer region is at least 5 (e.g., at least 10, at least 15, at least 20) ribonucleotides in length. Each spacer region may be, e.g., from 5 to 500 (e.g., 10, 20, 30, 40, 50, 60, 70, 80, 90, 100, 150, 200, 250, 300, 350, 400, 450, or 500) ribonucleotides in length. The first spacer region, the second spacer region, or the first spacer region and the second spacer region may include a polyA sequence. The first spacer region, the second spacer region, or the first spacer region and the second spacer region may include a polyA-C sequence. The first spacer region, the second spacer region, or the first spacer region and the second spacer region may include a polyA-G sequence. The first spacer region, the second spacer region, or the first spacer region and the second spacer region may include a polyA-T sequence. The first spacer region, the second spacer region, or the first spacer region and the second spacer region may include a random sequence.

In some embodiments, the linear polyribonucleotide is from 50 to 20,000, e.g., 100 to 20,000, e.g., 200 to 20,000, e.g., 300 to 20,000 (e.g., 50, 100, 200, 300, 400, 500, 600, 700, 800, 900, 1,000, 1,100, 1,200, 1,300, 1,400, 1,500, 1,600, 1,700, 1,800, 1,900, 2,000, 2,500, 3,000, 3,500, 4,000, 5,000, 6,000, 7,000, 8,000, 9,000, 10,000, 11,000, 12,000, 13,000, 14,000, 15,000, 16,000, 17,000, 18,000, 19,000, or 20,000) ribonucleotides in length. In embodiments, the linear polyribonucleotide is, e.g., at least 50, at least 100, at least 200, at least 300, at least 400, at least 500, at least 1,000, at least 2,000, at least 3,000, at least 4,000, or at least 5,000 ribonucleotides in length.

In another aspect, the invention features a DNA vector including an RNA polymerase promoter operably linked to a DNA sequence that encodes the linear polyribonucleotide of any of the embodiments described herein.

In another aspect, the invention features a circular polyribonucleotide (e.g., a covalently closed circular polyribonucleotide) produced from the linear polyribonucleotide or the DNA vector of any of the embodiments described herein.

In another aspect, the invention features a circular polyribonucleotide (e.g., a covalently closed circular polyribonucleotide) having a splice junction joining a 5' exon fragment and a 3' exon fragment. The 3' exon fragment includes a first annealing region including 2 to 50, e.g., 5 to 50, e.g., 6 to 50, e.g., 7 to 50, e.g., 8 to 50 (e.g., from 10 to 30, 10 to 20, or 10 to 15, e.g., 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50) ribonucleotides, and the 5' exon fragment includes a second annealing region including 2 to 50, e.g., 5 to 50, e.g., 6 to 50, e.g., 7 to 50, e.g., 8 to 50 (e.g., from 10 to 30, 10 to 20, or 10 to 15, e.g., 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50) ribonucleotides. In embodiment, the first annealing region and the second annealing region include from 80% to 100% (e.g., 80%, 85%, 90%, 95%, 97%, 99%, or 100%) complementarity. In embodiments the first annealing region and the second annealing region include from zero to 10

(e.g., 0, 1, 2, 3, 4, 5, 6, 7, 8, 9, or 10) mismatched base pairs (bp). In embodiments, the circular polynucleotide further include a polyribonucleotide cargo. In embodiments, the polyribonucleotide cargo includes an expression (or coding) sequence, a non-coding sequence, or a combination of an expression (or coding) sequence and a non-coding sequence. In embodiments, the polyribonucleotide cargo includes an expression (coding) sequence encoding a polypeptide. In embodiments, the polyribonucleotide includes an IRES operably linked to an expression sequence encoding a polypeptide. In some embodiments, the circular polyribonucleotide further includes a spacer region between the IRES and the 3' exon fragment or the 5' exon fragment. The spacer region may be, e.g., at least 5 (e.g., at least 10, at least 15, at least 20) ribonucleotides in length ribonucleotides in length. The spacer region may be, e.g., from 5 to 500 (e.g., 10, 20, 30, 40, 50, 60, 70, 80, 90, 100, 150, 200, 250, 300, 350, 400, 450, or 500) ribonucleotides. In some embodiments, the spacer region includes a polyA sequence. In some embodiments, the spacer region includes a polyA-C sequence. In some embodiments, the spacer region includes a polyA-G sequence. In some embodiments, the spacer region includes a polyA-T sequence. In some embodiments, the spacer region includes a random sequence.

In some embodiments, the circular polyribonucleotide is from 50 to 20,000, e.g., 100 to 20,000, e.g., 200 to 20,000, e.g., 300 to 20,000 (e.g., 50, 100, 200, 300, 400, 500, 600, 700, 800, 900, 1,000, 1,100, 1,200, 1,300, 1,400, 1,500, 1,600, 1,700, 1,800, 1,900, 2,000, 2,500, 3,000, 3,500, 4,000, 5,000, 6,000, 7,000, 8,000, 9,000, 10,000, 11,000, 12,000, 13,000, 14,000, 15,000, 16,000, 17,000, 18,000, 19,000, or 20,000) ribonucleotides in length. In embodiments, the circular polyribonucleotide is, e.g., at least 500, at least 1,000, at least 2,000, at least 3,000, at least 4,000, or at least 5,000 ribonucleotides in length.

In some embodiments, the circular polyribonucleotide is produced from a linear polyribonucleotide or vector as described herein.

In another aspect, the invention features a method of expressing a polypeptide in a cell by providing a linear polyribonucleotide, a DNA vector, or a circular polyribonucleotide as described herein to the cell. The method further includes allowing the cellular machinery to express the polypeptide from the polyribonucleotide.

In another aspect, the invention features a method of producing a circular polyribonucleotide as described herein by providing a linear polyribonucleotide as described herein under conditions suitable for self-splicing of the linear polyribonucleotide to produce the circular polyribonucleotide.

Definitions

To facilitate the understanding of this disclosure, a number of terms are defined below. Terms defined herein have meanings as commonly understood by a person of ordinary skill in the areas relevant to the disclosure. Terms such as "a", "an," and "the" are not intended to refer to only a singular entity but include the general class of which a specific example may be used for illustration. The term "or" is used to mean "and/or" unless explicitly indicated to refer to alternatives only or the alternative are mutually exclusive, although the disclosure supports a definition that refers to only alternatives and "and/or". The terminology herein is used to describe specific embodiments, but their usage is not to be taken as limiting, except as outlined in the claims.

As used herein, any values provided in a range of values include both the upper and lower bounds, and any values contained within the upper and lower bounds.

As used herein, the term "about" refers to a value that is within +10% of a recited value.

As used herein, the term "carrier" is a compound, composition, reagent, or molecule that facilitates the transport or delivery of a composition (e.g., a circular polyribonucleotide) into a cell by a covalent modification of the circular polyribonucleotide, via a partially or completely encapsulating agent, or a combination thereof. Non-limiting examples of carriers include carbohydrate carriers (e.g., an anhydride-modified phytoglycogen or glycogen-type material), nanoparticles (e.g., a nanoparticle that encapsulates or is covalently linked binds to the circular polyribonucleotide), liposomes, fusosomes, ex vivo differentiated reticulocytes, exosomes, protein carriers (e.g., a protein covalently linked to the circular polyribonucleotide), or cationic carriers (e.g., a cationic lipopolymer or transfection reagent).

As used herein, the terms "circular polyribonucleotide" and "circular RNA" are used interchangeably and mean a polyribonucleotide molecule that has a structure having no free ends (i.e., no free 3' or 5' ends), for example a polyribonucleotide molecule that forms a circular or end-less structure through covalent or non-covalent bonds. The circular polyribonucleotide may be, e.g., a covalently closed polyribonucleotide.

As used herein, the term "circularization efficiency" is a measurement of resultant circular polyribonucleotide versus its non-circular starting material.

As used herein, the terms "disease," "disorder," and "condition" each refer to a state of sub-optimal health, for example, a state that is or would typically be diagnosed or treated by a medical professional.

By "heterologous" is meant to occur in a context other than in the naturally occurring (native) context. A "heterologous" polynucleotide sequence indicates that the polynucleotide sequence is being used in a way other than what is found in that sequence's native genome. For example, a "heterologous promoter" is used to drive transcription of a sequence that is not one that is natively transcribed by that promoter; thus, a "heterologous promoter" sequence is often included in an expression construct by means of recombinant nucleic acid techniques. The term "heterologous" is also used to refer to a given sequence that is placed in a non-naturally occurring relationship to another sequence; for example, a heterologous coding or non-coding nucleotide sequence is commonly inserted into a genome by genomic transformation techniques, resulting in a genetically modified or recombinant genome.

As used herein "increasing fitness" or "promoting fitness" of a subject refers to any favorable alteration in physiology, or of any activity carried out by a subject organism, as a consequence of administration of a peptide or polypeptide described herein, including, but not limited to, any one or more of the following desired effects: (1) increased tolerance of biotic or abiotic stress by about 10%, 20%, 30%, 40%, 50%, 60%, 70%, 80%, 90%, 95%, 99%, 100% or more; (2) increased yield or biomass by about 10%, 20%, 30%, 40%, 50%, 60%, 70%, 80%, 90%, 95%, 99%, 100% or more; (3) modified flowering time by about 10%, 20%, 30%, 40%, 50%, 60%, 70%, 80%, 90%, 95%, 99%, 100% or more; (4) increased resistance to pests or pathogens by about 10%, 20%, 30%, 40%, 50%, 60%, 70%, 80%, 90%, 95%, 99%, 100% or more, (4) increased resistance to herbicides by about 10%, 20%, 30%, 40%, 50%, 60%, 70%, 80%, 90%, 95%, 99%, 100% or more; (5) increasing a population of a subject organism (e.g., an agriculturally important insect) by about 10%, 20%, 30%, 40%, 50%, 60%, 70%, 80%, 90%, 95%, 99%, 100% or more; (6) increasing the reproductive rate of a subject organism (e.g., insect, e.g., bee or silkworm) by about 10%, 20%, 30%, 40%, 50%, 60%, 70%, 80%, 90%, 95%, 99%, 100% or more; (7) increasing the mobility of a subject organism (e.g., insect, e.g., bee or silkworm) by about 10%, 20%, 30%, 40%, 50%, 60%, 70%, 80%, 90%, 95%, 99%, 100% or more; (8) increasing the body weight of a subject organism (e.g., insect, e.g., bee or silkworm) by about 10%, 20%, 30%, 40%, 50%, 60%, 70%, 80%, 90%, 95%, 99%, 100% or more; (9) increasing the metabolic rate or activity of a subject organism (e.g., insect, e.g., bee or silkworm) by about 10%, 20%, 30%, 40%, 50%, 60%, 70%, 80%, 90%, 95%, 99%, 100% or more; (10) increasing pollination (e.g., number of plants pollinated in a given amount of time) by a subject organism (e.g., insect, e.g., bee or silkworm) by about 10%, 20%, 30%, 40%, 50%, 60%, 70%, 80%, 90%, 95%, 99%, 100% or more; (11) increasing production of subject organism (e.g., insect, e.g., bee or silkworm) byproducts (e.g., honey from a honeybee or silk from a silkworm) by about 10%, 20%, 30%, 40%, 50%, 60%, 70%, 80%, 90%, 95%, 99%, 100% or more; (12) increasing nutrient content of the subject organism (e.g., insect) (e.g., protein, fatty acids, or amino acids) by about 10%, 20%, 30%, 40%, 50%, 60%, 70%, 80%, 90%, 95%, 99%, 100% or more; or (13) increasing a subject organism's resistance to pesticides (e.g., a neonicotinoid (e.g., imidacloprid) or an organophosphorus insecticide (e.g., a phosphorothioate, e.g., fenitrothion)) by about 10%, 20%, 30%, 40%, 50%, 60%, 70%, 80%, 90%, 95%, 99%, 100% or more, (14) increasing health or reducing disease of a subject organism such as a human or non-human animal. An increase in host fitness can be determined in comparison to a subject organism to which the modulating agent has not been administered. Conversely, "decreasing fitness" of a subject refers to any unfavorable alteration in physiology, or of any activity carried out by a subject organism, as a consequence of administration of a peptide or polypeptide described herein, including, but not limited to, any one or more of the following intended effects: (1) decreased tolerance of biotic or abiotic stress by about 10%, 20%, 30%, 40%, 50%, 60%, 70%, 80%, 90%, 95%, 99%, 100% or more; (2) decreased yield or biomass by about 10%, 20%, 30%, 40%, 50%, 60%, 70%, 80%, 90%, 95%, 99%, 100% or more; (3) modified flowering time by about 10%, 20%, 30%, 40%, 50%, 60%, 70%, 80%, 90%, 95%, 99%, 100% or more; (4) decreased resistance to pests or pathogens by about 10%, 20%, 30%, 40%, 50%, 60%, 70%, 80%, 90%, 95%, 99%, 100% or more, (4) decreased resistance to herbicides by about 10%, 20%, 30%, 40%, 50%, 60%, 70%, 80%, 90%, 95%, 99%, 100% or more; (5) decreasing a population of a subject organism (e.g., an agriculturally important insect) by about 10%, 20%, 30%, 40%, 50%, 60%, 70%, 80%, 90%, 95%, 99%, 100% or more; (6) decreasing the reproductive rate of a subject organism (e.g., insect, e.g., bee or silkworm) by about 10%, 20%, 30%, 40%, 50%, 60%, 70%, 80%, 90%, 95%, 99%, 100% or more; (7) decreasing the mobility of a subject organism (e.g., insect, e.g., bee or silkworm) by about 10%, 20%, 30%, 40%, 50%, 60%, 70%, 80%, 90%, 95%, 99%, 100% or more; (8) decreasing the body weight of a subject organism (e.g., insect, e.g., bee or silkworm) by about 10%, 20%, 30%, 40%, 50%, 60%, 70%, 80%, 90%, 95%, 99%, 100% or more; (9) decreasing the metabolic rate or activity of a subject organism (e.g., insect, e.g., bee or silkworm) by about 10%, 20%, 30%, 40%, 50%, 60%, 70%, 80%, 90%, 95%, 99%, 100% or more; (10) decreasing pollination (e.g., number of plants pollinated in a given amount of time) by a subject organism (e.g., insect, e.g., bee or silkworm) by about 10%, 20%, 30%, 40%, 50%, 60%, 70%, 80%, 90%, 95%, 99%, 100% or more; (11) decreasing production of subject organism (e.g., insect, e.g., bee or silkworm) byproducts (e.g., honey from a honeybee or silk from a silkworm) by about 10%, 20%, 30%, 40%, 50%, 60%, 70%, 80%, 90%, 95%, 99%, 100% or more; (12) decreasing nutrient content of the subject organism (e.g., insect) (e.g., protein, fatty acids, or amino acids) by about 10%, 20%, 30%, 40%, 50%, 60%, 70%, 80%, 90%, 95%, 99%, 100% or more; or (13) decreasing a subject organism's resistance to pesticides (e.g., a neonicotinoid (e.g., imidacloprid) or an organophosphorus insecticide (e.g., a phosphorothioate, e.g., fenitrothion)) by about 10%, 20%, 30%, 40%, 50%, 60%, 70%, 80%, 90%, 95%, 99%, 100% or more, (14) decreasing health or reducing disease of a subject organism such as a human or non-human animal. A decrease in host fitness can be determined in comparison to a subject organism to which the modulating agent has not been administered. It will be apparent to one of skill in the art that certain changes in the physiology, phenotype, or activity of a subject, e.g., modification of flowering time in a plant, can be considered to increase fitness of the subject or to decrease fitness of the subject, depending on the context (e.g., to adapt to a change in climate or other environmental conditions). For example, a delay in flowering time (e.g., about 10%, 20%, 30%, 40%, 50%, 60%, 70%, 80%, 90%, 95%, 99%, 100% fewer plants in a population flowering at a given calendar date) can be a beneficial adaptation to later or cooler springtimes and thus be considered to increase a plant's fitness; conversely, the same delay in flowering time in the context of earlier or warmer springtimes can be considered to decrease a plant's fitness.

As used herein, the terms "linear RNA" or "linear polyribonucleotide" or "linear polyribonucleotide molecule" are used interchangeably and mean polyribonucleotide molecule having a 5' and 3' end. One or both of the 5' and 3' ends may be free ends or joined to another moiety. Linear RNA includes RNA that has not undergone circularization (e.g., is pre-circularized) and can be used as a starting material for circularization.

As used herein, the term "modified ribonucleotide" means a nucleotide with at least one modification to the sugar, the nucleobase, or the internucleoside linkage.

As used herein, the term "naked delivery" is a formulation for delivery to a cell without the aid of a carrier and without covalent modification to a moiety that aids in delivery to a cell. A naked delivery formulation is free from any transfection reagents, cationic carriers, carbohydrate carriers, nanoparticle carriers, or protein carriers. For example, naked delivery formulation of a circular polyribonucleotide is a formulation that comprises a circular polyribonucleotide without covalent modification and is free from a carrier.

The term "pharmaceutical composition" is intended to also disclose that the circular or linear polyribonucleotide included within a pharmaceutical composition can be used for the treatment of the human or animal body by therapy.

The term "polynucleotide" as used herein means a molecule including one or more nucleic acid subunits, or nucleotides, and can be used interchangeably with "nucleic acid" or "oligonucleotide". A polynucleotide can include one or more nucleotides selected from adenosine (A), cytosine (C), guanine (G), thymine (T) and uracil (U), or variants thereof. A nucleotide can include a nucleoside and at least 1, 2, 3, 4, 5, 6, 7, 8, 9, 10, or more phosphate (PO3) groups. A nucleotide can include a nucleobase, a five-carbon sugar (either ribose or deoxyribose), and one or more phosphate groups. Ribonucleotides are nucleotides in which the sugar is ribose. Polyribonucleotides or ribonucleic acids, or RNA, can refer to macromolecules that include multiple ribonucleotides that are polymerized via phosphodiester bonds. Deoxyribonucleotides are nucleotides in which the sugar is deoxyribose. As used herein, a polyribonucleotide sequence that recites thymine (T) is understood to represent uracil (U).

As used herein, the term "polyribonucleotide cargo" herein includes any sequence including at least one polyribonucleotide. In embodiments, the polyribonucleotide cargo includes one or multiple expression sequences, wherein each expression sequence encodes a polypeptide. In embodiments, the polyribonucleotide cargo includes one or multiple noncoding sequences, such as a polyribonucleotide having regulatory or catalytic functions. In embodiments, the polyribonucleotide cargo includes a combination of expression and noncoding sequences. In embodiments, the polyribonucleotide cargo includes one or more polyribonucleotide sequence described herein, such as one or multiple regulatory elements, internal ribosomal entry site (IRES) elements, or spacer sequences.

As used interchangeably herein, the terms "polyA" or "polyA sequence" refer to an untranslated, contiguous region of a nucleic acid molecule of at least 5 nucleotides in length and consisting of adenosine residues. In some embodiments, a polyA sequence is at least 10, at least 15, at least 20, at least 30, at least 40, or at least 50 nucleotides in length. In some embodiments, a polyA sequence is located 3' to (e.g., downstream of) an open reason frame (e.g., an open reading frame encoding a polypeptide), and the polyA sequence is 3' to a termination element (e.g., a Stop codon) such that the polyA is not translated. In some embodiments, a polyA sequence is located 3' to a termination element and a 3' untranslated region.

As used herein, the elements of a nucleic acid are "operably connected" if they are positioned on the vector such that they can be transcribed to form a linear RNA that can then be circularized into a circular RNA using the methods provided herein.

Polydeoxyribonucleotides or deoxyribonucleic acids, or DNA, means macromolecules that include multiple deoxyribonucleotides that are polymerized via phosphodiester bonds. A nucleotide can be a nucleoside monophosphate or a nucleoside polyphosphate. A nucleotide means a deoxyribonucleoside polyphosphate, such as, e.g., a deoxyribonucleoside triphosphate (dNTP), which can be selected from deoxyadenosine triphosphate (dATP), deoxycytidine triphosphate (dCTP), deoxyguanosine triphosphate (dGTP), uridine triphosphate (dUTP) and deoxythymidine triphosphate (dTTP) dNTPs, that include detectable tags, such as luminescent tags or markers (e.g., fluorophores). A nucleotide can include any subunit that can be incorporated into a growing nucleic acid strand. Such subunit can be an A, C, G, T, or U, or any other subunit that is specific to one or more complementary A, C, G, T or U, or complementary to a purine (i.e., A or G, or variant thereof) or a pyrimidine (i.e., C, T or U, or variant thereof). In some examples, a polynucleotide is deoxyribonucleic acid (DNA), ribonucleic acid (RNA), or derivatives or variants thereof. In some cases, a polynucleotide is a short interfering RNA (siRNA), a microRNA (miRNA), a plasmid DNA (pDNA), a short hairpin RNA (shRNA), small nuclear RNA (snRNA), messenger RNA (mRNA), precursor mRNA (pre-mRNA), antisense RNA (asRNA), to name a few, and encompasses both the nucleotide sequence and any structural embodiments thereof, such as single-stranded, double-stranded, triple-stranded, helical, hairpin, etc. In some cases, a polynucleotide molecule is circular. A polynucleotide can have various lengths. A nucleic acid molecule can have a length of at least about 10 bases, 20 bases, 30 bases, 40 bases, 50 bases, 100 bases, 200 bases, 300 bases, 400 bases, 500 bases, 1 kilobase (kb), 2 kb, 3, kb, 4 kb, 5 kb, 10 kb, 50 kb, or more. A polynucleotide can be isolated from a cell or a tissue. Embodiments of polynucleotides include isolated and purified DNA/RNA molecules, synthetic DNA/RNA molecules, and synthetic DNA/RNA analogs.

Embodiments of polynucleotides, e.g., polyribonucleotides or polydeoxyribonucleotides, include polynucleotides that contain one or more nucleotide variants, including nonstandard nucleotide(s), non-natural nucleotide(s), nucleotide analog(s) or modified nucleotides. Examples of modified nucleotides include, but are not limited to diaminopurine, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, 2,6-diaminopurine and the like. In some cases, nucleotides include modifications in their phosphate moieties, including modifications to a triphosphate moiety. Non-limiting examples of such modifications include phosphate chains of greater length (e.g., a phosphate chain having, 4, 5, 6, 7, 8, 9, 10 or more phosphate moieties) and modifications with thiol moieties (e.g., alpha-thiotriphosphate and beta-thiotriphosphates). In embodiments, nucleic acid molecules are modified at the base moiety (e.g., at one or more atoms that typically are available to form a hydrogen bond with a complementary nucleotide or at one or more atoms that are not typically capable of forming a hydrogen bond with a complementary nucleotide), sugar moiety or phosphate backbone. In embodiments, nucleic acid molecules contain amine-modified groups, such as amino allyl 1-dUTP (aa-dUTP) and aminohexylacrylamide-dCTP (aha-dCTP) to allow covalent attachment of amine reactive moieties, such as N-hydroxysuccinimide esters (NHS). Alternatives to standard DNA base pairs or RNA base pairs in the oligonucleotides of the present disclosure can provide higher density in bits per cubic mm, higher safety (resistant to accidental or purposeful synthesis of natural toxins), easier discrimination in photo-programmed polymerases, or lower secondary structure. Such alternative base pairs compatible with natural and mutant polymerases for de novo or amplification synthesis are described in Betz K, Malyshev DA, Lavergne T, Welte W, Diederichs K, Dwyer TJ, Ordoukhanian P, Romesberg FE, Marx A. Nat. Chem. Biol. 2012 July;8 (7): 612-4, which is herein incorporated by reference for all purposes.

As used herein, "polypeptide" means a polymer of amino acid residues (natural or unnatural) linked together most often by peptide bonds. The term, as used herein, refers to proteins, polypeptides, and peptides of any size, structure, or function. Polypeptides can include gene products, naturally occurring polypeptides, synthetic polypeptides, homologs, orthologs, paralogs, fragments and other equivalents, variants, and analogs of the foregoing. A polypeptide can be a single molecule or a multi-molecular complex such as a dimer, trimer, or tetramer. They can also include single chain or multichain polypeptides such as antibodies or insulin and can be associated or linked. Most commonly disulfide linkages are found in multichain polypeptides. The term polypeptide can also apply to amino acid polymers in which one or more amino acid residues are an artificial chemical analogue of a corresponding naturally occurring amino acid.

As used herein, the term "plant-modifying polypeptide" refers to a polypeptide that can alter the genetic properties (e.g., increase gene expression, decrease gene expression, or otherwise alter the nucleotide sequence of DNA or RNA), epigenetic properties, or biochemical or physiological properties of a plant in a manner that results in a change in the plant's physiology or phenotype, e.g., an increase or a decrease in plant fitness.

As used herein, the term "regulatory element" is a moiety, such as a nucleic acid sequence, that modifies expression of an expression sequence within the circular or linear polyribonucleotide.

As used herein, a "spacer" refers to any contiguous nucleotide sequence (e.g., of one or more nucleotides) that provides distance or flexibility between two adjacent polynucleotide regions.

As used herein, the term "sequence identity" is determined by alignment of two peptide or two nucleotide sequences using a global or local alignment algorithm. Sequences are referred to as "substantially identical" or "essentially similar" when they share at least a certain minimal percentage of sequence identity when optimally aligned (e.g., when aligned by programs such as GAP or BESTFIT using default parameters). GAP uses the Needleman and Wunsch global alignment algorithm to align two sequences over their entire length, maximizing the number of matches and minimizes the number of gaps. Generally, the GAP default parameters are used, with a gap creation penalty=50 (nucleotides)/8 (proteins) and gap extension penalty=3 (nucleotides)/2 (proteins). For nucleotides the default scoring matrix used is nwsgapdna, and for proteins the default scoring matrix is Blosum62 (Henikoff & Henikoff, 1992, PNAS 89, 915-919). Sequence alignments and scores for percentage sequence identity are determined, e.g., using computer programs, such as the GCG Wisconsin Package, Version 10.3, available from Accelrys Inc., 9685 Scranton Road, San Diego, CA 92121-3752 USA, or EmbossWin version 2.10.0 (using the program "needle"). Alternatively or additionally, percent identity is determined by searching against databases, e.g., using algorithms such as FASTA, BLAST, etc. Sequence identity refers to the sequence identity over the entire length of the sequence.

As used herein, "structured" with regard to RNA refers to an RNA sequence that is predicted by the RNAFold software or similar predictive tools to form a structure (e.g., a hairpin loop) with itself or other sequences in the same RNA molecule.

As used herein, the term "subject" refers to an organism, such as an animal, plant, or microbe. In embodiments, the subject is a vertebrate animal (e.g., mammal, bird, fish, reptile, or amphibian). In embodiments, the subject is a human. In embodiments, the subject is a non-human mammal. In embodiments, the subject is a non-human mammal such as a non-human primate (e.g., monkeys, apes), ungulate (e.g., cattle, buffalo, bison, sheep, goat, pig, camel, llama, alpaca, deer, horses, donkeys), carnivore (e.g., dog, cat), rodent (e.g., rat, mouse), or lagomorph (e.g., rabbit). In embodiments, the subject is a bird, such as a member of the avian taxa Galliformes (e.g., chickens, turkeys, pheasants, quail), Anseriformes (e.g., ducks, geese), Paleaognathae (e.g., ostriches, emus), Columbiformes (e.g., pigeons, doves), or Psittaciformes (e.g., parrots). In embodiments, the subject is an invertebrate such as an arthropod (e.g, insects, arachnids, crustaceans), a nematode, an annelid, a helminth, or a mollusc. In embodiments, the subject is an invertebrate agricultural pest or an invertebrate that is parasitic on an invertebrate or vertebrate host. In embodiments, the subject is a plant, such as an angiosperm plant (which can be a dicot or a monocot) or a gymnosperm plant (e.g., a conifer, a cycad, a gnetophyte, a Ginkgo), a fern, horsetail, clubmoss, or a bryophyte. In embodiments, the subject is a eukaryotic alga (unicellular or multicellular). In embodiments, the subject is a plant of agricultural or horticultural importance, such as row crop plants, fruit-producing plants and trees, vegetables, trees, and ornamental plants including ornamental flowers, shrubs, trees, groundcovers, and turf grasses.

As used herein, the term "treat," or "treating," refers to a prophylactic or therapeutic treatment of a disease or disorder (e.g., an infectious disease, a cancer, a toxicity, or an allergic reaction) in a subject. The effect of treatment can include reversing, alleviating, reducing severity of, curing, inhibiting the progression of, reducing the likelihood of recurrence of the disease or one or more symptoms or manifestations of the disease or disorder, stabilizing (i.e., not worsening) the state of the disease or disorder, or preventing the spread of the disease or disorder as compared to the state or the condition of the disease or disorder in the absence of the therapeutic treatment. Embodiments include treating plants to control a disease or adverse condition caused by or associated with an invertebrate pest or a microbial (e.g., bacterial, fungal, oomycete, or viral) pathogen. Embodiments include treating a plant to increase the plant's innate defense or immune capability to tolerate pest or pathogen pressure.

As used herein, the term "termination element" is a moiety, such as a nucleic acid sequence, that terminates translation of the expression sequence in the circular or linear polyribonucleotide.

As used herein, the term "translation efficiency" is a rate or amount of protein or peptide production from a ribonucleotide transcript. In some embodiments, translation efficiency can be expressed as amount of protein or peptide produced per given amount of transcript that codes for the protein or peptide, e.g., in a given period of time, e.g., in a given translation system, e.g., an cell-free translation system like rabbit reticulocyte lysate.

As used herein, the term "translation initiation sequence" is a nucleic acid sequence that initiates translation of an expression sequence in the circular or linear polyribonucleotide.

As used herein, the term "therapeutic polypeptide" refers to a polypeptide that when administered to or expressed in a subject provides some therapeutic benefit. In embodiments, a therapeutic polypeptide is used to treat or prevent a disease, disorder, or condition in a subject by administration of the therapeutic peptide to a subject or by expression in a subject of the therapeutic polypeptide. In alternative embodiments, a therapeutic polypeptide is expressed in a cell and the cell is administered to a subject to provide a therapeutic benefit.

As used herein, a "vector" means a piece of DNA, that is synthesized (e.g., using PCR), or that is taken from a virus, plasmid, or cell of a higher organism into which a foreign DNA fragment can be or has been inserted for cloning or expression purposes. In some embodiments, a vector can be stably maintained in an organism. A vector can include, for example, an origin of replication, a selectable marker or reporter gene, such as antibiotic resistance or GFP, or a multiple cloning site (MCS). The term includes linear DNA fragments (e.g., PCR products, linearized plasmid fragments), plasmid vectors, viral vectors, cosmids, bacterial artificial chromosomes (BACs), yeast artificial chromosomes (YACs), and the like. In one embodiment, the vectors provided herein include a multiple cloning site (MCS). In another embodiment, the vectors provided herein do not include an MCS.

BRIEF DESCRIPTION OF THE DRAWINGS

FIGS. 10A and 10B are schematic drawings showing the structures of an exemplary Tetrahymena permuted intron-exon with an annealing region of 6 nucleotides (FIG. 9A) and an exemplary Tetrahymena permuted intron-exon with an extended annealing region (FIG. 9B).

FIG. 19 is a table showing exemplary modifications for various permuted intron-exon with an annealing region and having the sequences of SEQ ID NOs: 92-99. Bolding identifies the original annealing region; italics and underlining identify exemplary modifications for extended annealing.

DETAILED DESCRIPTION

Figure 1A:
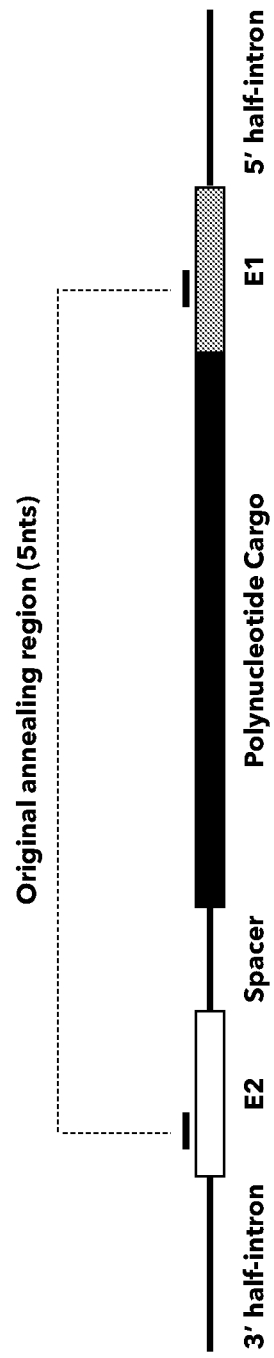
FIGS. 1A and 1B are schematic drawings showing an exemplary *Anabaena* permuted intron-exon with an annealing region of 5 nucleotides (FIG. 1A) and an exemplary *Anabaena* permuted intron-exon with an extended annealing region (FIG. 1B).

The present invention features compositions and methods for producing a circular polyribonucleotide (circular RNA). Circular polyribonucleotides described herein are particularly useful for delivering a polynucleotide cargo (e.g., encoding a gene or protein) to a target cell.

A circular polyribonucleotide may be produced from a linear polyribonucleotide in which the ends are self-spliced together, thereby forming the circular polyribonucleotide. The linear RNA molecules described herein include, from 5' to 3', (A) a 3' half of Group I catalytic intron fragment; (B) a 3' splice site; (C) a 3' exon fragment; (D) a polyribonucleotide cargo; (E) a 5' exon fragment; (F) a 5' splice site; and (G) a 5' half of Group I catalytic intron fragment. The polyribonucleotide includes a first annealing region that has from 2 to 50, e.g., from 8 to 50 ribonucleotides and is present within (A) the 3' half of Group I catalytic intron fragment; (B) the 3' splice site; or (C) the 3' exon fragment. The polyribonucleotide also includes a second annealing region that has from 2 to 50, e.g., from 8 to 50 ribonucleotides and is present within (E) the 5' exon fragment; (F) the 5' splice site; or (G) the 5' half of Group I catalytic intron fragment. The first annealing region has from 80% to 100% complementarity with the second annealing region or has from zero to 10 mismatched base pairs. These features allow the first annealing region to hybridize to the second annealing region, thus bringing the splice sites near the 5' and 3' ends of the linear polyribonucleotide into close proximity. Once the splice sites are nearby, the polyribonucleotide is able to self-splice the 3' and 5' splice sites, thus forming the circular polyribonucleotide.

By including the first annealing region within, for example, (A) the 3' half of Group I catalytic intron fragment; (B) the 3' splice site; or (C) the 3' exon fragment, and the second annealing region within, for example, (E) the 5' exon fragment; (F) the 5' splice site; or (G) the 5' half of Group I catalytic intron fragment, the linear molecule exhibits increased circularization efficiency and splicing fidelity as compared to other polyribonucleotide constructs that lack these features. Furthermore, by using an autocatalytic self-splicing intron, the linear molecule does not need to be treated with an exogenous enzyme, such as a ligase, to produce the circular polyribonucleotide. This is particularly advantageous for producing a circular product in a single pot reaction. The molecules, methods of producing, and uses thereof are described in more detail below.

Polynucleotides

The disclosure features circular polyribonucleotide compositions and methods of making circular polyribonucleotides. In some embodiments, a circular polyribonucleotide is produced from a linear polyribonucleotide (e.g., by self-splicing compatible ends of the linear polyribonucleotide). In some embodiments, a linear polyribonucleotide is transcribed from a deoxyribonucleotide template (e.g., a vector, a linearized vector, or a cDNA). Accordingly, the disclosure features deoxyribonucleotides, linear polyribonucleotides, and circular polyribonucleotides and compositions thereof useful in the production of circular polyribonucleotides.

Template Deoxyribonucleotides

The present invention features a template deoxyribonucleotide for making circular RNA. The deoxyribonucleotide includes the following, operably linked in a 5'-to-3' orientation: (A) a 3' half of Group I catalytic intron fragment; (B) a 3' splice site; (C) a 3' exon fragment; (D) a polyribonucleotide cargo; (E) a 5' exon fragment; (F) a 5' splice site; and (G) a 5' half of Group I catalytic intron fragment. In embodiments, the deoxyribonucleotide includes further elements, e.g., outside of or between any of elements (A), (B), (C), (D), (E), (F), or (G). In embodiments, any of the elements (A), (B), (C), (D), (E), (F), or (G) is separated from each other by a spacer sequence, as described herein.

In embodiments, the deoxyribonucleotide is, for example, a circular DNA vector, a linearized DNA vector, or a linear DNA (e.g., a cDNA, e.g., produced from a DNA vector).

In some embodiments, the deoxyribonucleotide further includes an RNA polymerase promoter operably linked to a sequence encoding a linear RNA described herein. In embodiments, the RNA polymerase promoter is heterologous to the sequence encoding the linear RNA. In some embodiments, the RNA polymerase promoter is a T7 promoter, a T6 promoter, a T4 promoter, a T3 promoter, an SP6 virus promoter, or an SP3 promoter.

In some embodiments, the deoxyribonucleotide includes a multiple-cloning site (MCS).

In some embodiments, the deoxyribonucleotide is used to produce circular RNA with the size range of about 100 to about 20,000 nucleotides. In some embodiments, the circular RNA is at least 100, 500, 550, 600, 650, 700, 750, 800, 850, 900, 950, 1,000, 1,100, 1,200, 1,300, 1,400, 1,500, 1,600 1,700, 1,800, 1,900, 2,000, 2,500, 3,000, 3,500, 4,000, 4,500 or 5,000 nucleotides in size. In some embodiments, the circular RNA is no more than 20,000, 15,000 10,000, 9,000, 8,000, 7,000, 6,000, 5,000 or 4,000 nucleotides in size.

Linear Polyribonucleotides

The present invention also features linear polyribonucleotides including the following, operably linked in a 5'-to-3' orientation: (A) a 3' half of Group I catalytic intron fragment; (B) a 3' splice site; (C) a 3' exon fragment; (D) a polyribonucleotide cargo; (E) a 5' exon fragment; (F) a 5' splice site; and (G) a 5' half of Group I catalytic intron fragment. In embodiments, the linear polyribonucleotide includes further elements, e.g., outside of or between any of elements (A), (B), (C), (D), (E), (F), or (G). For example, any of elements (A), (B), (C), (D), (E), (F), or (G) may be separated by a spacer sequence, as described herein.

In certain embodiments, provided herein is a method of generating linear RNA by performing transcription in a cell-free system (e.g., in vitro transcription) using a deoxyribonucleotide (e.g., a vector, linearized vector, or cDNA) provided herein as a template (e.g., a vector, linearized vector, or cDNA provided herein with an RNA polymerase promoter positioned upstream of the region that codes for the linear RNA).

In embodiments, a deoxyribonucleotide template is transcribed to a produce a linear RNA containing the components described herein. Upon expression, the linear polyribonucleotide produces a splicing-compatible polyribonucleotide, which may be self-spliced in order to produce a circular polyribonucleotide.

In some embodiments, the linear polyribonucleotide is from 50 to 20,000, 100 to 20,000, 200 to 20,000, 300 to 20,000 (e.g., 50, 100, 200, 300, 400, 500, 600, 700, 800, 900, 1,000, 1,100, 1,200, 1,300, 1,400, 1,500, 1,600, 1,700, 1,800, 1,900, 2,000, 2,500, 3,000, 3,500, 4,000, 5,000, 6,000, 7,000, 8,000, 9,000, 10,000, 11,000, 12,000, 13,000, 14,000, 15,000, 16,000, 17,000, 18,000, 19,000, or 20,000) ribonucleotides in length. In embodiments, the linear polyribonucleotide is, e.g., at least 500, at least 1,000, at least 2,000, at least 3,000, at least 4,000, or at least 5,000 ribonucleotides in length.

Circular Polyribonucleotides

In some embodiments, the invention features a circular polyribonucleotide (e.g., a covalently closed circular polyribonucleotide). In embodiments, the circular polyribonucleotide includes a splice junction joining a 5' exon fragment and a 3' exon fragment. In embodiments, the 3' exon fragment includes the first annealing region having from 2 to 50, e.g., from 8 to 50 (e.g., from 10 to 30, 10 to 20, or 10 to 15, e.g., 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50) ribonucleotides, and the 5' exon fragment includes the second annealing region having from 2 to 50, e.g., from 8 to 50 (e.g., from 10 to 30, 10 to 20, or 10 to 15, e.g., 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50) ribonucleotides. In embodiments, the first annealing region and the second annealing region include from 80% to 100% (e.g., 80%, 85%, 90%, 95%, 97%, 99%, or 100%) complementarity. In embodiments, the first annealing region and the second annealing region include from zero to 10 (e.g., 0, 1, 2, 3, 4, 5, 6, 7, 8, 9, or 10) mismatched base pairs.

In embodiments, the circular polynucleotide further includes a polyribonucleotide cargo. In embodiments, the polyribonucleotide cargo includes an expression (or coding) sequence, a non-coding sequence, or a combination of an expression (coding) sequence and a non-coding sequence. In embodiments, the polyribonucleotide cargo includes an expression (coding) sequence encoding a polypeptide. In embodiments, the polyribonucleotide includes an IRES operably linked to an expression sequence encoding a polypeptide. In some embodiments, the IRES is located upstream of the expression sequence. In some embodiments, the IRES is located downstream of the expression sequence. In some embodiments, the circular polyribonucleotide further includes a spacer region between the IRES and the 3' exon fragment or the 5' exon fragment. The spacer region may be, e.g., at least 5 (e.g., at least 10, at least 15, at least 20) ribonucleotides in length ribonucleotides in length. The spacer region may be, e.g., from 5 to 500 (e.g., 10, 20, 30, 40, 50, 60, 70, 80, 90, 100, 150, 200, 250, 300, 350, 400, 450, or 500) ribonucleotides. In some embodiments, the spacer region includes a polyA sequence. In some embodiments, the spacer region includes a polyA-C sequence. In some embodiments, the spacer region includes a polyA-G sequence. In some embodiments, the spacer region includes a polyA-T sequence. In some embodiments, the spacer region includes a random sequence. In some embodiments, the first annealing region and the second annealing region are joined, thereby forming a circular polyribonucleotide.

In some embodiments, the circular RNA is a produced by a deoxyribonucleotide template or a linear RNA described herein. In some embodiments, the circular RNA is produced by any of the methods described herein.

In some embodiments, the circular polyribonucleotide is at least about 20 nucleotides, at least about 30 nucleotides, at least about 40 nucleotides, at least about 50 nucleotides, at least about 75 nucleotides, at least about 100 nucleotides, at least about 200 nucleotides, at least about 300 nucleotides, at least about 400 nucleotides, at least about 500 nucleotides, at least about 1,000 nucleotides, at least about 2,000 nucleotides, at least about 5,000 nucleotides, at least about 6,000 nucleotides, at least about 7,000 nucleotides, at least about 8,000 nucleotides, at least about 9,000 nucleotides, at least about 10,000 nucleotides, at least about 12,000 nucleotides, at least about 14,000 nucleotides, at least about 15,000 nucleotides, at least about 16,000 nucleotides, at least about 17,000 nucleotides, at least about 18,000 nucleotides, at least about 19,000 nucleotides, or at least about 20,000 nucleotides.

In some embodiments, the circular polyribonucleotide is of a sufficient size to accommodate a binding site for a ribosome. In some embodiments, the size of a circular polyribonucleotide is a length sufficient to encode useful polypeptides, e.g., at least 20,000 nucleotides, at least 15,000 nucleotides, at least 10,000 nucleotides, at least 7,500 nucleotides, at least 5,000 nucleotides, at least 4,000 nucleotides, at least 3,000 nucleotides, at least 2,000 nucleotides, at least 1,000 nucleotides, at least 500 nucleotides, at least 1400 nucleotides, at least 300 nucleotides, at least 200 nucleotides, or at least 100 nucleotides may be produced.

In some embodiments, the circular polyribonucleotide includes one or more elements described elsewhere herein. In some embodiments, the elements are separated from one another by a spacer sequence. In some embodiments, the elements are separated from one another by 1 ribonucleotide, 2 nucleotides, about 5 nucleotides, about 10 nucleotides, about 15 nucleotides, about 20 nucleotides, about 30 nucleotides, about 40 nucleotides, about 50 nucleotides, about 60 nucleotides, about 80 nucleotides, about 100 nucleotides, about 150 nucleotides, about 200 nucleotides, about 250 nucleotides, about 300 nucleotides, about 400 nucleotides, about 500 nucleotides, about 600 nucleotides, about 700 nucleotides, about 800 nucleotides, about 900 nucleotides, about 1000 nucleotides, up to about 1 kb, at least about 1000 nucleotides, or any amount of nucleotides therebetween. In some embodiments, one or more elements are contiguous with one another, e.g., lacking a spacer element.

In some embodiments, the circular polyribonucleotide includes one or more repetitive elements described elsewhere herein. In some embodiments, the circular polyribonucleotide includes one or more modifications described elsewhere herein. In one embodiment, the circular RNA contains at least one nucleoside modification. In one embodiment, up to 100% of the nucleosides of the circular RNA are modified. In one embodiment, at least one nucleoside modification is a uridine modification or an adenosine modification.

As a result of its circularization, the circular polyribonucleotide may include certain characteristics that distinguish it from linear RNA. For example, the circular polyribonucleotide is less susceptible to degradation by exonuclease as compared to linear RNA. As such, the circular polyribonucleotide is more stable than a linear RNA, especially when incubated in the presence of an exonuclease. The increased stability of the circular polyribonucleotide compared with linear RNA makes circular polyribonucleotide more useful as a cell transforming reagent to produce polypeptides and can be stored more easily and for longer than linear RNA. The stability of the circular polyribonucleotide treated with exonuclease can be tested using methods standard in art which determine whether RNA degradation has occurred (e.g., by gel electrophoresis). Moreover, unlike linear RNA, the circular polyribonucleotide is less susceptible to dephosphorylation when the circular polyribonucleotide is incubated with phosphatase, such as calf intestine phosphatase.

Annealing Regions

Polynucleotide compositions described herein may include two or more annealing regions, e.g., two or more annealing regions described herein. An annealing region, or pair of annealing regions, are those that contain a portion with a high degree of complementarity that promotes hybridization under suitable conditions.

An annealing region includes at least a region of complementary as described herein. The high degree of complementarity of the complementary region promotes the association of annealing region pairs. When a first annealing region (e.g., a 5' annealing region) is located at or near the 5' end of a linear RNA and a second annealing region (e.g., a 3' annealing region) is located at or near the 3' end of a linear RNA, association of the annealing regions brings the 5' and 3' and the corresponding intron fragments into proximity. In some embodiments, this favor circularization of the linear RNA by splicing of the 3' and 5' splice sites. In some embodiments, the annealing regions described herein strengthen naturally occurring annealing regions, e.g., to promote self-splicing.

An annealing region may be altered by introducing one or more (e.g., 1, 2, 3, 4, 5, 6, 7, 8, 9, 10, 11, 12, 13, 14, 15, 16, 17, 18, 19, 20, or more) mutations into the polyribonucleotide sequence. For example, an annealing region may be extended by introducing one or more point mutations into a first annealing region and/or a second annealing region to increase the length of complementarity between the first and second annealing regions. The annealing region may also be altered by inserting one or more (e.g., 1, 2, 3, 4, 5, 6, 7, 8, 9, 10, 11, 12, 13, 14, 15, 16, 17, 18, 19, 20, or more) nucleotides into the polyribonucleotide. In embodiments, an annealing region is extended by inserting one or more nucleotides into a first annealing region and/or a second annealing region to increase the length of complementarity between the first and second annealing regions. In embodiments, the annealing region is extended by introducing one or more point mutations into a first annealing and/or a second region and inserting one or more nucleotides into the first annealing and/or the second annealing region to increase the length of complementarity. Altering the annealing region may alter the secondary structure of the polyribonucleotide by favoring a bulge or mismatched region with the original sequence to preferentially form a stem or stem loop structure with the altered sequence.

The polyribonucleotide includes a first annealing region that has from 2 to 50, 5 to 50, 6 to 50, 7 to 50, or 8 to 50 (e.g., from 10 to 30, 10 to 20, or 10 to 15, e.g., at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50) ribonucleotides and is present within (A) the 3' half of Group I catalytic intron fragment; (B) the 3' splice site; or (C) the 3' exon fragment. The polyribonucleotide also includes a second annealing region that has from 2 to 50, 5 to 50, 6 to 50, 7 to 50, or 8 to 50 (e.g., from 10 to 30, 10 to 20, or 10 to 15, e.g., at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50) ribonucleotides and is present within (E) the 5' exon fragment; (F) the 5' splice site; or (G) the 5' half of Group I catalytic intron fragment. The first annealing region has from 80% to 100% (e.g., 85% to 100%, e.g., 90% to 100%, e.g., 80%, 85%, 90%, 95%, 97%, 99%, or 100%) complementarity with the second annealing region or has from zero to 10 e.g., (0, 1, 2, 3, 4, 5, 6, 7, 8, 9, or 10) mismatched base pairs.

In some embodiments, the first annealing region and the second annealing region are 100% complementary.

In some embodiments, the first annealing region has at least 80% (e.g., at least 85%, 90%, 95%, 97%, 99%, or 100%) sequence identity to the sequence of 5'-TCCGT-3' (SEQ ID NO: 1), and the second annealing region has at least 80% (e.g., at least 85%, 90%, 95%, 97%, 99%, or 100%) sequence identity to the sequence of 5'-ACGGA-3' (SEQ ID NO: 2).

In some embodiments, the first annealing region has at least 80% (e.g., at least 85%, 90%, 95%, 97%, 99%, or 100%) sequence identity to the sequence of 5'-TCCGTAGCGTCT-3' (SEQ ID NO: 5), and the second annealing region has at least 80% (e.g., at least 85%, 90%, 95%, 97%, 99%, or 100%) sequence identity to the sequence of 5'-AGACGCTACGGA-3' (SEQ ID NO: 6).

In some embodiments, the first annealing region has at least 80% (e.g., at least 85%, 90%, 95%, 97%, 99%, or 100%) sequence identity to the sequence of 5'-TCCGTAGCGTCTAAACG-3' (SEQ ID NO: 22), and the second annealing region has at least 80% (e.g., at least 85%, 90%, 95%, 97%, 99%, or 100%) sequence identity to the sequence of 5'-CGTTTAGACGCTACGGA-3' (SEQ ID NO: 23).

In some embodiments, the first annealing region has at least 80% (e.g., at least 85%, 90%, 95%, 97%, 99%, or 100%) sequence identity to the sequence of 5'-TCCGTAGCGTCTAAACGGTCGT-3'(SEQ ID NO: 24), and the second annealing region has at least 80% (e.g., at least 85%, 90%, 95%, 97%, 99%, or 100%) sequence identity to the sequence of 5'-ACGACCGTTTAGACGCTACGGA-3' (SEQ ID NO: 25).

In some embodiments, the first annealing region has at least 80% (e.g., at least 85%, 90%, 95%, 97%, 99%, or 100%) sequence identity to the sequence of '-TCCGTAGCGTCTAAACGGTCGTGTGGG-3' (SEQ ID NO: 26), and the second annealing region has at least 80% (e.g., at least 85%, 90%, 95%, 97%, 99%, or 100%) sequence identity to the sequence of 5'-CCCACACGACCGTTTAGACGCTACGGA-3' (SEQ ID NO: 27).

In some embodiments, the first annealing region has at least 80% (e.g., at least 85%, 90%, 95%, 97%, 99%, or 100%) sequence identity to the sequence of 5'-AAGGTA-3' (SEQ ID NO: 13) , and the second annealing region has at least 80% (e.g., at least 85%, 90%, 95%, 97%, 99%, or 100%) sequence identity to the sequence of 5'-TACCTT-3' (SEQ ID NO: 14).

In some embodiments, the first annealing region has at least 80% (e.g., at least 85%, 90%, 95%, 97%, 99%, or 100%) sequence identity to the sequence of 5'-AAGGTAAATATT-3'(SEQ ID NO: 16), and the second annealing region has at least 80% (e.g., at least 85%, 90%, 95%, 97%, 99%, or 100%) sequence identity to the sequence of 5=-AATATTTACCTT-3' (SEQ ID NO: 17).

In some embodiments, the first annealing region has the sequence of 5'-CT-3', and the second annealing region has the sequence of 5'-AG-3'.

In some embodiments, the first annealing region has at least 80% (e.g., at least 85%, 90%, 95%, 97%, 99%, or 100%) sequence identity to the sequence of 5'-CTCAATT-3' (SEQ ID NO: 20), and the second annealing region has at least 80% (e.g., at least 85%, 90%, 95%, 97%, 99%, or 100%) sequence identity to the sequence of 5'-AATTGAG-3' (SEQ ID NO: 21).

In some embodiments, (A) or (C) includes the first annealing region and (E) or (G) includes the second annealing region.

In some embodiments, the 3' exon fragment of (C) includes the first annealing region and the 5' exon fragment of (E) includes the second annealing region.

In some embodiments, the 3' half of Group I catalytic intron fragment of (A) includes the first annealing region and the 5' exon fragment of (E) includes the second annealing region.

In some embodiments, the 3' exon fragment of (C) includes the first annealing region and the 5' half of Group I catalytic intron fragment includes the second annealing region.

In some embodiments, first annealing region and the second annealing region include zero or one mismatched base pair.

In embodiments, an annealing region further includes a non-complementary region as described below. A non-complementary region may be added to the complementary region to allow for the ends of the RNA to remain flexible, unstructured, or less structured than the complementarity region.

In some embodiments, each annealing region includes 2 to 100, 5 to 100, or 6 to 100 ribonucleotides (e.g., 6 to 80, 6 to 50, 6 to 30, 6 to 20, 10 to 100, 10 to 80, 10 to 50, or 10 to 30 ribonucleotides). In some embodiments, a 5' annealing region includes 2 to 100, 5 to 100, 6 to 100 ribonucleotides (e.g., 6 to 80, 6 to 50, 6 to 30, 6 to 20, 10 to 100, 10 to 80, 10 to 50, or 10 to 30 ribonucleotides). In some embodiments, a 3' annealing region includes 6 to 100 ribonucleotides (e.g., 6 to 80, 6 to 50, 6 to 30, 6 to 20, 10 to 100, 10 to 80, 10 to 50, or 10 to 30 ribonucleotides). In some embodiments, the polyribonucleotide does not include an annealing region 3' to (A) that includes partial or complete nucleic acid complementarity with an annealing region 5' to (G).

In some embodiments, the polyribonucleotide does not include a further annealing region, e.g., in addition to the first annealing region and second annealing region.

Complementary Regions

A complementary region is a region that favors association with a corresponding complementary region, under suitable conditions. For example, a pair of complementary regions may share a high degree of sequence complementarity (e.g., a first complementary region is the reverse complement of a second complementary region, at least in part). When two complementary regions associate (e.g., hybridize), they may form a highly structured secondary structure, such as a stem or stem loop.

In some embodiments, the polyribonucleotide includes a 5' complementary region and a 3' complementary region. In some embodiments, the 5' complementary region has from 2 to 50, e.g., 5 to 50 ribonucleotides (e.g., 5-40, 5-30, 5-20, 5-10, 10-50, 10-40, 10-30, 10-20, or 20-50, e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 ribonucleotides). In some embodiments, the 3' complementary region has from 2 to 50, e.g., 5 to 50 ribonucleotides (e.g., 5-40, 5-30, 5-20, 5-10, 10-50, 10-40, 10-30, 10-20, or 20-50, e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 ribonucleotides).

In some embodiments, the 5' complementary region and the 3' complementary region have from 50% to 100% sequence complementarity (e.g., from 60%-100%, 70%- 100%, 80%-100%, 90%-100%, or 100%, e.g., 80%, 85%, 90%, 95%, 97%, 99%, or 100% sequence complementarity).

In some embodiments, the 5' complementary region and the 3' complementary region have a free energy of binding of less than-5 kcal/mol (e.g., less than-10 kcal/mol, less than-20 kcal/mol, or less than −30 kcal/mol).

In some embodiments, the 5' complementary region and the 3' complementary region have a Tm of binding of at least 10° C., at least 15° C., at least 20° C., at least 30° C., at least 40° C., at least 50° C., at least 60° C., at least 70° C., at least 80° C., or at least 90° C.

In some embodiments, the 5' complementary region and the 3' complementary region include at least one but no more than 10 mismatches, e.g., 10, 9, 8, 7, 6, 5, 4, 3, or 2 mismatches, or 1 mismatch (i.e., when the 5' complementary region and the 3' complementary region hybridize to each other). A mismatch can be, e.g., a nucleotide in the 5' complementary region and a nucleotide in the 3' complementary region that are opposite each other (i.e., when the 5' complementary region and the 3' complementary region are hybridized) but that do not form a Watson-Crick base-pair. A mismatch can be, e.g., an unpaired nucleotide that forms a kink or bulge in either the 5' complementary region or the 3' complementary region. In some embodiments, the 5' complementary region and the 3' complementary region do not include any mismatches.

Non-Complementary Regions

A non-complementary region is a region that disfavors association with a corresponding non-complementary region, under suitable conditions. For example, a pair of non-complementary regions may share a low degree of sequence complementarity (e.g., a first non-complementary region is not a reverse complement of a second non-complementary region). When two non-complementary regions are in proximity, they do not form a highly structured secondary structure, such as a stem or stem loop.

In some embodiments, the polyribonucleotide includes a 5' non-complementary region and a 3' non-complementary region. In some embodiments, the 5' non-complementary region has from 5 to 50 ribonucleotides (e.g., 5-40, 5-30, 5-20, 5-10, 10-50, 10-40, 10-30, 10-20, or 20-50 ribonucleotides). In some embodiments, the 3' non-complementary region has from 5 to 50 ribonucleotides (e.g., 5-40, 5-30, 5-20, 5-10, 10-50, 10-40, 10-30, 10-20, or 20-50 ribonucleotides).

In some embodiments the 5' non-complementary region is located 5' to the 5' complementary region (e.g., between the 5' catalytic intron fragment and the 5' complementary region). In some embodiments, the 3' non-complementary region is located 3' to the 3' complementary region (e.g., between the 3' complementary region and the 3' catalytic intron fragment).

In some embodiments, the 5' non-complementary region and the 3' non-complementary region have from 0% to 50% sequence complementarity (e.g., from 0%-40%, 0%-30%, 0%-20%, 0%-10%, or 0% sequence complementarity).

In some embodiments, the 5' non-complementary region and the 3' non-complementary region have a free energy of binding of greater than-5 kcal/mol.

In some embodiments, the 5' complementary region and the 3' complementary region have a Tm of binding of less than 10° C.

In some embodiments, the 5' non-complementary region and the 3' non-complementary region include at least 1, 2, 3, 4, 5, 6, 7, 8, 9, or 10 mismatches.

Catalytic Introns

The polyribonucletides described herein include catalytic intron fragments, such as (A) a 3' half of Group I catalytic intron fragment and (G) a 5' half of Group I catalytic intron fragment. The first and second annealing regions may be positioned within the catalytic intron fragments. Group I catalytic introns are self-splicing ribozymes that catalyze their own excision from mRNA, tRNA, and rRNA precursors via two-metal ion phorphoryl transfer mechanism. Importantly, the RNA itself self-catalyzes the intron removal without the requirement of an exogenous enzyme, such as a ligase.

In some embodiments, the 3' half of Group I catalytic intron fragment of (A) and the 5' half of Group I catalytic intron fragment of (G) are from a cyanobacterium Anabaena pre-tRNA-Leu gene, or a Tetrahymena pre-rRNA.

In some embodiments, the 3' half of Group I catalytic intron fragment of (A) and the 5' half of Group I catalytic intron fragment of (G) are from a Cyanobacterium Anabaena pre-tRNA-Leu gene, and the 3' exon fragment of (C) includes the first annealing region and the 5' exon fragment of (E) includes the second annealing region. The first annealing region may include, e.g., from 5 to 50, e.g., from 10 to 15 (e.g., 10, 11, 12, 13, 14, or 15) ribonucleotides and the second annealing region may include, e.g., from 5 to 50, e.g., from 10 to 15 (e.g., 10, 11, 12, 13, 14, or 15) ribonucleotides.

In some embodiments, the 3' half of Group I catalytic intron fragment of (A) and the 5' half of Group I catalytic intron fragment of (G) are from a Tetrahymena pre-rRNA, and the 3' half of Group I catalytic intron fragment of (A) includes the first annealing region and the 5' exon fragment of (E) includes the second annealing region. In some embodiments, the 3' exon of (B) includes the first annealing region and the 5' half of Group I catalytic intron fragment of (G) includes the second annealing region. The first annealing region may include, e.g., from 6 to 50, e.g., from 10 to 16 (e.g., 10, 11, 12, 13, 14, 15, or 16) ribonucleotides, and the second annealing region may include, e.g., from 6 to 50, e.g., from 10 to 16 (e.g., 10, 11, 12, 13, 14, 15, or 16) ribonucleotides.

In some embodiments, the 3' half of Group I catalytic intron fragment of (A) and the 5' half of Group I catalytic intron fragment of (G) are from a cyanobacterium Anabaena pre-tRNA-Leu gene, a Tetrahymena pre-rRNA, or a T4 phage td gene.

In some embodiments, the 3' half of Group I catalytic intron fragment of (A) and the 5' Group I catalytic intron fragment of (G) are from a T4 phage td gene. The 3' exon fragment of (C) may include the first annealing region and the 5' half of Group I catalytic intron fragment of (G) may include the second annealing region. The first annealing region may include, e.g., from 2 to 16, e.g., 10 to 16 (e.g., 2, 3, 4, 5, 6, 7, 8, 9, 10, 11, 12, 13, 14, 15, or 16) ribonucleotides, and the second annealing region may include, e.g., from 2 to 16, e.g., 10 to 16 (e.g., 2, 3, 4, 5, 6, 7, 8, 9, 10, 11, 12, 13, 14, 15, or 16) ribonucleotides.

In some embodiments, the 3' half of Group I catalytic intron fragment of (A) is the 5' terminus of the linear polynucleotide.

In some embodiments, the 5' half of Group I catalytic intron fragment of (G) is the 3' terminus of the linear polyribonucleotide.

In some embodiments, the 3' half of Group I catalytic intron fragment of (A) has at least 80% (e.g., at least 85%, 90%, 95%, 97%, 99%, or 100%) sequence identity to the sequence of 5'- AACAACAGATAACTTACAGCTAGTCG-GAAGGTGCAGAGACTCGACGGGAGCTACCCTAAC-GTCAAGACGAGGGTAAAGAGAGAGTCCAATTCT-CAAAGCCAATAGGCAGTAGCGAAAGCTGCGG-GAGAATG-3' (SEQ ID NO: 28).

In some embodiments, the 5' half of Group I catalytic intron fragment of (G) has at least 80% (e.g., at least 85%, 90%, 95%, 97%, 99%, or 100%) sequence identity to the sequence of 5'- AAATAATTGAGCCTTAGAGAAGAAAT-TCTTTAAGTGGATGCTCTCAAACTCAGGGAAAC-CTAAATCTAGCTATAGACAAGGCAATCCTGAGC-CAAGCCGAAGTAGTAATTAGTAAGTT-3' (SEQ ID NO: 29).

In some embodiments, the 3' half of Group I catalytic intron fragment of (A) has the sequence of SEQ ID NO: 28 and the 5' half of Group I catalytic intron fragment of (G) has the sequence of SEQ ID NO: 29.

In some embodiments, the 3' half of Group I catalytic intron fragment of (A) has at least 80% (e.g., at least 85%, 90%, 95%, 97%, 99%, or 100%) sequence identity to the sequence of 5'- CTTCTGTTGATATGGATGCAGTTCA-CAGACTAAATGTCGGTCGGGGAAGATGTATTCTT-CTCATAAGATATAGTCGGACCTCTCCTTAATGG-GAGCTAGCGGATGAAGTGATGCAACACTG-GAGCCGCTGGGAACTAATTTGTATGCGAAAGTAT-ATTGATTAGTTTTGGAGTACTCG-3' (SEQ ID NO: 30).

In some embodiments, the 5' half of Group I catalytic intron fragment of (G) has at least 80% (e.g., at least 85%, 90%, 95%, 97%, 99%, or 100%) sequence identity to the sequence of 5'- AAATAGCAATATTTACCTTTGGAGG-GAAAAGTTATCAGGCATGCACCTGGTAGCTAG-TCTTTAAACCAATAGATTGCATCGGTTTAAAA-GGCAAGACCGTCAAATTGCGGGAAAGGGGTCAA-CAGCCGTTCAGTACCAAGTCTCAGGGGAAACTTT-GAGATGGCCTTGCAAAGGGTATGGTAATAAGCTGA-CGGACATGGTCCTAACCACGCAGCCAAGTCC-TAAGTCA ACAGAT-3' (SEQ ID NO: 31).

In some embodiments, the 3' half of Group I catalytic intron fragment of (A) has the sequence of SEQ ID NO: 30 and the 5' half of Group I catalytic intron fragment of (G) has the sequence of SEQ ID NO: 31.

In some embodiments, the 3' half of Group I catalytic intron fragment of (A) has at least 80% (e.g., at least 85%, 90%, 95%, 97%, 99%, or 100%) sequence identity to the sequence of 5'- GGTTCTACATAAATGCCTAACGAC-TATCCCTTTGGGGAGTAGGGTCAAGTGACTCGA-AACGATAGACAACTTGCTTTAACAAGTTGGAGA-TATAGTCTGCTCTGCATGGTGACATGCAGCTGGA-TATAATTCCGGGGTAAGATTAACGACCTTATCTGAA-CATAATG-3' (SEQ ID NO: 32).

In some embodiments, the 5' half of Group I catalytic intron fragment of (G) has at least 80% (e.g., at least 85%, 90%, 95%, 97%, 99%, or 100%) sequence identity to the sequence of 5'-TAATTGAGGCCTGAGTATAAGG-TGACTTATACTTGTAATCTATCTAAACGGGGAAC-CTCTCTAGTAGACAATCCCGTGCTAAATTGTAGG-ACT- 3' (SEQ ID NO: 33).

In some embodiments, the 3' half of Group I catalytic intron fragment of (A) has the sequence of SEQ ID NO: 32 and the 5' half of Group I catalytic intron fragment of (G) has the sequence of SEQ ID NO: 33.

In some embodiments, the 3' half of Group I catalytic intron fragment of (A) has at least 80% (e.g., at least 85%, 90%, 95%, 97%, 99%, or 100%) sequence identity to the sequence of 5'- TAAACAACTAACAGCTTTAGAAG-GTGCAGAGACTAGACGGGAGCTACCCTAACGGAT-TCAGCCGAGGGTAAAGGGATAGTCCAATTCTCAA CATCGCGATTGTTGATGGCAGCGAAAGTTGC-AGA-GAGAATGAAAATCCGCTGACTGTAAAGGTCGT-GAGGGTTCGAGTCCCTCCGCCCCCA-3' (SEQ ID NO: 80).

In some embodiments, the 5' half of Group I catalytic intron fragment of (G) has at least 80% (e.g., at least 85%, 90%, 95%, 97%, 99%, or 100%) sequence identity to the sequence of 5=-ACGGTAGACGCAGCGGACTTAGAA-AACTGGGCCTCGATCGCGAAAGGGATCGAGTG-GCAGCTCTCA AACTCAGGGAAACCTAAAACTTTA-AACATTMAAGTCATGGCAATCCTGAGCCAAGC-TAAAGC-3' (SEQ ID NO: 81).

In some embodiments, the 3' half of Group I catalytic intron fragment of (A) has the sequence of SEQ ID NO: 80 and the 5' half of Group I catalytic intron fragment of (G) has the sequence of SEQ ID NO: 81.

In some embodiments, the 3' half of Group I catalytic intron fragment of (A) has at least 80% (e.g., at least 85%, 90%, 95%, 97%, 99%, or 100%) sequence identity to the sequence of 5'- TTAAACTCAAAATTTAAAATCCCAA-ATTCAAAATTCCGGGAAGGTGCAGAGACTCGAC-GGGAGCTACCCTAACGTAAAGCCGAGGGTAAAGG-GAGAGTCCAATTCTCAAAGCCTGAAGTTGCT-GAAGCAACAAGGCAGTAGTGAAAGCTGCGA-GAGAATGAAAATCCGTTGACTGTAAAAAGTCGT-GGGGGTTCAAGTCCCCCCACCCCC-3' (SEQ ID NO: 82).

In some embodiments, the 5' half of Group I catalytic intron fragment of (G) has at least 80% (e.g., at least 85%, 90%, 95%, 97%, 99%, or 100%) sequence identity to the sequence of 5'- ATGGTAGACGCTACGGACTTAGA-AAACTGAGCCTTGATAGAGAAATCTTTTAAGTG-GAAGCTCTCAAATTCAGGGAAACCTAAATCTGA-ATACAGATATGGCAATCCTGAGCCAAGCCC-AGAAAATTTAGACTTGAGATTTGATTTTGGAG-3' (SEQ ID NO: 83).

In some embodiments, the 3' half of Group I catalytic intron fragment of (A) has the sequence of SEQ ID NO: 82 and the 5' half of Group I catalytic intron fragment of (G) has the sequence of SEQ ID NO: 83.

In some embodiments, the 3' half of Group I catalytic intron fragment of (A) has at least 80% (e.g., at least 85%, 90%, 95%, 97%, 99%, or 100%) sequence identity to the sequence of 5'- GGCTTTCAATTTGAAATCAGAAATT-CAAAATTCAGGGAAGGTGCAGAGACTCGACGG-GAGCTACCCTAACGTAAAGGCGAGGGTAAAGG-GAGAGTCCAATTCTTAAAGCCTGAAGTTGTGCA-AGCAACAAGGCAACAGTGAAAGCTGTGGAAGAAT-GAAAATCCGTTGACCTTAAACGGTCGTGGGGGTT-CAAGTCCCCCACCCCC-3' (SEQ ID NO: 84).

In some embodiments, the 5' half of Group I catalytic intron fragment of (G) has at least 80% (e.g., at least 85%, 90%, 95%, 97%, 99%, or 100%) sequence identity to the sequence of 5'- ATGGTAGACGCTACGGACTTAGA-AAACTGAGCCTTGATAGAGAAATCTTTCAAGTG-GAAGCTCTCAAATTCAGGGAAACCTAAATCT-GAATACAGATATGGCAATCCTGAGCCAAGCCCG-GAAATTTTAGAATCAAGATTTTATTTT-3' (SEQ ID NO: 85).

In some embodiments, the 3' half of Group I catalytic intron fragment of (A) has the sequence of SEQ ID NO: 84 and the 5' half of Group I catalytic intron fragment of (G) has the sequence of SEQ ID NO: 85.

In some embodiments, the 3' half of Group I catalytic intron fragment of (A) has at least 80% (e.g., at least 85%, 90%, 95%, 97%, 99%, or 100%) sequence identity to the sequence of 5'- AGAAATGGAGAAGGTGTAGAGACTG-GAAGGCAGGCACCCTAACGTTAAAGGCGAGGGT-GAAGGGACAGTCCAGACCACAAACCAG- TAAA-TCTGGGCAGCGAAAGCTGTAGATGGTAAGCAT-AACCCGAAGGTCAGTGGTTCAAATCCACTTCC-CGCCACCAAATTAAAAAAACAATAA-3' (SEQ ID NO: 86).

In some embodiments, the 5' half of Group I catalytic intron fragment of (G) has at least 80% (e.g., at least 85%, 90%, 95%, 97%, 99%, or 100%) sequence identity to the sequence of 5'- AGAAATGGAGAAGGTGTAGAGACTG-GAAGGCAGGCACCCTAACGTTAAAGGCGAGGGT-GAAGGGACAGTCCAGACCACAAACCAGTAAAT-CTGGGCAGCGAAAGCTGTAGATGGTAAGCAT-AACCCGAAGGTCAGTGGTTCAAATCCACTTCC-CGCCACCAAATTAAAAAAACAATAA-3' (SEQ ID NO: 87).

In some embodiments, the 3' half of Group I catalytic intron fragment of (A) has the sequence of SEQ ID NO: 86 and the 5' half of Group I catalytic intron fragment of (G) has the sequence of SEQ ID NO: 87.

In some embodiments, the 3' half of Group I catalytic intron fragment of (A) has at least 80% (e.g., at least 85%, 90%, 95%, 97%, 99%, or 100%) sequence identity to the sequence of 5'- ACAACAGATAACTTACTAACTTA-CAGCTAGTCGGAAGGTGCAGAGACTCGACGG-GAGCTACCCTAACGTCAAGACGAGGGTAAA-GAGAGAGTCCAATTCTCAAAGCCAATAGG-CAGTAGCGAAAGCTGCGGGAGAATGAAAATCC-GTAGCGTCTAAACGGTCGTGTGGGTT-CAAGTCCCTCCACCCCCA-3' (SEQ ID NO: 88).

In some embodiments, the 5' half of Group I catalytic intron fragment of (G) has at least 80% (e.g., at least 85%, 90%, 95%, 97%, 99%, or 100%) sequence identity to the sequence of 5=- AGACGCTACGGACTTAAATAATT-GAGCCTTAGAGAAGAAATTCTTTAAGTGGATGCT-CTCAAACTCAGGGAAACCTAAATCTAGCTATA-GACAAGGCAATCCTGAGCCAAGCCGAAG-TAGTAATTAGTAAGTTAGTAAGTT-3' (SEQ ID NO: 89).

In some embodiments, the 3' half of Group I catalytic intron fragment of (A) has the sequence of SEQ ID NO: 88 and the 5' half of Group I catalytic intron fragment of (G) has the sequence of SEQ ID NO: 89.

In some embodiments, the 3' half of Group I catalytic intron fragment of (A) has at least 80% (e.g., at least 85%, 90%, 95%, 97%, 99%, or 100%) sequence identity to the sequence of 5'- AACAACAGATAACTTACTAGTTACTA-GTCGGAAGGTGCAGAGACTCGACGGGAGCTACC-CTAACGTCAAGACGAGGGTAAAGAGAGAGTC-CAATTCTCAAAGCCAATAGGCAGTAGCGAAAGCT-GCGGGAGAATGAAAATCCGTAGCGTCTAAACG-GTCGTGTGGGTTCAAGTCCCTCCACCCCCA-3' (SEQ ID NO: 90).

In some embodiments, the 5' half of Group I catalytic intron fragment of (G) has at least 80% (e.g., at least 85%, 90%, 95%, 97%, 99%, or 100%) sequence identity to the sequence of 5'- AGACGCTACGGACTTAAATAATTGAG-CCTTAGAGAAGAAATTCTTTAAGTGGATGCTCTC-AAACTCAGGGAAACCTAAATCTAGCTATAGACA-AGGCAATCCTGAGCCAAGCCGAAGTAGTAATT-AGTAAGTT-3' (SEQ ID NO: 91).

In some embodiments, the 3' half of Group I catalytic intron fragment of (A) has the sequence of SEQ ID NO: 90 and the 5' half of Group I catalytic intron fragment of (G) has the sequence of SEQ ID NO: 91.

Splice Sites

The polyribonucleotides described herein include splice sites, such as (B) a 3' splice site; and (F) a 5' splice site. The splice site may be from a cyanobacterium *Anabaena* pre-tRNA-Leu gene, a Tetrahymena pre-rRNA, or a T4 phage td gene.

In some embodiments the 3' splice site (e.g., between the 3' half of Group I catalytic intron fragment and the 3' exon fragment has the sequence of AGAATG ↓AAAATC (SEQ ID NO: 34) where the arrow denotes the cut site. In some embodiments, the 5' splice site (e.g., between the 5' exon fragment and the 5' half of Group I catalytic intron fragment has the sequence of GGACTT↓AAATAA (SEQ ID NO: 35) where the arrow denotes the cut site.

In some embodiments the 3' splice site (e.g., between the 3' half of Group I catalytic intron fragment and the 3' exon fragment has the sequence TACTCG ↓TAAGGT (SEQ ID NO: 36) where the arrow denotes the cut site. In some embodiments, the 5' splice site (e.g., between the 5' exon fragment and the 5' half of Group I catalytic intron fragment has the sequence of CTCTCT↓AAATAG (SEQ ID NO: 37) where the arrow denotes the cut site.

In some embodiments the 3' splice site (e.g., between the 3' half of Group I catalytic intron fragment and the 3' exon fragment has the sequence of ATAATG ↓CTACCG (SEQ ID NO: 38) where the arrow denotes the cut site. In some embodiments, the 5' splice site (e.g., between the 5' exon fragment and the 5' half of Group I catalytic intron fragment has the sequence of TTGGGT↓TAATTG (SEQ ID NO: 39) where the arrow denotes the cut site.

Exon Fragments

The polyribonucleotides described herein include an exon fragment, such as (C) a 3' exon fragment; and (E) a 5' exon fragment.

In some embodiments, the 3' exon fragment of (C) has at least 80% (e.g., at least 85%, 90%, 95%, 97%, 99%, or 100%) sequence identity to the sequence of 5'-AAAATCCGTTGACCTTAAACGGTCGTGTGGGTT-CAAGTCCCTCCACCCCA-3' (SEQ ID NO: 40).

In some embodiments, the 3' exon fragment of (C) has at least 80% (e.g., at least 85%, 90%, 95%, 97%, 99%, or 100%) sequence identity to the sequence of 5'-AAAATCCGTAGCGTCTAAACGGTCGTGTGGGTT-CAAGTCCCTCCACCCCA-3' (SEQ ID NO: 41).

In some embodiments, the 5' exon fragment of (E) has at least 80% (e.g., at least 85%, 90%, 95%, 97%, 99%, or 100%) sequence identity to the sequence of 5'-AGACGC-TACGGACTT-3' (SEQ ID NO: 42).

In some embodiments, the 5' exon fragment of (E) has at least 80% (e.g., at least 85%, 90%, 95%, 97%, 99%, or 100%) sequence identity to the sequence of 5'-CGTTTA-GACGCTACGGACTT-3' (SEQ ID NO: 43).

In some embodiments, the 5' exon fragment of (E) has at least 80% (e.g., at least 85%, 90%, 95%, 97%, 99%, or 100%) sequence identity to the sequence of 5'-ACGACCGTTTAGACGCTACGGACTT-3' (SEQ ID NO: 44).

In some embodiments, the 5' exon fragment of (E) has at least 80% (e.g., at least 85%, 90%, 95%, 97%, 99%, or 100%) sequence identity to the sequence of 5'-CC-CACACGACCGTTTAGACGCTACGGACTT-3' (SEQ ID NO: 45).

In some embodiments, the 3' exon fragment of (C) has at least 80% (e.g., at least 85%, 90%, 95%, 97%, 99%, or 100%) sequence identity to the sequence of 5'-TAAGGTAGC-3' (SEQ ID NO: 46).

In some embodiments, the 3' exon fragment of (C) has at least 80% (e.g., at least 85%, 90%, 95%, 97%, 99%, or 100%) sequence identity to the sequence of 5'-TAGGTAAATATTGC-3' (SEQ ID NO: 47).

In some embodiments, the 5' exon fragment of (E) has at least 80% (e.g., at least 85%, 90%, 95%, 97%, 99%, or 100%) sequence identity to the sequence of 5'-ATGACTCTCT-3' (SEQ ID NO: 48).

In some embodiments, the 3' exon fragment of (C) has at least 80% (e.g., at least 85%, 90%, 95%, 97%, 99%, or 100%) sequence identity to the sequence of 5'-CTACCGTT-TAATATT-3' (SEQ ID NO: 49).

In some embodiments, the 3' exon fragment of (C) has at least 80% (e.g., at least 85%, 90%, 95%, 97%, 99%, or 100%) sequence identity to the sequence of 5'-CTCAATTT-TAATATT-3' (SEQ ID NO: 50).

In some embodiments, the 5' exon fragment of (E) has at least 80% (e.g., at least 85%, 90%, 95%, 97%, 99%, or 100%) sequence identity to the sequence of 5'-AGTTTTCTTGGGT-3' (SEQ ID NO: 51).

Polyribonucleotide Cargo

A polyribonucleotide cargo described herein includes any sequence including at least one polyribonucleotide. In some embodiments, the polyribonucleotide cargo of (D) includes an expression sequence, a non-coding sequence, or an expression sequence and a non-coding sequence. In some embodiments, the polyribonucleotide cargo of (D) includes an expression sequence encoding a polypeptide. In some embodiments, the polyribonucleotide cargo of (D) includes an IRES operably linked to an expression sequence encoding a polypeptide. In some embodiments, the polyribonucleotide cargo of (D) includes an expression sequence that encodes a polypeptide that has a biological effect on a subject.

A polyribonucleotide cargo may, for example, include at least about 40 nucleotides, at least about 50 nucleotides, at least about 75 nucleotides, at least about 100 nucleotides, at least about 200 nucleotides, at least about 300 nucleotides, at least about 400 nucleotides, at least about 500 nucleotides, at least about 1,000 nucleotides, at least about 2,000 nucleotides, at least about 5,000 nucleotides, at least about 6,000 nucleotides, at least about 7,000 nucleotides, at least about 8,000 nucleotides, at least about 9,000 nucleotides, at least about 10,000 nucleotides, at least about 12,000 nucleotides, at least about 14,000 nucleotides, at least about 15,000 nucleotides, at least about 16,000 nucleotides, at least about 17,000 nucleotides, at least about 18,000 nucleotides, at least about 19,000 nucleotides, or at least about 20,000 nucleotides. In some embodiments, the polyribonucleotides cargo includes from 1-20,000 nucleotides, 1-10,000 nucleotides, 1-5,000 nucleotides, 100-20,000 nucleotide, 100-10,000 nucleotides, 100-5,000 nucleotides, 500-20,000 nucleotides, 500-10,000 nucleotides, 500-5,000 nucleotides, 1,000-20,000 nucleotides, 1,000-10,000 nucleotides, or 1,000-5,000 nucleotides.

In embodiments, the polyribonucleotide cargo includes one or multiple expression (or coding) sequences, wherein each expression (or coding) sequence encodes a polypeptide. In embodiments, the polyribonucleotide cargo includes one or multiple noncoding sequences. In embodiments, the polyribonucleotide cargo consists entirely of non-coding sequence(s). In embodiments, the polyribonucleotide cargo includes a combination of expression (or coding) and non-coding sequences.

In some embodiments, polyribonucleotides made as described herein are used as effectors in therapy or agriculture. For example, a circular polyribonucleotide made by the methods described herein (e.g., the cell-free methods described herein) may be administered to a subject (e.g., in a pharmaceutical, veterinary, or agricultural composition). In another example, a circular polyribonucleotide made by the methods described herein (e.g., the cell-free methods described herein) may be delivered to a cell.

In some embodiments, the polyribonucleotide includes any feature, or any combination of features as disclosed in International Patent Publication No. WO2019/118919, which is hereby incorporated by reference in its entirety.

Polypeptide Expression Sequences

In some embodiments, the polyribonucleotide described herein (e.g., the polyribonucleotide cargo of the circular polyribonucleotide) includes one or more expression (or coding) sequences, wherein each expression sequence encodes a polypeptide. In some embodiments, the circular polyribonucleotide includes two, three, four, five, six, seven, eight, nine, ten or more expression (or coding) sequences.

Each encoded polypeptide may be linear or branched. In various embodiments, the polypeptide has a length from about 5 to about 40,000 amino acids, about 15 to about 35,000 amino acids, about 20 to about 30,000 amino acids, about 25 to about 25,000 amino acids, about 50 to about 20,000 amino acids, about 100 to about 15,000 amino acids, about 200 to about 10,000 amino acids, about 500 to about 5,000 amino acids, about 1,000 to about 2,500 amino acids, or any range therebetween. In some embodiments, the polypeptide has a length of less than about 40,000 amino acids, less than about 35,000 amino acids, less than about 30,000 amino acids, less than about 25,000 amino acids, less than about 20,000 amino acids, less than about 15,000 amino acids, less than about 10,000 amino acids, less than about 9,000 amino acids, less than about 8,000 amino acids, less than about 7,000 amino acids, less than about 6,000 amino acids, less than about 5,000 amino acids, less than about 4,000 amino acids, less than about 3,000 amino acids, less than about 2,500 amino acids, less than about 2,000 amino acids, less than about 1,500 amino acids, less than about 1,000 amino acids, less than about 900 amino acids, less than about 800 amino acids, less than about 700 amino acids, less than about 600 amino acids, less than about 500 amino acids, less than about 400 amino acids, less than about 300 amino acids, or less may be useful.

Polypeptides included herein may include naturally occurring polypeptides or non-naturally occurring polypeptides. In some embodiments, the polypeptide is or includes a functional fragment or variant of a reference polypeptide (e.g., an enzymatically active fragment or variant of an enzyme). For example, the polypeptide may be a functionally active variant of any of the polypeptides described herein with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, e.g., over a specified region or over the entire sequence, to a sequence of a polypeptide described herein or a naturally occurring polypeptide. In some instances, the polypeptide may have at least 50% (e.g., at least 50%, 60%, 70%, 80%, 90%, 95%, 97%, 99%, or greater) identity to a protein of interest.

Some examples of a polypeptide include, but are not limited to, a fluorescent tag or marker, an antigen, a therapeutic polypeptide, or a polypeptide for agricultural applications.

A therapeutic polypeptide may be a hormone, a neurotransmitter, a growth factor, an enzyme (e.g., oxidoreductase, metabolic enzyme, mitochondrial enzyme, oxygenase, dehydrogenase, ATP-independent enzyme, lysosomal enzyme, desaturase), a cytokine, an antigen binding polypeptide (e.g., antigen binding antibody or antibody-like fragments, such as single chain antibodies, nanobodies or other Ig heavy chain or light chain containing polypeptides), an Fc fusion protein, an anticoagulant, a blood factor, a bone morphogenetic protein, an interferon, an interleukin, and a thrombolytic.

A polypeptide for agricultural applications may be a bacteriocin, a lysin, an antimicrobial polypeptide, an antifungal polypeptide, a nodule C-rich peptide, a bacteriocyte regulatory peptide, a peptide toxin, a pesticidal polypeptide (e.g., insecticidal polypeptide or nematocidal polypeptide), an antigen binding polypeptide (e.g., antigen binding antibody or antibody-like fragments, such as single chain antibodies, nanobodies or other Ig heavy chain or light chain containing polypeptides), an enzyme (e.g., nuclease, amylase, cellulase, peptidase, lipase, chitinase), a peptide pheromone, and a transcription factor.

In some cases, the circular polyribonucleotide expresses a non-human protein.

In some embodiments, the circular polyribonucleotide expresses an antibody, e.g., an antibody fragment, or a portion thereof. In some embodiments, the antibody expressed by the circular polyribonucleotide can be of any isotype, such as IgA, IgD, IgE, IgG, IgM. In some embodiments, the circular polyribonucleotide expresses a portion of an antibody, such as a light chain, a heavy chain, a Fc fragment, a CDR (complementary determining region), a Fv fragment, or a Fab fragment, a further portion thereof. In some embodiments, the circular polyribonucleotide expresses one or more portions of an antibody. For instance, the circular polyribonucleotide can include more than one expression (or coding) sequence, each of which expresses a portion of an antibody, and the sum of which can constitute the antibody. In some cases, the circular polyribonucleotide includes one expression sequence coding for the heavy chain of an antibody, and another expression sequence coding for the light chain of the antibody. In some cases, when the circular polyribonucleotide is expressed in a cell or a cell-free environment, the light chain and heavy chain can be subject to appropriate modification, folding, or other post-translation modification to form a functional antibody.

In embodiments, polypeptides include multiple polypeptides, e.g., multiple copies of one polypeptide sequence, or multiple different polypeptide sequences. In embodiments, multiple polypeptides are connected by linker amino acids or spacer amino acids.

In embodiments, the polynucleotide cargo includes a sequence encoding a signal peptide. Many signal peptide sequences have been described, for example, the Tat (Twin-arginine translocation) signal sequence is typically an N-terminal peptide sequence containing a consensus SRRxFLK "twin-arginine" motif, which serves to translocate a folded protein containing such a Tat signal peptide across a lipid bilayer. See also, e.g., the Signal Peptide Database publicly available at www [dot] signalpeptide [dot] de. Signal peptides are also useful for directing a protein to specific organelles; see, e.g., the experimentally determined and computationally predicted signal peptides disclosed in the Spdb signal peptide database, publicly available at proline [dot] bic [dot] nus [dot] edu [dot] sg/spdb.

In embodiments, the polynucleotide cargo includes sequence encoding a cell-penetrating peptide (CPP). Hundreds of CPP sequences have been described; see, e.g., the database of cell-penetrating peptides, CPPsite, publicly available at crdd [dot] osdd [dot] net/raghava/cppsite/. An example of a commonly used CPP sequence is a poly-arginine sequence, e.g., octoarginine or nonoarginine, which can be fused to the C-terminus of the CGI peptide.

In embodiments, the polynucleotide cargo includes sequence encoding a self-assembling peptide; see, e.g., Miki et al. (2021) Nature Communications, 21:3412, DOI: 10.1038/s41467-021-23794-6.

In some embodiments, the expression (or coding) sequence includes a poly-A sequence (e.g., at the 3' end of an expression sequence). In some embodiments, the length of a poly-A sequence is greater than 10 nucleotides in length. In one embodiment, the poly-A sequence is greater than 15 nucleotides in length (e.g., at least or greater than about 10, 15, 20, 25, 30, 35, 40, 45, 50, 55, 60, 70, 80, 90, 100, 120, 140, 160, 180, 200, 250, 300, 350, 400, 450, 500, 600, 700, 800, 900, 1,000, 1,100, 1,200, 1,300, 1,400, 1,500, 1,600, 1,700, 1,800, 1,900, 2,000, 2,500, and 3,000 nucleotides). In some embodiments, the poly-A sequence is designed according to the descriptions of the poly-A sequence in [0202]-[0204] of International Patent Publication No. WO2019/118919A1, which is incorporated herein by reference in its entirety. In some embodiments, the expression sequence lacks a poly-A sequence (e.g., at the 3' end of an expression sequence).

In some embodiments, a circular polyribonucleotide includes a polyA, lacks a polyA, or has a modified polyA to modulate one or more characteristics of the circular polyribonucleotide. In some embodiments, the circular polyribonucleotide lacking a polyA or having modified polyA improves one or more functional characteristics, e.g., immunogenicity (e.g., the level of one or more marker of an immune or inflammatory response), half-life, and/or expression efficiency.

Therapeutic Polypeptides

In some embodiments, the circular polyribonucleotide described herein (e.g., the polyribonucleotide cargo of the circular polyribonucleotide) includes at least one expression sequence encoding a therapeutic polypeptide. A therapeutic polypeptide is a polypeptide that when administered to or expressed in a subject provides some therapeutic benefit. Administration to a subject or expression in a subject of a therapeutic polypeptide may be used to treat or prevent a disease, disorder, or condition or a symptom thereof. In some embodiments, the circular polyribonucleotide encodes two, three, four, five, six, seven, eight, nine, ten or more therapeutic polypeptides.

In some embodiments, the circular polyribonucleotide includes an expression sequence encoding a therapeutic protein. The protein may treat the disease in the subject in need thereof. In some embodiments, the therapeutic protein can compensate for a mutated, under-expressed, or absent protein in the subject in need thereof. In some embodiments, the therapeutic protein can target, interact with, or bind to a cell, tissue, or virus in the subject in need thereof.

A therapeutic polypeptide can be a polypeptide that can be secreted from a cell, or localized to the cytoplasm, nucleus, or membrane compartment of a cell.

A therapeutic polypeptide may be a hormone, a neurotransmitter, a growth factor, an enzyme (e.g., oxidoreductase, metabolic enzyme, mitochondrial enzyme, oxygenase, dehydrogenase, ATP-independent enzyme, lysosomal enzyme, desaturase), a cytokine, a transcription factor, an antigen binding polypeptide (e.g., antigen binding antibody or antibody-like fragments, such as single chain antibodies, nanobodies or other Ig heavy chain or light chain containing polypeptides), an Fc fusion protein, an anticoagulant, a blood factor, a bone morphogenetic protein, an interferon, an interleukin, a thrombolytic, an antigen (e.g., a tumor, viral, or bacterial antigen), a nuclease (e.g., an endonuclease such as a Cas protein, e.g., Cas9), a membrane protein (e.g., a chimeric antigen receptor (CAR), a transmembrane receptor, a G-protein-coupled receptor (GPCR), a receptor tyrosine kinase (RTK), an antigen receptor, an ion channel, or a membrane transporter), a secreted protein, a gene editing protein (e.g., a CRISPR-Cas, TALEN, or zinc finger), or a gene writing protein (see, e.g., International Patent Publication No. WO2020/047124, incorporated in its entirety herein by reference).

In some embodiments, the therapeutic polypeptide is an antibody, e.g., a full-length antibody, an antibody fragment, or a portion thereof. In some embodiments, the antibody expressed by the circular polyribonucleotide can be of any isotype, such as IgA, IgD, IgE, IgG, IgM. In some embodiments, the circular polyribonucleotide expresses a portion of an antibody, such as a light chain, a heavy chain, a Fc fragment, a CDR (complementary determining region), a Fv fragment, or a Fab fragment, a further portion thereof. In some embodiments, the circular polyribonucleotide expresses one or more portions of an antibody. For instance, the circular polyribonucleotide can include more than one expression sequence, each of which expresses a portion of an antibody, and the sum of which can constitute the antibody. In some cases, the circular polyribonucleotide includes one expression sequence coding for the heavy chain of an antibody, and another expression sequence coding for the light chain of the antibody. When the circular polyribonucleotide is expressed in a cell, the light chain and heavy chain can be subject to appropriate modification, folding, or other post-translation modification to form a functional antibody.

In some embodiments, circular polyribonucleotides made as described herein are used as effectors in therapy or agriculture. For example, a circular polyribonucleotide made by the methods described herein (e.g., the cell-free methods described herein) may be administered to a subject (e.g., in a pharmaceutical, veterinary, or agricultural composition). In embodiments, the subject is a vertebrate animal (e.g., mammal, bird, fish, reptile, or amphibian). In embodiments, the subject is a human. In embodiments, the method subject is a non-human mammal. In embodiments, the subject is a non-human mammal such as a non-human primate (e.g., monkeys, apes), ungulate (e.g., cattle, buffalo, sheep, goat, pig, camel, llama, alpaca, deer, horses, donkeys), carnivore (e.g., dog, cat), rodent (e.g., rat, mouse), or lagomorph (e.g., rabbit). In embodiments, the subject is a bird, such as a member of the avian taxa Galliformes (e.g., chickens, turkeys, pheasants, quail), Anseriformes (e.g., ducks, geese), Paleaognathae (e.g., ostriches, emus), Columbiformes (e.g., pigeons, doves), or Psittaciformes (e.g., parrots). In embodiments, the subject is an invertebrate such as an arthropod (e.g, insects, arachnids, crustaceans), a nematode, an annelid, a helminth, or a mollusc. In embodiments, the subject is an invertebrate agricultural pest or an invertebrate that is parasitic on an invertebrate or vertebrate host. In embodiments, the subject is a plant, such as an angiosperm plant (which can be a dicot or a monocot) or a gymnosperm plant (e.g., a conifer, a cycad, a gnetophyte, a Ginkgo), a fern, horsetail, clubmoss, or a bryophyte. In embodiments, the subject is a eukaryotic alga (unicellular or multicellular). In embodiments, the subject is a plant of agricultural or horticultural importance, such as row crop plants, fruit-producing plants and trees, vegetables, trees, and ornamental plants including ornamental flowers, shrubs, trees, groundcovers, and turf grasses.

Secreted Polypeptide Effectors

In some embodiments, the circular polyribonucleotide described herein (e.g., the polyribonucleotide cargo of the circular polyribonucleotide) includes at least one coding sequence encoding a secreted polypeptide effector. Exemplary secreted polypeptide effectors or proteins that may be expressed include, e.g., cytokines and cytokine receptors, polypeptide hormones and receptors, growth factors, clotting factors, therapeutic replacement enzymes and therapeutic non-enzymatic effectors, regeneration, repair, and fibrosis factors, transformation factors, and proteins that stimulate cellular regeneration, non-limiting examples of which are described herein, e.g., in the tables below.

Cytokines and Cytokine Receptors

In some embodiments, an effector described herein comprises a cytokine of Table 1, or a functional variant or fragment thereof, e.g., a protein having at least 80%, 85%, 90%, 95%, 967%, 98%, 99% identity to a protein sequence disclosed in Table 1 by reference to its UniProt ID. In some embodiments, the functional variant binds to the corresponding cytokine receptor with a Kd of no more than 10%, 20%, 30%, 40%, or 50% higher or lower than the Kd of the corresponding wild-type cytokine for the same receptor under the same conditions. In some embodiments, the effector comprises a fusion protein comprising a first region (e.g., a cytokine polypeptide of Table 1 or a functional variant or fragment thereof) and a second, heterologous region. In some embodiments, the first region is a first cytokine polypeptide of Table 1. In some embodiments, the second region is a second cytokine polypeptide of Table 1, wherein the first and second cytokine polypeptides form a cytokine heterodimer with each other in a wild-type cell. In some embodiments, the polypeptide of Table 1 or functional variant thereof comprises a signal sequence, e.g., a signal sequence that is endogenous to the effector, or a heterologous signal sequence.

In some embodiments, an effector described herein comprises an antibody or fragment thereof that binds a cytokine of Table 1. In some embodiments, the antibody molecule comprises a signal sequence.

TABLE 1

Exemplary cytokines and cytokine receptors

| Cytokine | Cytokine receptor(s) | Entrez Gene ID[1] | UniProt ID[2] |
|---|---|---|---|
| IL-1α, IL-1β, or a heterodimer thereof | IL-1 type 1 receptor, IL-1 type 2 receptor | 3552, 3553 | P01583, P01584 |
| IL-1Ra | IL-1 type 1 receptor, IL-1 type 2 receptor | 3454, 3455 | P17181, P48551 |
| IL-2 | IL-2R | 3558 | P60568 |
| IL-3 | IL-3 receptor α + β c (CD131) | 3562 | P08700 |
| IL-4 | IL-4R type I, IL-4R type II | 3565 | P05112 |
| IL-5 | IL-5R | 3567 | P05113 |
| IL-6 | IL-6R (sIL-6R) gp130 | 3569 | P05231 |
| IL-7 | IL-7R and sIL-7R | 3574 | P13232 |
| IL-8 | CXCR1 and CXCR2 | 3576 | P10145 |
| IL-9 | IL-9R | 3578 | P15248 |
| IL-10 | IL-10R1/IL-10R2 complex | 3586 | P22301 |
| IL-11 | IL-11Rα 1 gp130 | 3589 | P20809 |
| IL-12 (e.g., p35, p40, or a heterodimer thereof) | IL-12Rβ1 and IL-12Rβ2 | 3593, 3592 | P29459, P29460 |
| IL-13 | IL-13R1α1 and IL-13R1α2 | 3596 | P35225 |
| IL-14 | IL-14R | 30685 | P40222 |
| IL-15 | IL-15R | 3600 | P40933 |
| IL-16 | CD4 | 3603 | Q14005 |
| IL-17A | IL-17RA | 3605 | Q16552 |
| IL-17B | IL-17RB | 27190 | Q9UHF5 |
| IL-17C | IL-17RA to IL-17RE | 27189 | Q9P0M4 |
| IL-17D | SEF | 53342 | Q8TAD2 |
| IL-17F | IL-17RA, IL-17RC | 112744 | Q96PD4 |
| IL-18 | IL-18 receptor | 3606 | Q14116 |
| IL-19 | IL-20R1/IL-20R2 | 29949 | Q9UHD0 |
| IL-20 | L-20R1/IL-20R2 and IL-22R1/IL-20R2 | 50604 | Q9NYY1 |
| IL-21 | IL-21R | 59067 | Q9HBE4 |
| IL-22 | IL-22R | 50616 | Q9GZX6 |
| IL-23 (e.g., p19, p40, or a heterodimer thereof) | IL-23R | 51561 | Q9NPF7 |
| IL-24 | IL-20R1/IL-20R2 and IL-22R1/IL-20R2 | 11009 | Q13007 |
| IL-25 | IL-17RA and IL-17RB | 64806 | Q9H293 |
| IL-26 | IL-10R2 chain and IL-20R1 chain | 55801 | Q9NPH9 |
| IL-27 (e.g., p28, EBI3, or a heterodimer thereof) | WSX-1 and gp130 | 246778 | Q8NEV9 |
| IL-28A, IL-28B, and IL29 | IL-28R1/IL-10R2 | 282617, 282618 | Q8IZI9, Q8IU54 |
| IL-30 | IL6R/gp130 | 246778 | Q8NEV9 |
| IL-31 | IL-31RA/OSMRβ | 386653 | Q6EBC2 |
| IL-32 | | 9235 | P24001 |
| IL-33 | ST2 | 90865 | O95760 |
| IL-34 | Colony-stimulating factor 1 receptor | 146433 | Q6ZMJ4 |
| IL-35 (e.g., p35, EBI3, or a heterodimer thereof) | IL-12Rβ2/gp130; IL-12Rβ2/IL-12Rβ2; gp130/gp130 | 10148 | Q14213 |
| IL-36 | IL-36Ra | 27179 | Q9UHA7 |
| IL-37 | IL-18Rα and IL-18BP | 27178 | Q9NZH6 |
| IL-38 | IL-1R1, IL-36R | 84639 | Q8WWZ1 |
| IFN-α | IFNAR | 3454 | P17181 |

TABLE 1-continued

Exemplary cytokines and cytokine receptors

| Cytokine | Cytokine receptor(s) | Entrez Gene ID[1] | UniProt ID[2] |
|---|---|---|---|
| IFN-β | IFNAR | 3454 | P17181 |
| IFN-γ | IFNGR1/IFNGR2 | 3459 | P15260 |
| TGF-β | TβR-I and βBR-II | 7046, 7048 | P36897, P37173 |
| TNF-α | TNFR1, TNFR2 | 7132, 7133 | P19438, P20333 |

[1]Sequence available on the NCBI database on the world wide web internet site "ncbi.nlm.nih.gov/gene"; Maglott D, et al. Gene: a gene-centered information resource at NCBI. Nucleic Acids Res. 2014. pii: gku1055.
[2]Sequence available on the Uniprot database on the world wide web internet site "uniprot.org/uniprot/"; UniProt: the universal protein knowledgebase in 2021.Nucleic Acids Res. 49:D1 (2021).

Polypeptide Hormones and Receptors

In some embodiments, an effector described herein comprises a hormone of Table 2, or a functional variant thereof, e.g., a protein having at least 80%, 85%, 90%, 95%, 967%, 98%, 99% identity to a protein sequence disclosed in Table 2 by reference to its UniProt ID. In some embodiments, the functional variant binds to the corresponding receptor with a Kd of no more than 10%, 20%, 30%, 40%, or 50% higher than the Kd of the corresponding wild-type hormone for the same receptor under the same conditions. In some embodiments, the polypeptide of Table 2 or functional variant thereof comprises a signal sequence, e.g., a signal sequence that is endogenous to the effector, or a heterologous signal sequence.

In some embodiments, an effector described herein comprises an antibody molecule (e.g., an scFv) that binds a hormone of Table 2. In some embodiments, an effector described herein comprises an antibody molecule (e.g., an scFv) that binds a hormone receptor of Table 2. In some embodiments, the antibody molecule comprises a signal sequence.

TABLE 2

Exemplary polypeptide hormones and receptors

| Hormone | Receptor | Entrez Gene ID[1] | UniProt ID[2] |
|---|---|---|---|
| Natriuretic Peptide, e.g., Atrial Natriuretic Peptide (ANP) | NPRA, NPRB, NPRC | 4878 | P01160 |
| Brain Natriuretic Peptide (BNP) | NPRA, NPRB | 4879 | P16860 |
| C-type natriuretic peptide (CNP) | NPRB | 4880 | P23582 |
| Growth hormone (GH) | GHR | 2690 | P10912 |
| Prolactin (PRL) | PRLR | 5617 | P01236 |
| Thyroid-stimulating hormone (TSH) | TSH receptor | 7253 | P16473 |
| Adrenocorticotropic hormone (ACTH) | ACTH receptor | 5443 | P01189 |
| Follicle-stimulating hormone (FSH) | FSHR | 2492 | P23945 |
| Luteinizing hormone (LH) | LHR | 3973 | P22888 |
| Antidiuretic hormone (ADH) | Vasopressin receptors, e.g., V2; AVPR1A; AVPR1B; AVPR3; AVPR2 | 554 | P30518 |
| Oxytocin | OXTR | 5020 | P01178 |
| Calcitonin | Calcitonin receptor (CT) | 796 | P01258 |
| Parathyroid hormone (PTH) | PTH1R and PTH2R | 5741 | P01270 |
| Insulin | Insulin receptor (IR) | 3630 | P01308 |
| Glucagon | Glucagon receptor | 2641 | P01275 |
| GIP | GIPR | 2695 | P09681 |
| Fibroblast growth factor 19 (FGF19) | FGFR4 | 9965 | O95750 |
| Fibroblast growth factor 21 (FGF21) | FGFR1c, 2c, 3c | 26291 | Q9NSA1 |
| Fibroblast growth factor 23 (FGF23) | FGFR1, 2, 4 | 8074 | Q9GZV9 |
| Melanocyte-stimulating hormone (alpha- MSH) | MC1R, MC4R, MC5R | | |
| Melanocyte-stimulating hormone (beta- MSH) | MC4R | | |
| Melanocyte-stimulating hormone (gamma- MSH) | MC1R, MC3R, MC4R, MC5R | | |
| Proopiomelanocortin POMC (alpha- beta-, gamma-, MSH precursor) | MC1R, MC3R, MC4R, MC5R | 5443 | P01189 |
| Glycoprotein hormones alpha chain (CGA) | | 1081 | P01215 |
| Follicle-stimulating hormone beta (FSHB) | FSHR | 2488 | P01225 |

TABLE 2-continued

Exemplary polypeptide hormones and receptors

| Hormone | Receptor | Entrez Gene ID[1] | UniProt ID[2] |
|---------|----------|-------------------|---------------|
| Leptin | LEPR | 3952 | P41159 |
| Ghrelin | GHSR | 51738 | Q9UBU3 |

[1]Sequence available on the NCBI database on the world wide web internet site "ncbi.nlm.nih.gov/gene", Maglott D, et al. Gene: a gene-centered information resource at NCBI. Nucleic Acids Res. 2014. pii: gku1055.
[2]Sequence available on the Uniprot database on the world wide web internet site "uniprot.org/uniprot/"; UniProt: the universal protein knowledgebase in 2021.Nucleic Acids Res. 49:D1 (2021).

Growth Factors

In some embodiments, an effector described herein comprises a growth factor of Table 3, or a functional variant thereof, e.g., a protein having at least 80%, 85%, 90%, 95%, 967%, 98%, 99% identity to a protein sequence disclosed in Table 3 by reference to its UniProt ID. In some embodiments, the functional variant binds to the corresponding receptor with a Kd of no more than 10%, 20%, 30%, 40%, or 50% higher than the Kd of the corresponding wild-type growth factor for the same receptor under the same conditions. In some embodiments, the polypeptide of Table 3 or functional variant thereof comprises a signal sequence, e.g., a signal sequence that is endogenous to the effector, or a heterologous signal sequence.

In some embodiments, an effector described herein comprises an antibody or fragment thereof that binds a growth factor of Table 3. In some embodiments, an effector described herein comprises an antibody molecule (e.g., an scFv) that binds a growth factor receptor of Table 3. In some embodiments, the antibody molecule comprises a signal sequence.

TABLE 3

Exemplary growth factors

| | | Entrez Gene ID[1] | UniProt ID[2] |
|---|---|---|---|
| PDGF family | | | |
| PDGF (e.g., PDGF-1, PDGF-2, or a heterodimer thereof) | PDGF receptor, e.g., PDGFRα, PDGFRβ | 5156 | P16234 |
| CSF-1 | CSF1R | 1435 | P09603 |
| SCF | CD117 | 3815 | P10721 |
| VEGF family | | | |
| VEGF (e.g., isoforms VEGF 121, VEGF 165, VEGF 189, and VEGF 206) | VEGFR-1, VEGFR-2 | 2321 | P17948 |
| VEGF-B | VEGFR-1 | 2321 | P17949 |
| VEGF-C | VEGFR-2 and VEGFR-3 | 2324 | P35916 |
| PIGF | VEGFR-1 | 5281 | Q07326 |
| EGF family | | | |
| EGF | EGFR | 1950 | P01133 |
| TGF-α | EGFR | 7039 | P01135 |
| amphiregulin | EGFR | 374 | P15514 |
| HB-EGF | EGFR | 1839 | Q99075 |
| betacellulin | EGFR, ErbB-4 | 685 | P35070 |
| epiregulin | EGFR, ErbB-4 | 2069 | O14944 |
| Heregulin | EGFR, ErbB-4 | 3084 | Q02297 |
| FGF family | | | |
| FGF-1, FGF-2, FGF-3, FGF-4, FGF-5, FGF-6, FGF-7, FGF-8, FGF-9 | FGFR1, FGFR2, FGFR3, and FGFR4 | 2246, 2247, 2248, 2249, 2250, 2251, 2252, 2253, 2254 | P05230, P09038, P11487, P08620, P12034, P10767, P21781, P55075, P31371 |
| Insulin family | | | |
| Insulin | IR | 3630 | P01308 |
| IGF-I | IGF-I receptor, IGF-II receptor | 3479 | P05019 |
| IGF-II | IGF-II receptor | 3481 | P01344 |
| HGF family | | | |
| HGF | MET receptor | 3082 | P14210 |
| MSP | RON | 4485 | P26927 |
| Neurotrophin family | | | |
| NGF | LNGFR, trkA | 4803 | P01138 |
| BDNF | trkB | 627 | P23560 |
| NT-3 | trkA, trkB, trkC | 4908 | P20783 |
| NT-4 | trkA, trkB | 4909 | P34130 |
| NT-5 | trkA, trkB | 4909 | P34130 |

TABLE 3-continued

Exemplary growth factors

| | | Entrez Gene ID[1] | UniProt ID[2] |
|---|---|---|---|
| Angiopoietin family | | | |
| ANGPT1 | HPK-6/TEK | 284 | Q15389 |
| ANGPT2 | HPK-6/TEK | 285 | O15123 |
| ANGPT3 | HPK-6/TEK | 9068 | O95841 |
| ANGPT4 | HPK-6/TEK | 51378 | Q9Y264 |
| ANGPTL2 | LILRB2 & integrin α5β1 | 23452 | Q9UKU9 |
| ANGPTL3 | LPL | 27329 | Q9Y5C1 |
| ANGPTL4 | | 51129 | Q9BY76 |
| ANGPTL8 | PirB | 55908 | Q6UXH0 |

[1]Sequence available on the NCBI database on the world wide web internet site "ncbi.nlm.nih.gov/gene", Maglott D, et al. Gene: a gene-centered information resource at NCBI. Nucleic Acids Res. 2014. pii: gku1055.
[2]Sequence available on the Uniprot database on the world wide web internet site "uniprot.org/uniprot/"; UniProt: the universal protein knowledgebase in 2021.Nucleic Acids Res. 49:D1 (2021).

Clotting Factors

In some embodiments, an effector described herein comprises a polypeptide of Table 4, or a functional variant thereof, e.g., a protein having at least 80%, 85%, 90%, 95%, 967%, 98%, 99% identity to a protein sequence disclosed in Table 4 by reference to its UniProt ID. In some embodiments, the functional variant catalyzes the same reaction as the corresponding wild-type protein, e.g., at a rate no less than 10%, 20%, 30%, 40%, or 50% lower or higher than the wild-type protein. In some embodiments, the polypeptide of Table 4 or functional variant thereof comprises a signal sequence, e.g., a signal sequence that is endogenous to the effector, or a heterologous signal sequence.

TABLE 4

Clotting-associated factors

| Effector | Indication | Entrez Gene ID[1] | UniProt ID[2] |
|---|---|---|---|
| Factor I (fibrinogen) | Afibrinogenomia | 2243, 2266, 2244 | P02671, P02679, P02675 |
| Factor II | Factor II Deficiency | 2147 | P00734 |
| Factor IX | Hemophilia B | 2158 | P00740 |
| Factor V | Owren's disease | 2153 | P12259 |
| Factor VIII | Hemophilia A | 2157 | P00451 |
| Factor X | Stuart-Prower Factor Deficiency | 2159 | P00742 |
| Factor XI | Hemophilia C | 2160 | P03951 |
| Factor XIII | Fibrin Stabilizing factor deficiency | 2162, 2165 | P00488, P05160 |
| VWF | von Willebrand disease | 7450 | P04275 |

[1]Sequence available on the NCBI database on the world wide web internet site "ncbi.nlm.nih.gov/gene", Maglott D, et al. Gene: a gene-centered information resource at NCBI. Nucleic Acids Res. 2014. pii: gku1055.
[2]Sequence available on the Uniprot database on the world wide web internet site "uniprot.org/uniprot/"; UniProt: the universal protein knowledgebase in 2021.Nucleic Acids Res. 49:D1 (2021).

Therapeutic Replacement Enzymes

In some embodiments, an effector described herein comprises an enzyme of Table 5, or a functional variant thereof, e.g., a protein having at least 80%, 85%, 90%, 95%, 967%, 98%, 99% identity to a protein sequence disclosed in Table 5 by reference to its UniProt ID. In some embodiments, the functional variant catalyzes the same reaction as the corresponding wild-type protein, e.g., at a rate no less or no more than 10%, 20%, 30%, 40%, or 50% lower than the wild-type protein.

TABLE 5

Exemplary enzymatic effectors for enzyme deficiency

| Effector | Deficiency | Entrez Gene ID[1] | UniProt ID[2] |
|---|---|---|---|
| 3-methylcrotonyl-CoA carboxylase | 3-methylcrotonyl-CoA carboxylase deficiency | 56922, 64087 | Q96RQ3, Q9HCC0 |
| Acetyl-CoA-glucosaminide N-acetyltransferase | Mucopolysaccharidosis MPS III (Sanfilippo's syndrome) Type III-C | 138050 | Q68CP4 |
| ADAMTS13 | Thrombotic Thrombocytopeniaurpura | 11093 | Q76LX8 |
| adenine phosphoribosyltransferase | Adenine phosphoribosyltransferase deficiency | 353 | P07741 |
| Adenosine deaminase | Adenosine deaminase deficiency | 100 | P00813 |
| ADP-ribose protein hydrolase | Glutamyl ribose-5-phosphate storage disease | 26119, 54936 | Q5SW96, |
| alpha glucosidase | Glycogen storage disease type 2 (Pompe's disease) | 2548 | P10253 |
| Arginase | Familial hyperargininemia | 383, 384 | P05089, P78540 |
| Arylsulfatase A | Metachromatic leukodystrophy | 410 | P15289 |
| Cathepsin K | Pycnodysostosis | 1513 | P43235 |
| Ceramidase | Farber's disease (lipogranulomatosis) | 125981, 340485, 55331 | Q8TDN7, Q5QJU3, Q9NUN7 |
| Cystathionine B synthase | Homocystinuria | 875 | P35520 |
| Dolichol-P-mannose synthase | Congenital disorders of N-glycosylation CDG Ie | 8813, 54344 | O60762, Q9P2X0 |

TABLE 5-continued

Exemplary enzymatic effectors for enzyme deficiency

| Effector | Deficiency | Entrez Gene ID[1] | UniProt ID[2] |
|---|---|---|---|
| Dolicho-P-Glc: Man9GlcNAc2-PP-dolichol glucosyltransferase | Congenital disorders of N-glycosylation CDG Ic | 84920 | Q5BKT4 |
| Dolicho-P-Man: Man5GlcNAc2-PP-dolichol mannosyltransferase | Congenital disorders of N-glycosylation CDG Id | 10195 | Q92685 |
| Dolichyl-P-glucose: Glc-1-Man-9-GlcNAc-2-PP-dolichyl-α-3-glucosyltransferase | Congenital disorders of N-glycosylation CDG Ih | 79053 | Q9BVK2 |
| Dolichyl-P-mannose: Man-7-GlcNAc-2-PP-dolichyl-α-6-mannosyltransferase | Congenital disorders of N-glycosylation CDG Ig | 79087 | Q9BV10 |
| Factor II | Factor II Deficiency | 2147 | P00734 |
| Factor IX | Hemophilia B | 2158 | P00740 |
| Factor V | Owren's disease | 2153 | P12259 |
| Factor VIII | Hemophilia A | 2157 | P00451 |
| Factor X | Stuart-Prower Factor Deficiency | 2159 | P00742 |
| Factor XI | Hemophilia C | 2160 | P03951 |
| Factor XIII | Fibrin Stabilizing factor deficiency | 2162, 2165 | P00488, P05160 |
| Galactosamine-6-sulfate sulfatase | Mucopolysaccharidosis MPS IV (Morquio's syndrome) Type IV-A | 2588 | P34059 |
| Galactosylceramide β-galactosidase | Krabbe's disease | 2581 | P54803 |
| Ganglioside β-galactosidase | GM1 gangliosidosis, generalized | 2720 | P16278 |
| Ganglioside β-galactosidase | GM2 gangliosidosis | 2720 | P16278 |
| Ganglioside β-galactosidase | Sphingolipidosis Type I | 2720 | P16278 |
| Ganglioside β-galactosidase | Sphingolipidosis Type II (juvenile type) | 2720 | P16278 |
| Ganglioside β-galactosidase | Sphingolipidosis Type III (adult type) | 2720 | P16278 |
| Glucosidase I | Congenital disorders of N-glycosylation CDG IIb | 2548 | P10253 |
| Glucosylceramide β-glucosidase | Gaucher's disease | 2629 | P04062 |
| Heparan-S-sulfate sulfamidase | Mucopolysaccharidosis MPS III (Sanfilippo's syndrome) Type III-A | 6448 | P51688 |
| homogentisate oxidase | Alkaptonuria | 3081 | Q93099 |
| Hyaluronidase | Mucopolysaccharidosis MPS IX (hyaluronidase deficiency) | 3373, 8692, 8372, 23553 | Q12794, Q12891, O43820, Q2M3T9 |
| Iduronate sulfate sulfatase | Mucopolysaccharidosis MPS II (Hunter's syndrome) | 3423 | P22304 |
| Lecithin-cholesterol acyltransferase (LCAT) | Complete LCAT deficiency, Fish-eye disease, atherosclerosis, hypercholesterolemia | 3931 | 606967 |
| Lysine oxidase | Glutaric acidemia type I | 4015 | P28300 |
| Lysosomal acid lipase | Cholesteryl ester storage disease (CESD) | 3988 | P38571 |
| Lysosomal acid lipase | Lysosomal acid lipase deficiency | 3988 | P38571 |
| lysosomal acid lipase | Wolman's disease | 3988 | P38571 |
| Lysosomal pepstatin-insensitive peptidase | Ceroid lipofuscinosis Late infantile form (CLN2, Jansky-Bielschowsky disease) | 1200 | O14773 |
| Mannose (Man) phosphate (P) isomerase | Congenital disorders of N-glycosylation CDG Ib | 4351 | P34949 |
| Mannosyl-α-1,6-glycoprotein-β-1,2-N-acetylglucosminyltransferase | Congenital disorders of N-glycosylation CDG IIa | 4247 | Q10469 |
| Metalloproteinase-2 | Winchester syndrome | 4313 | P08253 |
| methylmalonyl-CoA mutase | Methylmalonic acidemia (vitamin b12 non-responsive) | 4594 | P22033 |
| N-Acetyl galactosamine β-4-sulfate sulfatase (arylsulfatase B) | Mucopolysaccharidosis MPS VI (Maroteaux-Lamy syndrome) | 411 | P15848 |
| N-acetyl-D-glucosaminidase | Mucopolysaccharidosis MPS III (Sanfilippo's syndrome) Type III-B | 4669 | P54802 |
| N-Acetyl-galactosaminidase | Schindler's disease Type I (infantile severe form) | 4668 | P17050 |
| N-Acetyl-galactosaminidase | Schindler's disease Type II (Kanzaki disease, adult-onset form) | 4668 | P17050 |
| N-Acetyl-galactosaminidase | Schindler's disease Type III (intermediate form) | 4668 | P17050 |
| N-acetyl-glucosaminine- | Mucopolysaccharidosis MPS III (Sanfilippo's syndrome) | 2799 | P15586 |

TABLE 5-continued

Exemplary enzymatic effectors for enzyme deficiency

| Effector | Deficiency | Entrez Gene ID[1] | UniProt ID[2] |
|---|---|---|---|
| 6-sulfate sulfatase | Type III-D | | |
| N-acetylglucosaminyl-1-phosphotransferase | Mucolipidosis ML III (pseudo-Hurler's polydystrophy) | 79158 | Q3T906 |
| N-Acetylglucosaminyl-1-phosphotransferase catalytic subunit | Mucolipidosis ML II (I-cell disease) | 79158 | Q3T906 |
| N-acetylglucosaminyl-1-phosphotransferase, substrate-recognition subunit | Mucolipidosis ML III (pseudo-Hurler's polydystrophy) Type III-C | 84572 | Q9UJJ9 |
| N-Aspartylglucosaminidase | Aspartylglucosaminuria | 175 | P20933 |
| Neuraminidase 1 (sialidase) | Sialidosis | 4758 | Q99519 |
| Palmitoyl-protein thioesterase-1 | Ceroid lipofuscinosis Adult form (CLN4, Kufs' disease) | 5538 | P50897 |
| Palmitoyl-protein thioesterase-1 | Ceroid lipofuscinosis Infantile form (CLN1, Santavuori-Haltia disease) | 5538 | P50897 |
| Phenylalanine hydroxylase | Phenylketonuria | 5053 | P00439 |
| Phosphomannomutase-2 | Congenital disorders of N-glycosylation CDG 1a (solely neurologic and neurologic-multivisceral forms) | 5373 | O15305 |
| Porphobilinogen deaminase | Acute Intermittent Porphyria | 3145 | P08397 |
| Purine nucleoside phosphorylase | Purine nucleoside phosphorylase deficiency | 4860 | P00491 |
| pyrimidine 5' nucleotidase | Hemolytic anemia and/or pyrimidine 5' nucleotidase deficiency | 51251 | Q9H0P0 |
| Sphingomyelinase | Niemann-Pick disease type A | 6609 | P17405 |
| Sphingomyelinase | Niemann-Pick disease type B | 6609 | P17405 |
| Sterol 27-hydroxylase | Cerebrotendinous xanthomatosis (cholestanol lipidosis) | 1593 | Q02318 |
| Thymidine phosphorylase | Mitochondrial neurogastrointestinal encephalomyopathy (MNGIE) | 1890 | P19971 |
| Trihexosylceramide α-galactosidase | Fabry's disease | 2717 | P06280 |
| tyrosinase, e.g., OCA1 | albinism, e.g., ocular albinism | 7299 | P14679 |
| UDP-GlcNAc:dolichyl-P NAcGlc phosphotransferase | Congenital disorders of N-glycosylation CDG Ij | 1798 | Q9H3H5 |
| UDP-N-acetylglucosamine-2-epimerase/N-acetylmannosamine kinase, sialin | Sialuria French type | 10020 | Q9Y223 |
| Uricase | Lesch-Nyhan syndrome, gout | 391051 | No protein |
| uridine diphosphate glucuronyl-transferase (e.g., UGT1A1) | Crigler-Najjar syndrome | 54658 | P22309 |
| α-1,2-Mannosyltransferase | Congenital disorders of N-glycosylation CDG II (608776) | 79796 | Q9H6U8 |
| α-1,2-Mannosyltransferase | Congenital disorders of N-glycosylation, type I (pre-Golgi glycosylation defects) | 79796 | Q9H6U8 |
| α-1,3-Mannosyltransferase | Congenital disorders of N-glycosylation CDG Ii | 440138 | Q2TAA5 |
| α-D-Mannosidase | α-Mannosidosis, type I (severe) or II (mild) | 10195 | Q92685 |
| α-L-Fucosidase | Fucosidosis | 4123 | Q9NTJ4 |
| α-I-Iduronidase | Mucopolysaccharidosis MPS I H/S (Hurler-Scheie syndrome) | 2517 | P04066 |
| α-I-Iduronidase | Mucopolysaccharidosis MPS I-H (Hurler's syndrome) | 3425 | P35475 |
| α-I-Iduronidase | Mucopolysaccharidosis MPS I-S (Scheie's syndrome) | 3425 | P35475 |
| β-1,4-Galactosyltransferase | Congenital disorders of N-glycosylation CDG IId | 3425 | P35475 |
| β-1,4-Mannosyltransferase | Congenital disorders of N-glycosylation CDG Ik | 2683 | P15291 |
| β-D-Mannosidase | β-Mannosidosis | 56052 | Q9BT22 |
| β-Galactosidase | Mucopolysaccharidosis MPS IV (Morquio's syndrome) Type IV-B | 4126 | O00462 |
| β-Glucuronidase | Mucopolysaccharidosis MPS VII (Sly's syndrome) | 2720 | P16278 |
| β-Hexosaminidase A | Tay-Sachs disease | 2990 | P08236 |
| β-Hexosaminidase B | Sandhoff's disease | 3073 | P06865 |

[1] Sequence available on the NCBI database on the world wide web internet site "ncbi.nlm.nih.gov/gene", Maglott D, et al. Gene: a gene-centered information resource at NCBI. Nucleic Acids Res. 2014. pii: gku1055.
[2] Sequence available on the Uniprot database on the world wide web internet site "uniprot.org/uniprot/"; UniProt: the universal protein knowledgebase in 2021.Nucleic Acids Res. 49:D1 (2021).

Other Non-Enzymatic Effectors

In some embodiments, a therapeutic polypeptide described herein comprises a polypeptide of Table 6, or a functional variant thereof, e.g., a protein having at least 80%, 85%, 90%, 95%, 967%, 98%, 99% identity to a protein sequence disclosed in Table 6 by reference to its UniProt ID.

TABLE 6

Exemplary non-enzymatic effectors and corresponding indications

| Effector | Indication | Entrez Gene ID[1] | UniProt ID[2] |
|---|---|---|---|
| Survival motor neuron protein (SMN) | spinal muscular atrophy | 6606 | Q16637 |
| Dystrophin | muscular dystrophy (e.g., Duchenne muscular dystrophy or Becker muscular dystrophy) | 1756 | P11532 |
| Complement protein, e.g., Complement factor C1 | Complement Factor I deficiency | 3426 | P05156 |
| Complement factor H | Atypical hemolytic uremic syndrome | 3075 | P08603 |
| Cystinosin (lysosomal cystine transporter) | Cystinosis | 1497 | O60931 |
| Epididymal secretory protein 1 (HE1; NPC2 protein) | Niemann-Pick disease Type C2 | 10577 | P61916 |
| GDP-fucose transporter-1 | Congenital disorders of N-glycosylation CDG IIc (Rambam-Hasharon syndrome) | 55343 | Q96A29 |
| GM2 activator protein | GM2 activator protein deficiency (Tay-Sachs disease AB variant, GM2A) | 2760 | Q17900 |
| Lysosomal transmembrane CLN3 protein | Ceroid lipofuscinosis Juvenile form (CLN3, Batten disease, Vogt-Spielmeyer disease) | 1207 | Q13286 |
| Lysosomal transmembrane CLN5 protein | Ceroid lipofuscinosis Variant late infantile form, Finnish type (CLN5) | 1203 | O75503 |
| Na phosphate cotransporter, sialin | Infantile sialic acid storage disorder | 26503 | Q9NRA2 |
| Na phosphate cotransporter, sialin | Sialuria Finnish type (Salla disease) | 26503 | Q9NRA2 |
| NPC1 protein | Niemann-Pick disease Type C1/Type D | 4864 | O15118 |
| Oligomeric Golgi complex-7 | Congenital disorders of N-glycosylation CDG IIe | 91949 | P83436 |
| Prosaposin | Prosaposin deficiency | 5660 | P07602 |
| Protective protein/cathepsin A (PPCA) | Galactosialidosis (Goldberg's syndrome, combined neuraminidase and β-galactosidase deficiency) | 5476 | P10619 |
| Protein involved in mannose-P-dolichol utilization | Congenital disorders of N-glycosylation CDG If | 9526 | O75352 |
| Saposin B | Saposin B deficiency (sulfatide activator deficiency) | 5660 | P07602 |
| Saposin C | Saposin C deficiency (Gaucher's activator deficiency) | 5660 | P07602 |
| Sulfatase-modifying factor-1 | Mucosulfatidosis (multiple sulfatase deficiency) | 285362 | Q8NBK3 |
| Transmembrane CLN6 protein | Ceroid lipofuscinosis Variant late infantile form (CLN6) | 54982 | Q9NWW5 |
| Transmembrane CLN8 protein | Ceroid lipofuscinosis Progressive epilepsy with intellectual disability | 2055 | Q9UBY8 |
| VWF | von Willebrand disease | 7450 | P04275 |
| Factor I (fibrinogen) erythropoietin (hEPO) | Afibrinogenomia | 2243, 2244, 2266 | P02671, P02675, P02679 |

[1]Sequence available on the NCBI database on the world wide web internet site "ncbi.nlm.nih.gov/gene", Maglott D, et al. Gene: a gene-centered information resource at NCBI. Nucleic Acids Res. 2014. pii: gku1055.
[2]Sequence available on the Uniprot database on the world wide web internet site "uniprot.org/uniprot/"; UniProt: the universal protein knowledgebase in 2021.Nucleic Acids Res. 49:D1 (2021).

Regeneration, Repair and Fibrosis Factors

Therapeutic polypeptides described herein also include growth factors, e.g., as disclosed in Table 7, or functional variants thereof, e.g., a protein having at least 80%, 85%, 90%, 95%, 967%, 98%, 99% identity to a protein sequence disclosed in Table 7 by reference to its NCBI protein accession number. Also included are antibodies or fragments thereof against such growth factors, or miRNAs that promote regeneration and repair.

TABLE 7

Exemplary Regeneration, Repair, and Fibrosis Factors

| Target | NCBI Gene accession #[1] | NCBI Protein accession #[2] |
|---|---|---|
| VEGF-A | NG_008732 | NP_001165094 |
| NRG-1 | NG_012005 | NP_001153471 |
| FGF2 | NG_029067 | NP_001348594 |
| FGF1 | Gene ID: 2246 | NP_001341882 |
| miR199-3p | MIMAT0000232 | n/a |
| miR590-3p | MIMAT0004801 | n/a |
| miR17-92 | MI0000071 | On the world wide web internet site "ncbi.nlm.nih.gov/pmc/articles/PMC2732113/figure/F1/" |
| miR222 | MI0000299 | n/a |
| miR302-367 | MIR302A And MIR367 | On the world wide web internet site "ncbi.nlm.nih.gov/pmc/articles/PMC4400607/" |

[1] Sequence available on the world wide web internet site "ncbi.nlm.nih.gov/gene" (Maglott D, et al. Gene: a gene-centered information resource at NCBI. Nucleic Acids Res. 2014. Pii: gku1055.)
[2] Sequence available on the world wide web internet site "ncbi.nlm.nih.gov/protein/"

Transformation Factors

Therapeutic polypeptides described herein also include transformation factors, e.g., protein factors that transform fibroblasts into differentiated cell e.g., factors disclosed in Table 8 or functional variants thereof, e.g., a protein having at least 80%, 85%, 90%, 95%, 967%, 98%, 99% identity to a protein sequence disclosed in Table 8 by reference to its UniProt ID.

TABLE 8

Polypeptides indicated for organ repair by transforming fibroblasts

| Target | NCBI Gene accession #[1] | NCBI Protein accession #[2] |
|---|---|---|
| MESP1 | Gene ID: 55897 | EAX02066 |
| ETS2 | GeneID: 2114 | NP_005230 |
| HAND2 | GeneID: 9464 | NP_068808 |
| MYOCARDIN | GeneID: 93649 | NP_001139784 |
| ESRRA | Gene ID: 2101 | AAH92470 |
| miR1 | MI0000651 | n/a |
| miR133 | MI000450 | n/a |
| TGFb | GeneID: 7040 | NP_000651.3 |
| WNT | Gene ID: 7471 | NP_005421 |
| JAK | Gene ID: 3716 | NP_001308784 |
| NOTCH | GeneID: 4851 | XP_011517019 |

[1] Sequence available on the world wide web internet site "ncbi.nlm.nih.gov/gene" (Maglott D, et al. Gene: a gene-centered information resource at NCBI. Nucleic Acids Res. 2014. Pii: gku1055.)
[2] Sequence available on the world wide web internet site "ncbi.nlm.nih.gov/protein/"

Proteins that Stimulate Cellular Regeneration

Therapeutic polypeptides described herein also include proteins that stimulate cellular regeneration e.g., proteins disclosed in Table 9 or functional variants thereof, e.g., a protein having at least 80%, 85%, 90%, 95%, 967%, 98%, 99% identity to a protein sequence disclosed in Table 9 by reference to its UniProt ID.

TABLE 9

Exemplary proteins that stimulate cellular regeneration

| Target | Gene accession #[1] | Protein accession #[2] |
|---|---|---|
| MST1 | NG_016454 | NP_066278 |
| STK30 | Gene ID: 26448 | NP_036103 |
| MST2 | Gene ID: 6788 | NP_006272 |

TABLE 9-continued

Exemplary proteins that stimulate cellular regeneration

| Target | Gene accession #[1] | Protein accession #[2] |
|---|---|---|
| SAV1 | Gene ID: 60485 | NP_068590 |
| LATS1 | Gene ID: 9113 | NP_004681 |
| LATS2 | Gene ID: 26524 | NP_055387 |
| YAP1 | NG_029530 | NP_001123617 |
| CDKN2b | NG_023297 | NP_004927 |
| CDKN2a | NG_007485 | NP_478102 |

[1] Sequence available on the world wide web internet site "ncbi.nlm.nih.gov/gene" (Maglott D, et al. Gene: a gene-centered information resource at NCBI. Nucleic Acids Res. 2014. Pii: gku1055.)
[2] Sequence available on the world wide web internet site "ncbi.nlm.nih.gov/protein/"

In some embodiments, the circular polyribonucleotide comprises one or more expression sequences (coding sequences) and is configured for persistent expression in a cell of a subject in vivo. In some embodiments, the circular polyribonucleotide is configured such that expression of the one or more expression sequences in the cell at a later time point is equal to or higher than an earlier time point. In such embodiments, the expression of the one or more expression sequences may be either maintained at a relatively stable level or may increase over time. The expression of the expression sequences may be relatively stable for an extended period of time. For instance, in some cases, the expression of the one or more expression sequences in the cell over a time period of at least 7, 8, 9, 10, 12, 14, 16, 18, 20, 22, 23 or more days does not decrease by 50%, 45%, 40%, 35%, 30%, 25%, 20%, 15%, 10%, or 5%. In some cases, in some cases, the expression of the one or more expression sequences in the cell is maintained at a level that does not vary by more than 50%, 45%, 40%, 35%, 30%, 25%, 20%, 15%, 10%, or 5% for at least 7, 8, 9, 10, 12, 14, 16, 18, 20, 22, 23 or more days.

Plant-Modifying Polypeptides

In some embodiments, the polyribonucleotide described herein (e.g., the polyribonucleotide cargo of the polyribonucleotide) includes at least one expression sequence encoding a plant-modifying polypeptide. A plant-modifying polypeptide refers to a polypeptide that can alter the genetic properties (e.g., increase gene expression, decrease gene expression, or otherwise alter the nucleotide sequence of DNA or RNA), epigenetic properties, or physiological or biochemical properties of a plant in a manner that results in a change in the plant's physiology or phenotype, e.g., an increase or decrease in the plant's fitness. In some embodiments, the polyribonucleotide encodes two, three, four, five, six, seven, eight, nine, ten or more different plant-modifying polypeptides, or multiple copies of one or more plant-modifying polypeptides. A plant-modifying polypeptide may change the physiology or phenotype of, or increase or decrease the fitness of, a variety of plants, or can be one that effects such change(s) in one or more specific plants (e.g., a specific species or genera of plants).

Examples of polypeptides that can be used herein can include an enzyme (e.g., a metabolic recombinase, a helicase, an integrase, a RNAse, a DNAse, or a ubiquitination protein), a pore-forming protein, a signaling ligand, a cell penetrating peptide, a transcription factor, a receptor, an antibody, a nanobody, a gene editing protein (e.g., CRISPR-Cas endonuclease, TALEN, or zinc finger), riboprotein, a protein aptamer, or a chaperone.

Agricultural Polypeptides

In some embodiments, the polyribonucleotide described herein (e.g., the polyribonucleotide cargo of the polyribonucleotide) includes at least one expression sequence encoding an agricultural polypeptide. An agricultural polypeptide is a polypeptide that is suitable for an agricultural use. In embodiments, an agricultural polypeptide is applied to a plant or seed (e.g., by foliar spray, dusting, injection, or seed coating) or to the plant's environment (e.g., by soil drench or granular soil application), resulting in an alteration of the plant's physiology, phenotype, or fitness. Embodiments of an agricultural polypeptide include polypeptides that alter a level, activity, or metabolism of one or more microorganisms resident in or on a plant or non-human animal host, the alteration resulting in an increase in the host's fitness. In some embodiments the agricultural polypeptide is a plant polypeptide. In some embodiments, the agricultural polypeptide is an insect polypeptide. In some embodiments, the agricultural polypeptide has a biological effect when contacted with a non-human vertebrate animal, invertebrate animal, microbial, or plant cell.

In some embodiments, the polyribonucleotide encodes two, three, four, five, six, seven, eight, nine, ten or more agricultural polypeptides, or multiple copies of one or more agricultural polypeptides.

Embodiments of polypeptides useful in agricultural applications include, for example, bacteriocins, lysins, antimicrobial peptides, nodule C-rich peptides, and bacteriocyte regulatory peptides. Such polypeptides can be used to alter the level, activity, or metabolism of target microorganisms for increasing the fitness of insects, such as honeybees and silkworms. Embodiments of agriculturally useful polypeptides include peptide toxins, such as those naturally produced by entomopathogenic bacteria (e.g., *Bacillus thuringiensis, Photorhabdus luminescens, Serratia entomophila*, or *Xenorhabdus nematophila*), as is known in the art. Embodiments of agriculturally useful polypeptides include polypeptides (including small peptides such as cyclodipeptides or diketopiperazines) for controlling agriculturally important pests or pathogens, e.g., antimicrobial polypeptides or antifungal polypeptides for controlling diseases in plants, or pesticidal polypeptides (e.g., insecticidal polypeptides or nematicidal polypeptides) for controlling invertebrate pests such as insects or nematodes. Embodiments of agriculturally useful polypeptides include antibodies, nanobodies, and fragments thereof, e.g., antibody or nanobody fragments that retain at least some (e.g., at least 10%) of the specific binding activity of the intact antibody or nanobody. Embodiments of agriculturally useful polypeptides include transcription factors, e.g., plant transcription factors; see., e.g, the "AtTFDB" database listing the transcription factor families identified in the model plant *Arabidopsis thaliana*), publicly available at agris-knowledgebase [dot] org/AtTFDB/. Embodiments of agriculturally useful polypeptides include nucleases, for example, exonucleases or endonucleases (e.g., Cas nucleases such as Cas9 or Cas12a). Embodiments of agriculturally useful polypeptides further include cell-penetrating peptides, enzymes (e.g., amylases, cellulases, peptidases, lipases, chitinases), peptide pheromones (for example, yeast mating pheromones, invertebrate reproductive and larval signalling pheromones, see, e.g., Altstein (2004) Peptides, 25:1373-1376).

Internal Ribosomal Entry Sites

In some embodiments, the polyribonucleotide described herein (e.g., the polyribonucleotide cargo of the polyribonucleotide) includes one or more internal ribosome entry site (IRES) elements. In some embodiments, the IRES is operably linked to one or more expression sequences (e.g., each IRES is operably linked to one or more expression sequences). In embodiments, the IRES is located between a heterologous promoter and the 5' end of a coding sequence.

A suitable IRES element to include in a polyribonucleotide includes an RNA sequence capable of engaging a eukaryotic ribosome. In some embodiments, the IRES element is at least about 5 nt, at least about 8 nt, at least about 9 nt, at least about 10 nt, at least about 15 nt, at least about 20 nt, at least about 25 nt, at least about 30 nt, at least about 40 nt, at least about 50 nt, at least about 100 nt, at least about 200 nt, at least about 250 nt, at least about 350 nt, or at least about 500 nt.

In some embodiments, the IRES element is derived from the DNA of an organism including, but not limited to, a virus, a mammal, and a *Drosophila*. Such viral DNA may be derived from, but is not limited to, picornavirus complementary DNA (cDNA), with encephalomyocarditis virus (EMCV) cDNA and poliovirus cDNA. In one embodiment, *Drosophila* DNA from which an IRES element is derived includes, but is not limited to, an Antennapedia gene from *Drosophila melanogaster*.

In some embodiments, if present, the IRES sequence is an IRES sequence of Taura syndrome virus, *Triatoma* virus, Theiler's encephalomyelitis virus, simian Virus 40, *Solenopsis invicta* virus 1, *Rhopalosiphum padi* virus, Reticuloendotheliosis virus, fuman poliovirus 1, *Plautia* stall intestine virus, Kashmir bee virus, Human rhinovirus 2, Homalodisca coagulata virus-1, Human Immunodeficiency Virus type 1, Homalodisca coagulata virus-1, Himetobi P virus, Hepatitis C virus, Hepatitis A virus, Hepatitis GB virus, foot and mouth disease virus, Human enterovirus 71, Equine rhinitis virus, Ectropis obliqua picorna-like virus, Encephalomyocarditis virus (EMCV), *Drosophila* C Virus, Crucifer tobamo virus, Cricket paralysis virus, Bovine viral diarrhea virus 1, Black Queen Cell Virus, Aphid lethal paralysis virus, Avian encephalomyelitis virus, Acute bee paralysis virus, Hibiscus chlorotic ringspot virus, Classical swine fever virus, Human FGF2, Human SFTPA1, Human AML1/RUNX1, *Drosophila* antennapedia, Human AQP4, Human AT1R, Human BAG-I, Human BCL2, Human BiP, Human c-IAPI, Human c-myc, Human elF4G, Mouse NDST4L, Human LEF1, Mouse HIF1 alpha, Human n.myc, Mouse Gtx, Human p27kipl, Human PDGF2/c-sis, Human p53, Human Pim-I, Mouse Rbm3, *Drosophila* reaper, Canine Scamper, *Drosophila* Ubx, Human UNR, Mouse UtrA, Human VEGF-A, Human XIAP, Salivirus, Cosavirus, Parechovirus, *Drosophila* hairless, *S. cerevisiae* TFIID, *S. cerevisiae* YAP1, Human c-src, Human FGF-I, Simian picomavirus, Turnip crinkle virus, an aptamer to elF4G, Coxsackievirus B3 (CVB3) or Coxsackievirus A (CVB1/2). In yet another embodiment, the IRES is an IRES sequence of Coxsackievirus B3 (CVB3). In a further embodiment, the IRES is an IRES sequence of Encephalomyocarditis virus.

In some embodiments, the polyribonucleotide includes at least one IRES flanking at least one (e.g., 2, 3, 4, 5 or more) expression sequence. In some embodiments, the IRES flanks both sides of at least one (e.g., 2, 3, 4, 5 or more) expression sequence. In some embodiments, the polyribonucleotide includes one or more IRES sequences on one or both sides of each expression sequence, leading to separation of the resulting peptide(s) and or polypeptide(s).

In some embodiments, the polyribonucleotide cargo includes an IRES. For example, the polyribonucleotide cargo may include a circular RNA IRES, e.g., as described in Chen et al. Mol. Cell 81:1-19, 2021, which is hereby incorporated by reference in its entirety.

Regulatory Elements

In some embodiments, the polyribonucleotide described herein (e.g., the polyribonucleotide cargo of the polyribonucleotide) includes one or more regulatory elements. In some embodiments, the polyribonucleotide includes a regulatory element, e.g., a sequence that modifies expression of an expression sequence within the polyribonucleotide.

A regulatory element may include a sequence that is located adjacent to an expression sequence that encodes an expression product. A regulatory element may be linked operatively to the adjacent sequence. A regulatory element may increase an amount of product expressed as compared to an amount of the expressed product when no regulatory element exists. In addition, one regulatory element can increase an amount of products expressed for multiple expression sequences attached in tandem. Hence, one regulatory element can enhance the expression of one or more expression sequences. Multiple regulatory elements are well-known to persons of ordinary skill in the art.

In some embodiments, the regulatory element is a translation modulator. A translation modulator can modulate translation of the expression sequence in the polyribonucleotide. A translation modulator can be a translation enhancer or suppressor. In some embodiments, the polyribonucleotide includes at least one translation modulator adjacent to at least one expression sequence. In some embodiments, the polyribonucleotide includes a translation modulator adjacent each expression sequence. In some embodiments, the translation modulator is present on one or both sides of each expression sequence, leading to separation of the expression products, e.g., peptide(s) and or polypeptide(s).

In some embodiments, the regulatory element is a microRNA (miRNA) or a miRNA binding site.

Further examples of regulatory elements are described, e.g., in paragraphs-of International Patent Publication No. WO2019/118919, which is hereby incorporated by reference in its entirety.

Translation Initiation Sequences

In some embodiments, the polyribonucleotide described herein (e.g., the polyribonucleotide cargo of the polyribonucleotide) includes at least one translation initiation sequence. In some embodiments, the polyribonucleotide includes a translation initiation sequence operably linked to an expression sequence.

In some embodiments, the polyribonucleotide encodes a polypeptide and may include a translation initiation sequence, e.g., a start codon. In some embodiments, the translation initiation sequence includes a Kozak or Shine-Dalgamo sequence. In some embodiments, the polyribonucleotide includes the translation initiation sequence, e.g., Kozak sequence, adjacent to an expression sequence. In some embodiments, the translation initiation sequence is a non-coding start codon. In some embodiments, the translation initiation sequence, e.g., Kozak sequence, is present on one or both sides of each expression sequence, leading to separation of the expression products. In some embodiments, the polyribonucleotide includes at least one translation initiation sequence adjacent to an expression sequence. In some embodiments, the translation initiation sequence provides conformational flexibility to the polyribonucleotide. In some embodiments, the translation initiation sequence is within a substantially single stranded region of the polyribonucleotide. Further examples of translation initiation sequences are described in paragraphs-of International Patent Publication No. WO2019/118919, which is hereby incorporated by reference in its entirety.

The polyribonucleotide may include more than 1 start codon such as, but not limited to, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40, at least 50, at least 60 or more than 60 start codons. Translation may initiate on the first start codon or may initiate downstream of the first start codon.

In some embodiments, the polyribonucleotide may initiate at a codon which is not the first start codon, e.g., AUG. Translation of the polyribonucleotide may initiate at an alternative translation initiation sequence, such as, but not limited to

```
                                    (SEQ ID NO: 74)
        ACG, AGG, AAG, CTG/CUG, (SEQ ID NO: 75)
              GTG/GUG, (SEQ ID NO: 76)
              ATA/AUA, (SEQ ID NO: 77)
              ATT/AUU, (SEQ ID NO: 78)
              TTG/UUG.
```

In some embodiments, translation begins at an alternative translation initiation sequence under selective conditions, e.g., stress induced conditions. As a non-limiting example, the translation of the polyribonucleotide may begin at alternative translation initiation sequence, such as ACG. As another non-limiting example, the polyribonucleotide translation may begin at alternative translation initiation sequence, CTG/CUG (SEQ ID NO: 74). As another non-limiting example, the polyribonucleotide translation may begin at alternative translation initiation sequence,

GTG/GUG. (SEQ ID NO: 75)

As another non-limiting example, the polyribonucleotide may begin translation at a repeat-associated non-AUG (RAN) sequence, such as an alternative translation initiation sequence that includes short stretches of repetitive RNA e.g.,

CGG, GGGGCC, (SEQ ID NO: 79)

CAG, CTG.

Termination Elements

In some embodiments, the polyribonucleotide described herein (e.g., the polyribonucleotide cargo of the polyribonucleotide) includes least one termination element. In some embodiments, the polyribonucleotide includes a termination element operably linked to an expression sequence. In some embodiments, the polynucleotide lacks a termination element.

In some embodiments, the polyribonucleotide includes one or more expression sequences, and each expression sequence may or may not have a termination element. In some embodiments, the polyribonucleotide includes one or more expression sequences, and the expression sequences lack a termination element, such that the polyribonucleotide is continuously translated. Exclusion of a termination element may result in rolling circle translation or continuous expression of expression product.

In some embodiments, the circular polyribonucleotide includes one or more expression sequences, and each expression sequence may or may not have a termination element. In some embodiments, the circular polyribonucleotide includes one or more expression sequences, and the expression sequences lack a termination element, such that the circular polyribonucleotide is continuously translated. Exclusion of a termination element may result in rolling circle translation or continuous expression of expression product, e.g., peptides or polypeptides, due to lack of ribosome stalling or fall-off. In such an embodiment, rolling circle translation expresses a continuous expression product through each expression sequence. In some other embodiments, a termination element of an expression sequence can be part of a stagger element. In some embodiments, one or more expression sequences in the circular polyribonucleotide comprises a termination element. However, rolling circle translation or expression of a succeeding (e.g., second, third, fourth, fifth, etc.) expression sequence in the circular polyribonucleotide is performed. In such instances, the expression product may fall off the ribosome when the ribosome encounters the termination element, e.g., a stop codon, and terminates translation. In some embodiments, translation is terminated while the ribosome, e.g., at least one subunit of the ribosome, remains in contact with the circular polyribonucleotide.

In some embodiments, the circular polyribonucleotide includes a termination element at the end of one or more expression sequences. In some embodiments, one or more expression sequences comprises two or more termination elements in succession. In such embodiments, translation is terminated and rolling circle translation is terminated. In some embodiments, the ribosome completely disengages with the circular polyribonucleotide. In some such embodiments, production of a succeeding (e.g., second, third, fourth, fifth, etc.) expression sequence in the circular polyribonucleotide may require the ribosome to reengage with the circular polyribonucleotide prior to initiation of translation. Generally, termination elements include an in-frame nucleotide triplet that signals termination of translation, e.g., UAA, UGA, UAG. In some embodiments, one or more termination elements in the circular polyribonucleotide are frame-shifted termination elements, such as but not limited to, off-frame or −1 and +1 shifted reading frames (e.g., hidden stop) that may terminate translation. Frame-shifted termination elements include nucleotide triples, TAA, TAG, and TGA that appear in the second and third reading frames of an expression sequence. Frame-shifted termination elements may be important in preventing misreads of mRNA, which is often detrimental to the cell. In some embodiments, the termination element is a stop codon.

Further examples of termination elements are described in paragraphs-of International Patent Publication No. WO2019/118919, which is hereby incorporated by reference in its entirety.

Untranslated Regions

In some embodiments, a circular polyribonucleotide includes untranslated regions (UTRs). UTRs of a genomic region including a gene may be transcribed but not translated. In some embodiments, a UTR may be included upstream of the translation initiation sequence of an expression sequence described herein. In some embodiments, a UTR may be included downstream of an expression sequence described herein. In some instances, one UTR for first expression sequence is the same as or continuous with or overlapping with another UTR for a second expression sequence. In some embodiments, the intron is a human intron. In some embodiments, the intron is a full-length human intron, e.g., ZKSCAN1.

Exemplary untranslated regions are described in paragraphs-of International Patent Publication No. WO2019/118919, which is hereby incorporated by reference in its entirety.

In some embodiments, a circular polyribonucleotide includes a poly-A sequence. Exemplary poly-A sequences are described in paragraphs-of International Patent Publication No. WO2019/118919, which is hereby incorporated by reference in its entirety. In some embodiments, a circular polyribonucleotide lacks a poly-A sequence.

In some embodiments, a circular polyribonucleotide includes a UTR with one or more stretches of Adenosines and Uridines embedded within. These AU rich signatures may increase turnover rates of the expression product.

Introduction, removal, or modification of UTR AU rich elements (AREs) may be useful to modulate the stability, or immunogenicity (e.g., the level of one or more marker of an immune or inflammatory response) of the circular polyribonucleotide. When engineering specific circular polyribonucleotides, one or more copies of an ARE may be introduced to the circular polyribonucleotide and the copies of an ARE may modulate translation and/or production of an expression product. Likewise, AREs may be identified and removed or engineered into the circular polyribonucleotide to modulate the intracellular stability and thus affect translation and production of the resultant protein.

It should be understood that any UTR from any gene may be incorporated into the respective flanking regions of the circular polyribonucleotide.

In some embodiments, a circular polyribonucleotide lacks a 5'-UTR and is competent for protein expression from its one or more expression sequences. In some embodiments, the circular polyribonucleotide lacks a 3'-UTR and is competent for protein expression from its one or more expression sequences. In some embodiments, the circular polyribonucleotide lacks a poly-A sequence and is competent for protein expression from its one or more expression sequences. In some embodiments, the circular polyribonucleotide lacks a termination element and is competent for protein expression from its one or more expression sequences. In some embodiments, the circular polyribonucleotide lacks an internal ribosomal entry site and is competent for protein expression from its one or more expression sequences. In some embodiments, the circular polyribonucleotide lacks a cap and is competent for protein expression from its one or more expression sequences. In some embodiments, the circular polyribonucleotide lacks a 5'-UTR, a 3'-UTR, and an IRES, and is competent for protein expression from its one or more expression sequences. In some embodiments, the circular polyribonucleotide includes one or more of the following sequences: a sequence that encodes one or more miRNAs, a sequence that encodes one or more replication proteins, a sequence that encodes an exogenous gene, a sequence that encodes a therapeutic, a regulatory element (e.g., translation modulator, e.g., translation enhancer or suppressor), a translation initiation sequence, one or more regulatory nucleic acids that targets endogenous genes (e.g., siRNA, lncRNAs, shRNA), and a sequence that encodes a therapeutic mRNA or protein.

In some embodiments, a circular polyribonucleotide lacks a 5'-UTR. In some embodiments, the circular polyribonucleotide lacks a 3'-UTR. In some embodiments, the circular polyribonucleotide lacks a poly-A sequence. In some embodiments, the circular polyribonucleotide lacks a termination element. In some embodiments, the circular polyribonucleotide lacks an internal ribosomal entry site. In some embodiments, the circular polyribonucleotide lacks degradation susceptibility by exonucleases. In some embodiments, the fact that the circular polyribonucleotide lacks degradation susceptibility can mean that the circular polyribonucleotide is not degraded by an exonuclease, or only degraded in the presence of an exonuclease to a limited extent, e.g., that is comparable to or similar to in the absence of exonuclease. In some embodiments, the circular polyribonucleotide is not degraded by exonucleases. In some embodiments, the circular polyribonucleotide has reduced degradation when exposed to exonuclease. In some embodiments, the circular polyribonucleotide lacks binding to a cap-binding protein. In some embodiments, the circular polyribonucleotide lacks a 5' cap.

Stagger Elements

In some embodiments, the circular polyribonucleotide includes at least one stagger element adjacent to an expression sequence. In some embodiments, the circular polyribonucleotide includes a stagger element adjacent to each expression sequence. In some embodiments, the stagger element is present on one or both sides of each expression sequence, leading to separation of the expression products, e.g., peptide(s) and or polypeptide(s). In some embodiments, the stagger element is a portion of the one or more expression sequences. In some embodiments, the circular polyribonucleotide comprises one or more expression sequences, and each of the one or more expression sequences is separated from a succeeding expression sequence by a stagger element on the circular polyribonucleotide. In some embodiments, the stagger element prevents generation of a single polypeptide (a) from two rounds of translation of a single expression sequence or (b) from one or more rounds of translation of two or more expression sequences. In some embodiments, the stagger element is a sequence separate from the one or more expression sequences. In some embodiments, the stagger element comprises a portion of an expression sequence of the one or more expression sequences.

In some embodiments, the circular polyribonucleotide includes a stagger element. To avoid production of a continuous expression product, e.g., peptide or polypeptide, while maintaining rolling circle translation, a stagger element may be included to induce ribosomal pausing during translation. In some embodiments, the stagger element is at 3' end of at least one of the one or more expression sequences. The stagger element can be configured to stall a ribosome during rolling circle translation of the circular polyribonucleotide. The stagger element may include, but is not limited to a 2A-like, or CHYSEL (SEQ ID NO: 71) (cis-acting hydrolase element) sequence. In some embodiments, the stagger element encodes a sequence with a C-terminal consensus sequence that is $X_1X_2X_3EX_5NPGP$ (SEQ ID NO: 72), where $X_1$ is absent or G or H, $X_2$ is absent or D or G, $X_3$ is D or V or I or S or M, and $X_5$ is any amino acid. In some embodiments, this sequence comprises a non-conserved sequence of amino-acids with a strong alpha-helical propensity followed by the consensus sequence -D(V/I)EXNPGP (SEQ ID NO: 73), where x=any amino acid. Some nonlimiting examples of stagger elements includes GDVESNPGP SEQ ID NO: 52), GDIEENPGP (SEQ ID NO: 53), VEPNPGP (SEQ ID NO: 54), IETNPGP (SEQ ID NO: 55), GDIESNPGP (SEQ ID NO: 56), GDVELNPGP (SEQ ID NO: 57), GDIETNPGP (SEQ ID NO: 58), GDVENPGP (SEQ ID NO: 59), GDVEENPGP (SEQ ID NO: 60), GDVEQNPGP (SEQ ID NO: 61), IESNPGP (SEQ ID NO: 62), GDIELNPGP (SEQ ID NO: 63), HDIETNPGP (SEQ ID NO: 64), HDVETNPGP (SEQ ID NO: 65), HDVEMNPGP (SEQ ID NO: 66), GDMESNPGP (SEQ ID NO: 67), GDVETNPGP (SEQ ID NO: 68) GDIEQNPGP (SEQ ID NO: 69), and DSEFNPGP (SEQ ID NO: 70).

In some embodiments, the stagger element described herein cleaves an expression product, such as between G and P of the consensus sequence described herein. As one non-limiting example, the circular polyribonucleotide includes at least one stagger element to cleave the expression product. In some embodiments, the circular polyribonucleotide includes a stagger element adjacent to at least one expression sequence. In some embodiments, the circular polyribonucleotide includes a stagger element after each expression sequence. In some embodiments, the circular polyribonucleotide includes a stagger element is present on one or both sides of each expression sequence, leading to translation of individual peptide(s) and or polypeptide(s) from each expression sequence.

In some embodiments, a stagger element comprises one or more modified nucleotides or unnatural nucleotides that induce ribosomal pausing during translation. Unnatural nucleotides may include peptide nucleic acid (PNA), Morpholino and locked nucleic acid (LNA), as well as glycol nucleic acid (GNA) and threose nucleic acid (TNA). Examples such as these are distinguished from naturally occurring DNA or RNA by changes to the backbone of the molecule. Exemplary modifications can include any modification to the sugar, the nucleobase, the internucleoside linkage (e.g., to a linking phosphate/to a phosphodiester linkage/to the phosphodiester backbone), and any combination thereof that can induce ribosomal pausing during translation. Some of the exemplary modifications provided herein are described elsewhere herein.

In some embodiments, the stagger element is present in the circular polyribonucleotide in other forms. For example, in some exemplary circular polyribonucleotides, a stagger element comprises a termination element of a first expression sequence in the circular polyribonucleotide, and a nucleotide spacer sequence that separates the termination element from a first translation initiation sequence of an expression succeeding the first expression sequence. In some examples, the first stagger element of the first expression sequence is upstream of (5' to) a first translation initiation sequence of the expression succeeding the first expression sequence in the circular polyribonucleotide. In some cases, the first expression sequence and the expression sequence succeeding the first expression sequence are two separate expression sequences in the circular polyribonucleotide. The distance between the first stagger element and the first translation initiation sequence can enable continuous translation of the first expression sequence and its succeeding expression sequence.

In some embodiments, the first stagger element comprises a termination element and separates an expression product of the first expression sequence from an expression product of its succeeding expression sequences, thereby creating discrete expression products. In some cases, the circular polyribonucleotide comprising the first stagger element upstream of the first translation initiation sequence of the succeeding sequence in the circular polyribonucleotide is continuously translated, while a corresponding circular polyribonucleotide comprising a stagger element of a second expression sequence that is upstream of a second translation initiation sequence of an expression sequence succeeding the second expression sequence is not continuously translated. In some cases, there is only one expression sequence in the circular polyribonucleotide, and the first expression sequence and its succeeding expression sequence are the same expression sequence. In some exemplary circular polyribonucleotides, a stagger element comprises a first termination element of a first expression sequence in the circular polyribonucleotide, and a nucleotide spacer sequence that separates the termination element from a downstream translation initiation sequence. In some such examples, the first stagger element is upstream of (5' to) a first translation initiation sequence of the first expression sequence in the circular polyribonucleotide. In some cases, the distance between the first stagger element and the first translation initiation sequence enables continuous translation of the first expression sequence and any succeeding expression sequences.

In some embodiments, the first stagger element separates one round expression product of the first expression sequence from the next round expression product of the first expression sequences, thereby creating discrete expression products. In some cases, the circular polyribonucleotide comprising the first stagger element upstream of the first translation initiation sequence of the first expression sequence in the circular polyribonucleotide is continuously translated, while a corresponding circular polyribonucleotide comprising a stagger element upstream of a second translation initiation sequence of a second expression sequence in the corresponding circular polyribonucleotide is not continuously translated. In some cases, the distance between the second stagger element and the second translation initiation sequence is at least 2×, 3×, 4×, 5×, 6×, 7×, 8×, 9×, or 10× greater in the corresponding circular polyribonucleotide than a distance between the first stagger element and the first translation initiation in the circular polyribonucleotide. In some cases, the distance between the first stagger element and the first translation initiation is at least 2 nt, 3 nt, 4 nt, 5 nt, 6 nt, 7 nt, 8 nt, 9 nt, 10 nt, 11 nt, 12 nt, 13 nt, 14 nt, 15 nt, 16 nt, 17 nt, 18 nt, 19 nt, 20 nt, 25 nt, 30 nt, 35 nt, 40 nt, 45 nt, 50 nt, 55 nt, 60 nt, 65 nt, 70 nt, 75 nt, or greater. In some embodiments, the distance between the second stagger element and the second translation initiation is at least 2 nt, 3 nt, 4 nt, 5 nt, 6 nt, 7 nt, 8 nt, 9 nt, 10 nt, 11 nt, 12 nt, 13 nt, 14 nt, 15 nt, 16 nt, 17 nt, 18 nt, 19 nt, 20 nt, 25 nt, 30 nt, 35 nt, 40 nt, 45 nt, 50 nt, 55 nt, 60 nt, 65 nt, 70 nt, 75 nt, or greater than the distance between the first stagger element and the first translation initiation. In some embodiments, the circular polyribonucleotide comprises more than one expression sequence.

Examples of stagger elements are described in paragraphs of International Patent Publication No. WO2019/118919, which is hereby incorporated by reference in its entirety.

Non-Coding Sequences

In some embodiments, the polyribonucleotide described herein (e.g., the polyribonucleotide cargo of the polyribonucleotide) includes one or more non-coding sequence, e.g., a sequence that does not encode the expression of polypeptide. In some embodiments, the polyribonucleotide includes two, three, four, five, six, seven, eight, nine, ten or more than ten non-coding sequences. In some embodiments, the polyribonucleotide does not encode a polypeptide expression sequence.

Noncoding sequences can be natural or synthetic sequences. In some embodiments, a noncoding sequence can alter cellular behavior, such as e.g., lymphocyte behavior. In some embodiments, the noncoding sequences are antisense to cellular RNA sequences.

In some embodiments, the polyribonucleotide includes regulatory nucleic acids that are RNA or RNA-like structures typically from about 5-500 base pairs (bp) (depending on the specific RNA structure (e.g., miRNA 5-30 bp, lncRNA 200-500 bp) and may have a nucleobase sequence identical (complementary) or nearly identical (substantially complementary) to a coding sequence in an expressed target gene within the cell. In embodiments, the circular polyribonucleotide includes regulatory nucleic acids that encode an RNA precursor that can be processed to a smaller RNA, e.g., a miRNA precursor, which can be from about 50 to about 1000 bp, that can be processed to a smaller miRNA intermediate or a mature miRNA.

Long non-coding RNAs (lncRNA) are defined as non-protein coding transcripts longer than 100 nucleotides. Many lncRNAs are characterized as tissue specific. Divergent lncRNAs that are transcribed in the opposite direction to nearby protein-coding genes include a significant proportion (e.g., about 20% of total lncRNAs in mammalian genomes) and possibly regulate the transcription of the nearby gene. In one embodiment, the polyribonucleotide provided herein includes a sense strand of a lncRNA. In one embodiment, the polyribonucleotide provided herein includes an antisense strand of a lncRNA.

In embodiments, the polyribonucleotide encodes a regulatory nucleic acid that is substantially complementary, or fully complementary, to all or to at least one fragment of an endogenous gene or gene product (e.g., mRNA). In embodiments, the regulatory nucleic acids complement sequences at the boundary between introns and exons, in between exons, or adjacent to an exon, to prevent the maturation of newly generated nuclear RNA transcripts of specific genes into mRNA for transcription. The regulatory nucleic acids that are complementary to specific genes can hybridize with the mRNA for that gene and prevent its translation. The antisense regulatory nucleic acid can be DNA, RNA, or a derivative or hybrid thereof. In some embodiments, the regulatory nucleic acid includes a protein-binding site that can bind to a protein that participates in regulation of expression of an endogenous gene or an exogenous gene.

In embodiments, the polyribonucleotide encodes a regulatory RNA that hybridizes to a transcript of interest wherein the regulatory RNA has a length of from about 5 to 30 nucleotides, from about 10 to 30 nucleotides, or about 11, 12, 13, 14, 15, 16, 17, 18, 19, 20, 21, 22, 23, 24, 25, 26, 27, 28, 29, 30 or more than 30 nucleotides. In embodiments, the degree of sequence identity of the regulatory RNA to the targeted transcript is at least 75%, at least 80%, at least 85%, at least 90%, or at least 95%.

In embodiments, the polyribonucleotide encodes a microRNA (miRNA) molecule identical to about 5 to about 25 contiguous nucleotides of a target gene or encodes a precursor to that miRNA. In some embodiments, the miRNA has a sequence that allows the mRNA to recognize and bind to a specific target mRNA. In embodiments, miRNA sequence commences with the dinucleotide AA, includes a GC-content of about 30-70% (about 30-60%, about 40-60%, or about 45%-55%), and does not have a high percentage identity to any nucleotide sequence other than the target in the genome of the subject (e.g., a mammal) in which it is to be introduced, for example as determined by standard BLAST search.

In some embodiments, the polyribonucleotide includes at least one miRNA (or miRNA precursor), e.g., 2, 3, 4, 5, 6, or more miRNAs or miRNA precursors. In some embodiments, the polyribonucleotide includes a sequence that encodes a miRNA (or its precursor) having at least about 75%, 80%, 85%, 90% 95%, 96%, 97%, 98%, or 99% or 100% nucleotide sequence complementarity to a target sequence.

siRNAs and shRNAs resemble intermediates in the processing pathway of the endogenous microRNA (miRNA) genes. In some embodiments, siRNAs can function as miRNAs and vice versa. MicroRNAs, like siRNAs, use RISC to downregulate target genes, but unlike siRNAs, most animal miRNAs do not cleave the mRNA. Instead, miRNAs reduce protein output through translational suppression or polyA removal and mRNA degradation. Known miRNA binding sites are within mRNA 3' UTRs; miRNAs seem to target sites with near-perfect complementarity to nucleotides 2-8 from the miRNA's 5' end. This region is known as the seed region. Because mature siRNAs and miRNAs are interchangeable, exogenous siRNAs downregulate mRNAs with seed complementarity to the siRNA.

Lists of known miRNA sequences can be found in databases maintained by research organizations, such as Wellcome Trust Sanger Institute, Penn Center for Bioinformatics, Memorial Sloan Kettering Cancer Center, and European Molecule Biology Laboratory, among others. Known effective siRNA sequences and cognate binding sites are also well represented in the relevant literature. RNAi molecules are readily designed and produced by technologies known in the art. In addition, there are computational tools that increase the chance of finding effective and specific sequence motifs.

Protein-Binding Sequences

In some embodiments, a circular polyribonucleotide includes one or more protein binding sites that enable a protein, e.g., a ribosome, to bind to an internal site in the RNA sequence. By engineering protein binding sites, e.g., ribosome binding sites, into the circular polyribonucleotide, the circular polyribonucleotide may evade or have reduced detection by the host's immune system, have modulated degradation, or modulated translation, by masking the circular polyribonucleotide from components of the host's immune system.

In some embodiments, a circular polyribonucleotide includes at least one immunoprotein binding site, for example to evade immune responses, e.g., CTL (cytotoxic T lymphocyte) responses. In some embodiments, the immunoprotein binding site is a nucleotide sequence that binds to an immunoprotein and aids in masking the circular polyribonucleotide as exogenous. In some embodiments, the immunoprotein binding site is a nucleotide sequence that binds to an immunoprotein and aids in hiding the circular polyribonucleotide as exogenous or foreign.

Traditional mechanisms of ribosome engagement to linear RNA involve ribosome binding to the capped 5' end of an RNA. From the 5' end, the ribosome migrates to an initiation codon, whereupon the first peptide bond is formed. According to the present disclosure, internal initiation (i.e., cap-independent) of translation of the circular polyribonucleotide does not require a free end or a capped end. Rather, a ribosome binds to a non-capped internal site, whereby the ribosome begins polypeptide elongation at an initiation codon. In some embodiments, the circular polyribonucleotide includes one or more RNA sequences including a ribosome binding site, e.g., an initiation codon.

Natural 5'UTRs bear features which play roles in for translation initiation. They harbor signatures like Kozak sequences which are commonly known to be involved in the process by which the ribosome initiates translation of many genes. Kozak sequences have the consensus CCR(A/G) CCAUGG (SEQ ID NO: 79), where R is a purine (adenine or guanine) three bases upstream of the start codon (AUG), which is followed by another 'G'. 5'UTR also have been known to form secondary structures which are involved in elongation factor binding.

In some embodiments, a circular polyribonucleotide encodes a protein binding sequence that binds to a protein. In some embodiments, the protein binding sequence targets or localizes the circular polyribonucleotide to a specific target. In some embodiments, the protein binding sequence specifically binds an arginine-rich region of a protein.

In some embodiments, the protein binding site includes, but is not limited to, a binding site to the protein such as ACIN1, AGO, APOBEC3F, APOBEC3G, ATXN2, AUH, BCCIP, CAPRIN1, CELF2, CPSF1, CPSF2, CPSF6, CPSF7, CSTF2, CSTF2T, CTCF, DDX21, DDX3, DDX3X, DDX42, DGCR8, EIF3A, EIF4A3, EIF4G2, ELAVL1, ELAVL3, FAM120A, FBL, FIP1L1, FKBP4, FMR1, FUS, FXR1, FXR2, GNL3, GTF2F1, HNRNPA1, HNRNPA2B1, HNRNPC, HNRNPK, HNRNPL, HNRNPM, HNRNPU, HNRNPUL1, IGF2BP1, IGF2BP2, IGF2BP3, ILF3, KHDRBS1, LARP7, LIN28A, LIN28B, m6A, MBNL2, METTL3, MOV10, MSI1, MSI2, NONO, NONO-, NOP58, NPM1, NUDT21, PCBP2, POLR2A, PRPF8, PTBP1, RBFOX2, RBM10, RBM22, RBM27, RBM47, RNPS1, SAFB2, SBDS, SF3A3, SF3B4, SIRT7, SLBP, SLTM, SMNDC1, SND1, SRRM4, SRSF1, SRSF3, SRSF7, SRSF9, TAF15, TARDBP, TIA1, TNRC6A, TOP3B, TRA2A, TRA2B, U2AF1, U2AF2, UNK, UPF1, WDR33, XRN2, YBX1, YTHDC1, YTHDF1, YTHDF2, YWHAG, ZC3H7B, PDK1, AKT1, and any other protein that binds RNA.

Spacer Sequences

In some embodiments, the polyribonucleotide described herein includes one or more spacer sequences. A spacer refers to any contiguous nucleotide sequence (e.g., of one or more nucleotides) that provides distance or flexibility between two adjacent polynucleotide regions. Spacers may be present in between any of the nucleic acid elements described herein. Spacers may also be present within a nucleic acid element described herein.

For example, wherein a nucleic acid includes any two or more of the following elements: (A) a 3' half of Group I catalytic intron fragment; (B) a 3' splice site; (C) a 3' exon fragment; (D) a polyribonucleotide cargo; (E) a 5' exon fragment; (F) a 5' splice site; and (G) a 5' half of Group I catalytic intron fragment; a spacer region may be present between any one or more of the elements. Any of elements (A), (B), (C), (D), (E), (F), or (G) may be separated by a spacer sequence, as described herein. For example, there may be a spacer between (A) and (B), between (B) and (C), between (C) and (D), between (D) and (E), between (E) and (F), or between (F) and (G).

In some embodiments, the polyribonucleotide further includes a first spacer region between the 5' exon fragment of (C) and the polyribonucleotide cargo of (D). The spacer may be, e.g., at least 5 (e.g., at least 10, at least 15, at least 20) ribonucleotides in length. In some embodiments, the polyribonucleotide further includes a second spacer region between the polyribonucleotide cargo of (D) and the 5' exon fragment of (E). The spacer may be, e.g., at least 5 (e.g., at least 10, at least 15, at least 20) ribonucleotides in length. In some embodiments, each spacer region is at least 5 (e.g., at least 10, at least 15, at least 20) ribonucleotides in length. Each spacer region may be, e.g., from 5 to 500 (e.g., 10, 20, 30, 40, 50, 60, 70, 80, 90, 100, 150, 200, 250, 300, 350, 400, 450, or 500) ribonucleotides in length. The first spacer region, the second spacer region, or the first spacer region and the second spacer region may include a polyA sequence. The first spacer region, the second spacer region, or the first spacer region and the second spacer region may include a polyA-C sequence. In some embodiments, the first spacer region, the second spacer region, or the first spacer region and the second spacer region includes a polyA-G sequence. In some embodiments, the first spacer region, the second spacer region, or the first spacer region and the second spacer region includes a polyA-T sequence. In some embodiments, the first spacer region, the second spacer region, or the first spacer region and the second spacer region includes a random sequence.

Spacers may also be present within a nucleic acid region described herein. For example, a polynucleotide cargo region may include one or multiple spacers. Spacers may separate regions within the polynucleotide cargo.

In some embodiments, the spacer sequence can be, for example, at least 10 nucleotides in length, at least 15 nucleotides in length, or at least 30 nucleotides in length. In some embodiments, the spacer sequence is at least 7, 8, 9, 10, 11, 12, 13, 14, 15, 16, 17, 18, 19, 20, 25 or 30 nucleotides in length. In some embodiments, the spacer sequence is no more than 100, 90, 80, 70, 60, 50, 45, 40, 35 or 30 nucleotides in length. In some embodiments the spacer sequence is from 20 to 50 nucleotides in length. In certain embodiments, the spacer sequence is 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleotides in length.

The spacer sequences can be polyA sequences, polyA-C sequences, polyC sequences, or poly-U sequences.

In some embodiments, the spacer sequences can be polyA-T, polyA-C, polyA-G, or a random sequence.

A spacer sequences may be used to separate an IRES from adjacent structural elements to martini the structure and function of the IRES or the adjacent element. A spacer can be specifically engineered depending on the IRES. In some embodiments, an RNA folding computer software, such as RNAFold, can be utilized to guide designs of the various elements of the vector, including the spacers.

In some embodiments, the polyribonucleotide includes a 5' spacer sequence (e.g., between the 5' annealing region and the polyribonucleotide cargo). In some embodiments, the 5' spacer sequence is at least 10 nucleotides in length. In another embodiment, the 5' spacer sequence is at least 15 nucleotides in length. In a further embodiment, the 5' spacer sequence is at least 30 nucleotides in length. In some embodiments, the 5' spacer sequence is at least 7, 8, 9, 10, 11, 12, 13, 14, 15, 16, 17, 18, 19, 20, 25 or 30 nucleotides in length. In some embodiments, the 5' spacer sequence is no more than 100, 90, 80, 70, 60, 50, 45, 40, 35 or 30 nucleotides in length. In some embodiments the 5' spacer sequence is between 20 and 50 nucleotides in length. In certain embodiments, the 5' spacer sequence is 10, 11, 12, 13, 14, 15, 16, 17, 18, 19, 20, 21, 22, 23, 24, 25, 26, 27, 28, 29, 30, 31, 32, 33, 34, 35, 36 37, 38, 39, 40, 41, 42, 43, 44, 45, 46, 47, 48, 49 or 50 nucleotides in length. In one embodiment, the 5' spacer sequence is a polyA sequence. In another embodiment, the 5' spacer sequence is a polyA-C sequence. In some embodiments, the 5' spacer sequence includes a polyA-G sequence. In some embodiments, the 5' spacer sequence includes a polyA-T sequence. In some embodiments, the 5' spacer sequence includes a random sequence.

In some embodiments, the polyribonucleotide includes a 3' spacer sequence (e.g., between the 3' annealing region and the polyribonucleotide cargo). In some embodiments, the 3' spacer sequence is at least 10 nucleotides in length. In another embodiment, the 3' spacer sequence is at least 15 nucleotides in length. In a further embodiment, the 3' spacer sequence is at least 30 nucleotides in length. In some embodiments, the 3' spacer sequence is at least 7, 8, 9, 10, 11, 12, 13, 14, 15, 16, 17, 18, 19, 20, 25 or 30 nucleotides in length. In some embodiments, the 3' spacer sequence is no more than 100, 90, 80, 70, 60, 50, 45, 40, 35 or 30 nucleotides in length. In some embodiments the 3' spacer sequence is from 20 to 50 nucleotides in length. In certain embodiments, the 3' spacer sequence is 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleotides in length. In one embodiment, the 3' spacer sequence is a polyA sequence. In another embodiment, the 5' spacer sequence is a polyA-C sequence. In some embodiments, the 5' spacer sequence includes a polyA-G sequence. In some embodiments, the 5' spacer sequence includes a polyA-T sequence. In some embodiments, the 5' spacer sequence includes a random sequence.

In one embodiment, the polyribonucleotide includes a 5' spacer sequence, but not a 3' spacer sequence. In another embodiment, the polyribonucleotide includes a 3' spacer sequence, but not a 5' spacer sequence. In another embodiment, the polyribonucleotide includes neither a 5' spacer sequence, nor a 3' spacer sequence. In another embodiment, the polyribonucleotide does not include an IRES sequence. In a further embodiment, the polyribonucleotide does not include an IRES sequence, a 5' spacer sequence or a 3' spacer sequence.

In some embodiments, the spacer sequence includes at least 3 ribonucleotides, at least 4 ribonucleotides, at least 5 ribonucleotides, at least about 8 ribonucleotides, at least about 10 ribonucleotides, at least about 12 ribonucleotides, at least about 15 ribonucleotides, at least about 20 ribonucleotides, at least about 25 ribonucleotides, at least about 30 ribonucleotides, at least about 40 ribonucleotides, at least about 50 ribonucleotides, at least about 60 ribonucleotides, at least about 70 ribonucleotides, at least about 80 ribonucleotides, at least about 90 ribonucleotides, at least about 100 ribonucleotides, at least about 120 ribonucleotides, at least about 150 ribonucleotides, at least about 200 ribonucleotides, at least about 250 ribonucleotides, at least about 300 ribonucleotides, at least about 400 ribonucleotides, at least about 500 ribonucleotides, at least about 600 ribonucleotides, at least about 700 ribonucleotides, at least about 800 ribonucleotides, at least about 900 ribonucleotides, or at least about 100 ribonucleotides.

Methods of Production

Methods of Production in a Cell-Free System

The disclosure also provides methods of producing a circular RNA. For example, a deoxyribonucleotide template may be transcribed in a cell-free system (e.g., by in vitro transcription) to a produce a linear RNA. The linear polyribonucleotide produces a splicing-compatible polyribonucleotide, which may be self-spliced to produce a circular polyribonucleotide.

In some embodiments, the disclosure provides a method of producing a circular polyribonucleotide (e.g., in a cell-free system) by providing a linear polyribonucleotide; and self-splicing linear polyribonucleotide under conditions suitable for splicing of the 3' and 5' splice sites of the linear polyribonucleotide; thereby producing a circular polyribonucleotide.

In some embodiments, the disclosure provides a method of producing a circular polyribonucleotide by providing a deoxyribonucleotide encoding the linear polyribonucleotide; transcribing the deoxyribonucleotide in a cell-free system to produce the linear polyribonucleotide; optionally purifying the splicing-compatible linear polyribonucleotide; and self-splicing the linear polyribonucleotide under conditions suitable for splicing of the 3' and 5' splice sites of the linear polyribonucleotide, thereby producing a circular polyribonucleotide.

In some embodiments, the disclosure provides a method of producing a circular polyribonucleotide by providing a deoxyribonucleotide encoding a linear polyribonucleotide; transcribing the deoxyribonucleotide in a cell-free system to produce the linear polyribonucleotide, wherein the transcribing occurs in a solution under conditions suitable for splicing of the 3' and 5' splice sites of the linear polyribonucleotide, thereby producing a circular polyribonucleotide. In some embodiments, the linear polyribonucleotide comprises a 5' split-intron and a 3' split-intron (e.g., a self-splicing construct for producing a circular polyribonucleotide). In some embodiments, the linear polyribonucleotide comprises a 5' annealing region and a 3' annealing region.

Suitable conditions for in vitro transcriptions and or self-splicing may include any conditions (e.g., a solution or a buffer, such as an aqueous buffer or solution) that mimic physiological conditions in one or more respects. In some embodiments, suitable conditions include between 0.1-100 mM Mg2+ ions or a salt thereof (e.g., 1-100 mM, 1-50 mM, 1-20 mM, 5-50 mM, 5-20 mM, or 5-15 mM). In some embodiments, suitable conditions include between 1-1000 mM K+ ions or a salt thereof such as KCl (e.g., 1-1000 mM, 1-500 mM, 1-200 mM, 50-500 mM, 100-500 mM, or 100-300 mM). In some embodiments, suitable conditions include between 1-1000 mM Cl-ions or a salt thereof such as KCl (e.g., 1-1000 mM, 1-500 mM, 1-200 mM, 50-500 mM, 100-500 mM, or 100-300 mM). In some embodiments, suitable conditions include between 0.1-100 mM Mn2+ ions or a salt thereof such as MnCl2 (e.g., 0.1-100 mM, 0.1-50 mM, 0.1-20 mM, 0.1-10 mM, 0.1-5 mM, 0.1-2 mM, 0.5-50 mM, 0.5-20 mM, 0.5-15 mM, 0.5-5 mM, 0.5-2 mM, or 0.1-10 mM). In some embodiments, suitable conditions include dithiothreitol (DTT) (e.g., 1-1000 UM, 1-500 UM, 1-200UM, 50-500UM, 100-500UM, 100-300UM, 0.1-100 mM, 0.1-50 mM, 0.1-20 mM, 0.1-10 mM, 0.1-5 mM, 0.1-2 mM, 0.5-50 mM, 0.5-20 mM, 0.5-15 mM, 0.5-5 mM, 0.5-2 mM, or 0.1-10 mM). In some embodiments, suitable conditions include between 0.1 mM and 100 mM ribonucleoside triphosphate (NTP) (e.g., 0.1-100 mM, 0.1-50 mM, 0.1-10 mM, 1-100 mM, 1-50 mM, or 1-10 mM). In some embodiments, suitable conditions include a pH of 4 to 10 (e.g., pH of 5 to 9, pH of 6 to 9, or pH of 6.5 to 8.5). In some embodiments, suitable conditions include a temperature of 4° C. to 50° C. (e.g., 10° C. to 40° C., 15° C. to 40° C., 20° C. to 40° C., or 30° C. to 40° C.), In some embodiments the linear polyribonucleotide is produced from a deoxyribonucleic acid, e.g., a deoxyribonucleic acid described herein, such as a DNA vector, a linearized DNA vector, or a cDNA. In some embodiments, the linear polyribonucleotide is transcribed from the deoxyribonucleic acid by transcription in a cell-free system (e.g., in vitro transcription).

Methods of Production in a Cell

The disclosure also provides methods of producing a circular RNA in a cell, e.g., a prokaryotic cell or a eukaryotic cell. In some embodiments, an exogenous polyribonucleotide is provided to a cell (e.g., a linear polyribonucleotide described herein or a DNA molecule encoding for the transcription of a linear polyribonucleotide described here). The linear polyribonucleotides may be transcribed in the cell from an exogenous DNA molecule provided to the cell. The linear polyribonucleotide may be transcribed in the cell from an exogenous recombinant DNA molecule transiently provided to the cell. In some embodiments, the exogenous DNA molecule does not integrate into the cell's genome. In some embodiments, the linear polyribonucleotide is transcribed in the cell from a recombinant DNA molecule that is incorporated into the cell's genome.

In some embodiments, the cell is a prokaryotic cell. In some embodiments, the prokaryotic cell including the polyribonucleotides described herein may be a bacterial cell or an archaeal cell. For example, the prokaryotic cell including the polyribonucleotides described herein may be *E coli*, halophilic archaea (e.g., *Haloferax* volcaniii), *Sphingomonas*, cyanobacteria (e.g., *Synechococcus elongatus, Spirulina* (Arthrospira) spp., and *Synechocystis* spp.), *Streptomyces*, actinomycetes (e.g., Nonomuraea, Kitasatospora, or Thermobifida), *Bacillus* spp. (e.g., *Bacillus subtilis, Bacillus anthracis, Bacillus cereus*), betaproteobacteria (e.g., *Burkholderia*), alphaproteobacterial (e.g., *Agrobacterium*), *Pseudomonas* (e.g., *Pseudomonas putida*), and enterobacteria. The prokaryotic cells may be grown in a culture medium. The prokaryotic cells may be contained in a bioreactor.

In some embodiments, the cell is a eukaryotic cell. In some embodiments, the eukaryotic cell including the polyribonucleotides described herein is a unicellular eukaryotic cell. In some embodiments, the unicellular eukaryotic is a unicellular fungal cell such as a yeast cell (e.g., *Saccharomyces cerevisiae* and other *Saccharomyces* spp., Brettanomyces spp., *Schizosaccharomyces* spp., Torulaspora spp, and *Pichia* spp.). In some embodiments, the unicellular eukaryotic cell is a unicellular animal cell. A unicellular animal cell may be a cell isolated from a multicellular animal and grown in culture, or the daughter cells thereof. In some embodiments, the unicellular animal cell may be dedifferentiated. In some embodiments, the unicellular eukaryotic cell is a unicellular plant cell. A unicellular plant cell may be a cell isolated from a multicellular plant and grown in culture, or the daughter cells thereof. In some embodiments, the unicellular plant cell may be dedifferentiated. In some embodiments, the unicellular plant cell is from a plant callus. In embodiments, the unicellular cell is a plant cell protoplast. In some embodiments, the unicellular eukaryotic cell is a unicellular eukaryotic algal cell, such as a unicellular green alga, a diatom, a euglenid, or a dinoflagellate. Non-limiting examples of unicellular eukaryotic algae of interest include *Dunaliella salina, Chlorella vulgaris, Chlorella* zofingiensis, Haematococcus pluvialis, *Neochloris oleoabundans* and other *Neochloris* spp., Protosiphon botryoides, *Botryococcus braunii, Cryptococcus* spp., *Chlamydomonas reinhardtii* and other *Chlamydomonas* spp. In some embodiments, the unicellular eukaryotic cell is a protist cell. In some embodiments, the unicellular eukaryotic cell is a protozoan cell.

In some embodiments, the eukaryotic cell is a cell of a multicellular eukaryote. For example, the multicellular eukaryote may be selected from the group consisting of a vertebrate animal, an invertebrate animal, a multicellular fungus, a multicellular alga, and a multicellular plant. In some embodiments, the eukaryotic organism is a human. In some embodiments, the eukaryotic organism is a non-human vertebrate animal. In some embodiments, the eukaryotic organism is an invertebrate animal. In some embodiments, the eukaryotic organism is a multicellular fungus. In some embodiments, the eukaryotic organism is a multicellular plant. In embodiments, the eukaryotic cell is a cell of a human or a cell of a non-human mammal such as a non-human primate (e.g., monkeys, apes), ungulate (e.g., bovids including cattle, buffalo, bison, sheep, goat, and musk ox; pig; camelids including camel, llama, and alpaca; deer, antelope; and equids including horse and donkey), carnivore (e.g., dog, cat), rodent (e.g., rat, mouse, guinea pig, hamster, squirrel), or lagomorph (e.g., rabbit, hare). In embodiments, the eukaryotic cell is a cell of a bird, such as a member of the avian taxa Galliformes (e.g., chickens, turkeys, pheasants, quail), Anseriformes (e.g., ducks, geese), Paleaognathae (e.g., ostriches, emus), Columbiformes (e.g., pigeons, doves), or Psittaciformes (e.g., parrots). In embodiments, the eukaryotic cell is a cell of an arthropod (e.g., insects, arachnids, crustaceans), a nematode, an annelid, a helminth, or a mollusc. In embodiments, the eukaryotic cell is a cell of a multicellular plant, such as an angiosperm plant (which can be a dicot or a monocot) or a gymnosperm plant (e.g., a conifer, a cycad, a gnetophyte, a Ginkgo), a fern, horsetail, clubmoss, or a bryophyte. In embodiments, the eukaryotic cell is a cell of a eukaryotic multicellular alga.

The eukaryotic cells may be grown in a culture medium. The eukaryotic cells may be contained in a bioreactor.

Methods of Purification

One or more purification steps may be included in the methods described herein. For example, in some embodiments, the linear polyribonucleotide is substantively enriched or pure (e.g., purified) prior to self-splicing the linear polyribonucleotide. In other embodiments, the linear polyribonucleotide is not purified prior to self-splicing the linear polyribonucleotide. In some embodiments, the resulting circular RNA is purified.

Purification may include separating or enriching the desired reaction product from one or more undesired components, such as any unreacted stating material, byproducts, enzymes, or other reaction components. For example, purification of linear polyribonucleotide following transcription in a cell-free system (e.g., in vitro transcription) may include separation or enrichment from the DNA template prior to self-splicing the linear polyribonucleotide. Purification of the circular RNA product following splicing may be used to separate or enrich the circular RNA from its corresponding linear RNA. Methods of purification of RNA are known to those of skill in the art and include enzymatic purification or by chromatography.

In some embodiments, the methods of purification result in a circular polyribonucleotide that has less than 50% (e.g., less than 40%, 30%, 20%, 10%, 5%, 4%, 3%, 2%, or 1%) linear polyribonucleotides.

Bioreactors

In some embodiments, any method of producing a circular polyribonucleotide described herein may be performed in a bioreactor. A bioreactor refers to any vessel in which a chemical or biological process is carried out which involves organisms or biochemically active substances derived from such organisms. Bioreactors may be compatible with the cell-free methods for production of circular RNA described herein. A vessel for a bioreactor may include a culture flask, a dish, or a bag that may be single use (disposable), autoclavable, or sterilizable. A bioreactor may be made of glass, or it may be polymer-based, or it may be made of other materials.

Examples of bioreactors include, without limitation, stirred tank (e.g., well mixed) bioreactors and tubular (e.g., plug flow) bioreactors, airlift bioreactors, membrane stirred tanks, spin filter stirred tanks, vibromixers, fluidized bed reactors, and membrane bioreactors. The mode of operating the bioreactor may be a batch or continuous processes. A bioreactor is continuous when the reagent and product streams are continuously being fed and withdrawn from the system. A batch bioreactor may have a continuous recirculating flow, but no continuous feeding of reagents or product harvest.

Some methods of the present disclosure are directed to large-scale production of circular polyribonucleotides. For large-scale production methods, the method may be performed in a volume of 1 liter (L) to 50 L, or more (e.g., 5 L, 10 L, 15 L, 20 L, 25 L, 30 L, 35 L, 40 L, 45 L, 50 L, or more). In some embodiments, the method may be performed in a volume of 5 L to 10 L, 5 L to 15 L, 5 L to 20 L, 5 L to 25 L, 5 L to 30 L, 5 L to 35 L, 5 L to 40 L, 5 L to 45 L, 10 L to 15 L, 10 L to 20 L, 10 L to 25 L, 20 L to 30 L, 10 L to 35 L, 10 L to 40 L, 10 L to 45 L, 10 L to 50 L, 15 L to 20 L, 15 L to 25 L, 15 L to 30 L, 15 L to 35 L, 15 L to 40 L, 15 L to 45 L, or 15 to 50 L.

In some embodiments, a bioreactor may produce at least 1 g of circular RNA. In some embodiments, a bioreactor may produce 1-200 g of circular RNA (e.g., 1-10 g, 1-20 g, 1-50 g, 10-50 g, 10-100 g, 50-100 g, of 50-200 g of circular RNA). In some embodiments, the amount produced is measured per liter (e.g., 1-200 g per liter), per batch or reaction (e.g., 1-200 g per batch or reaction), or per unit time (e.g., 1-200 g per hour or per day).

In some embodiments, more than one bioreactor may be utilized in series to increase the production capacity (e.g., one, two, three, four, five, six, seven, eight, or nine bioreactors may be used in series).

Methods of Use

In some embodiments, circular polyribonucleotides made as described herein are used as effectors in therapy or agriculture.

For example, a circular polyribonucleotide made by the methods described herein may be administered to a subject (e.g., in a pharmaceutical, veterinary, or agricultural composition). In some embodiments, the subject is a vertebrate animal (e.g., mammal, bird, fish, reptile, or amphibian). In some embodiments, the subject is a human. In some embodiments, the subject is a non-human mammal. In embodiments, the subject is a non-human mammal is such as a non-human primate (e.g., monkeys, apes), ungulate (e.g., cattle, buffalo, sheep, goat, pig, camel, llama, alpaca, deer, horses, donkeys), carnivore (e.g., dog, cat), rodent (e.g., rat, mouse), or lagomorph (e.g., rabbit). In embodiments, the subject is a bird, such as a member of the avian taxa Galliformes (e.g., chickens, turkeys, pheasants, quail), Anseriformes (e.g., ducks, geese), Paleaognathae (e.g., ostriches, emus), Columbiformes (e.g., pigeons, doves), or Psittaciformes (e.g., parrots). In embodiments, the subject is an invertebrate such as an arthropod (e.g., insects, arachnids, crustaceans), a nematode, an annelid, a helminth, or a mollusk. In embodiments, the subject is an invertebrate agricultural pest or an invertebrate that is parasitic on an invertebrate or vertebrate host. In embodiments, the subject is a plant, such as an angiosperm plant (which can be a dicot or a monocot) or a gymnosperm plant (e.g., a conifer, a cycad, a gnetophyte, a Ginkgo), a fern, horsetail, clubmoss, or a bryophyte. In embodiments, the subject is a eukaryotic alga (unicellular or multicellular). In embodiments, the subject is a plant of agricultural or horticultural importance, such as row crop plants, fruit-producing plants and trees, vegetables, trees, and ornamental plants including ornamental flowers, shrubs, trees, groundcovers, and turf grasses.

In some embodiments, the disclosure provides a method of modifying a subject by providing to the subject a composition or formulation described herein. In some embodiments, the composition or formulation is or includes a nucleic acid molecule (e.g., a DNA molecule or an RNA molecule described herein), and the polynucleotide is provided to a eukaryotic subject. In some embodiments, the composition or formulation is or includes a eukaryotic or prokaryotic cell including a nucleic acid described herein.

In some embodiments, the disclosure provides a method of treating a condition in a subject in need thereof by providing to the subject a composition or formulation described herein. In some embodiments, the composition or formulation is or includes a nucleic acid molecule (e.g., a DNA molecule or an RNA molecule described herein), and the polynucleotide is provided to a eukaryotic subject. In some embodiments, the composition or formulation is or includes a eukaryotic or prokaryotic cell including a nucleic acid described herein.

In some embodiments, the disclosure provides a method of providing a circular polyribonucleotide to a subject by providing a eukaryotic or prokaryotic cell include a polynucleotide described herein to the subject.

Formulations

In some embodiments of the present disclosure a circular polyribonucleotide described herein may be formulated in composition, e.g., a composition for delivery to a cell, a plant, an invertebrate animal, a non-human vertebrate animal, or a human subject, e.g., an agricultural, veterinary, or pharmaceutical composition. In some embodiments, the circular polyribonucleotide is formulated in a pharmaceutical composition. In some embodiments, a composition includes a circular polyribonucleotide and a diluent, a carrier, an adjuvant, or a combination thereof. In a particular embodiment, a composition includes a circular polyribonucleotide described herein and a carrier or a diluent free of any carrier. In some embodiments, a composition including a circular polyribonucleotide with a diluent free of any carrier is used for naked delivery of the circular polyribonucleotide to a subject.

Salts

In some cases, a composition or pharmaceutical composition provided herein comprises one or more salts. For controlling the tonicity, a physiological salt such as sodium salt can be included a composition provided herein. Other salts can comprise potassium chloride, potassium dihydrogen phosphate, disodium phosphate, and/or magnesium chloride, or the like. In some cases, the composition is formulated with one or more pharmaceutically acceptable salts. The one or more pharmaceutically acceptable salts can comprise those of the inorganic ions, such as, for example, sodium, potassium, calcium, magnesium ions, and the like. Such salts can comprise salts with inorganic or organic acids, such as hydrochloric acid, hydrobromic acid, phosphoric acid, nitric acid, sulfuric acid, methanesulfonic acid, p-toluenesulfonic acid, acetic acid, fumaric acid, succinic acid, lactic acid, mandelic acid, malic acid, citric acid, tartaric acid, or maleic acid. The polyribonucleotide can be present in either linear or circular form.

Buffers/pH

A composition or pharmaceutical composition provided herein can comprise one or more buffers, such as a Tris buffer; a borate buffer; a succinate buffer; a histidine buffer (e.g., with an aluminum hydroxide adjuvant); or a citrate buffer. Buffers, in some cases, are included in the 5-20 mM range.

A composition or pharmaceutical composition provided herein can have a pH between about 5.0 and about 8.5, between about 6.0 and about 8.0, between about 6.5 and about 7.5, or between about 7.0 and about 7.8. The composition or pharmaceutical composition can have a pH of about 7. The polyribonucleotide can be present in either linear or circular form.

Detergents/Surfactants

A composition or pharmaceutical composition provided herein can comprise one or more detergents and/or surfactants, depending on the intended administration route, e.g., polyoxyethylene sorbitan esters surfactants (commonly referred to as "Tweens"), e.g., polysorbate 20 and polysorbate 80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1,2-ethanediyl) groups, e.g., octoxynol-9 (Triton X-100, or t-octylphenoxypolyethoxyethanol); (octylphenoxy) polyethoxyethanol (IGEPAL CA-630/NP-40); phospholipids such as phosphatidylcholine (lecithin); nonylphenol ethoxylates, such as the Tergitol™ NP series; polyoxyethylene fatty ethers derived from lauryl, cetyl, stearyl and oleyl alcohols (known as Brij surfactants), such as triethyleneglycol monolauryl ether (Brij 30); and sorbitan esters (commonly known as "SPANs"), such as sorbitan trioleate (Span 85) and sorbitan monolaurate, an octoxynol (such as octoxynol-9 (Triton X-100) or t-octylphenoxypolyethoxyethanol), a cetyl trimethyl ammonium bromide ("CTAB"), or sodium deoxycholate. The one or more detergents and/or surfactants can be present only at trace amounts. In some cases, the composition can include less than 1 mg/ml of each of octoxynol-10 and polysorbate 80. Non-ionic surfactants can be used herein. Surfactants can be classified by their "HLB" (hydrophile/lipophile balance). In some cases, surfactants have a HLB of at least 10, at least 15, and/or at least 16. The polyribonucleotide can be present in either linear or circular form.

Diluents

In some embodiments, a composition of the disclosure includes a circular polyribonucleotide and a diluent. In some embodiments, a composition of the disclosure includes a linear polyribonucleotide and a diluent.

A diluent can be a non-carrier excipient. A non-carrier excipient serves as a vehicle or medium for a composition, such as a circular polyribonucleotide as described herein. A non-carrier excipient serves as a vehicle or medium for a composition, such as a linear polyribonucleotide as described herein. Non-limiting examples of a non-carrier excipient include solvents, aqueous solvents, non-aqueous solvents, dispersion media, diluents, dispersions, suspension aids, surface active agents, isotonic agents, thickening agents, emulsifying agents, preservatives, polymers, peptides, proteins, cells, hyaluronidases, dispersing agents, granulating agents, disintegrating agents, binding agents, buffering agents (e.g., phosphate buffered saline (PBS)), lubricating agents, oils, and mixtures thereof. A non-carrier excipient can be any one of the inactive ingredients approved by the United States Food and Drug Administration (FDA) and listed in the Inactive Ingredient Database that does not exhibit a cell-penetrating effect. A non-carrier excipient can be any inactive ingredient suitable for administration to a non-human animal, for example, suitable for veterinary use. Modification of compositions suitable for administration to humans in order to render the compositions suitable for administration to various animals is well understood, and the ordinarily skilled veterinary pharmacologist can design and/or perform such modification with merely ordinary, if any, experimentation.

In some embodiments, the circular polyribonucleotide may be delivered as a naked delivery formulation, such as including a diluent. A naked delivery formulation delivers a circular polyribonucleotide, to a cell without the aid of a carrier and without modification or partial or complete encapsulation of the circular polyribonucleotide, capped polyribonucleotide, or complex thereof.

A naked delivery formulation is a formulation that is free from a carrier and wherein the circular polyribonucleotide is without a covalent modification that binds a moiety that aids in delivery to a cell or without partial or complete encapsulation of the circular polyribonucleotide. In some embodiments, a circular polyribonucleotide without a covalent modification that binds a moiety that aids in delivery to a cell is a polyribonucleotide that is not covalently bound to a protein, small molecule, a particle, a polymer, or a biopolymer. A circular polyribonucleotide without covalent modification that binds a moiety that aids in delivery to a cell does not contain a modified phosphate group. For example, a circular polyribonucleotide without a covalent modification that binds a moiety that aids in delivery to a cell does not contain phosphorothioate, phosphoroselenates, boranophosphates, boranophosphate esters, hydrogen phosphonates, phosphoramidates, phosphorodiamidates, alkyl or aryl phosphonates, or phosphotriesters.

In some embodiments, a naked delivery formulation is free of any or all of: transfection reagents, cationic carriers, carbohydrate carriers, nanoparticle carriers, or protein carriers. In some embodiments, a naked delivery formulation is free from phtoglycogen octenyl succinate, phytoglycogen beta-dextrin, anhydride-modified phytoglycogen beta-dextrin, lipofectamine, polyethylenimine, poly(trimethylenimine), poly(tetramethylenimine), polypropylenimine, aminoglycoside-polyamine, dideoxy-diamino-b-cyclodextrin, spermine, spermidine, poly(2-dimethylamino)ethyl methacrylate, poly(lysine), poly(histidine), poly(arginine), cationized gelatin, dendrimers, chitosan, 1,2-Dioleoyl-3-Trimethylammonium-Propane (DOTAP), N-[1-(2,3-dioleoyloxy)propyl]-N,N,N-trimethylammonium chloride (DOTMA), I-[2-(oleoyloxy)ethyl]-2-oleyl-3-(2-hydroxyethyl) imidazolinium chloride (DOTIM), 2,3-dioleyloxy-N-[2 (sperminecarboxamido)ethyl]-N,N-dimethyl-I-propanaminium trifluoroacetate (DOSPA), 3B-[N-(N↓N'-Dimethylaminoethane)-carbamoyl] Cholesterol Hydrochloride (DC-Cholesterol HCl), diheptadecylamidoglycyl spermidine (DOGS), N,N-distearyl-N,N-dimethylammonium bromide (DDAB), N-(1,2-dimyristyloxyprop-3-yl)-N,N-dimethyl-N-hydroxyethyl ammonium bromide (DMRIE), N,N-dioleyl-N,N-dimethylammonium chloride (DODAC), human serum albumin (HSA), low-density lipoprotein (LDL), high-density lipoprotein (HDL), or globulin.

In certain embodiments, a naked delivery formulation includes a non-carrier excipient. In some embodiments, a non-carrier excipient includes an inactive ingredient that does not exhibit a cell-penetrating effect. In some embodiments, a non-carrier excipient includes a buffer, for example PBS. In some embodiments, a non-carrier excipient is a solvent, a non-aqueous solvent, a diluent, a suspension aid, a surface-active agent, an isotonic agent, a thickening agent, an emulsifying agent, a preservative, a polymer, a peptide, a protein, a cell, a hyaluronidase, a dispersing agent, a granulating agent, a disintegrating agent, a binding agent, a buffering agent, a lubricating agent, or an oil.

In some embodiments, a naked delivery formulation includes a diluent. A diluent may be a liquid diluent or a solid diluent. In some embodiments, a diluent is an RNA solubilizing agent, a buffer, or an isotonic agent. Examples of an RNA solubilizing agent include water, ethanol, methanol, acetone, formamide, and 2-propanol. Examples of a buffer include 2-(N-morpholino) ethanesulfonic acid (MES), Bis-Tris, 2-[(2-amino-2-oxoethyl)-(carboxymethyl)amino]acetic acid (ADA), N-(2-Acetamido)-2-aminoethanesulfonic acid (ACES), piperazine-N,N'-bis(2-ethane-sulfonic acid) (PIPES), 2-[1,3-dihydroxy-2-(hydroxymethyl) propan-2-yllamino]ethanesulfonic acid (TES), 3-(N-morpholino) propanesulfonic acid (MOPS), 4-(2-hydroxyethyl)-1-piperazineethanesulfonic acid (HEPES), Tris, Tricine, Gly-Gly, Bicine, or phosphate. Examples of an isotonic agent include glycerin, mannitol, polyethylene glycol, propylene glycol, trehalose, or sucrose.

Carriers

In some embodiments, a composition of the disclosure includes a circular polyribonucleotide and a carrier. In some embodiments, a composition of the disclosure includes a linear polyribonucleotide and a carrier.

In certain embodiments, a composition includes a circular polyribonucleotide as described herein in a vesicle or other membrane-based carrier. In certain embodiments, a composition includes a linear polyribonucleotide as described herein in a vesicle or other membrane-based carrier.

In other embodiments, a composition includes the circular polyribonucleotide in or via a cell, vesicle or other membrane-based carrier. In other embodiments, a composition includes the linear polyribonucleotide in or via a cell, vesicle or other membrane-based carrier. In one embodiment, a composition includes the circular polyribonucleotide in liposomes or other similar vesicles. In one embodiment, a composition includes the linear polyribonucleotide in liposomes or other similar vesicles. Liposomes are spherical vesicle structures composed of a uni- or multilamellar lipid bilayer surrounding internal aqueous compartments and a relatively impermeable outer lipophilic phospholipid bilayer. Liposomes may be anionic, neutral, or cationic. Liposomes are biocompatible, nontoxic, can deliver both hydrophilic and lipophilic drug molecules, protect their cargo from degradation by plasma enzymes, and transport their load across biological membranes and the blood brain barrier (BBB) (see, e.g., Spuch and Navarro, Journal of Drug Delivery, vol. 2011, Article ID 469679, 12 pages, 2011. doi: 10.1155/2011/469679 for review).

Vesicles can be made from several different types of lipids; however, phospholipids are most commonly used to generate liposomes as drug carriers. Methods for preparation of multilamellar vesicle lipids are known in the art (see for example U.S. Pat. No. 6,693,086, the teachings of which relating to multilamellar vesicle lipid preparation are incorporated herein by reference). Although vesicle formation can be spontaneous when a lipid film is mixed with an aqueous solution, it can also be expedited by applying force in the form of shaking by using a homogenizer, sonicator, or an extrusion apparatus (see, e.g., Spuch and Navarro, Journal of Drug Delivery, vol. 2011, Article ID 469679, 12 pages, 2011. doi: 10.1155/2011/469679 for review). Extruded lipids can be prepared by extruding through filters of decreasing size, as described in Templeton et al., Nature Biotech, 15:647-652, 1997, the teachings of which relating to extruded lipid preparation are incorporated herein by reference.

In certain embodiments, a composition of the disclosure includes a circular polyribonucleotide and lipid nanoparticles, for example lipid nanoparticles described herein. In certain embodiments, a composition of the disclosure includes a linear polyribonucleotide and lipid nanoparticles. Lipid nanoparticles are another example of a carrier that provides a biocompatible and biodegradable delivery system for a circular polyribonucleotide molecule as described herein. Lipid nanoparticles are another example of a carrier that provides a biocompatible and biodegradable delivery system for a linear polyribonucleotide molecule as described herein. Nanostructured lipid carriers (NLCs) are modified solid lipid nanoparticles (SLNs) that retain the characteristics of the SLN, improve drug stability and loading capacity, and prevent drug leakage. Polymer nanoparticles (PNPs) are an important component of drug delivery. These nanoparticles can effectively direct drug delivery to specific targets and improve drug stability and controlled drug release. Lipid-polymer nanoparticles (PLNs), a new type of carrier that combines liposomes and polymers, may also be employed. These nanoparticles possess the complementary advantages of PNPs and liposomes. A PLN is composed of a core-shell structure; the polymer core provides a stable structure, and the phospholipid shell offers good biocompatibility. As such, the two components increase the drug encapsulation efficiency rate, facilitate surface modification, and prevent leakage of water-soluble drugs. For a review, see, e.g., Li et al. 2017, Nanomaterials 7, 122; doi: 10.3390/nano7060122.

Additional non-limiting examples of carriers include carbohydrate carriers (e.g., an anhydride-modified phytoglycogen or glycogen-type material), protein carriers (e.g., a protein covalently linked to the circular polyribonucleotide or a protein covalently linked to the linear polyribonucleotide), or cationic carriers (e.g., a cationic lipopolymer or transfection reagent). Non-limiting examples of carbohydrate carriers include phtoglycogen octenyl succinate, phytoglycogen beta-dextrin, and anhydride-modified phytoglycogen beta-dextrin. Non-limiting examples of cationic carriers include lipofectamine, polyethylenimine, poly(trimethylenimine), poly(tetramethylenimine), polypropylenimine, aminoglycoside-polyamine, dideoxy-diamino-b-cyclodextrin, spermine, spermidine, poly(2-dimethylamino) ethyl methacrylate, poly(lysine), poly(histidine), poly (arginine), cationized gelatin, dendrimers, chitosan, 1,2-Dioleoyl-3-Trimethylammonium-Propane (DOTAP), N-[1-(2,3-dioleoyloxy) propyl]-N,N,N-trimethylammonium chloride (DOTMA), I-[2-(oleoyloxy)ethyl]-2-oleyl-3-(2-hydroxyethyl) imidazolinium chloride (DOTIM), 2,3-dioleyloxy-N-[2 (sperminecarboxamido)ethyl]-N,N-dimethyl-I-propanaminium trifluoroacetate (DOSPA), 3B-[N-(N↓N'-Dimethylaminoethane)-carbamoyl] Cholesterol Hydrochloride (DC-Cholesterol HCl), diheptadecylamidoglycyl spermidine (DOGS), N,N-distearyl-N,N-dimethylammonium bromide (DDAB), N-(1,2-dimyristyloxyprop-3-yl)-N,N-dimethyl-N-hydroxyethyl ammonium bromide (DMRIE), and N,N-dioleyl-N,N-dimethylammonium chloride (DODAC). Non-limiting examples of protein carriers include human serum albumin (HSA), low-density lipoprotein (LDL), high-density lipoprotein (HDL), or globulin.

Exosomes can also be used as drug delivery vehicles for a circular RNA composition or preparation described herein. Exosomes can be used as drug delivery vehicles for a linear polyribonucleotide composition or preparation described herein. For a review, see Ha et al. July 2016. Acta Pharmaceutica *Sinica* B. Volume 6, Issue 4, Pages 287-296; https://doi.org/10.1016/j.apsb.2016.02.001.

Ex vivo differentiated red blood cells can also be used as a carrier for a circular RNA composition or preparation described herein. Ex vivo differentiated red blood cells can also be used as a carrier for a linear polyribonucleotide composition or preparation described herein. See, e.g., International Patent Publication Nos. WO2015/073587; WO2017/123646; WO2017/123644; WO2018/102740; WO2016/183482; WO2015/153102; WO2018/151829; WO2018/009838; Shi et al. 2014. Proc Natl Acad Sci USA. 111 (28): 10131-10136; U.S. Pat. No. 9,644,180; Huang et al. 2017. Nature Communications 8:423; Shi et al. 2014. Proc Natl Acad Sci USA. 111 (28): 10131-10136.

Fusosome compositions, e.g., as described in International Patent Publication No. WO2018/208728, can also be used as carriers to deliver a circular polyribonucleotide molecule described herein. Fusosome compositions, e.g., as described in WO2018/208728, can also be used as carriers to deliver a linear polyribonucleotide molecule described herein.

Virosomes and virus-like particles (VLPs) can also be used as carriers to deliver a circular polyribonucleotide molecule described herein to targeted cells. Virosomes and virus-like particles (VLPs) can also be used as carriers to deliver a linear polyribonucleotide molecule described herein to targeted cells.

Plant nanovesicles and plant messenger packs (PMPs), e.g., as described in International Patent Publication Nos. WO2011/097480, WO2013/070324, WO2017/004526, or WO2020/041784 can also be used as carriers to deliver the circular RNA composition or preparation described herein. Plant nanovesicles and plant messenger packs (PMPs) can also be used as carriers to deliver a linear polyribonucleotide composition or preparation described herein.

Microbubbles can also be used as carriers to deliver a circular polyribonucleotide molecule described herein.

Microbubbles can also be used as carriers to deliver a linear polyribonucleotide molecule described herein. See, e.g., U.S. Pat. No. 7,115,583; Beeri, R. et al., Circulation. 2002 Oct. 1;106 (14): 1756-1759; Bez, M. et al., Nat Protoc. 2019 April; 14 (4): 1015-1026; Hernot, S. et al., Adv Drug Deliv Rev. 2008 Jun. 30; 60 (10): 1153-1166; Rychak, J. J. et al., Adv Drug Deliv Rev. 2014 June; 72:82-93. In some embodiments, microbubbles are albumin-coated perfluorocarbon microbubbles.

The carrier including the circular polyribonucleotides described herein may include a plurality of particles. The particles may have median article size of 30 to 700 nanometers (e.g., 30 to 50, 50 to 100, 100 to 200, 200 to 300, 300 to 400, 400 to 500, 500 to 600, 600 to 700, 100 to 500, 50 to 500, or 200 to 700 nanometers). The size of the particle may be optimized to favor deposition of the payload, including the circular polyribonucleotide into a cell. Deposition of the circular polyribonucleotide into certain cell types may favor different particle sizes. For example, the particle size may be optimized for deposition of the circular polyribonucleotide into antigen presenting cells. The particle size may be optimized for deposition of the circular polyribonucleotide into dendritic cells. Additionally, the particle size may be optimized for depositions of the circular polyribonucleotide into draining lymph node cells.

Lipid Nanoparticles

The compositions, methods, and delivery systems provided by the present disclosure may employ any suitable carrier or delivery modality described herein, including, in certain embodiments, lipid nanoparticles (LNPs). Lipid nanoparticles, in some embodiments, comprise one or more ionic lipids, such as non-cationic lipids (e.g., neutral or anionic, or zwitterionic lipids); one or more conjugated lipids (such as PEG-conjugated lipids or lipids conjugated to polymers described in Table 5 of WO2019217941; incorporated herein by reference in its entirety); one or more sterols (e.g., cholesterol).

Lipids that can be used in nanoparticle formations (e.g., lipid nanoparticles) include, for example those described in Table 4 of WO2019217941, which is incorporated by reference—e.g., a lipid-containing nanoparticle can comprise one or more of the lipids in Table 4 of WO2019217941. Lipid nanoparticles can include additional elements, such as polymers, such as the polymers described in Table 5 of WO2019217941, incorporated by reference.

In some embodiments, conjugated lipids, when present, can include one or more of PEG-diacylglycerol (DAG) (such as I-(monomethoxy-polyethyleneglycol)-2,3-dimyristoylglycerol (PEG-DMG)), PEG-dialkyloxypropyl (DAA), PEG-phospholipid, PEG-ceramide (Cer), a pegylated phosphatidylethanoloamine (PEG-PE), PEG succinate diacylglycerol (PEGS-DAG) (such as 4-0-(2',3'-di(tetradecanoyloxy) propyl-I-0-(w-methoxy (polyethoxy)ethyl) butanedioate (PEG-S-DMG)), PEG dialkoxypropylcarbam, N-(carbonyl-methoxypoly ethylene glycol 2000)-1,2-distearoyl-sn-glycero-3-phosphoethanolamine sodium salt, and those described in Table 2 of WO2019051289 (incorporated by reference), and combinations of the foregoing.

In some embodiments, sterols that can be incorporated into lipid nanoparticles include one or more of cholesterol or cholesterol derivatives, such as those in WO2009/127060 or US2010/0130588, which are incorporated by reference. Additional exemplary sterols include phytosterols, including those described in Eygeris et al. (2020), dx.doi.org/10.1021/acs.nanolett.0c01386, incorporated herein by reference.

In some embodiments, the lipid particle comprises an ionizable lipid, a non-cationic lipid, a conjugated lipid that inhibits aggregation of particles, and a sterol. The amounts of these components can be varied independently and to achieve desired properties. For example, in some embodiments, the lipid nanoparticle comprises an ionizable lipid is in an amount from about 20 mol % to about 90 mol % of the total lipids (in other embodiments it may be 20-70% (mol), 30-60% (mol) or 40-50% (mol); about 50 mol % to about 90 mol % of the total lipid present in the lipid nanoparticle), a non-cationic lipid in an amount from about 5 mol % to about 30 mol % of the total lipids, a conjugated lipid in an amount from about 0.5 mol % to about 20 mol % of the total lipids, and a sterol in an amount from about 20 mol % to about 50 mol % of the total lipids. The ratio of total lipid to nucleic acid can be varied as desired. For example, the total lipid to nucleic acid (mass or weight) ratio can be from about 10:1 to about 30:1.

In some embodiments, the lipid to nucleic acid ratio (mass/mass ratio; w/w ratio) can be in the range of from about 1:1 to about 25:1, from about 10:1 to about 14:1, from about 3:1 to about 15:1, from about 4:1 to about 10:1, from about 5:1 to about 9:1, or about 6:1 to about 9:1. The amounts of lipids and nucleic acid can be adjusted to provide a desired N/P ratio, for example, N/P ratio of 3, 4, 5, 6, 7, 8, 9, 10 or higher. Generally, the lipid nanoparticle formulation's overall lipid content can range from about 5 mg/ml to about 30 mg/mL.

Some non-limiting example of lipid compounds that may be used (e.g., in combination with other lipid components) to form lipid nanoparticles for the delivery of compositions described herein, e.g., nucleic acid (e.g., RNA (e.g., circular polyribonucleotide, linear polyribonucleotide)) described herein includes,

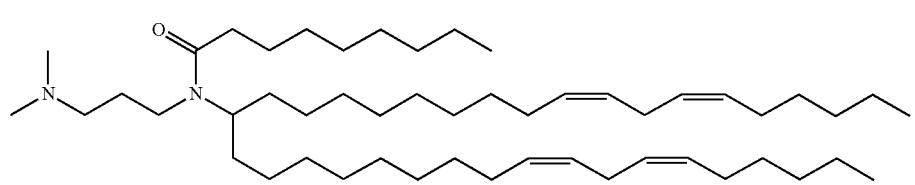

(i)

In some embodiments an LNP comprising Formula (i) is used to deliver a polyribonucleotide (e.g., a circular polyribonucleotide, a linear polyribonucleotide) composition described herein to cells.

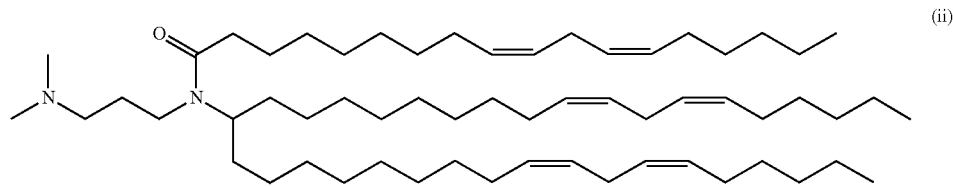 [SMILES: CCCCC/C=C\C/C=C\CCCCCCCCC(CCCCCCCC/C=C\C/C=C\CCCCC)N(CCCN(C)C)C(=O)CCCCCCC/C=C\C/C=C\CCCCC]
(ii)

In some embodiments an LNP comprising Formula (ii) is used to deliver a polyribonucleotide (e.g., a circular polyribonucleotide, a linear polyribonucleotide) composition described herein to cells.

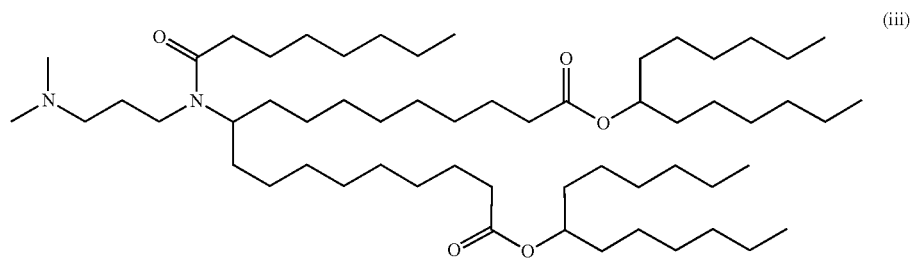 [SMILES: CCCCCCCC(=O)N(CCCN(C)C)C(CCCCCCCCC(=O)OC(CCCCCC)CCCCCC)CCCCCCCCC(=O)OC(CCCCCC)CCCCCC]
(iii)

In some embodiments an LNP comprising Formula (iii) is used to deliver a polyribonucleotide (e.g., a circular polyribonucleotide, a linear polyribonucleotide) composition described herein to cells.

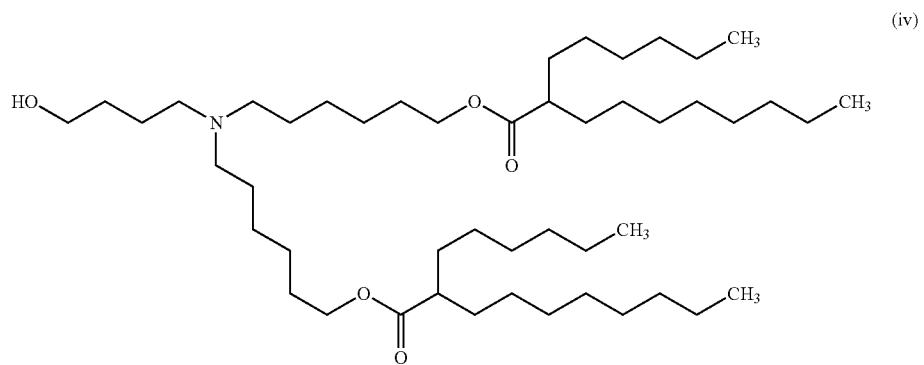 [SMILES: CCCCCCCCC(CCCCCC)C(=O)OCCCCCCN(CCCCO)CCCCCCOC(=O)C(CCCCCC)CCCCCCCC]
(iv)

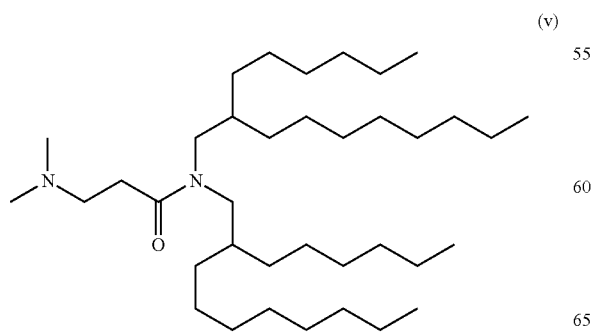
(v)

In some embodiments an LNP comprising Formula (v) is used to deliver a polyribonucleotide (e.g., a circular polyribonucleotide, a linear polyribonucleotide) composition described herein to cells.

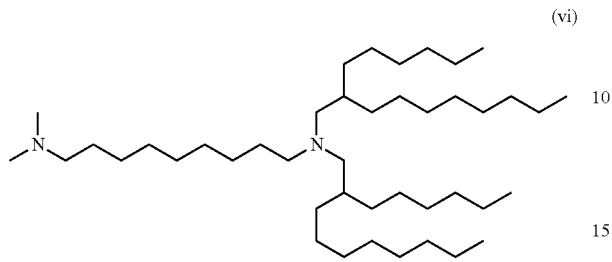

(vi)

In some embodiments an LNP comprising Formula (vi) is used to deliver a polyribonucleotide (e.g., a circular polyribonucleotide, a linear polyribonucleotide) composition described herein to cells.

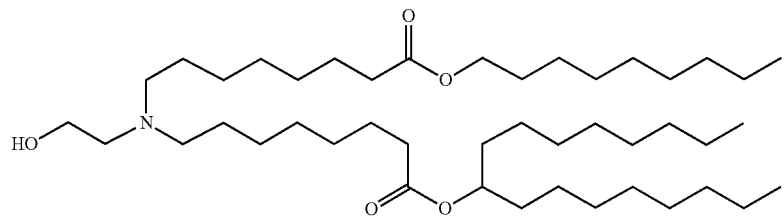

(vii)

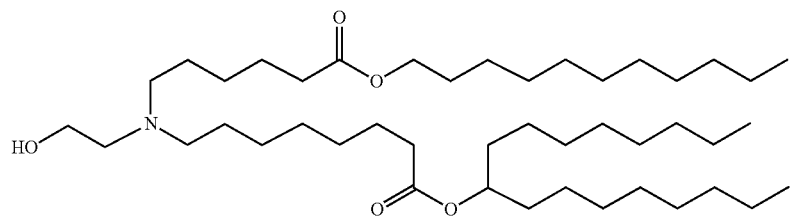

(viii)

In some embodiments an LNP comprising Formula (viii) is used to deliver a polyribonucleotide (e.g., a circular polyribonucleotide, a linear polyribonucleotide) composition described herein to cells.

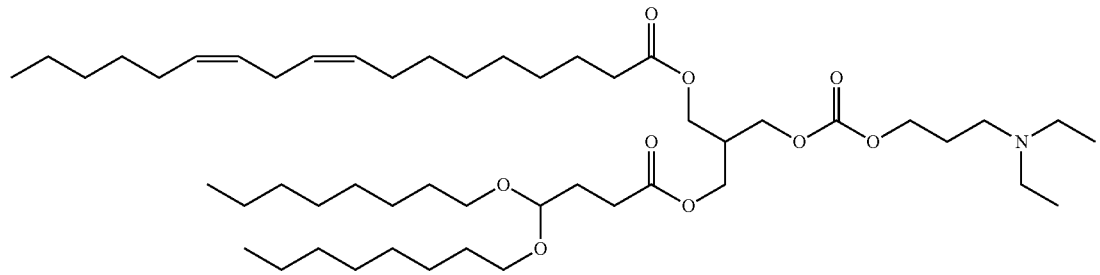

(ix)

In some embodiments an LNP comprising Formula (ix) is used to deliver a polyribonucleotide (e.g., a circular polyribonucleotide, a linear polyribonucleotide) composition described herein to cells.

(x)

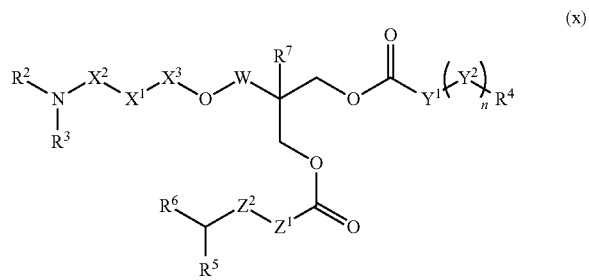

wherein
$X^1$ is O, $NR^1$, or a direct bond, $X^2$ is C2-5 alkylene, $X^3$ is C(=O) or a direct bond, $R^1$ is H or Me, $R^3$ is C1-3 alkyl, $R^2$ is C1-3 alkyl, or $R^2$ taken together with the nitrogen atom to which it is attached and 1-3 carbon atoms of $X^2$ form a 4-, 5-, or 6-membered ring, or $X^1$ is $NR^1$, $R^1$ and $R^2$ taken together with the nitrogen atoms to which they are attached form a 5- or 6-membered ring, or $R^2$ taken together with $R^3$ and the nitrogen atom to which they are attached form a 5-, 6-, or 7-membered ring, Y1 is C2-12 alkylene, Y2 is selected from

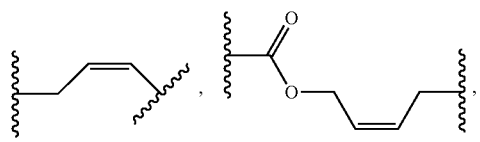

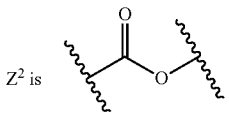 [SMILES: *OC(*)=O]

(in either orientation), (in either orientation), (in either orientation), n is 0 to 3, $R^4$ is C1-15 alkyl, $Z^1$ is C1-6 alkylene or a direct bond, $Z^2$ is 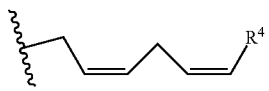

(in either orientation) or absent, provided that if $Z^1$ is a direct bond, $Z^2$ is absent;
$R^5$ is C5-9 alkyl or C6-10 alkoxy, $R^6$ is C5-9 alkyl or C6-10 alkoxy, W is methylene or a direct bond, and $R^7$ is H or Me, or a salt thereof, provided that if $R^3$ and $R^2$ are C2 alkyls, $X^1$ is O, $X^2$ is linear C3 alkylene, $X^3$ is C(=O), $Y^1$ is linear Ce alkylene, $(Y^2)$ n-$R^4$ is

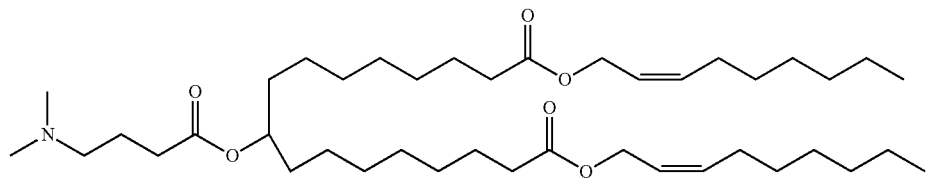

$R^4$ is linear C5 alkyl, $Z^1$ is C2 alkylene, $Z^2$ is absent, W is methylene, and $R^7$ is H, then $R^5$ and $R^6$ are not Cx alkoxy.

In some embodiments an LNP comprising Formula (xii) is used to deliver a polyribonucleotide (e.g., a circular polyribonucleotide, a linear polyribonucleotide) composition described herein to cells.

(xi)

In some embodiments an LNP comprising Formula (xi) is used to deliver a polyribonucleotide (e.g., a circular polyribonucleotide, a linear polyribonucleotide) composition described herein to cells.

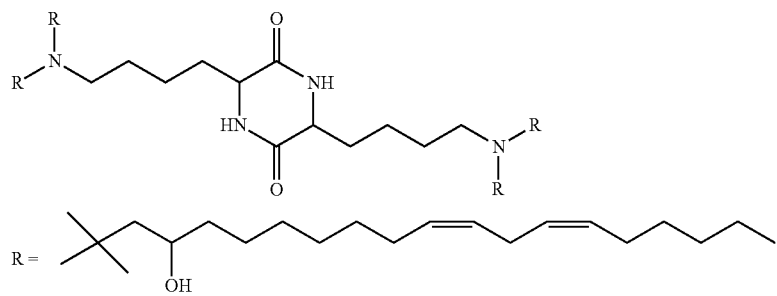

OF-O2 where R = 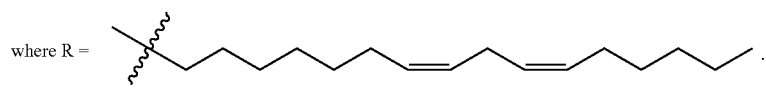
(xii)
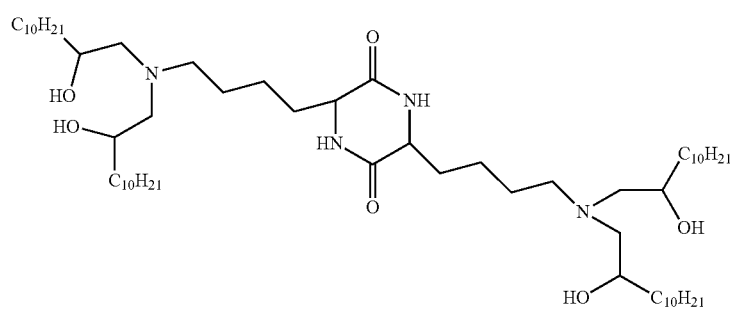
(xiii)
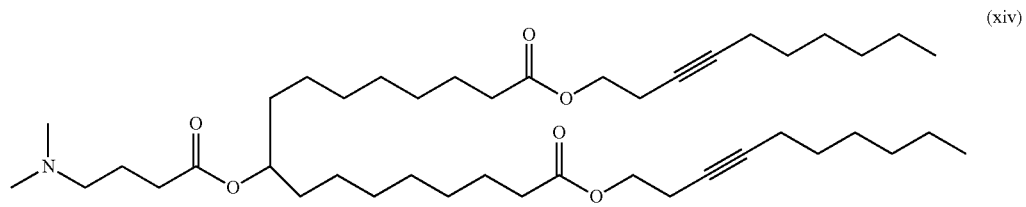
(xiv)
In some embodiments an LNP comprises a compound of Formula (xiii) and a compound of Formula (xiv).
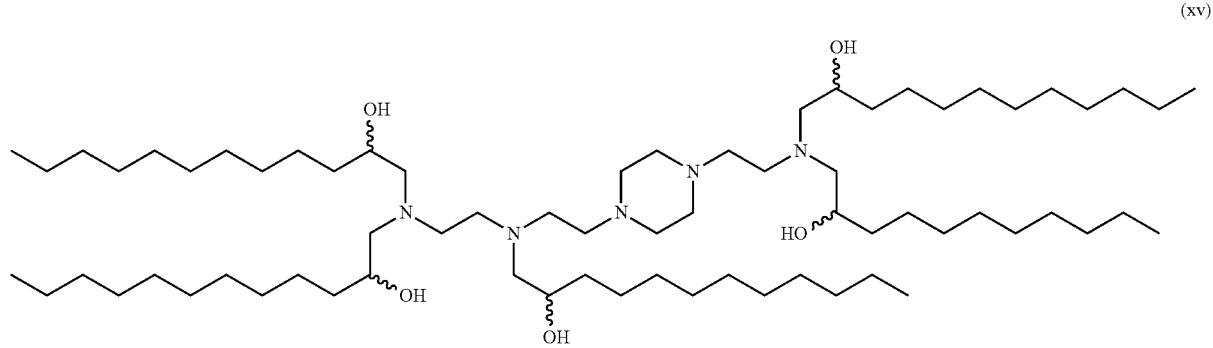 [SMILES: CCCCCCCCCCC(O)CN(CCN1CCN(CCN(CC(O)CCCCCCCCC)CC(O)CCCCCCCCCC)CC1)CCN(CC(O)CCCCCCCCCC)CC(O)CCCCCCCCCC]
(xv)
In some embodiments an LNP comprising Formula (xv) is used to deliver a polyribonucleotide (e.g., a circular polyribonucleotide, a linear polyribonucleotide) composition described herein to cells.
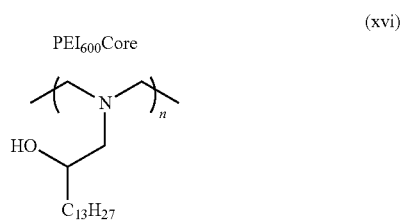
(xvi)

In some embodiments an LNP comprising a formulation of Formula (xvi) is used to deliver a polyribonucleotide (e.g., a circular polyribonucleotide, a linear polyribonucleotide) composition described herein to cells.
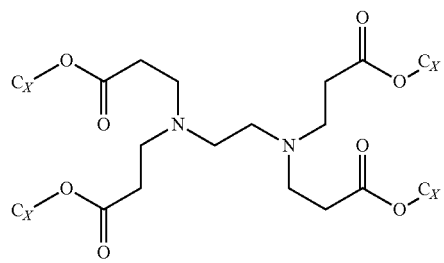
(xvii)
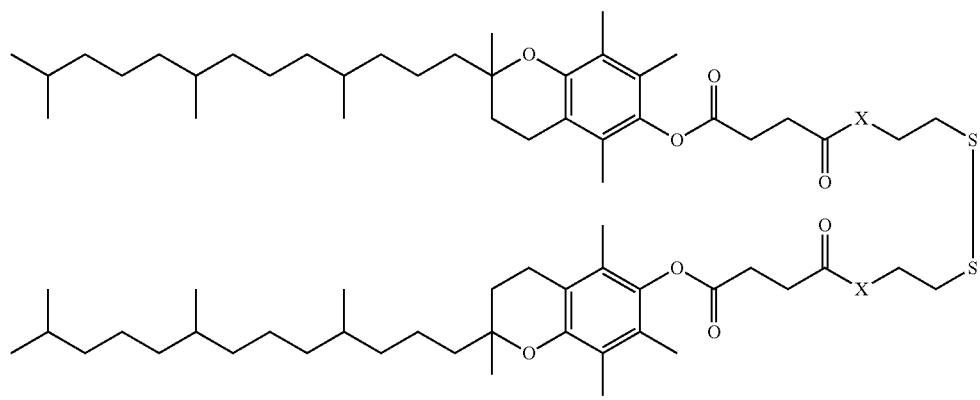
(xviii)(a)
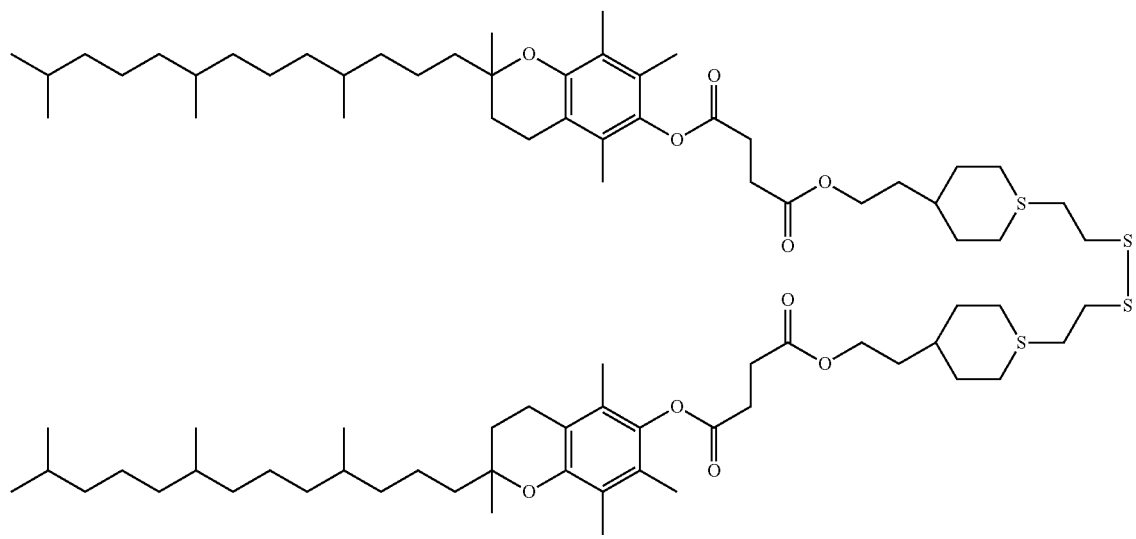
(xviii)(b)
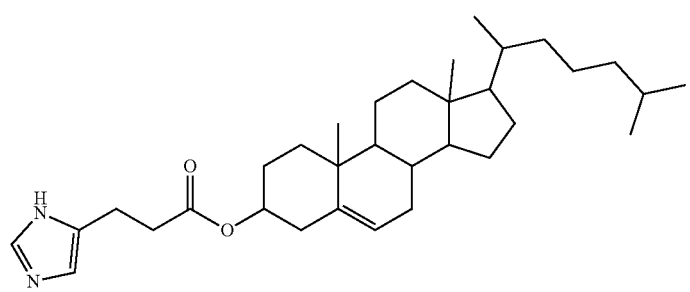
(xix)

X = amino structure where X = 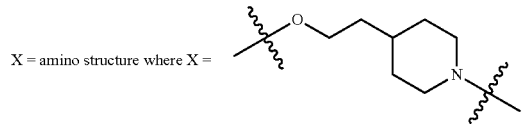

In some embodiments, a lipid compound used to form lipid nanoparticles for the delivery of compositions described herein, e.g., nucleic acid (e.g., RNA (e.g., circular polyribonucleotide, linear polyribonucleotide)) described herein is made by one of the following reactions:

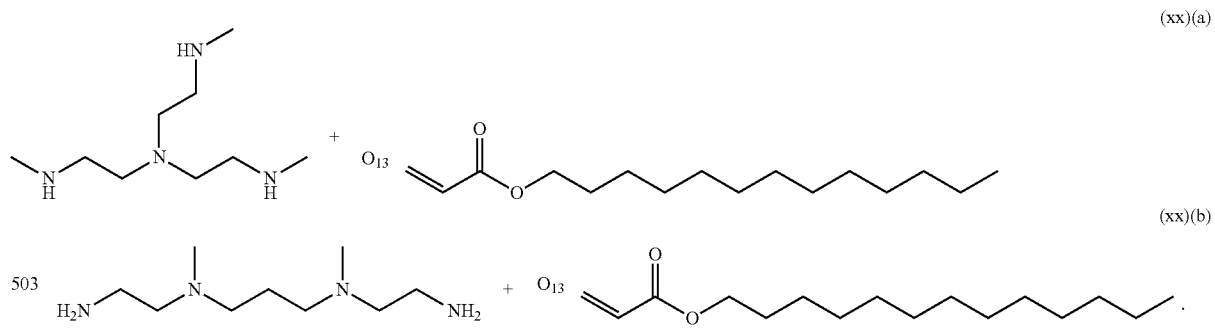

In some embodiments an LNP comprising Formula (xxi) is used to deliver a polyribonucleotide (e.g., a circular polyribonucleotide, a linear polyribonucleotide) composition described herein to cells. In some embodiments the LNP of Formula (xxi) is an LNP described by WO2021113777 (e.g., a lipid of Formula (1) such as a lipid of Table 1 of WO2021113777).

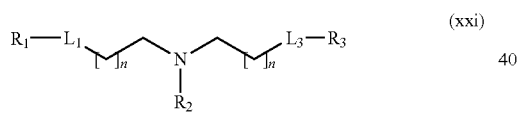

wherein each n is independently an integer from 2-15; $L_1$ and $L_3$ are each independently —OC(O)—* or —C(O)O—*, wherein "*" indicates the attachment point to $R_1$ or $R_3$;

$R_1$ and $R_5$ are each independently a linear or branched $C_9$-$C_{20}$ alkyl or $C_9$-$C_{20}$ alkenyl, optionally substituted by one or more substituents selected from a group consisting of oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl) (alkyl)aminoalkyl, heterocyclyl, heteroaryl, alkylheteroaryl, alkynyl, alkoxy, amino, dialkylamino, aminoalkylcarbonylamino, aminocarbonylalkylamino, (aminocarbonylalkyl) (alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl) (alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkyl sulfonyl, and alkyl sulfonealkyl; and $R^2$ is selected from a group consisting of:

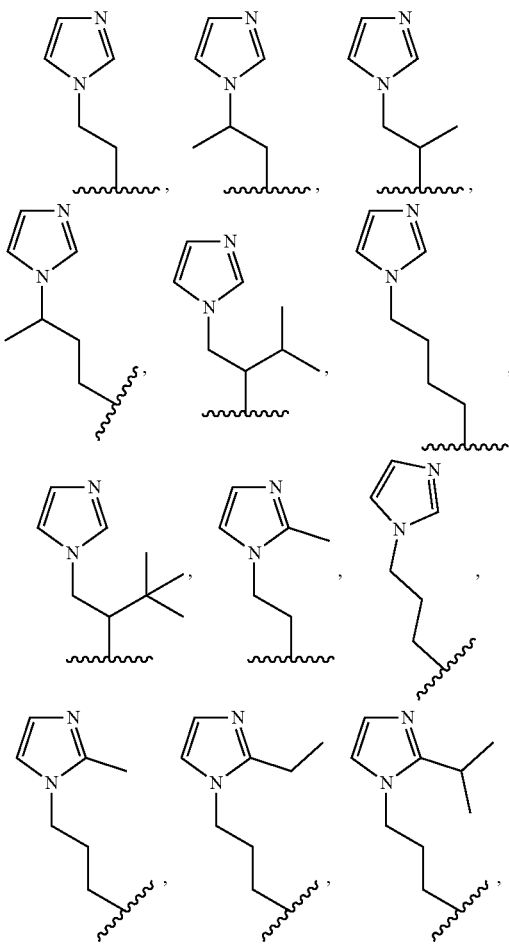

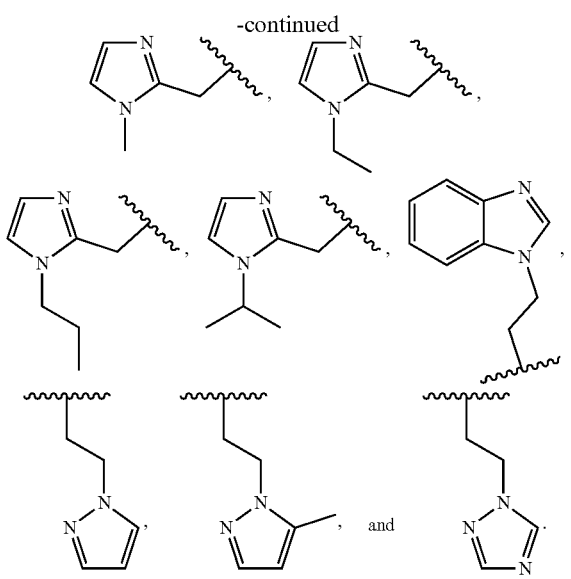

In some embodiments an LNP comprising Formula (xxii) is used to deliver a polyribonucleotide (e.g., a circular polyribonucleotide, a linear polyribonucleotide) composition described herein to cells. In some embodiments the LNP of Formula (xxii) is an LNP described by WO2021113777 (e.g., a lipid of Formula (2) such as a lipid of Table 2 of WO2021113777).

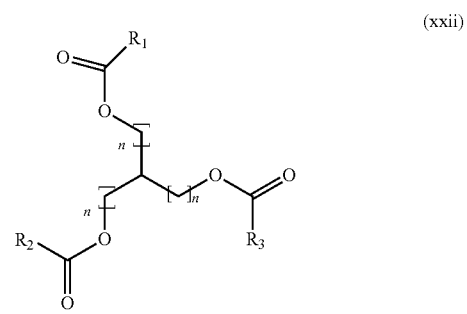

wherein
each n is independently an integer from 1-15;
$R_1$ and $R_2$ are each independently selected from a group consisting of:

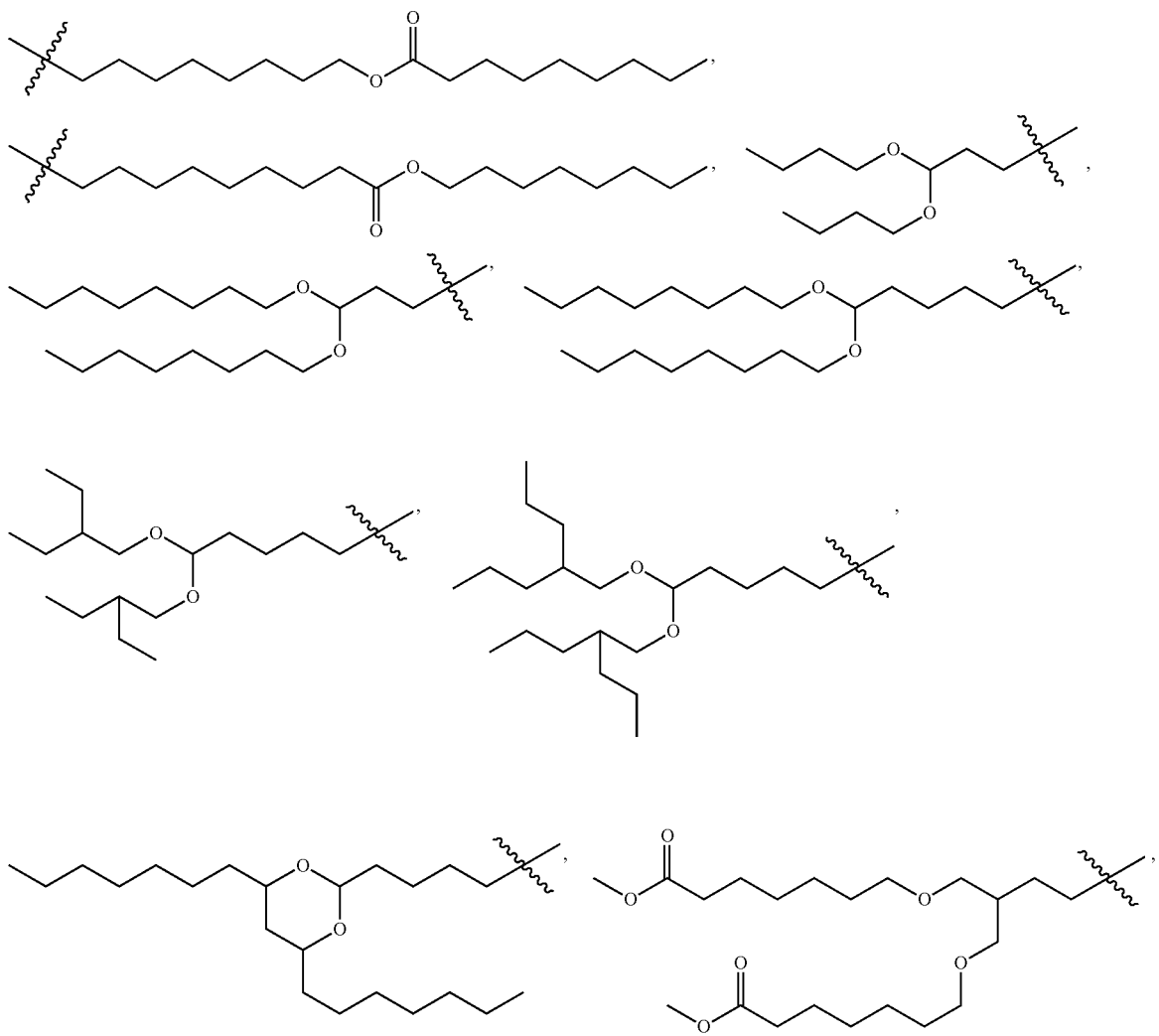

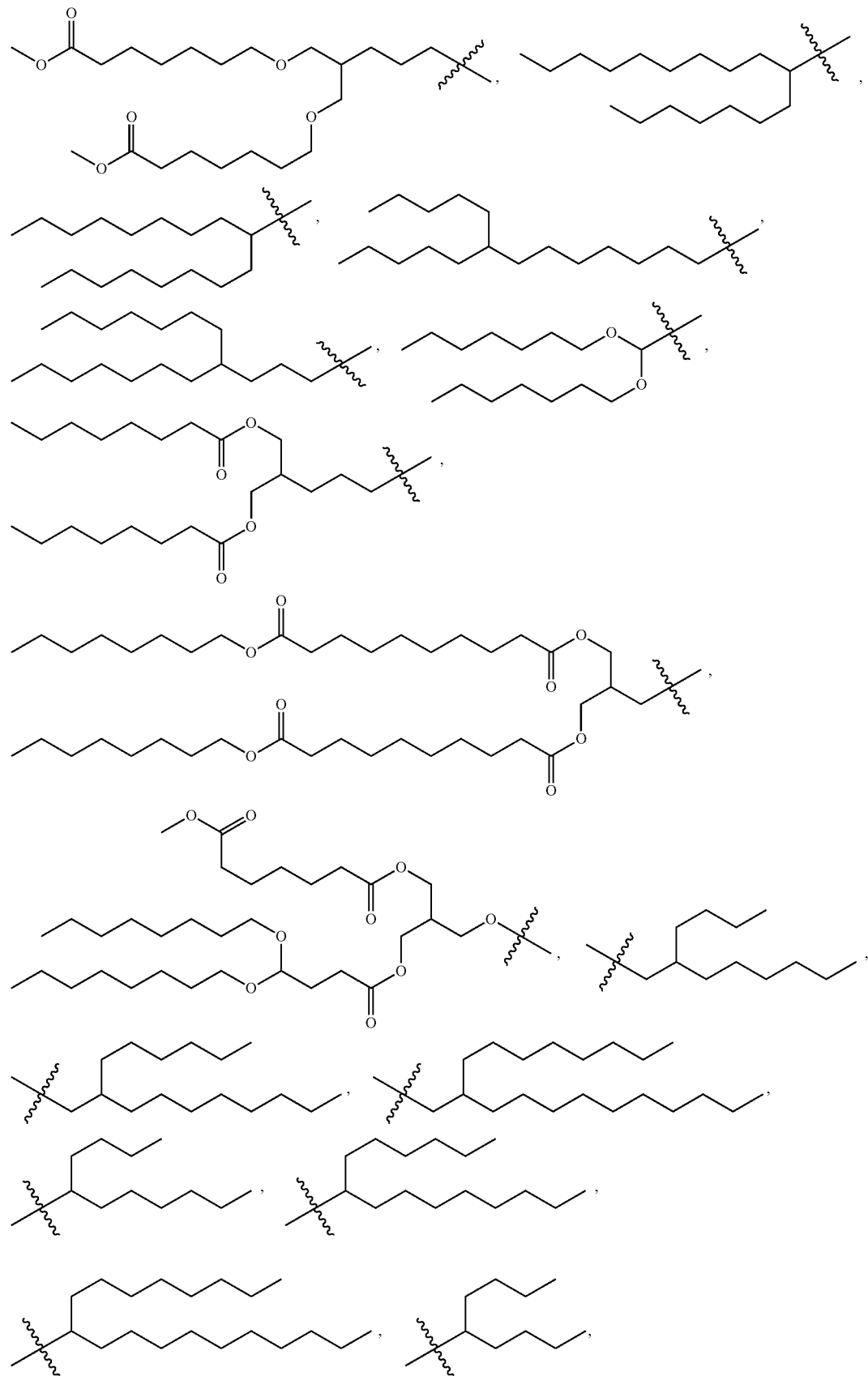

$R^3$ is selected from a group consisting of:

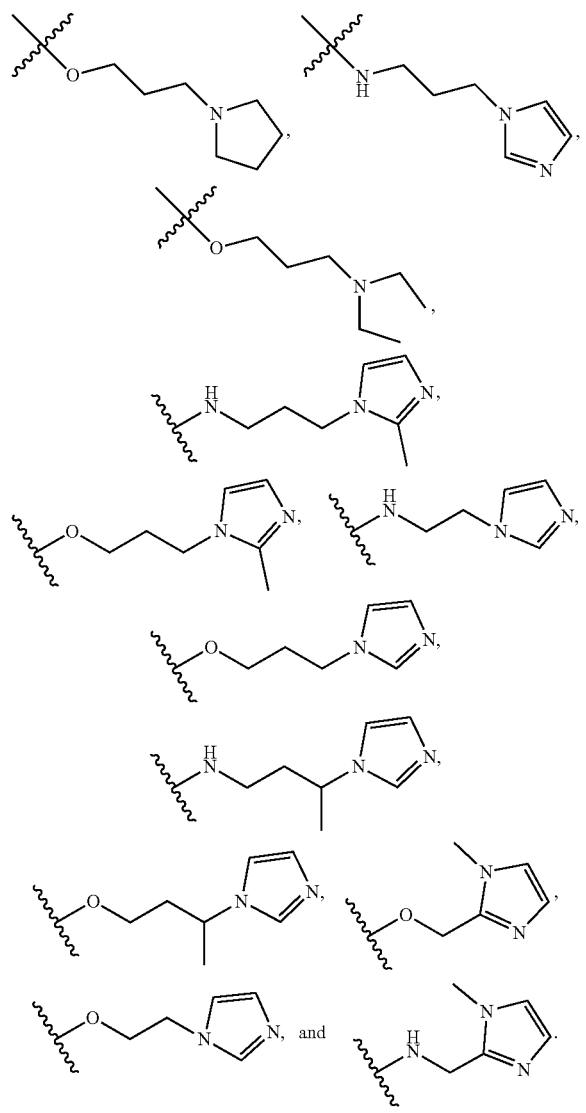

In some embodiments an LNP comprising Formula (xxiii) is used to deliver a polyribonucleotide (e.g., a circular polyribonucleotide, a linear polyribonucleotide) composition described herein to cells. In some embodiments the LNP of Formula (xxiii) is an LNP described by WO2021113777 (e.g., a lipid of Formula (3) such as a lipid of Table 3 of WO2021113777).

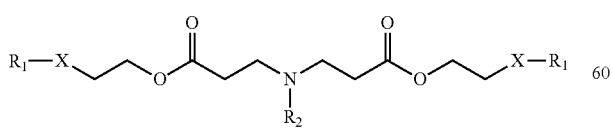

(xxiii)

wherein

X is selected from —O—, —S—, or —OC(O)—*, wherein * indicates the attachment point to $R_1$;

$R_1$ is selected from a group consisting of:

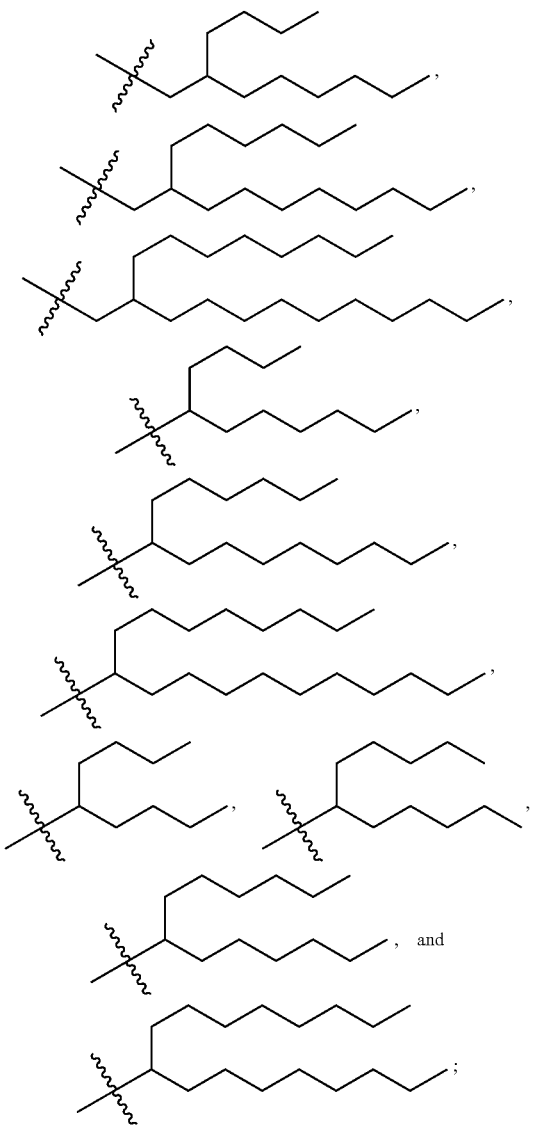

and $R^2$ is selected from a group consisting of:

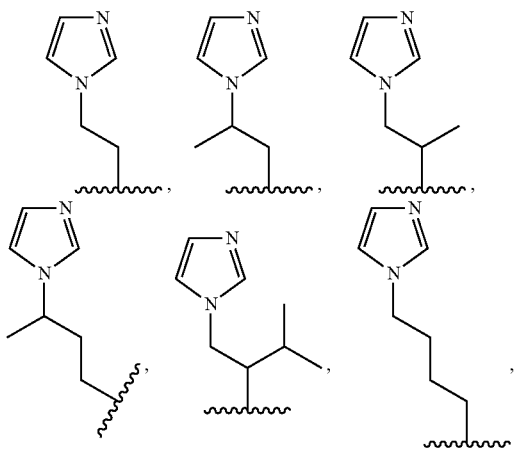

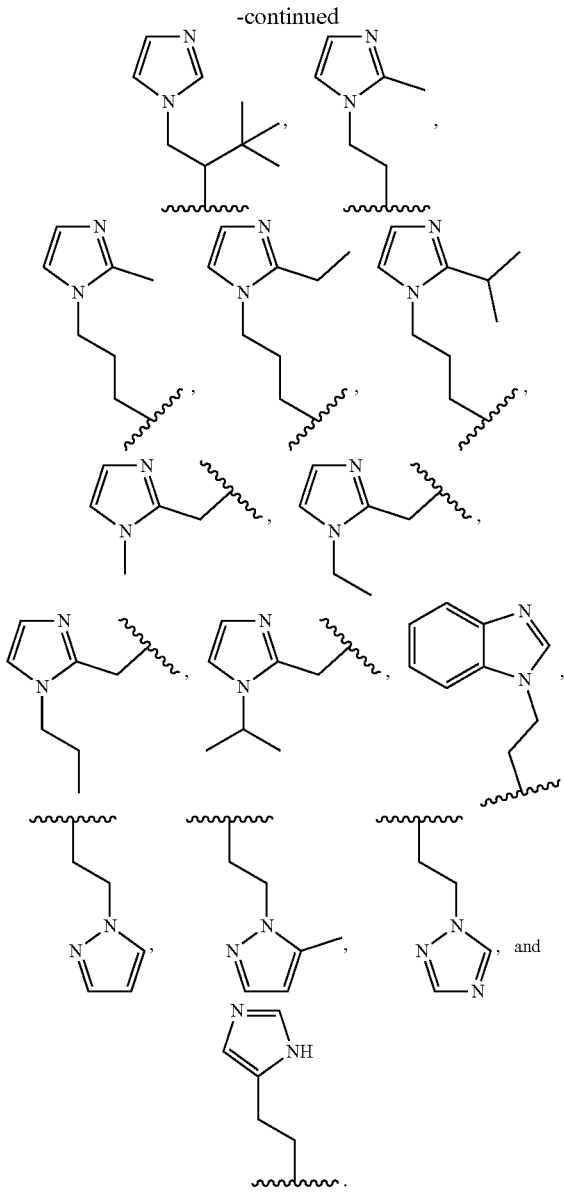

In some embodiments, a composition described herein (e.g., a nucleic acid (e.g., a circular polyribonucleotide, a linear polyribonucleotide) or a protein) is provided in an LNP that comprises an ionizable lipid. In some embodiments, the ionizable lipid is heptadecan-9-yl 8-((2-hydroxyethyl) (6-oxo-6-(undecyloxy) hexyl)amino) octanoate (SM-102); e.g., as described in Example 1 of U.S. Pat. No. 9,867,888 (incorporated by reference herein in its entirety). In some embodiments, the ionizable lipid is 9Z,12Z)-3-((4, 4-bis(octyloxy) butanoyl)oxy)-2-((((3-(diethylamino) propoxy) carbonyl)oxy)methyl) propyl octadeca-9,12-dienoate (LP01), e.g., as synthesized in Example 13 of WO2015/095340 (incorporated by reference herein in its entirety). In some embodiments, the ionizable lipid is Di((Z)-non-2-en-1-yl) 9-((4-dimethylamino) butanoyl)oxy) heptadecanedioate ($L_{319}$), e.g., as synthesized in Example 7, 8, or 9 of US2012/0027803 (incorporated by reference herein in its entirety). In some embodiments, the ionizable lipid is 1,1'-((2-(4-(2-((2-(Bis(2-hydroxydodecyl)amino) ethyl) (2-hydroxydodecyl)amino)ethyl) piperazin-1-yl) ethyl) azanediyl)bis(dodecan-2-ol) (C12-200), e.g., as synthesized in Examples 14 and 16 of WO2010/053572 (incorporated by reference herein in its entirety). In some embodiments, the ionizable lipid is Imidazole cholesterol ester (ICE) lipid (3S, 10R, 13R, 17R)-10, 13-dimethyl-17-((R)-6-methylheptan-2-yl)-2, 3, 4, 7, 8, 9, 10, 11, 12, 13, 14, 15, 16, 17-tetradecahydro-IH-cyclopenta[a] phenanthren-3-yl 3-(1H-imidazol-4-yl) propanoate, e.g., Structure (I) from WO2020/106946 (incorporated by reference herein in its entirety).

In some embodiments, an ionizable lipid may be a cationic lipid, an ionizable cationic lipid, e.g., a cationic lipid that can exist in a positively charged or neutral form depending on pH, or an amine-containing lipid that can be readily protonated. In some embodiments, the cationic lipid is a lipid capable of being positively charged, e.g., under physiological conditions. Exemplary cationic lipids include one or more amine group(s) which bear the positive charge. In some embodiments, the lipid particle comprises a cationic lipid in formulation with one or more of neutral lipids, ionizable amine-containing lipids, biodegradable alkyne lipids, steroids, phospholipids including polyunsaturated lipids, structural lipids (e.g., sterols), PEG, cholesterol, and polymer conjugated lipids. In some embodiments, the cationic lipid may be an ionizable cationic lipid. An exemplary cationic lipid as disclosed herein may have an effective pKa over 6.0. In embodiments, a lipid nanoparticle may comprise a second cationic lipid having a different effective pKa (e.g., greater than the first effective pKa), than the first cationic lipid. A lipid nanoparticle may comprise between 40 and 60 mol percent of a cationic lipid, a neutral lipid, a steroid, a polymer conjugated lipid, and a therapeutic agent, e.g., a nucleic acid (e.g., RNA (e.g., a circular polyribonucleotide, a linear polyribonucleotide)) described herein, encapsulated within or associated with the lipid nanoparticle. In some embodiments, the nucleic acid is co-formulated with the cationic lipid. The nucleic acid may be adsorbed to the surface of an LNP, e.g., an LNP comprising a cationic lipid. In some embodiments, the nucleic acid may be encapsulated in an LNP, e.g., an LNP comprising a cationic lipid. In some embodiments, the lipid nanoparticle may comprise a targeting moiety, e.g., coated with a targeting agent. In embodiments, the LNP formulation is biodegradable. In some embodiments, a lipid nanoparticle comprising one or more lipid described herein, e.g., Formula (i), (ii), (ii), (vii) and/or (ix) encapsulates at least 1%, at least 5%, at least 10%, at least 20%, at least 30%, at least 40%, at least 50%, at least 60%, at least 70%, at least 80%, at least 90%, at least 92%, at least 95%, at least 97%, at least 98% or 100% of an RNA molecule.

Exemplary ionizable lipids that can be used in lipid nanoparticle formulations include, without limitation, those listed in Table 1 of WO2019051289, incorporated herein by reference. Additional exemplary lipids include, without limitation, one or more of the following formulae: X of US2016/0311759; I of US20150376115 or in US2016/0376224; I, II or III of US20160151284; I, IA, II, or IIA of US20170210967; I-c of US20150140070; A of US2013/0178541; I of US2013/0303587 or US2013/0123338; I of US2015/0141678; II, III, IV, or V of US2015/0239926; I of US2017/0119904; I or II of WO2017/117528; A of US2012/0149894; A of US2015/0057373; A of WO2013/116126; A of US2013/0090372; A of US2013/0274523; A of US2013/0274504; A of US2013/0053572; A of WO2013/016058; A of WO2012/162210; I of US2008/042973; I, II, III, or IV of US2012/01287670; I or II of US2014/0200257; I, II, or III of US2015/0203446; I or III of US2015/0005363; I, IA, IB, IC, ID, II, IIA, IIB, IIC, IID, or III-XXIV of US2014/0308304; of US2013/0338210; I, II, III, or IV of WO2009/132131; A of US2012/01011478; I or XXXV of US2012/0027796; XIV or XVII of US2012/0058144; of US2013/0323269; I of US2011/0117125; I, II, or III of US2011/0256175; I, II, III, IV, V, VI, VII, VIII, IX, X, XI, XII of US2012/0202871; I, II, III, IV, V, VI, VII, VIII, X, XII, XIII, XIV, XV, or XVI of US2011/0076335; I or II of US2006/008378; I of US2013/0123338; I or X-A-Y-Z of US2015/0064242; XVI, XVII, or XVIII of US2013/0022649; I, II, or III of US2013/0116307; I, II, or III of US2013/0116307; I or II of US2010/0062967; I-X of US2013/0189351; I of US2014/0039032; V of US2018/0028664; I of US2016/0317458; I of US2013/0195920; 5, 6, or 10 of U.S. Pat. No. 10,221,127; III-3 of WO2018/081480; 1-5 or 1-8 of WO2020/081938; 18 or 25 of U.S. Pat. No. 9,867,888; A of US2019/0136231; II of WO2020/219876; 1 of US2012/0027803; OF-02 of US2019/0240349; 23 of U.S. Pat. No. 10,086,013; cKK-E12/A6 of Miao et al (2020); C12-200 of WO2010/053572; 7C1 of Dahlman et al (2017); 304-013 or 503-013 of Whitehead et al; TS-P4C2 of U.S. Pat. No. 9,708,628; I of WO2020/106946; I of WO2020/106946; and (1), (2), (3), or (4) of WO2021/113777. Exemplary lipids further include a lipid of any one of Tables 1-16 of WO2021/113777.

In some embodiments, the ionizable lipid is MC3 (6Z, 9Z,28Z,3 1Z)-heptatriaconta-6,9,28,3 1-tetraen-19-yl-4-(dimethylamino) butanoate (DLin-MC3-DMA or MC3), e.g., as described in Example 9 of WO2019051289A9 (incorporated by reference herein in its entirety). In some embodiments, the ionizable lipid is the lipid ATX-002, e.g., as described in Example 10 of WO2019051289A9 (incorporated by reference herein in its entirety). In some embodiments, the ionizable lipid is (13Z,16Z)-A,A-dimethyl-3-nonyldocosa-13, 16-dien-I-amine (Compound 32), e.g., as described in Example 11 of WO2019051289A9 (incorporated by reference herein in its entirety). In some embodiments, the ionizable lipid is Compound 6 or Compound 22, e.g., as described in Example 12 of WO2019051289A9 (incorporated by reference herein in its entirety).

Exemplary non-cationic lipids include, but are not limited to, distearoyl-sn-glycero-phosphoethanolamine, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoylphosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), monomethyl-phosphatidylethanolamine (such as 16-O-monomethyl PE), dimethyl-phosphatidylethanolamine (such as 16-O-dimethyl PE), 18-I-trans PE, I-stearoyl-2-oleoyl-phosphatidyethanolamine (SOPE), hydrogenated soy phosphatidylcholine (HSPC), egg phosphatidylcholine (EPC), dioleoylphosphatidylserine (DOPS), sphingomyelin (SM), dimyristoyl phosphatidylcholine (DMPC), dimyristoyl phosphatidylglycerol (DMPG), distearoylphosphatidylglycerol (DSPG), dierucoylphosphatidylcholine (DEPC), palmitoyloleoylphosphatidylglycerol (POPG), dielaidoyl-phosphatidylethanolamine (DEPE), lecithin, phosphatidylethanolamine, lysolecithin, lysophosphatidylethanolamine, phosphatidylserine, phosphatidylinositol, sphingomyelin, egg sphingomyelin (ESM), cephalin, cardiolipin, phosphatidicacid, cerebrosides, dicetylphosphate, lysophosphatidylcholine, dilinoleoylphosphatidylcholine, or mixtures thereof. It is understood that other diacylphosphatidylcholine and diacylphosphatidylethanolamine phospholipids can also be used. The acyl groups in these lipids are preferably acyl groups derived from fatty acids having C10-C24 carbon chains, e.g., lauroyl, myristoyl, paimitoyl, stearoyl, or oleoyl. Additional exemplary lipids, in certain embodiments, include, without limitation, those described in Kim et al. (2020) dx.doi.org/10.1021/acs.nanolett.0c01386, incorporated herein by reference. Such lipids include, in some embodiments, plant lipids found to improve liver transfection with mRNA (e.g., DGTS).

Other examples of non-cationic lipids suitable for use in the lipid nanoparticles include, without limitation, nonphosphorous lipids such as, e.g., stearylamine, dodeeylamine, hexadecylamine, acetyl palmitate, glycerol ricinoleate, hexadecyl stereate, isopropyl myristate, amphoteric acrylic polymers, triethanolamine-lauryl sulfate, alkyl-aryl sulfate polyethyloxylated fatty acid amides, dioctadecyl dimethyl ammonium bromide, ceramide, sphingomyelin, and the like. Other non-cationic lipids are described in WO2017/099823 or US patent publication US2018/0028664, the contents of which is incorporated herein by reference in their entirety.

In some embodiments, the non-cationic lipid is oleic acid or a compound of Formula I, II, or IV of US2018/0028664, incorporated herein by reference in its entirety. The non-cationic lipid can comprise, for example, 0-30% (mol) of the total lipid present in the lipid nanoparticle. In some embodiments, the non-cationic lipid content is 5-20% (mol) or 10-15% (mol) of the total lipid present in the lipid nanoparticle. In embodiments, the molar ratio of ionizable lipid to the neutral lipid ranges from about 2:1 to about 8:1 (e.g., about 2:1, 3:1, 4:1, 5:1, 6:1, 7:1, or 8:1).

In some embodiments, the lipid nanoparticles do not comprise any phospholipids.

In some aspects, the lipid nanoparticle can further comprise a component, such as a sterol, to provide membrane integrity. One exemplary sterol that can be used in the lipid nanoparticle is cholesterol and derivatives thereof. Non-limiting examples of cholesterol derivatives include polar analogues such as 5a-cholestanol, 53-coprostanol, cholesteryl-(2-hydroxy)-ethyl ether, cholesteryl-(4'-hydroxy)-butyl ether, and 6-ketocholestanol; non-polar analogues such as 5a-cholestane, cholestenone, 5a-cholestanone, 5p-cholestanone, and cholesteryl decanoate; and mixtures thereof. In some embodiments, the cholesterol derivative is a polar analogue, e.g., cholesteryl-(4'-hydroxy)-butyl ether. Exemplary cholesterol derivatives are described in PCT publication WO2009/127060 and US patent publication US2010/0130588, each of which is incorporated herein by reference in its entirety.

In some embodiments, the component providing membrane integrity, such as a sterol, can comprise 0-50% (mol) (e.g., 0-10%, 10-20%, 20-30%, 30-40%, or 40-50%) of the total lipid present in the lipid nanoparticle. In some embodiments, such a component is 20-50% (mol) 30-40% (mol) of the total lipid content of the lipid nanoparticle.

In some embodiments, the lipid nanoparticle can comprise a polyethylene glycol (PEG) or a conjugated lipid molecule. Generally, these are used to inhibit aggregation of lipid nanoparticles and/or provide steric stabilization. Exemplary conjugated lipids include, but are not limited to, PEG-lipid conjugates, polyoxazoline (POZ)-lipid conjugates, polyamide-lipid conjugates (such as *ATTA*-lipid conjugates), cationic-polymer lipid (CPL) conjugates, and mixtures thereof. In some embodiments, the conjugated lipid molecule is a PEG-lipid conjugate, for example, a (methoxy polyethylene glycol)-conjugated lipid.

Exemplary PEG-lipid conjugates include, but are not limited to, PEG-diacylglycerol (DAG) (such as 1-(monomethoxy-polyethyleneglycol)-2,3-dimyristoylglycerol (PEG-DMG)), PEG-dialkyloxypropyl (DAA), PEG-phospholipid, PEG-ceramide (Cer), a pegylated phosphatidylethanoloamine (PEG-PE), PEG succinate diacylglycerol (PEGS-DAG) (such as 4-0-(2',3'-di(tetradecanoyloxy) propyl-1-0-(w-methoxy (polyethoxy)ethyl) butanedioate (PEG-S-DMG)), PEG dialkoxypropylcarbam, N-(carbonyl-methoxypolyethylene glycol 2000)-1,2-distearoyl-sn-glycero-3-phosphoethanolamine sodium salt, or a mixture thereof. Additional exemplary PEG-lipid conjugates are described, for example, in U.S. Pat. Nos. 5,885,613, 6,287,591, US2003/0077829, US2003/0077829, US2005/0175682, US2008/0020058, US2011/0117125, US2010/0130588, US2016/0376224, US2017/0119904, and US/099823, the contents of all of which are incorporated herein by reference in their entirety. In some embodiments, a PEG-lipid is a compound of Formula III, III-a-I, III-a-2, III-b-1, III-b-2, or V of US2018/0028664, the content of which is incorporated herein by reference in its entirety. In some embodiments, a PEG-lipid is of Formula II of US20150376115 or US2016/0376224, the content of both of which is incorporated herein by reference in its entirety. In some embodiments, the PEG-DAA conjugate can be, for example, PEG-dilauryloxypropyl, PEG-dimyristyloxypropyl, PEG-dipalmityloxypropyl, or PEG-distearyloxypropyl. The PEG-lipid can be one or more of PEG-DMG, PEG-dilaurylglycerol, PEG-dipalmitoylglycerol, PEG-disterylglycerol, PEG-dilaurylglycamide, PEG-dimyristylglycamide, PEG-dipalmitoylglycamide, PEG-disterylglycamide, PEG-cholesterol (1-[8'-(Cholest-5-en-3[beta]-oxy) carboxamido-3',6'-dioxaoctanyl] carbamoyl-[omega]-methyl-poly(ethylene glycol), PEG-DMB (3,4-Ditetradecoxylbenzyl-[omega]-methyl-poly(ethylene glycol) ether), and 1,2-dimyristoyl-sn-glycero-3-phosphoethanolamine-N-[methoxy (polyethylene glycol)-2000]. In some embodiments, the PEG-lipid comprises PEG-DMG, 1,2-dimyristoyl-sn-glycero-3-phosphoethanolamine-N-[methoxy (polyethylene glycol)-2000]. In some embodiments, the PEG-lipid comprises a structure selected from:

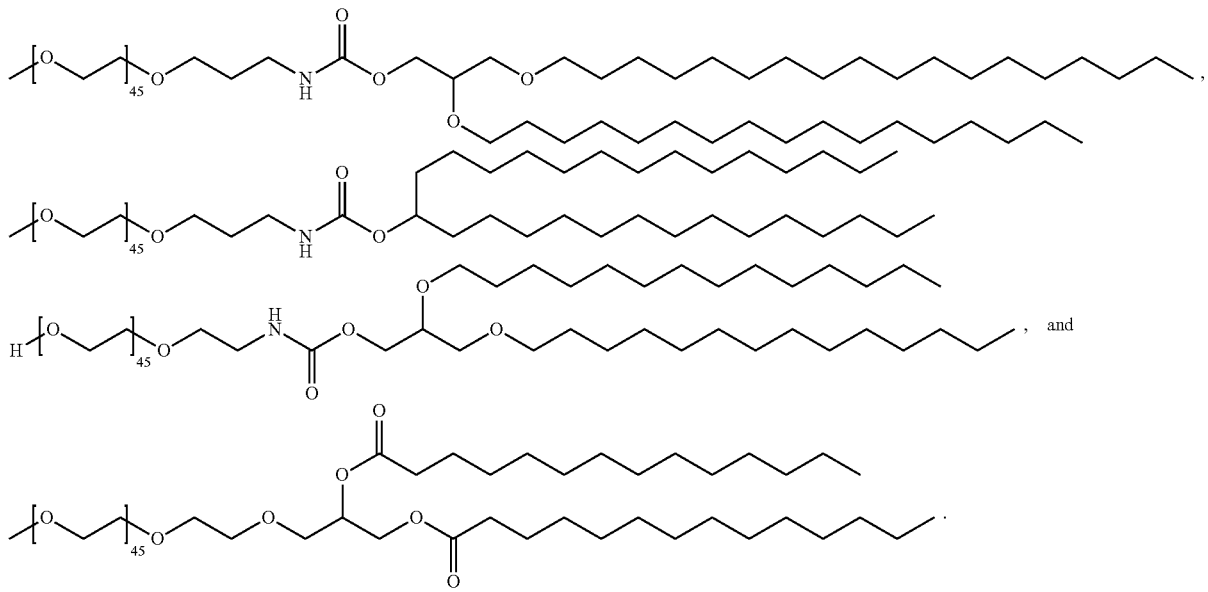

In some embodiments, lipids conjugated with a molecule other than a PEG can also be used in place of PEG-lipid. For example, polyoxazoline (POZ)-lipid conjugates, polyamide-lipid conjugates (such as ATTA-lipid conjugates), and cat-ionic-polymer lipid (GPL) conjugates can be used in place of or in addition to the PEG-lipid.

Exemplary conjugated lipids, i.e., PEG-lipids, (POZ)-lipid conjugates, ATTA-lipid conjugates and cationic polymer-lipids are described in the PCT and US patent applications listed in Table 2 of WO2019051289A9, the contents of all of which are incorporated herein by reference in their entirety.

In some embodiments, the PEG or the conjugated lipid can comprise 0-20% (mol) of the total lipid present in the lipid nanoparticle. In some embodiments, PEG or the conjugated lipid content is 0.5-10% or 2-5% (mol) of the total lipid present in the lipid nanoparticle. Molar ratios of the ionizable lipid, non-cationic-lipid, sterol, and PEG/conjugated lipid can be varied as needed. For example, the lipid particle can comprise 30-70% ionizable lipid by mole or by total weight of the composition, 0-60% cholesterol by mole or by total weight of the composition, 0-30% non-cationic-lipid by mole or by total weight of the composition and 1-10% conjugated lipid by mole or by total weight of the composition. Preferably, the composition comprises 30-40% ionizable lipid by mole or by total weight of the composition, 40-50% cholesterol by mole or by total weight of the composition, and 10-20% non-cationic-lipid by mole or by total weight of the composition. In some other embodiments, the composition is 50-75% ionizable lipid by mole or by total weight of the composition, 20-40% cholesterol by mole or by total weight of the composition, and 5 to 10% non-cationic-lipid, by mole or by total weight of the composition and 1-10% conjugated lipid by mole or by total weight of the composition. The composition may contain 60-70% ionizable lipid by mole or by total weight of the composition, 25-35% cholesterol by mole or by total weight of the composition, and 5-10% non-cationic-lipid by mole or by total weight of the composition. The composition may also contain up to 90% ionizable lipid by mole or by total weight of the composition and 2 to 15% non-cationic lipid by mole or by total weight of the composition. The formulation may also be a lipid nanoparticle formulation, for example comprising 8-30% ionizable lipid by mole or by total weight of the composition, 5-30% non-cationic lipid by mole or by total weight of the composition, and 0-20% cholesterol by mole or by total weight of the composition; 4-25% ionizable lipid by mole or by total weight of the composition, 4-25% non-cationic lipid by mole or by total weight of the composition, 2 to 25% cholesterol by mole or by total weight of the composition, 10 to 35% conjugate lipid by mole or by total weight of the composition, and 5% cholesterol by mole or by total weight of the composition; or 2-30% ionizable lipid by mole or by total weight of the composition, 2-30% non-cationic lipid by mole or by total weight of the composition, 1 to 15% cholesterol by mole or by total weight of the composition, 2 to 35% conjugate lipid by mole or by total weight of the composition, and 1-20% cholesterol by mole or by total weight of the composition; or even up to 90% ionizable lipid by mole or by total weight of the composition and 2-10% non-cationic lipids by mole or by total weight of the composition, or even 100% cationic lipid by mole or by total weight of the composition. In some embodiments, the lipid particle formulation comprises ionizable lipid, phospholipid, cholesterol and a PEG-ylated lipid in a molar ratio of 50:10:38.5: 1.5. In some other embodiments, the lipid particle formulation comprises ionizable lipid, cholesterol and a PEG-ylated lipid in a molar ratio of 60:38.5:1.5.

In some embodiments, the lipid particle comprises ionizable lipid, non-cationic lipid (e.g., phospholipid), a sterol (e.g., cholesterol) and a PEG-ylated lipid, where the molar ratio of lipids ranges from 20 to 70 mole percent for the ionizable lipid, with a target of 40-60, the mole percent of non-cationic lipid ranges from 0 to 30, with a target of 0 to 15, the mole percent of sterol ranges from 20 to 70, with a target of 30 to 50, and the mole percent of PEG-ylated lipid ranges from 1 to 6, with a target of 2 to 5.

In some embodiments, the lipid particle comprises ionizable lipid/non-cationic-lipid/sterol/conjugated lipid at a molar ratio of 50:10:38.5:1.5.

In an aspect, the disclosure provides a lipid nanoparticle formulation comprising phospholipids, lecithin, phosphatidylcholine and phosphatidylethanolamine.

In some embodiments, one or more additional compounds can also be included. Those compounds can be administered separately, or the additional compounds can be included in the lipid nanoparticles of the invention. In other words, the lipid nanoparticles can contain other compounds in addition to the nucleic acid or at least a second nucleic acid, different than the first. Without limitations, other additional compounds can be selected from the group consisting of small or large organic or inorganic molecules, monosaccharides, disaccharides, trisaccharides, oligosaccharides, polysaccharides, peptides, proteins, peptide analogs and derivatives thereof, peptidomimetics, nucleic acids, nucleic acid analogs and derivatives, an extract made from biological materials, or any combinations thereof.

In some embodiments, the LNPs comprise biodegradable, ionizable lipids. In some embodiments, the LNPs comprise (9Z,12Z)-3-((4,4-bis(octyloxy) butanoyl)oxy)-2-((((3-(diethylamino) propoxy) carbonyl)oxy)methyl) propyl octadeca-9,12-dienoate, also called 3-((4,4-bis(octyloxy) butanoyl)oxy)-2-((((3-(diethylamino) propoxy) carbonyl)oxy)methyl) propyl(9Z,12Z)-octadeca-9,12-dienoate) or another ionizable lipid. See, e.g., lipids of WO2019/067992, WO/2017/173054, WO2015/095340, and WO2014/136086, as well as references provided therein. In some embodiments, the term cationic and ionizable in the context of LNP lipids is interchangeable, e.g., wherein ionizable lipids are cationic depending on the pH.

In some embodiments, the average LNP diameter of the LNP formulation may be between 10s of nm and 100s of nm, e.g., measured by dynamic light scattering (DLS). In some embodiments, the average LNP diameter of the LNP formulation may be from about 40 nm to about 150 nm, such as about 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm. In some embodiments, the average LNP diameter of the LNP formulation may be from about 50 nm to about 100 nm, from about 50 nm to about 90 nm, from about 50 nm to about 80 nm, from about 50 nm to about 70 nm, from about 50 nm to about 60 nm, from about 60 nm to about 100 nm, from about 60 nm to about 90 nm, from about 60 nm to about 80 nm, from about 60 nm to about 70 nm, from about 70 nm to about 100 nm, from about 70 nm to about 90 nm, from about 70 nm to about 80 nm, from about 80 nm to about 100 nm, from about 80 nm to about 90 nm, or from about 90 nm to about 100 nm. In some embodiments, the average LNP diameter of the LNP formulation may be from about 70 nm to about 100 nm. In a particular embodiment, the average LNP diameter of the LNP formulation may be about 80 nm. In some embodiments, the average LNP diameter of the LNP formulation may be about 100 nm. In some embodiments, the average LNP diameter of the LNP formulation ranges from about 1 mm to about 500 mm, from about 5 mm to about 200 mm, from about 10 mm to about 100 mm, from about 20 mm to about 80 mm, from about 25 mm to about 60 mm, from about 30 mm to about 55 mm, from about 35 mm to about 50 mm, or from about 38 mm to about 42 mm.

A LNP may, in some instances, be relatively homogenous. A polydispersity index may be used to indicate the homogeneity of a LNP, e.g., the particle size distribution of the lipid nanoparticles. A small (e.g., less than 0.3) polydispersity index generally indicates a narrow particle size distribution. A LNP may have a polydispersity index from about 0 to about 0.25, such as 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, or 0.25. In some embodiments, the polydispersity index of a LNP may be from about 0.10 to about 0.20.

The zeta potential of a LNP may be used to indicate the electrokinetic potential of the composition. In some embodiments, the zeta potential may describe the surface charge of an LNP. Lipid nanoparticles with relatively low charges, positive or negative, are generally desirable, as more highly charged species may interact undesirably with cells, tissues, and other elements in the body. In some embodiments, the zeta potential of a LNP may be from about-10 mV to about +20 mV, from about-10 mV to about +15 mV, from about-10 mV to about +10 mV, from about-10 mV to about +5 mV, from about-10 mV to about 0 mV, from about-10 mV to about-5 mV, from about-5 mV to about +20 mV, from about-5 mV to about +15 mV, from about-5 mV to about +10 mV, from about-5 mV to about +5 mV, from about-5 mV to about 0 mV, from about 0 mV to about +20 mV, from about 0 mV to about +15 mV, from about 0 mV to about +10 mV, from about 0 mV to about +5 mV, from about +5 mV to about +20 mV, from about +5 mV to about +15 mV, or from about +5 mV to about +10 mV.

The efficiency of encapsulation of a protein and/or nucleic acid, describes the amount of protein and/or nucleic acid that is encapsulated or otherwise associated with a LNP after preparation, relative to the initial amount provided. The encapsulation efficiency is desirably high (e.g., close to 100%). The encapsulation efficiency may be measured, for example, by comparing the amount of protein or nucleic acid in a solution containing the lipid nanoparticle before and after breaking up the lipid nanoparticle with one or more organic solvents or detergents. An anion exchange resin may be used to measure the amount of free protein or nucleic acid (e.g., RNA) in a solution. Fluorescence may be used to measure the amount of free protein and/or nucleic acid (e.g., RNA) in a solution. For the lipid nanoparticles described herein, the encapsulation efficiency of a protein and/or nucleic acid may be at least 50%, for example 50%, 55%, 60%, 65%, 70%, 75%, 80%, 85%, 90%, 91%, 92%, 93%, 94%, 95%, 96%, 97%, 98%, 99%, or 100%. In some embodiments, the encapsulation efficiency may be at least 80%. In some embodiments, the encapsulation efficiency may be at least 90%. In some embodiments, the encapsulation efficiency may be at least 95%.

A LNP may optionally comprise one or more coatings. In some embodiments, a LNP may be formulated in a capsule, film, or table having a coating. A capsule, film, or tablet including a composition described herein may have any useful size, tensile strength, hardness or density.

Additional exemplary lipids, formulations, methods, and characterization of LNPs are taught by WO2020/061457 and WO2021/113777, each of which is incorporated herein by reference in its entirety. Further exemplary lipids, formulations, methods, and characterization of LNPs are taught by Hou et al. Lipid nanoparticles for mRNA delivery. Nat Rev Mater (2021). doi.org/10.1038/s41578-021-00358-0, which is incorporated herein by reference in its entirety (see, for example, exemplary lipids and lipid derivatives of FIG. 2 of Hou et al.).

In some embodiments, in vitro or ex vivo cell lipofections are performed using Lipofectamine MessengerMax (Thermo Fisher) or TransIT-mRNA Transfection Reagent (Mirus Bio). In certain embodiments, LNPs are formulated using the GenVoy_ILM ionizable lipid mix (Precision NanoSystems). In certain embodiments, LNPs are formulated using 2,2-dilinoleyl-4-dimethylaminoethyl-[1,3]-dioxolane (DLin-KC2-DMA) or dilinoleylmethyl-4-dimethylaminobutyrate (DLin-MC3-DMA or MC3), the formulation and in vivo use of which are taught in Jayaraman et al. Angew Chem Int Ed Engl 51 (34): 8529-8533 (2012), incorporated herein by reference in its entirety.

LNP formulations optimized for the delivery of CRISPR-Cas systems, e.g., Cas9-gRNA RNP, gRNA, Cas9 mRNA, are described in WO2019067992 and WO2019067910, both incorporated by reference, and are useful for delivery of circular polyribonucleotides and linear polyribonucleotides described herein.

Additional specific LNP formulations useful for delivery of nucleic acids (e.g., circular polyribonucleotides, linear polyribonucleotides) are described in U.S. Pat. Nos. 8,158,601 and 8,168,775, both incorporated by reference, which include formulations used in patisiran, sold under the name ONPATTRO.

Exemplary dosing of polyribonucleotide (e.g., a circular polyribonucleotide, a linear polyribonucleotide) LNP may include about 0.1, 0.25, 0.3, 0.5, 1, 2, 3, 4, 5, 6, 8, 10, or 100 mg/kg (RNA). Exemplary dosing of AAV comprising a polyribonucleotide (e.g., a circular polyribonucleotide, a linear polyribonucleotide) may include an MOI of about 1011, 1012, 1013, and 1014 vg/kg.

EXAMPLES

The following examples are put forth so as to provide those of ordinary skill in the art with a description of how the compositions and methods described herein may be used, made, and evaluated, and are intended to be purely exemplary of the disclosure and are not intended to limit the scope of what the inventors regard as their invention.

Example 1: Design of *Anabaena* Self-Splicing Permuted Intron-Exon (PIE) Construct with Extended Annealing Region This example describes the design of *Anabaena* self-splicing permuted intron-exon (PIE) sequences with extended annealing region to provide better circularization efficiency.

Figure 1B:
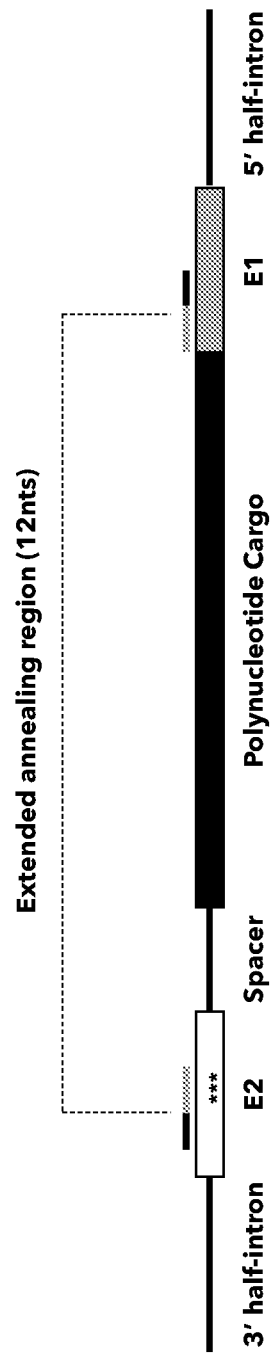

Schematics depicting exemplary designs of DNA constructs are provided in FIG. 1A and FIG. 1B. In this example, the constructs include, from 5' to 3': a 3' half of group I catalytic intron fragment (*Anabaena* 3' half-intron), a 3' splice site, a 3' exon fragment (*Anabaena* E2), a spacer element, a polynucleotide cargo, a 5' exon fragment (*Anabaena* E1), a 5' splice site, and a 5' half of group I catalytic intron fragment (*Anabaena* 5' half-intron). E2 has a 5 nucleotide complementary sequence (5'-TCCGT-3') (SEQ ID NO: 1) to E1 (5'-ACGGA-3') (SEQ ID NO: 2) (FIGS. 1A and 1B, black lines on the E2 and E1). To generate a construct that has an extended annealing region between E2 and E1, 5 nucleotides from E2 were mutated to have an extended 7 nucleotide annealing region with E1 (TGACCTT (SEQ ID NO: 3)→AGCGTCT (SEQ ID NO: 4), bold character represents mutated sequences) (FIG. 1B, gray line on the E2 and E1, asterisks in E2 represent mutation on the sequence). The total annealing region from *Anabaena* permuted intron-exon (PIE) with an extended annealing region is 12 nucleotides (E2; 5'-TCCGTAGCGTCT-3' (SEQ ID NO: 5), E1; 5'-AGACGCTACGGA-3' (SEQ ID NO: 6)) (FIG. 1B).

Figure 2B:
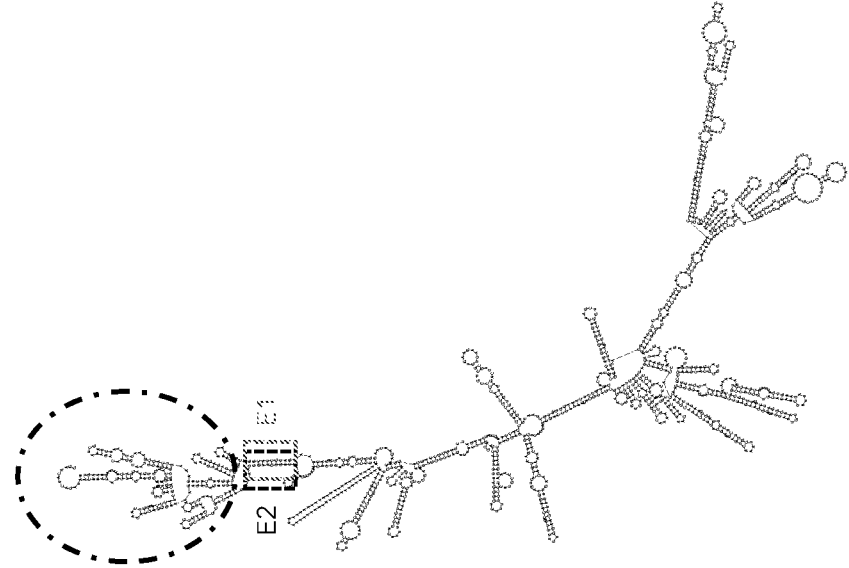
FIGS. 2A and 2B are schematic drawings showing the structures of an exemplary *Anabaena* permuted intron-exon with an annealing region of 5 nucleotides (FIG. 2A) and an exemplary *Anabaena* permuted intron-exon with an extended annealing region (FIG. 2B)
Figure 2A:
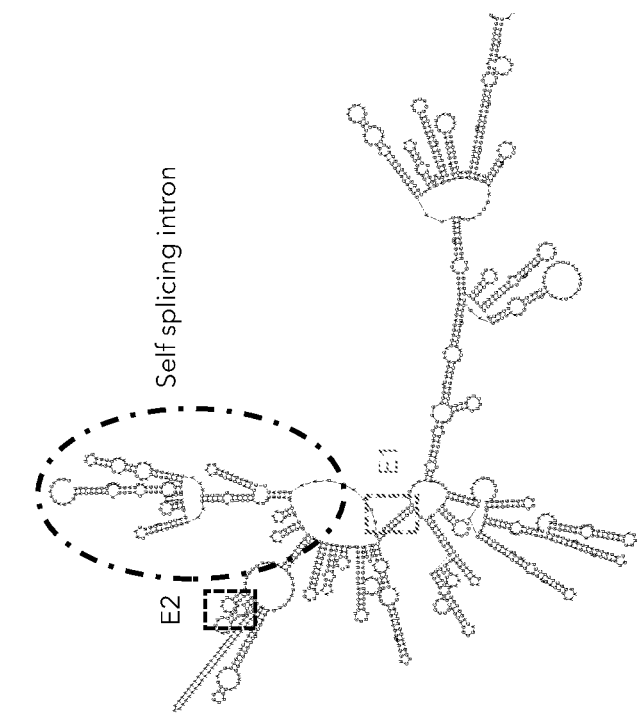

The RNA structure was estimated by RNA structure prediction tool, RNA fold (rna.tbi.univie.ac.at/cgi-bin/RNAWebSuite/RNAfold.cgi). Extension of E2-E1 interaction was generated by modifying sequence results in proper E2-E1 interaction and condensed self-splicing intron structure (FIGS. 2A and 2B).

Constructs that have the *Anabaena* PIE with an annealing region of 5 nucleotides (*Anabaena* 1) and annealing sequences with an extended annealing region (*Anabaena* 2) were designed to compare circularization efficiency. *Anabaena* PIE constructs described in Wesselhoeft, et al. 2018 (Nat. Commun. 9:2629) (*Anabaena* 3) were also used for comparison. In this example, the constructs were designed to include polyA50 as the spacer element, and a combination of an EMCV internal ribosome entry site (IRES) and an ORF as the polynucleotide cargo. Two different ORFs were tested: a *Gaussia* luciferase (Gluc) ORF (558 nucleotides) and a SARS-COV-2 spike protein ORF (3822nts). The size of circular RNA was 1.2 Kb with the Gluc ORF and 4.5 Kb with the SARS-COV-2 spike protein ORF.

Figure 3A:
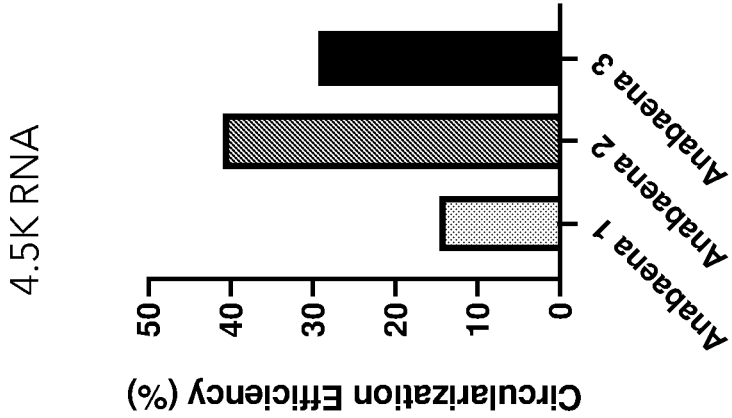
FIGS. 3A and 3B are graphs showing the circularization efficiency of *Anabaena* permuted intron-exon with an annealing region of 5 nucleotides (*Anabaena* 1), *Anabaena* permuted intron-exon with an extended annealing region (*Anabaena* 2), and *Anabaena* 3 with either a 1.2 Kb RNA (FIG. 3A) or a 4.5 Kb RNA (FIG. 3B).
Figure 3B:
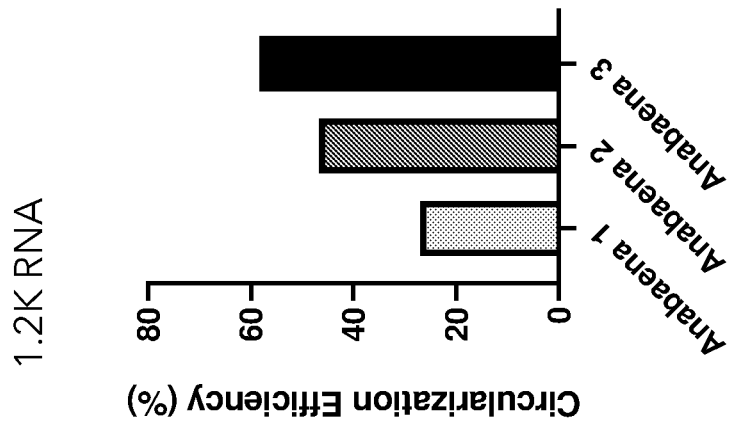

Unmodified linear RNA was synthesized by in vitro transcription using T7 RNA polymerase from a DNA template in the presence of 7.5 mM of NTP. Template DNA was removed by treating with DNase for 20 minutes. Synthesized linear RNA was purified with an RNA clean up kit (New England Biolabs, T2050). Self-splicing occurred during transcription; no additional reaction was required. To monitor self-splicing efficiency, 200 ng of column purified in vitro transcribed RNA was mixed with gel loading buffer II (Thermo Fisher, AM8546G) and heated at 95° C. for 3 minutes, then incubated on ice for 3 minutes. The samples were then separated by 6% Urea polyacrylamide gel electrophoresis (Urea PAGE), and the RNA band was stained using gel stain and visualized using an imaging system. Extending the annealing sequence from 5 nucleotides to 12 nucleotides increased circularization efficiency up to two-fold and showed similar circularization efficiency with *Anabaena* 3 in the case of the 1.2 Kb circular RNA (FIG. 3A). In the case of the 4.5 Kb circular RNA, *Anabaena* PIE with an extended annealing region (*Anabaena* 2) showed 40% better circularization efficiency as compared to *Anabaena* 3 and three-fold higher than *Anabaena* PIE with an annealing region of 5 nucleotides (*Anabaena* 1) (FIG. 3B)

*Anabaena* PIE designed to have an extended E2-E1 annealing sequence (*Anabaena* 2) showed 2-3-fold better circularization efficiency than *Anabaena* PIE with an annealing region of 5 nucleotides regardless of the size of the circular RNA (*Anabaena* 1). This shows similar circularization efficiency for the easier-to circularize 1.2 Kb construct and 40% better circularization efficiency for the difficult 4.5 Kb construct.

Example 2: Protein Expression from Circular RNA Generated by *Anabaena* Self-Splicing PIE with an Extended Annealing Region This example demonstrates protein expression from circular RNA generated by *Anabaena* self-splicing PIE with an extended annealing region.

In this example, constructs having *Anabaena* PIE with an annealing region of 5 nucleotides (*Anabaena* 1) and extended annealing sequences (*Anabaena* 2) were designed as described in Example 1 to compare protein expression. In this example, the constructs were designed to include polyA50 as the spacer element, and a combination of an EMCV IRES and an ORF as the polynucleotide cargo. Two different ORFs were tested: Gluc (558nts) and SARS-COV-2 spike protein (3822nts). *Anabaena* 3, as described in Example 1, was also tested for comparison.

Linear RNA was synthesized by in vitro transcription using T7 RNA polymerase in the presence of 7.5 mM of NTP. Template DNA was removed by treating with DNase for 20 minutes. Synthesized linear RNA was purified with an RNA clean up kit (New England Biolabs, T2050). Circular RNA encoding Gluc was purified by Urea PAGE, eluted in a buffer (0.5 M Sodium Acetate, 0.1% SDS, 1 mM EDTA), ethanol precipitated and resuspended in RNAse-free water. Circular RNA encoding spike protein from SARS-CoV-2 was purified by reverse phase chromatography and the fractions were buffer exchanged with sodium citrate and then water through ultrafiltration using Amicon Ultra Centrifugal filters (Sigma Aldrich).

To compare expression of circular RNA encoding Gluc, circular RNA generated by *Anabaena* 1 and *Anabaena* 2 were prepared. For comparison, circular RNA produced by *Anabaena* 3 was also prepared. Hela cells (10,000 cells per well in a 96 well plate) were transfected with 0.1 pmole of purified circular RNAs using LIPOFECTAMINER MessengerMAX transfection reagent (Invitrogen) according to the manufacturer's protocol. Cell culture media was harvested and replaced with fresh media at 24 hr, 48 hr and 72 hr timepoints to measure Gluc activity. To measure Gluc activity, 10 µl of harvested cell media was transferred to a white 96 well plate, and a bioluminescent reporter assay system was used according to the manufacturer's instruction (Pierce *Gaussia* Luciferase Flash Assay Kit, 16158, Thermo Scientific). The plate was read in a luminometer instrument (Promega).

To compare expression of circular RNA encoding SARS-COV-2 spike protein, circular RNA generated by *Anabaena* PIE with an annealing region of 5 nucleotides (*Anabaena* 1) and *Anabaena* PIE with an extended annealing region (*Anabaena* 2) were prepared. For comparison, circular RNA produced by *Anabaena* 3 was also prepared. Hela cells (1.2 million cells per well in a 6 well plate) were transfected with 4 pmol of purified circular RNA using LIPOFECTAMINE® MessengerMAX (Invitrogen) transfection agent according to manufacturer's instructions. After 48 hour transfection, cells were harvested by trypsinization and resuspended in cold serum-free media. Cells were then stained with anti-SARS-COV-2 RBD antibody for one hour and subsequently incubated with anti-mouse lgG1 antibody AF647 for 30 minutes. The stained population was measured by flow cytometry.

Figure 4:
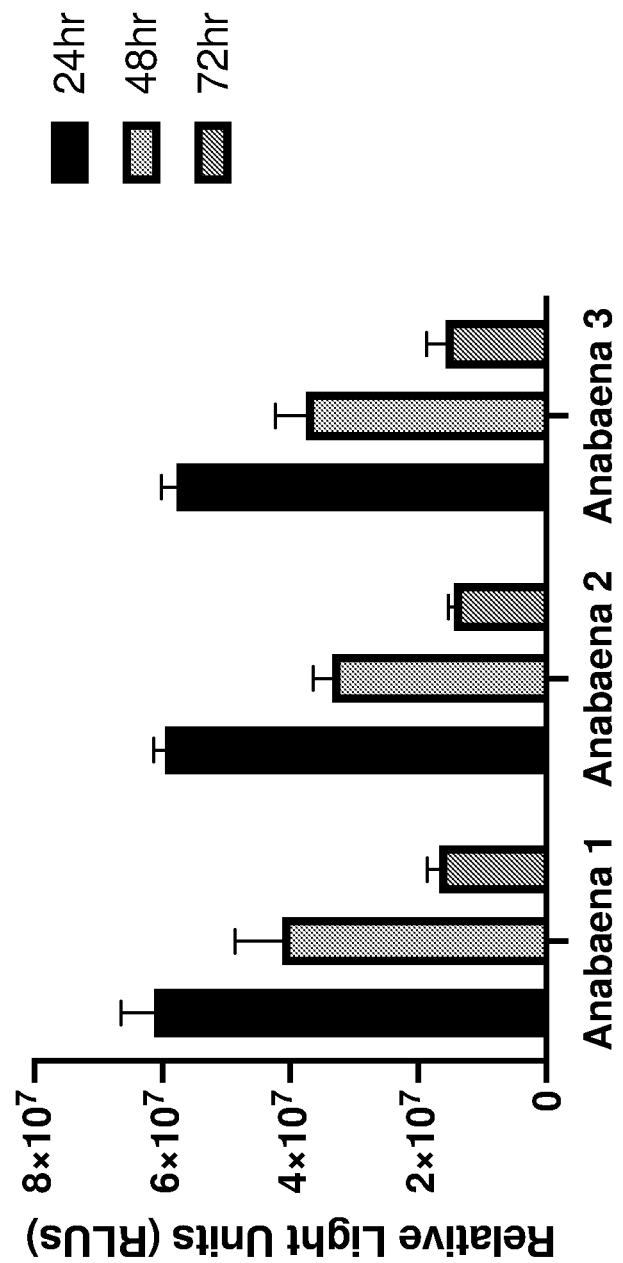
FIG. 4 is a graph showing relative expression of Gluc from circular RNA generated with *Anabaena* permuted intron-exon with an annealing region of 5 nucleotides (*Anabaena* 1), *Anabaena* permuted intron-exon with an extended annealing region (*Anabaena* 2), or *Anabaena* 3 at three different timepoints.
Figure 5:
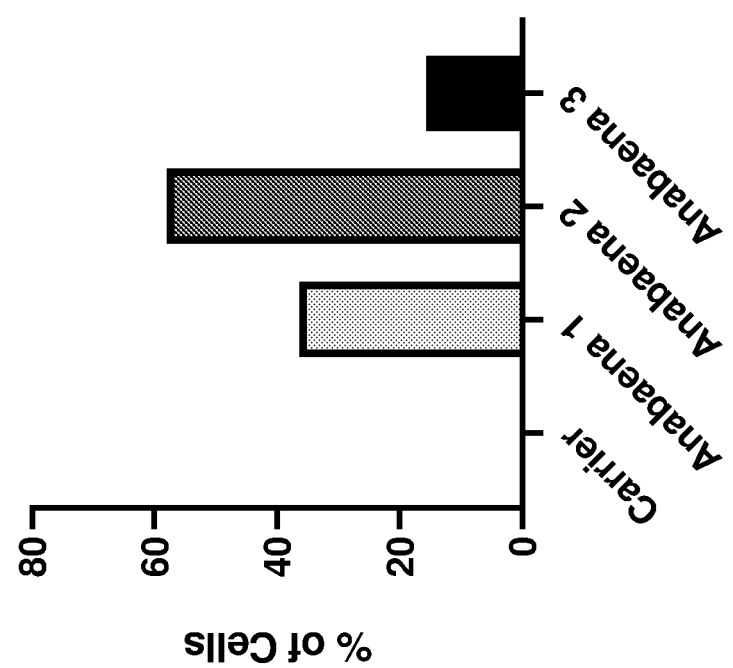
FIG. 5 is a graph showing relative expression SARS-COV-2 spike protein from circular RNA generated with *Anabaena* permuted intron-exon with an annealing region of 5 nucleotides (*Anabaena* 1), *Anabaena* permuted intron-exon with an extended annealing region (*Anabaena* 2), or *Anabaena* 3 at three different timepoints.

Circular RNA generated by *Anabaena* PIE with an extended annealing region (*Anabaena* 2) showed similar expression with circular RNA generated by *Anabaena* PIE with an annealing region of 5 nucleotides (*Anabaena* 1) and *Anabaena* 3-produced circular RNA when encoding Gluc as a polynucleotide cargo (FIG. 4). In the case of circular RNA encoding SARS-COV-2 spike protein, circular RNA generated by *Anabaena* 2 showed around three-fold better expression than *Anabaena* 3-produced circular RNA and 50% more expression than *Anabaena* 1 generated circular RNA (FIG. 5).

Example 3: The Effect of the Length of Annealing Region on Circularization Efficiency in *Anabaena* Self-Splicing PIE This example demonstrates the effect of the length of annealing region on the circularization efficiency in *Anabaena* self-splicing PIE.

Figure 6:
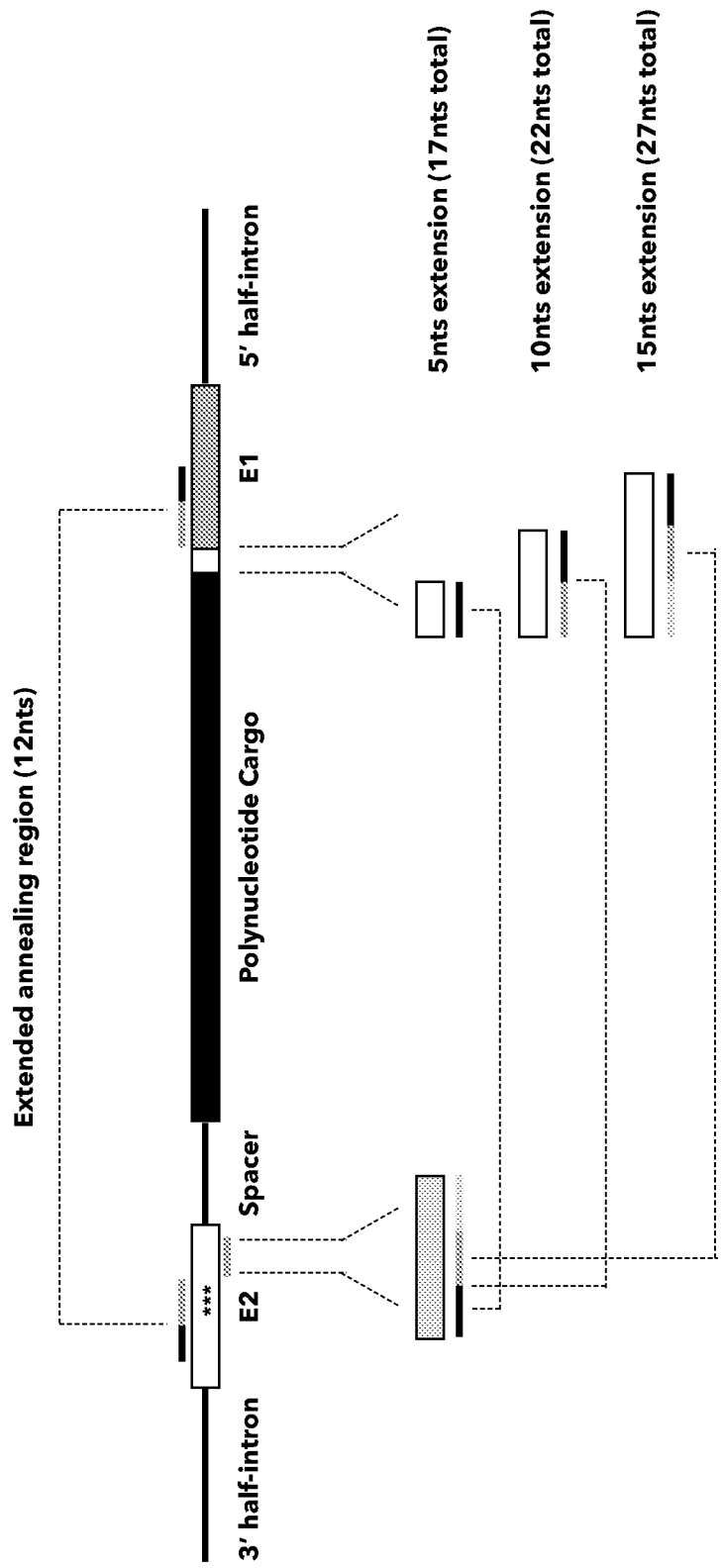
FIG. 6 is a schematic drawing showing exemplary designs of *Anabaena* permuted intron-exon with several extended annealing regions between E2 and E1.

In Example 1 above, we showed that extending the annealing region from 5 nucleotides to 12 nucleotides by mutating the E2 sequence augments circularization efficiency of *Anabaena* PIE. To examine the effect of the length of the annealing region on circularization efficiency, three additional constructs were designed to have a further extended annealing region between E2 and E1 by including additional sequences at the 5' end of E1 that are complementary to E2: (1) 5 nucleotide extension (5'-CGTTT-3') (SEQ ID NO: 7), (2) 10 nucleotide extension (5'-ACGACCGTTT-3') (SEQ ID NO: 8), and (3) 15 nucleotide extension (5'-CCCACACGACCGTTT-3') (SEQ ID NO: 9). The complementary sequence in E2 is a 5 nucleotide extension (5'-AAACG-3') (SEQ ID NO: 10), 10 nucleotide extension 5'-AAACGGTCGT-3') (SEQ ID NO: 11), or 15 nucleotide extension 5'-AAACGGTCGTGTGGG-3') (SEQ ID NO: 12), respectively. Total annealing sequence is 17 nucleotides, 22 nucleotides, or 27 nucleotides, respectively. A schematic depicting exemplary designs of DNA constructs with extended annealing regions between E2 and E1 is provided in FIG. 6.

Constructs with extended annealing sequences (*Anabaena* 2) and extended annealing region (5 nucleotide extension, 10 nucleotide extension and 15 nucleotide extension) were designed to compare circularization efficiency. In this example, the constructs were designed to include polyA50 as the spacer element, and a combination of an EMCV IRES and Gluc as the polynucleotide cargo. Linear RNA was synthesized by in vitro transcription using T7 RNA polymerase in the presence of 7.5 mM of NTP. Template DNA was removed by treating with DNase for 20 minutes. Synthesized linear RNA was purified with an RNA clean up kit (New England Biolabs, T2050).

Self-splicing occurred during transcription; no additional reaction was required. To monitor self-splicing efficiency, 200 ng of column purified in vitro transcribed RNA was mixed with gel loading buffer II (Thermo Fisher, AM8546G) and heated at 95° C. for 3 minutes, then incubated on ice for 3 minutes. The samples were then separated by 6% Urea PAGE, and the RNA band was stained using gel stain and visualized using an imaging system.

Figure 7:
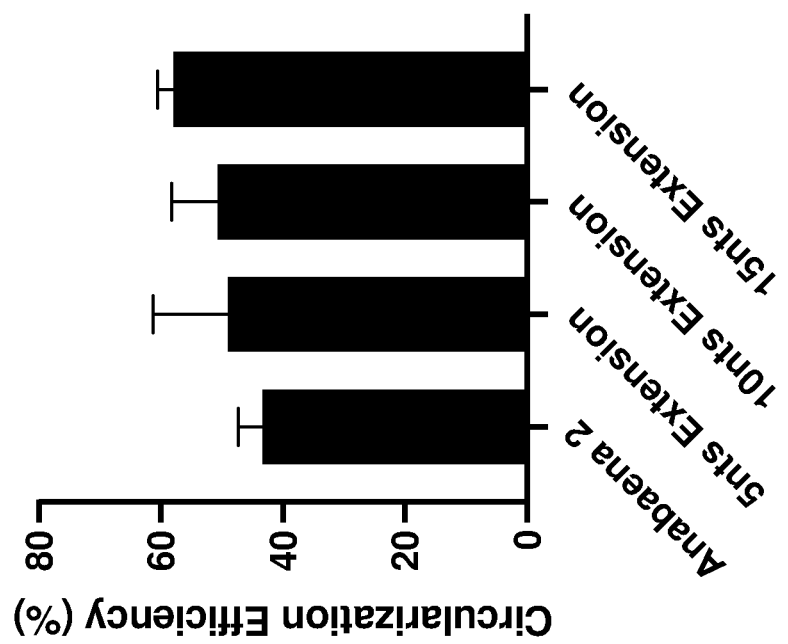
FIG. 7 is a graph showing circularization efficiency with the *Anabaena* permuted intron-exon with an extended annealing region (*Anabaena* 2), and *Anabaena* permuted intron-exon with further 5, 10, or 15 nucleotide extensions of the annealing region.

Further extending of the annealing region between E2 and E1 (5 nts extension, 10 nts extension, or 15 nts extension) showed comparable circularization efficiency with Anabaena PIE with an extended annealing region (Anabaena 2) (FIG. 7). A 15 nucleotide extension of annealing region showed 30% better circularization efficiency compared with Anabaena 2 (FIG. 7). This data indicates that the E2-E1 interaction is important for efficient circularization and further extending the annealing region can increase circularization efficiency.

Example 4: Protein Expression from Circular RNA Generated by *Anabaena* Self-Splicing PIE with Extended Annealing Sequence This example demonstrates protein expression from circular RNA generated by *Anabaena* self-splicing PIE with extended annealing sequence.

In this example, constructs with extended annealing sequences (*Anabaena* 2) and extended annealing region (5 nucleotide extension, 10 nucleotide extension, and 15 nucleotide extension) were designed as described in Example 3 to compare protein expression. In this example, the constructs were designed to include polyA50 as the spacer element, and a combination of an EMCV IRES and Gluc as the polynucleotide cargo.

Linear RNA was synthesized by in vitro transcription using T7 RNA polymerase in the presence of 7.5 mM of NTP. Template DNA was removed by treating with DNase for 20 minutes. Synthesized linear RNA was purified with an RNA clean up kit (New England Biolabs, T2050). Circular RNA encoding Gluc was purified by Urea PAGE, eluted in a buffer (0.5 M Sodium Acetate, 0.1% SDS, 1 mM EDTA), ethanol precipitated, and resuspended in RNAse-free water.

To compare expression of circular RNA encoding Gluc, circular RNA generated by *Anabaena* 2 and *Anabaena* PIE with a further extended annealing region (5 nucleotide extension, 10 nucleotide extension, or 15 nucleotide extension) were prepared as described in Example 3. Hela cells (10,000 cells per well in a 96 well plate) were transfected with 0.1 pmole of purified circular RNAs using LIPOFECTAMINE® MessengerMAX (Invitrogen) transfection agent according to manufacturer's instructions. Transfectants were prepared for each time points separately. At 6 hours, 24 hours and 48 hours, culture media was harvested. To measure Gluc activity, 10 µl of harvested cell media was transferred to a white 96 well plate and a bioluminescent reporter assay system was used according to the manufacturer's instruction (Pierce *Gaussia* Luciferase Flash Assay Kit, 16158, Thermo Scientific). The plate was read in a luminometer instrument (Promega).

Figure 8:
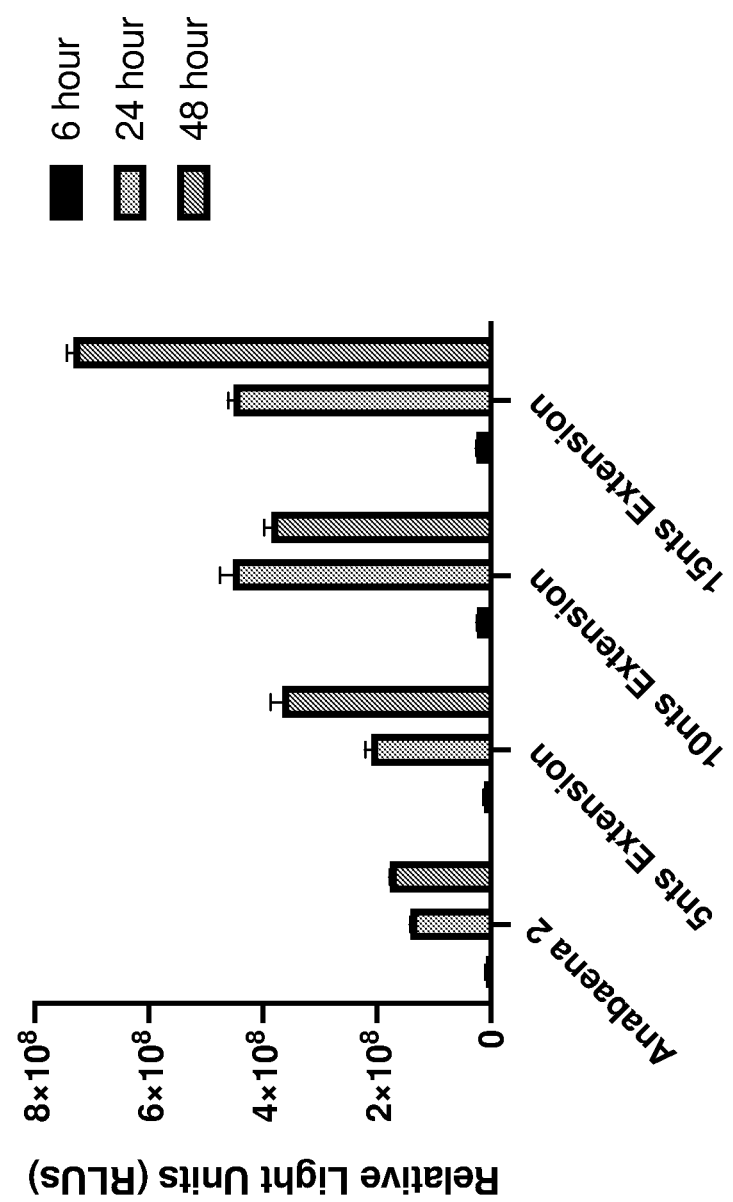
FIG. 8 is a graph showing expression with the *Anabaena* permuted intron-exon with an extended annealing region (*Anabaena* 2), and *Anabaena* permuted intron-exon with further 5, 10, or 15 nucleotide extensions of the annealing region at three different timepoints.

Circular RNA generated by *Anabaena* PIE with a further extended annealing region (5 nts extension, 10 nts extension, or 15 nts extension) showed similar or better expression than that of circular RNA generated by *Anabaena* 2 (FIG. 8). For example, circular RNA generated by *Anabaena* PIE with a 15 nucleotide extension (27 nucleotides total) showed threefold higher expression than *Anabaena* PIE with an extended annealing region of 12 nucleotides (*Anabaena* 2). This data indicates that annealing region extension is important for not only circularization efficiency but also for expression.

Example 5: Design of Tetrahymena Self-Splicing Permuted Intron-Exon (PIE) with Extended Annealing Region This example describes the design of Tetrahymena self-splicing permuted intron-exon (PIE) with extended annealing region.

Figures 9A, 9B:
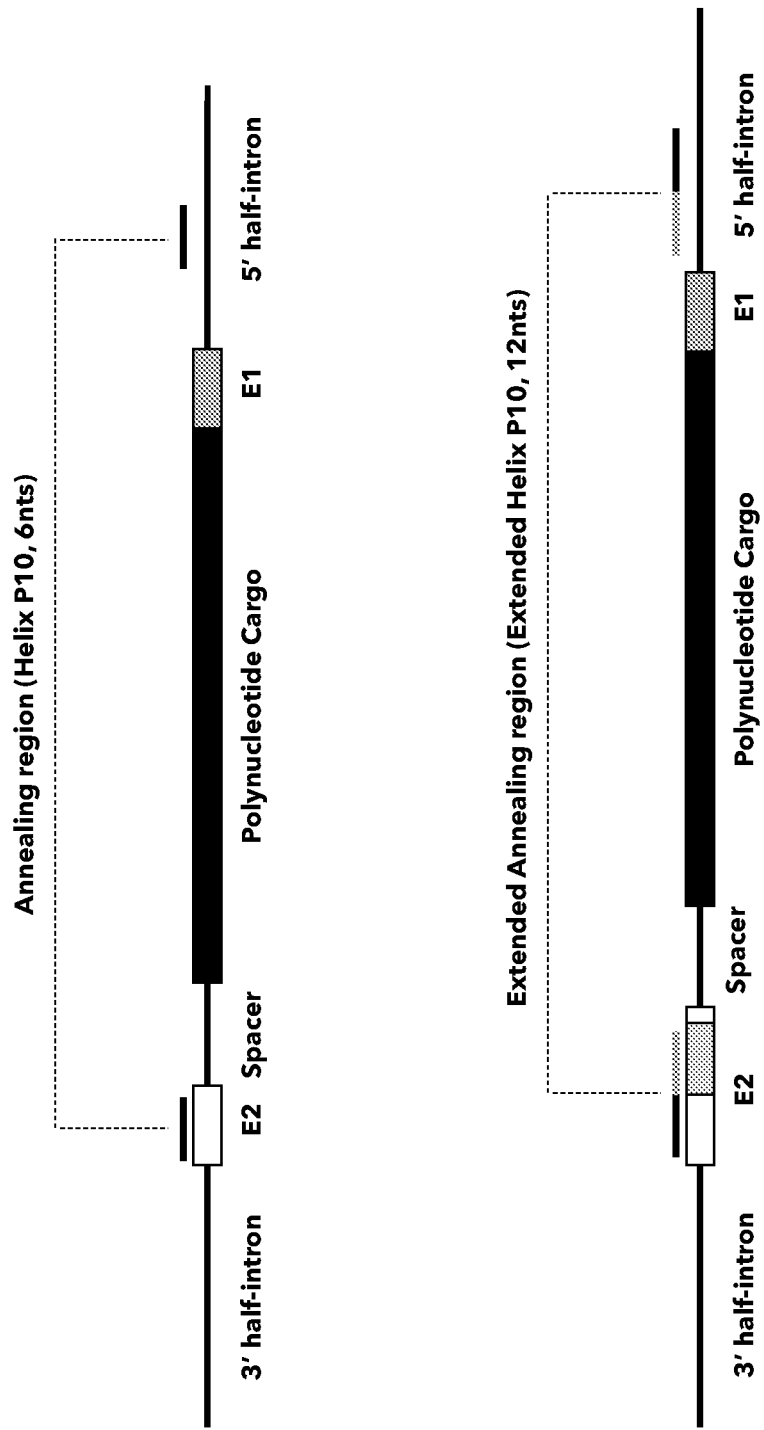
FIGS. 9A and 9B are schematic drawings showing an exemplary Tetrahymena permuted intron-exon with an annealing region of 6 nucleotides (FIG. 9A) and an exemplary Tetrahymena permuted intron-exon with an extended annealing region (FIG. 9B).

Schematics depicting exemplary designs of DNA constructs are provided in FIG. 9A and FIG. 9B.

In this example, the constructs include, from 5'-to-3': a 3' half of group I catalytic intron fragment (Tetrahymena 3' half-intron), a 3' splice site, a 3' exon fragment (Tetrahymena E2), a spacer element, a polynucleotide cargo, a 5' exon fragment (Tetrahymena E1), a 5' splice site, and a 5' half of group I catalytic intron fragment (Tetrahymena 5' half-intron). E2 has a 6 nucleotide complementary sequence (5'-AAGGTA-3') (SEQ ID NO: 13) to the 5' half-intron (5'-TACCTT-3') (SEQ ID NO: 14) that forms helix P10 (FIG. 9, black lines on E1 and 5' half-intron). To generate a construct that has an extended annealing region between E2 and 5' half-intron, 6 nucleotides were added to the 3' end of the annealing region in E2 (5'-AATATT-3' (SEQ ID NO; 15), gray box on E2 in FIGS. 9A and 9B). The total annealing region from Tetrahymena self-splicing PIE with extended annealing region is 12 nucleotides (E2; 5'-AAGGTAAAT-ATT-340 (SEQ ID NO: 16), 5'intron; 5'-AATATTTACCTT-3' (SEQ ID NO: 17), bold characters represent extended annealing region) (FIG. 9B).

The RNA structure was estimated by the RNA structure prediction tool, RNA fold (rna.tbi.univie.ac.at/cgi-bin/RNAWebSuite/RNAfold.cgi). Extension of E2-5' half-intron interaction by additional sequence resulted in proper helix P10 formation and condensed self-splicing intron structure (FIGS. 10A and 10B).

Constructs that have a Tetrahymena permuted intron-exon with an annealing region of 6 nucleotides (Tetrahymena 1) and extended annealing sequences (Tetrahymena 2) were designed to compare circularization efficiency. In this example, the constructs were designed to include polyA50 as the spacer element, and a combination of an EMCV IRES and hEPO ORF as the polynucleotide cargo. The size of the circular RNA was 1.2 Kb.

Linear RNA was synthesized by in vitro transcription using T7 RNA polymerase in the presence of 7.5 mM of NTP. Template DNA was removed by treating with DNase for 20 minutes. Synthesized linear RNA was purified with an RNA clean up kit (New England Biolabs, T2050).

Figure 11:
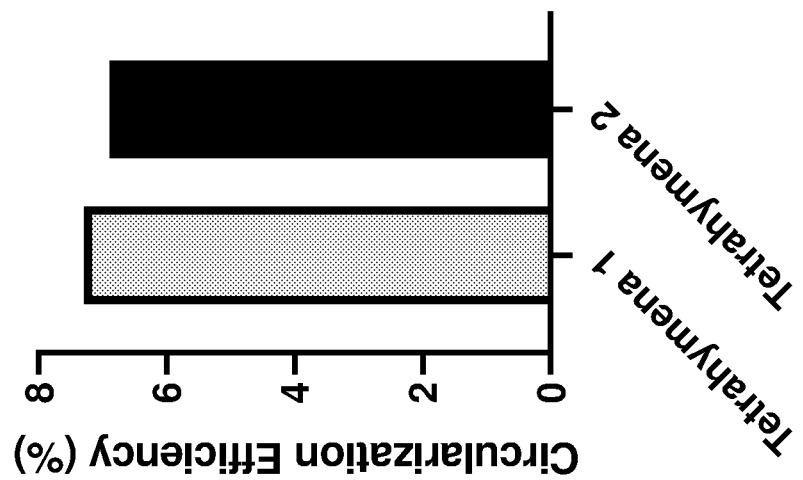
FIG. 11 is a graph showing circularization efficiency of Tetrahymena permuted intron-exon with an annealing region of 6 nucleotides (Tetrahymena 1) and Tetrahymena permuted intron-exon with an extended annealing region (Tetrahymena 2).

Self-splicing occurred during transcription; no additional reaction was required. To monitor circularization efficiency, 200 ng of column purified in vitro transcribed RNA was mixed with gel loading buffer II (Thermo Fisher, AM8546G) and heated at 95° C. for 3 minutes, then incubated on ice for 3 minutes. The samples were then separated by 6% Urea PAGE, and the RNA band was stained using gel stain and visualized using an imaging system. Extending the annealing sequence from 6 nucleotides to 12 nucleotides (Tetrahymena 2) showed similar circularization efficiency with a Tetrahymena self-splicing PIE with an annealing region of 6 nucleotides (Tetrahymena 1) (FIG. 11). This data indicate that circularization was not disrupted by extension of the annealing sequence in Tetrahymena self-splicing PIE.

Example 6: Protein Expression from Circular RNA Generated by Tetrahymena PIE with an Extended Annealing Region This example describes protein expression from circular RNA generated by Tetrahymena self-splicing PIE with an extended annealing region.

To compare protein expression, DNA constructs having a Tetrahymena self-splicing PIE with an annealing region of 6 nucleotides (Tetrahymena 1) and extended annealing sequences (Tetrahymena 2) are designed as described in Example 5. The constructs are designed to include a polyA50 as the spacer element, and a combination of an EMCV IRES, and Gluc ORF as the polynucleotide cargo.

Linear RNA is synthesized by in vitro transcription using T7 RNA polymerase in the presence of 7.5 mM of NTP. Template DNA is removed by treating with DNase. Synthesized linear RNA is purified with an RNA clean up kit (New England Biolabs, T2050). Circular RNA encoding Gluc is purified by Urea PAGE, eluted in a buffer (0.5 M Sodium Acetate, 0.1% SDS, 1 mM EDTA), ethanol precipitated, and resuspended in RNAse-free water.

To compare expression of circular RNA encoding Gluc, circular RNA generated by Tetrahymena PIE with an annealing region of 6 nucleotides (Tetrahymena 1) and Tetrahymena PIE with an extended annealing region (Tetrahymena 2) are prepared as described above. Hela cells (10,000 cells per well in a 96 well plate) are transfected with 0.1 pmoles of purified circular RNA using LIPOFECTAMINE® MessengerMAX (Invitrogen) transfection agent according to manufacturer's instructions. Transfectants are prepared for each time points separately. At 6 hours, 24 hours and 48 hours, culture media is harvested. To measure Gluc activity, harvested cell media is transferred to a white 96 well plate and a bioluminescent reporter assay system is used according to manufacturer's instructions. The plate is read in a luminometer instrument.

Example 7: Design of T4 Phage Self-Splicing Permuted Intron-Exon (PIE) with Extended Annealing Region This example describes the design of T4 phage self-splicing PIE with extended annealing region.

Figures 12A, 12B:
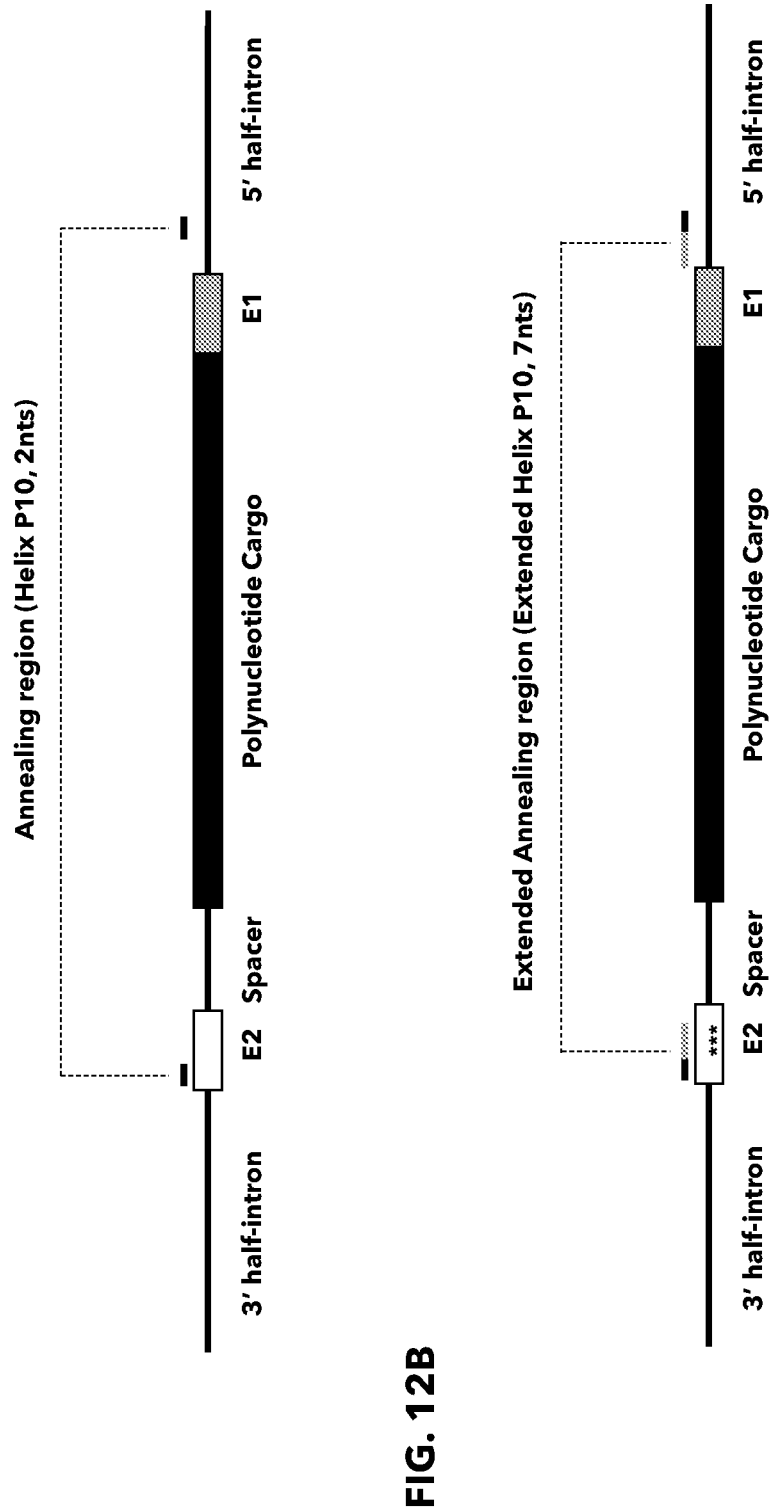
FIGS. 12A and 12B are schematic drawings showing an exemplary T4 phage permuted intron-exon with an annealing region of 2 nucleotides (FIG. 12A) and an exemplary T4 phage permuted intron-exon with an extended annealing region (FIG. 12B).

Schematics depicting exemplary designs of DNA constructs are provided in FIG. 12A and FIG. 12B. The construct includes, from 5'-to-3': a 3' half of group I catalytic intron fragment (T4 phage 3' half-intron), a 3' splice site, a 3' exon fragment (T4 phage E2), a spacer element, a polynucleotide cargo, a 5' exon fragment (T4 phage E1), a 5' splice site, and a 5' half of group I catalytic intron fragment (T4 phage 5' half-intron). E2 has a 2 nucleotide complementary sequence (5'-CT-3') to the 5' half-intron (5'-AG-3') that forms helix P10 (FIGS. 12A and 12B, black lines on E2 and 5' half-intron). To generate a construct that has an extended annealing region between E2 and 5' half-intron, 4 nucleotides from E2 were mutated to have an extended 5 nucleotide annealing region with the 5' half-intron (5'-ACCGT-3' (SEQ ID NO: 18)→5'-CAATT-3' (SEQ ID NO: 19), bold characters represent mutated sequences). The total annealing region from T4 phage PIE with an extended annealing region is 7 nucleotides (E2; 5'-CTCAATT-3' (SEQ ID NO: 20), 5' half-intron; 5'-AATTGAG-3' (SEQ ID NO: 21), bold characters represent extended annealing sequences) (FIGS. 12A and 12B).

To compare circularization efficiency, constructs that have T4 phage PIE with an annealing region of 2 nucleotides (T4 phage 1) and extended annealing sequences (T4 phage 2) were designed. In this example, the constructs were designed to include polyA50 as the spacer element, a combination of an EMCV IRES and Gluc ORF as the polynucleotide cargo. The size of the circular RNA was 1.2 K. Linear RNA was synthesized by in vitro transcription using T7 RNA polymerase in the presence of 7.5 mM of NTP. Template DNA was removed by treating with DNase. Synthesized linear RNA was purified with an RNA clean up kit (New England Biolabs, T2050).

Self-splicing occurred during transcription; no additional reaction is required. To monitor circularization efficiency, 200 ng of column purified in vitro transcribed RNA was mixed with gel loading buffer II (Thermo Fisher, AM8546G) and heated at 95° C. for 3 minutes, then incubated on ice for 3 minutes. The samples were then separated by 6% Urea PAGE, and the RNA band was stained using gel stain and visualized using an imaging system.

Figure 13:
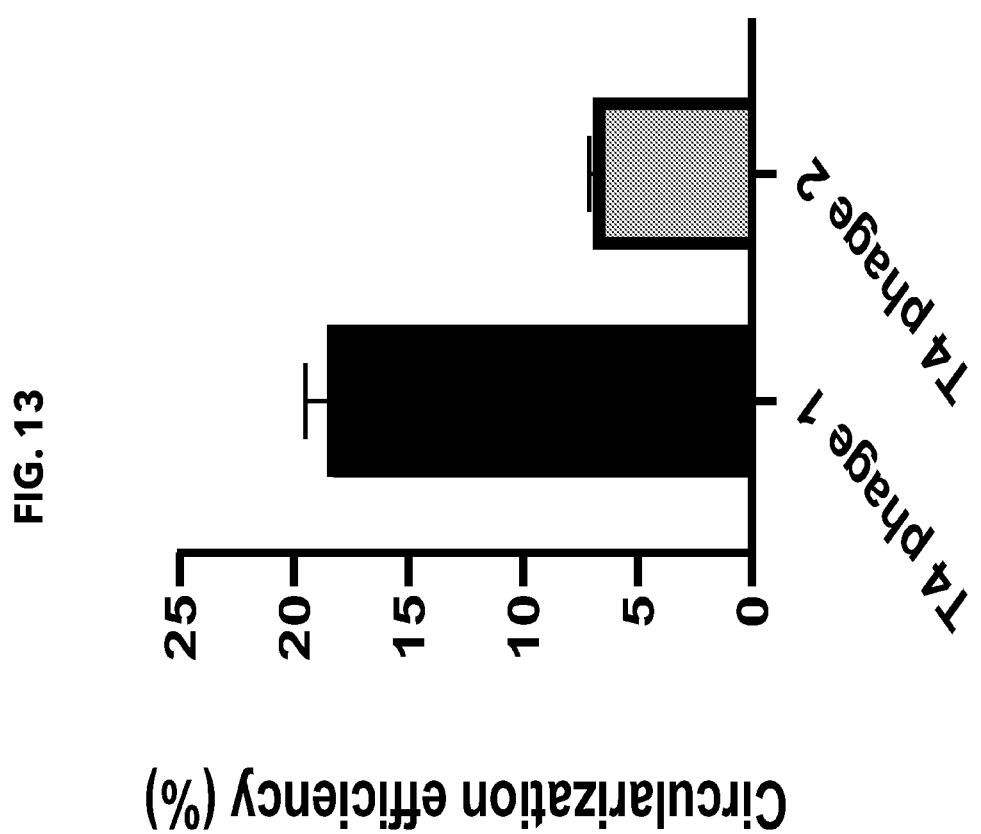
FIG. 13 is a graph showing circularization efficiency of T4 phage permuted intron-exon with an annealing region of 2 nucleotides (T4 phage 1) and T4 phage permuted intron-exon with an extended annealing region (T4 phage 2).

Extending the annealing sequence (T4 phage 2) showed similar circularization efficiency with a T4 phage self-splicing PIE with an annealing region of 6 nucleotides (T4 phage 1) (FIG. 13). This data indicate that circularization was not disrupted by extension of the annealing sequence in T4 phage self-splicing PIE.

Example 8: Protein Expression from Circular RNA Generated by T4 Phage Self-Splicing PIE with an Extended Annealing Region This example describes expression of circular RNA generated by T4 phage self-splicing PIE with an extended annealing region.

To compare protein expression, DNA constructs with T4 phage PIE with an annealing region of 2 nucleotides (T4 phage 1) and extended annealing sequences (T4 phage 2) are designed as described in Example 7. In this example, the constructs are designed to include polyA50 as the spacer element, and a combination of an EMCV IRES and Gluc ORF as the polynucleotide cargo.

Linear RNA is synthesized by in vitro transcription using T7 RNA polymerase in the presence of 7.5 mM of NTP. Template DNA is removed by treating with DNase. Synthesized linear RNA is purified with an RNA clean up kit (New England Biolabs, T2050). Circular RNA encoding Gluc is purified by Urea PAGE, eluted in a buffer (0.5 M Sodium Acetate, 0.1% SDS, 1 mM EDTA), ethanol precipitated, and resuspended in RNAse-free water.

To compare expression of circular RNA encoding Gluc, circular RNA generated by T4 phage PIE with an annealing region of 2 nucleotides (T4 phage 1) and T4 phage PIE with an extended annealing region (T4 page 2) are prepared as described above. HeLa cells (10,000 cells per well in a 96 well plate) are transfected with 0.1 pmole of purified circular RNAs using LIPOFECTAMINE® MessengerMAX (Invitrogen) transfection agent according to manufacturer's instructions. Transfectants are prepared for each time point separately. At 6 hours, 24 hours and 48 hours, culture media is harvested. To measure Gluc activity, harvested cell media is transferred to a white 96 well plate and a bioluminescent reporter assay system is used according to the manufacturer's instructions. The plate is read in a luminometer instrument.

Example 9: Design of Self-Splicing Permuted Intron-Exon (PIE) Construct with Extended Annealing Region This example describes the design of various self-splicing permuted intron-exon (PIE) sequences with extended annealing region to provide better circularization efficiency.

Figure 14A:
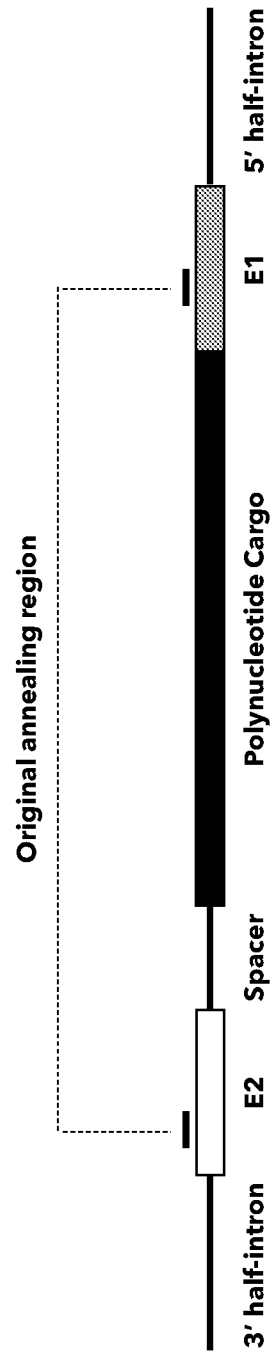
FIGS. 14A and 14B are schematic drawings showing an exemplary permuted intron-exon with an annealing region (FIG. 14A) and an exemplary permuted intron-exon with an extended annealing region (FIG. 14B).
Figure 14B:
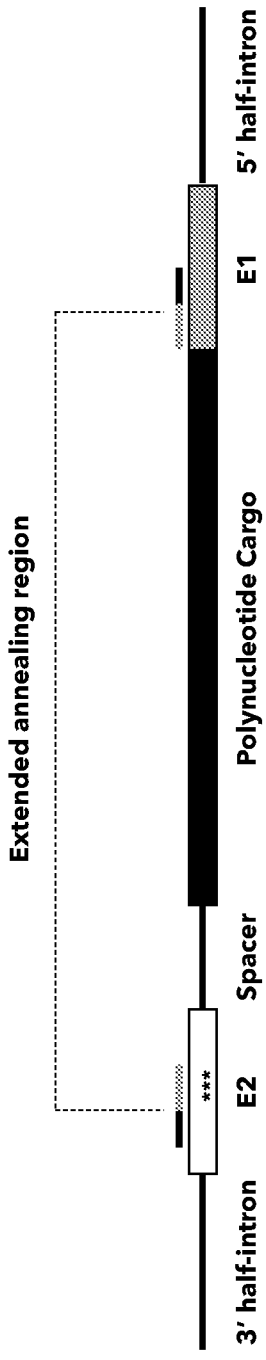
Figure 15B:
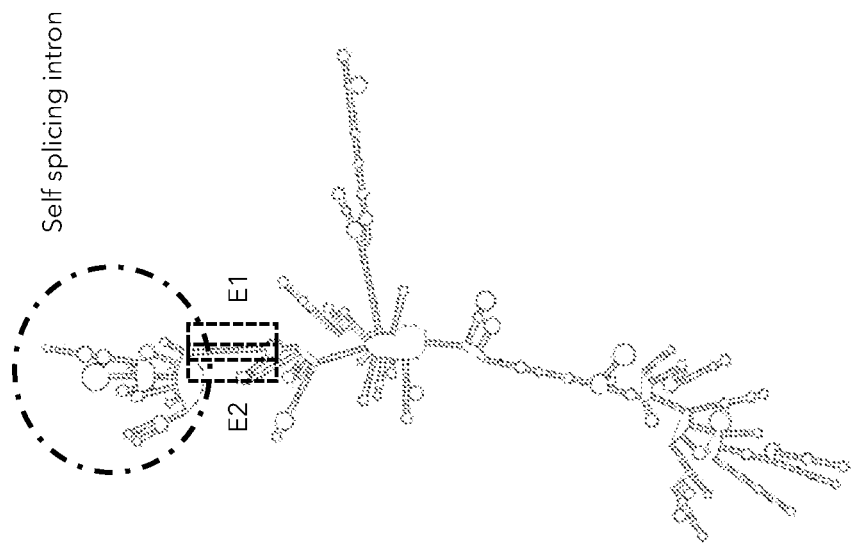
FIGS. 15A and 15B are schematic drawings showing the structures of an exemplary *Synechococcus* permuted intron-exon with an annealing region of 7 nucleotides (FIG. 15A) and an exemplary *Synechococcus* permuted intron-exon with a modified and extended annealing region (FIG. 15B).
Figure 15A:
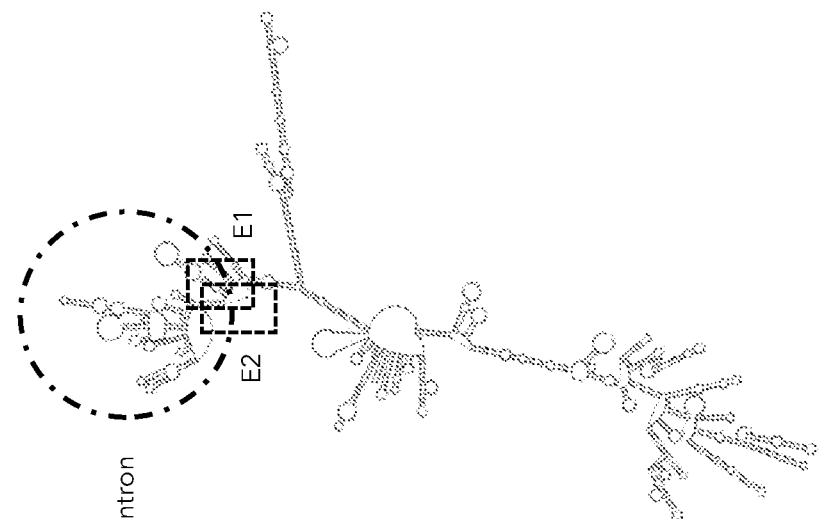
Figure 16B:
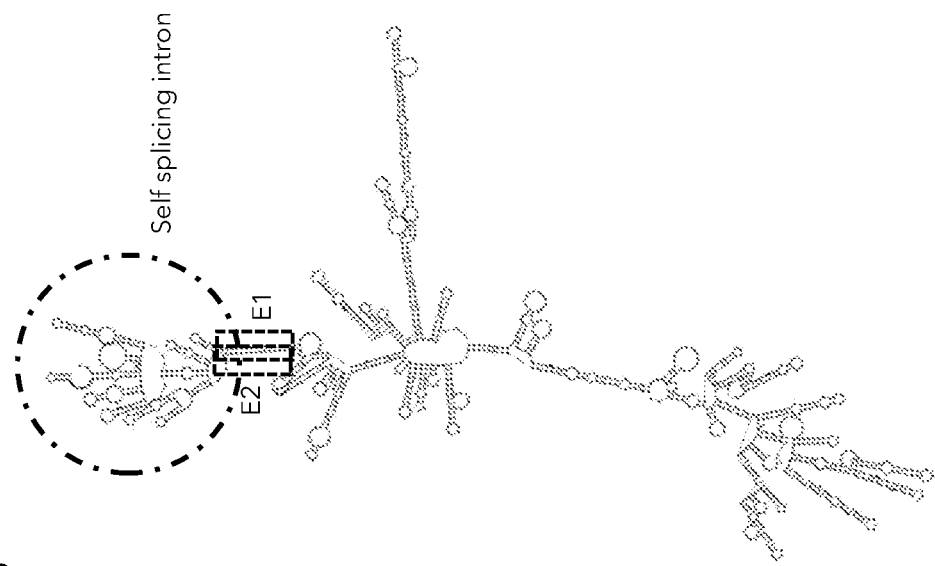
FIGS. 16A and 16B are schematic drawings showing the structures of an exemplary *Anabaena azollae* permuted intron-exon with an annealing region of 5 nucleotides (FIG. 16A) and an exemplary *Anabaena azollae* permuted intron-exon with a modified and extended annealing region (FIG. 16B).
Figure 16A:
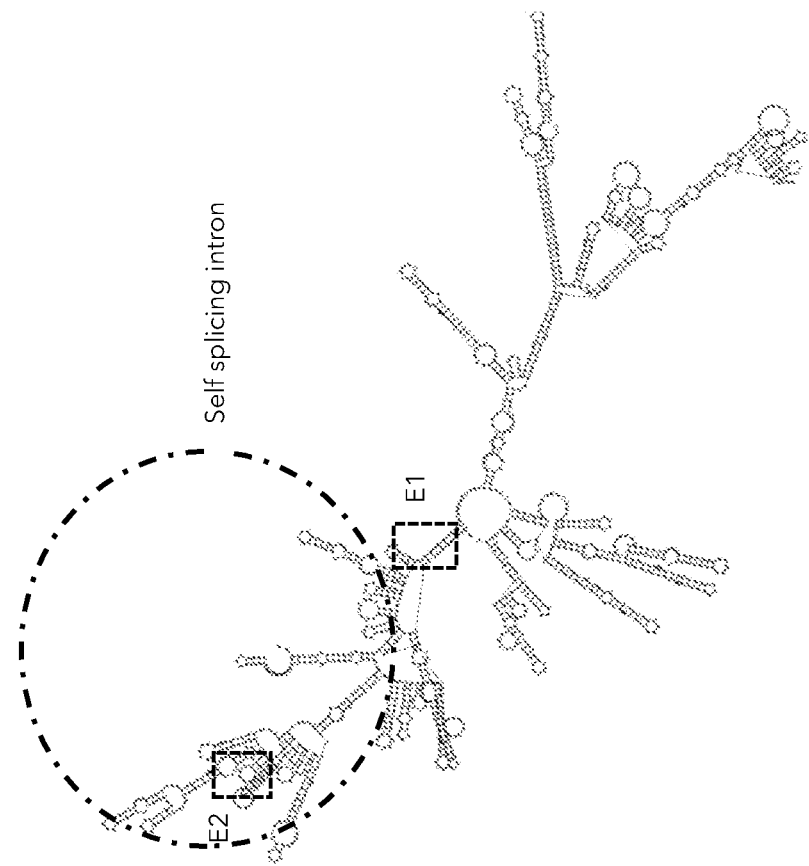
Figure 17B:
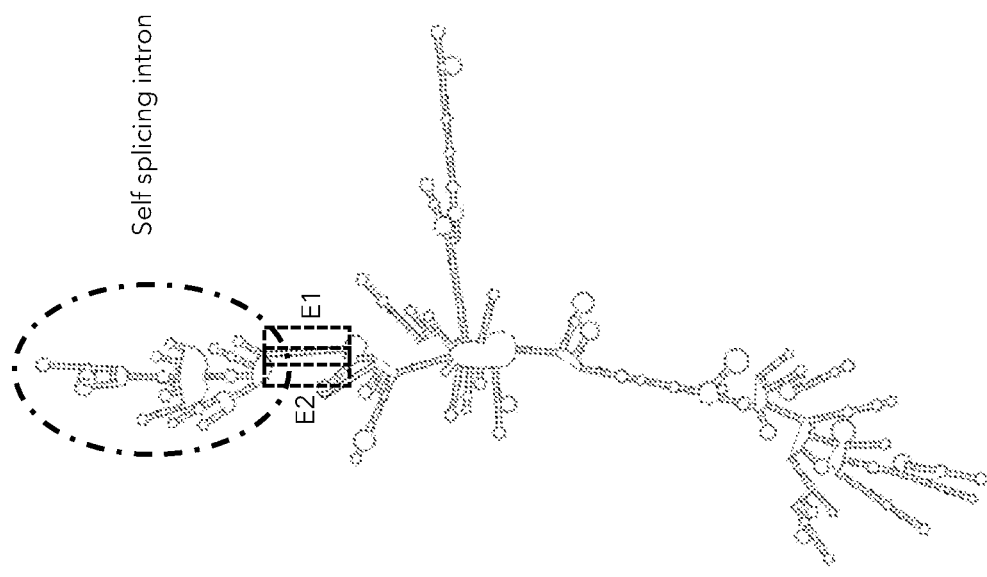
FIGS. 17A and 17B are schematic drawings showing the structures of an exemplary *Anabaena cylindrica* with an annealing region of 5 nucleotides (FIG. 17A) and an exemplary *Anabaena cylindrica* permuted intron-exon with a modified and extended annealing region (FIG. 17B).
Figure 17A:
Figure 18B:
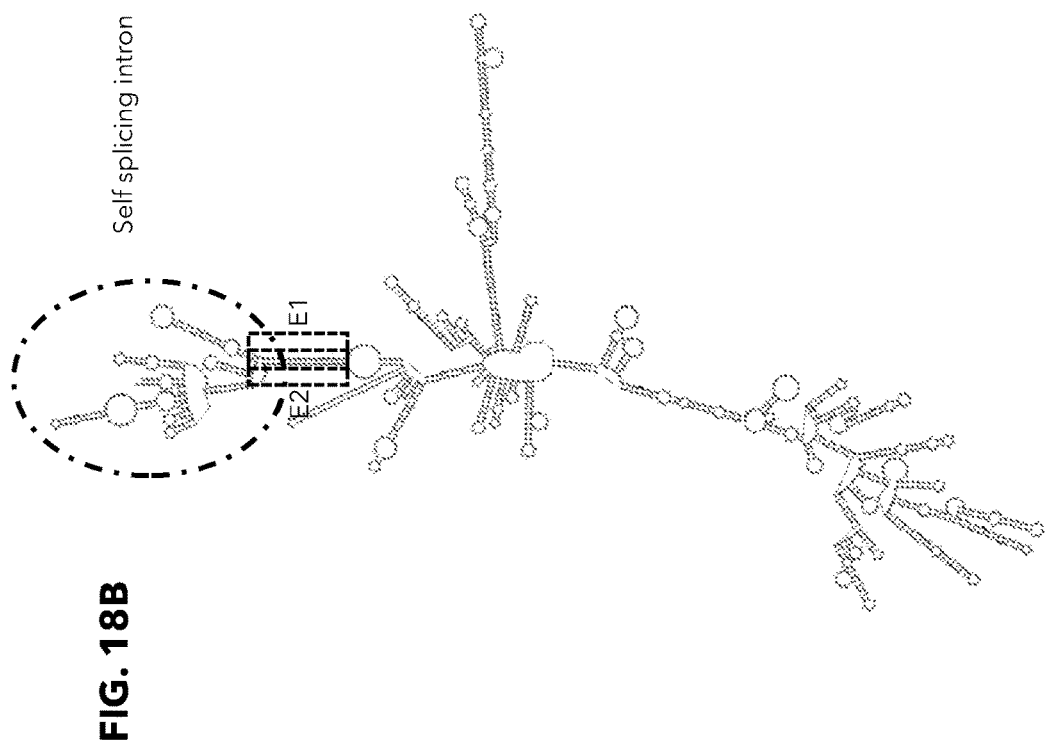
FIGS. 18A and 18B are schematic drawings showing the structures of an exemplary *Scytonema* permuted intron-exon with an annealing region of 5 nucleotides (FIG. 18A) and an exemplary *Scytonema* permuted intron-exon with a modified and extended annealing region (FIG. 18B).
Figure 18A:

Schematics depicting exemplary designs of DNA constructs are provided in FIG. 14A and FIG. 14B. In this example, the constructs include, from 5' to 3': a 3' half of group I catalytic intron fragment (3' half-intron), a 3' splice site, a 3' exon fragment (E2), a spacer element, a polynucleotide cargo, a 5' exon fragment (E1), a 5' splice site, and a 5' half of group I catalytic intron fragment (5' half-intron).

Different group I introns have different lengths of complementary sequence (FIG. 19). For example, E2 of *Synechococcus elongatus* PCC 6301 has a 7 nucleotide complementary sequence to E1 of *Synechococcus elongatus* PCC 6301; E2 of *Anabaena azollae, Anabaena cylindrica*, and *Scytonema hofmanni* have 5 nucleotides of complementary sequences to E1 of *Anabaena azollae, Anabaena cylindrica*, and *Scytonema hofmanni*, respectively. To generate a construct that has an extended annealing region between E2 and E1, sequences in E2 were mutated to have an extended annealing region with E1 as described in FIG. 19. The total annealing region from group I permuted intron-exon (PIE) with an extended annealing region is 17 nucleotides.

Original (1) and extended (2) annealing regions from FIG. 19 are as follows:

*Synechococcus* 1 TCCGCTGACTGTAAAGG (SEQ ID NO: 92)
*Synechococcus* 2 TCCGCTGCGTCTACCGT (SEQ ID NO: 93)
*Anabaena azollae* 1 TCCGTTGACTGTAAAAA (SEQ ID NO: (94)
*Anabaena azollae* 2 TCCGTAGCGTCTACCAT (SEQ ID NO: 95)
*Anabaena cylindrica* 1 TCCGTTGACCTTAAACG (SEQ ID NO: 96)
*Anabaena cylindrica* 2 TCCGTAGCGTCTACCAT (SEQ ID NO: 97)
*Scytonema* 1 CCCGAAGGTCAGTGGTT (SEQ ID NO: 98)
*Scytonema* 2 CCCGACGAGCTACCAGG (SEQ ID NO: 99)

The RNA structures were estimated by RNA structure prediction tool, RNA fold (rna.tbi.univie.ac.at/cgi-bin/RNAWebSuite/RNAfold.cgi). Extension of E2-E1 interaction was generated by modifying sequence results in proper E2-E1 interaction and condensed self-splicing intron structure (FIGS. 15A-15B, 16A-16B, 17A-17B, and 18A-18B).

Constructs that have the PIE with an original annealing region and annealing sequences with an extended annealing region were designed to compare circularization efficiency. For comparison, *Anabaena* 1 and *Anabaena* 2 constructs were also used. In this example, the constructs were designed to include a spacer element, and a combination of an EMCV IRES and a 3822 nucleotide ORF as the polynucleotide cargo. The size of the circular RNA was 4.5 Kb.

Unmodified linear RNA was synthesized by in vitro transcription using T7 RNA polymerase from a DNA template in the presence of 12.5 mM of NTP. Template DNA was removed by treating with DNase for 20 minutes. Synthesized linear RNA was purified with an RNA clean up kit (New England Biolabs, T2050). Self-splicing occurred during transcription; no additional reaction was required. To monitor self-splicing efficiency, column purified in vitro transcribed RNA was separated on an anionic exchange (AEX) column through HPLC. The percentage of linear and circular peaks were measured, and circularization efficiency was normalized with that of constructs that have the PIE with the original annealing region.

Figure 20:
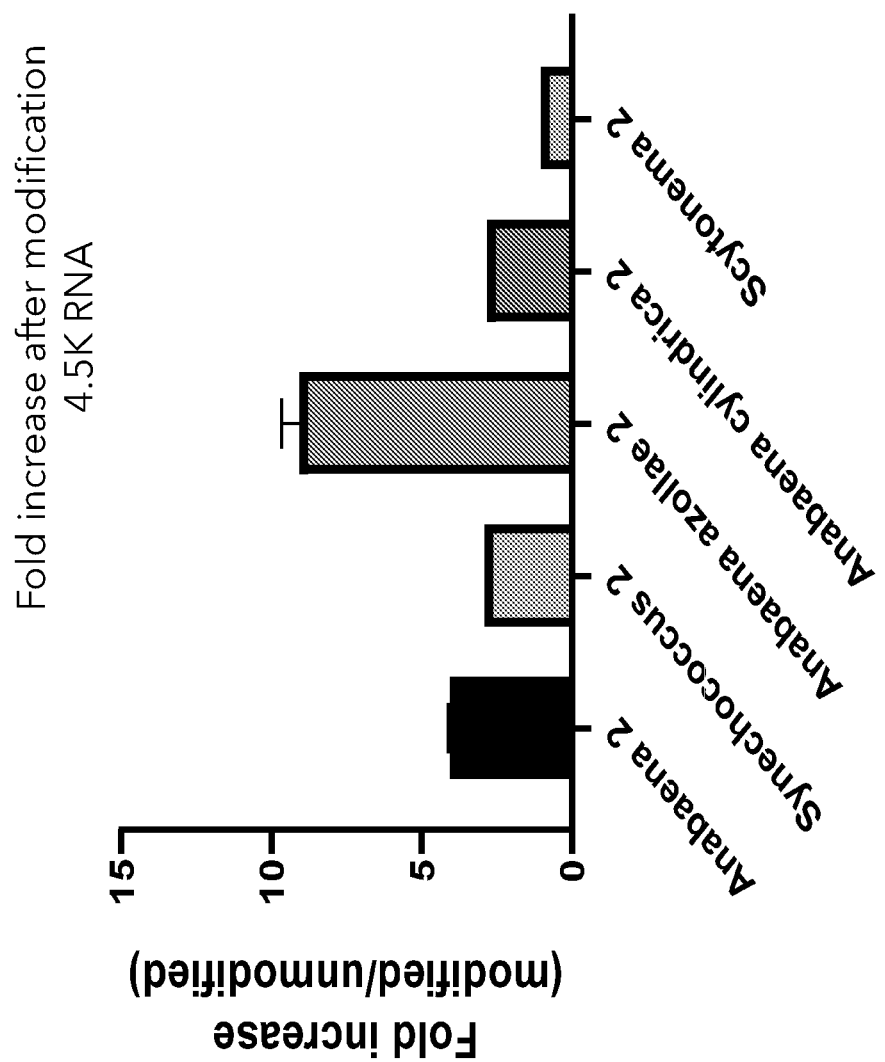
FIG. 20 is a graph showing fold increase of circularization of various modified permuted intron-exon with a 4.5 Kb RNA relative to the unmodified (original) permuted intron-exon with a 4.5 Kb RNA. Enhanced circularization efficiency is observed with group I introns with permuted intron-exon with extended E2-E1 annealing region.

Extending the annealing sequence increased circularization efficiency up to five-fold for *Anabaena* (*Anabaena* 2), *Synechococcus elongatus* PCC 6301 (*Synechococcus* 2), and *Anabaena cylindrica* (*Anabaena* cyclindrica 2), and up to ten-fold for *Anabaena azollae* (*Anabaena azollae* 2), but no increase in circularization efficiency was observed for *Scytonema hofmanni* (*Scytonema* 2) (FIG. 20). This shows that circularization efficiency can be increased by modifying other group I introns using the same or similar strategy as described herein for *Anabaena* intron.

Example 10: Design of *Anabaena* Self-Splicing Permuted Intron-Exon (PIE) Construct with Extended Stem Region to Enhance End to End Interaction This example describes the design of *Anabaena* self-splicing permuted intron-exon (PIE) sequences with extended stem region to provide better circularization efficiency by enhancing end to end interaction.

Figure 21A:
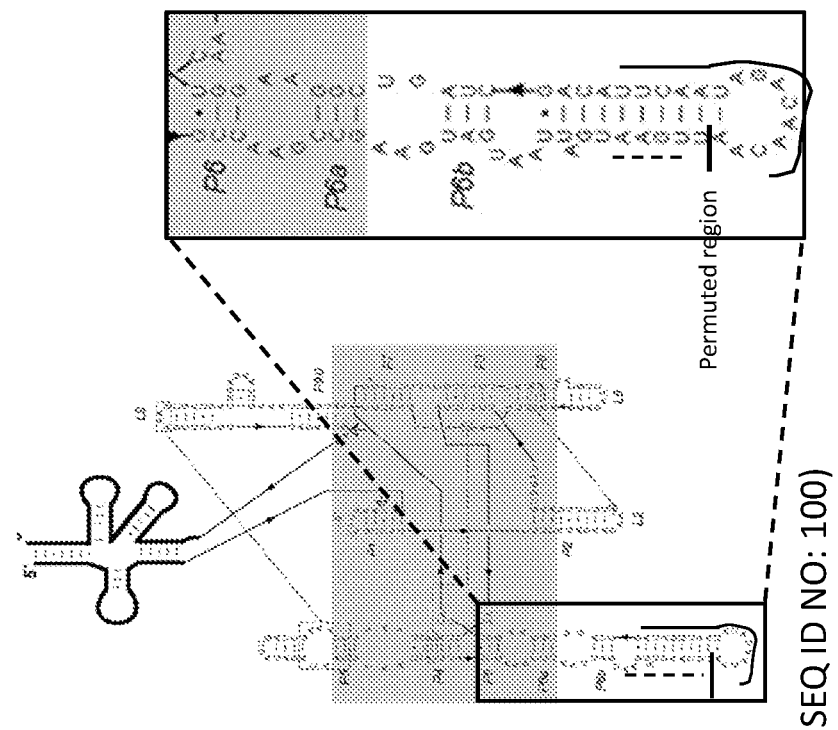
FIG. 21A is a schematic drawing showing secondary structure of *Anabaena* self-splicing intron (SEQ ID NO: 100). Permuting region in P6b is highlighted.
Figure 21B:
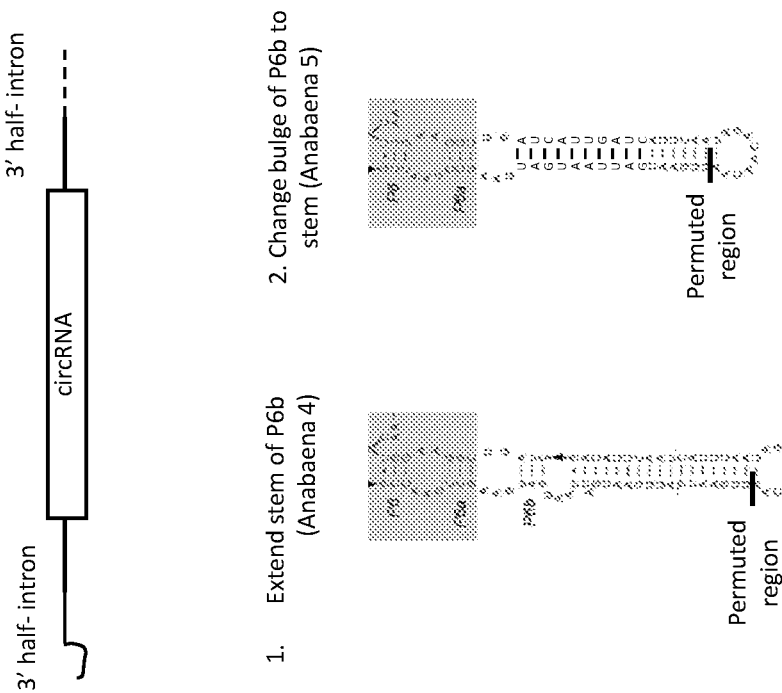
FIG. 21B are schematic drawings showing the structures of exemplary designs of *Anabaena* permuted intron-exon with an extended P6b stem (*Anabaena* 4; SEQ ID NO: 101) or with change of bulge of P6b to stem (*Anabaena* 5; SEQ ID NO: 102).

Schematics depicting exemplary designs of DNA constructs are provided in FIG. 21B. In this example, the constructs include, from 5' to 3': a 3' half of group I catalytic intron fragment (*Anabaena* 3' half-intron), a 3' splice site, a 3' exon fragment (*Anabaena* E2), a spacer element, a polynucleotide cargo, a 5' exon fragment (*Anabaena* E1), a 5' splice site, and a 5' half of group I catalytic intron fragment (*Anabaena* 5' half-intron). Two versions of constructs that have an extended stem region were designed. For design of *Anabaena* 4, an additional stem region (5'-GUAAGUU-3') was placed next each other. For design of *Anabaena* 5, a bulge region in P6b was filled to make a stem.

Unmodified linear RNA was synthesized by in vitro transcription using T7 RNA polymerase from a DNA template in the presence of 12.5 mM of NTP. Template DNA was removed by treating with DNase for 20 minutes. Synthesized linear RNA was purified with an RNA clean up kit (New England Biolabs, T2050). Self-splicing occurred during transcription; no additional reaction was required. To monitor self-splicing efficiency, column purified in vitro transcribed RNA was separated on an anionic exchange (AEX) column through HPLC. The percentage of linear and circular peaks were measured and circularization efficiency was normalized with that of the corresponding original constructs.

Figure 22:
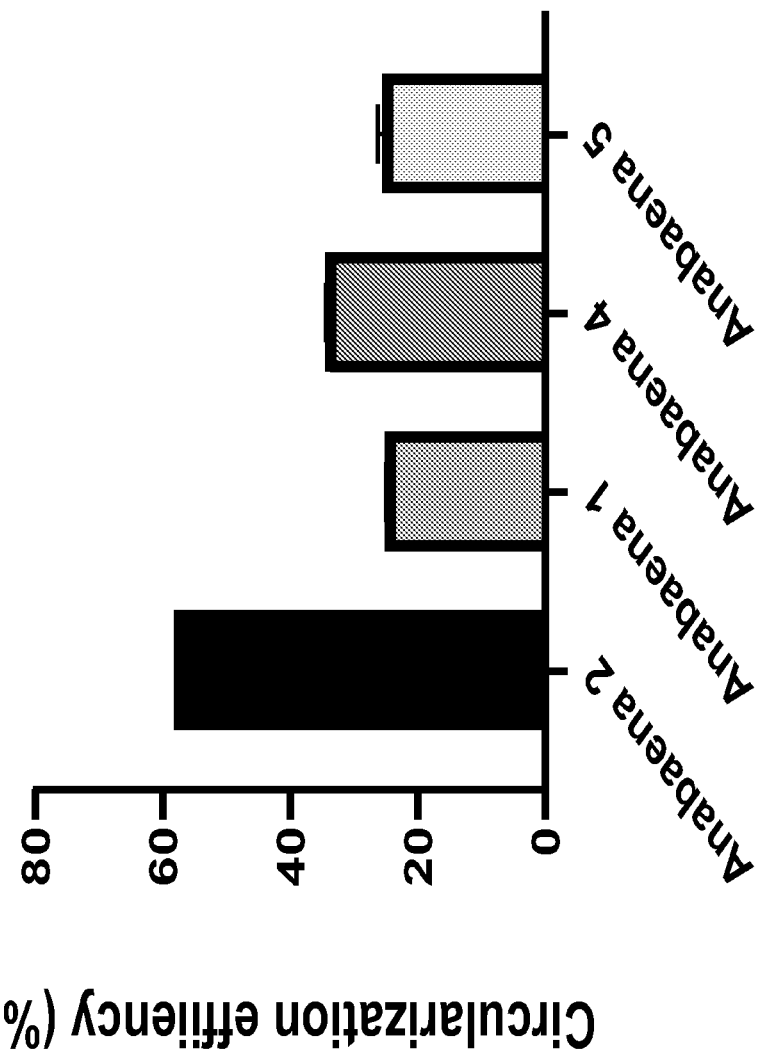
FIG. 22 is a graph showing circularization efficiency with the *Anabaena* permuted intron-exon with an extended annealing region (*Anabaena* 2), *Anabaena* permuted intron-exon with an annealing region of 5 nucleotides (*Anabaena* 1), *Anabaena* 4, and *Anabaena* 5.

Constructs with an extended stem region showed comparable circularization efficiency with constructs that have the *Anabaena* PIE with an extended annealing region (*Anabaena* 2) and constructs that have the *Anabaena* PIE with an annealing region of 5 nucleotides (*Anabaena* 1) (FIG. 22).

*Synechococcus elongatus* PCC 6301: 3' half-intron E2

(SEQ ID NO: 80)
TAAACAACTAACAGCTTTAGAAGGTGCAGAGACTAGACGGGAGCTACCC

TAACGGATTCAGCCGAGGGTAAAGGGATAGTCCAATTCTCAACATCGCG

ATTGTTGATGGCAGCGAAAGTTGCAGAGAGAATGAAAATCCGCTGACTG

TAAAGGTCGTGAGGGTTCGAGTCCCTCCGCCCCA

*Synechococcus elongatus* PCC 6301: E1 5' half-intron (SEQ ID NO: 81)
ACGGTAGACGCAGCGGACTTAGAAAACTGGGCCTCGATCGCGAAAGGGA

TCGAGTGGCAGCTCTCAAACTCAGGGAAACCTAAAACTTTAAACATTMA

AGTCATGGCAATCCTGAGCCAAGCTAAAGC

*Anabaena azollae:* 3' half-intron E2

(SEQ ID NO: 82)
TTAAACTCAAAATTTAAAATCCCAAATTCAAAATTCCGGGAAGGTGCAG

AGACTCGACGGGAGCTACCCTAACGTAAAGCCGAGGGTAAAGGGAGAGT

CCAATTCTCAAAGCCTGAAGTTGCTGAAGCAACAAGGCAGTAGTGAAAG

CTGCGAGAGAATGAAAATCCGTTGACTGTAAAAAGTCGTGGGGGTTCAA

GTCCCCCCACCCCC

*Anabaena azollae*: E1 5' half-intron (SEQ ID NO: 83)
ATGGTAGACGCTACGGACTTAGAAAACTGAGCCTTGATAGAGAAATCTT

TTAAGTGGAAGCTCTCAAATTCAGGGAAACCTAAATCTGAATACAGATA

TGGCAATCCTGAGCCAAGCCCAGAAAATTTAGACTTGAGATTTGATTTT

GGAG

*Anabaena cylindrica:* 3' half-intron E2

(SEQ ID NO: 84)
GGCTTTCAATTTGAAATCAGAAATTCAAAATTCAGGGAAGGTGCAGAGA

CTCGACGGGAGCTACCCTAACGTAAAGGCGAGGGTAAAGGGAGAGTCCA

ATTCTTAAAGCCTGAAGTTGTGCAAGCAACAAGGCAACAGTGAAAGCTG

TGGAAGAATGAAAATCCGTTGACCTTAAACGGTCGTGGGGGTTCAAGTC

CCCCCACCCCC

*Anabaena cylindrica*: E1 5' half-intron (SEQ ID NO: 85)
ATGGTAGACGCTACGGACTTAGAAAACTGAGCCTTGATAGAGAAATCTT

TCAAGTGGAAGCTCTCAAATTCAGGGAAACCTAAATCTGAATACAGATA

TGGCAATCCTGAGCCAAGCCCGGAAATTTTAGAATCAAGATTTTATTTT

*Scytonema hofmanni:* 3' half-intron E2

(SEQ ID NO: 86)
AGAAATGGAGAAGGTGTAGAGACTGGAAGGCAGGCACCCTAACGTTAAA

GGCGAGGGTGAAGGGACAGTCCAGACCACAAACCAGTAAATCTGGGCAG

CGAAAGCTGTAGATGGTAAGCATAACCCGAAGGTCAGTGGTTCAAATCC

ACTTCCCGCCACCAAATTAAAAAAACAATAA

*Scytonema hofmanni*: E1 5' half-intron (SEQ ID NO: 87)
AGAAATGGAGAAGGTGTAGAGACTGGAAGGCAGGCACCCTAACGTTAAA

GGCGAGGGTGAAGGGACAGTCCAGACCACAAACCAGTAAATCTGGGCAG

CGAAAGCTGTAGATGGTAAGCATAACCCGAAGGTCAGTGGTTCAAATCC

ACTTCCCGCCACCAAATTAAAAAAACAATAA

*Anabaena* 4: 3' half-intron E2

(SEQ ID NO: 88)
AACAACAGATAACTTACTAACTTACAGCTAGTCGGAAGGTGCAGAGACT

CGACGGGAGCTACCCTAACGTCAAGACGAGGGTAAAGAGAGAGTCCAAT

TCTCAAAGCCAATAGGCAGTAGCGAAAGCTGCGGGAGAATGAAAATCCG

TAGCGTCTAAACGGTCGTGTGGGTTCAAGTCCCTCCACCCCCA

*Anabaena* 4: E1 5' half-intron (SEQ ID NO: 89)
AGACGCTACGGACTTAAATAATTGAGCCTTAGAGAAGAAATTCTTTAAG

TGGATGCTCTCAAACTCAGGGAAACCTAAATCTAGCTATAGACAAGGCA

ATCCTGAGCCAAGCCGAAGTAGTAATTAGTAAGTTAGTAAGTT

*Anabaena* 5: 3' half-intron E2

(SEQ ID NO: 90)
AACAACAGATAACTTACTAGTTACTAGTCGGAAGGTGCAGAGACTCGAC

GGGAGCTACCCTAACGTCAAGACGAGGGTAAAGAGAGAGTCCAATTCTC

AAAGCCAATAGGCAGTAGCGAAAGCTGCGGGAGAATGAAAATCCGTAGC

GTCTAAACGGTCGTGTGGGTTCAAGTCCCTCCACCCCCA

*Anabaena* 5: E1 5' half-intron (SEQ ID NO: 91)
AGACGCTACGGACTTAAATAATTGAGCCTTAGAGAAGAAATTCTTTAAG

TGGATGCTCTCAAACTCAGGGAAACCTAAATCTAGCTATAGACAAGGCA

ATCCTGAGCCAAGCCGAAGTAGTAATTAGTAAGTT

OTHER EMBODIMENTS

While the invention has been described in connection with specific embodiments thereof, it will be understood that it is capable of further modifications and this application is intended to cover any variations, uses, or adaptations of the invention following, in general, the principles of the invention and including such departures from the invention that come within known or customary practice within the art to which the invention pertains and may be applied to the essential features hereinbefore set forth, and follows in the scope of the claims. Other embodiments are within the claims.

The invention claimed is:

1. A linear polyribonucleotide having the formula 5'-(A)-(B)-(C)-(D)-(E)-(F)-(G)-3', wherein: (A) comprises a 3' portion of Group I catalytic intron fragment; (B) comprises a 3' splice site; (C) comprises a 3' exon fragment comprising a first annealing region comprising from 8 to 50 ribonucleotides, wherein the first annealing region is flanked on each side by a portion of the 3' exon fragment, and wherein the 3' exon fragment of (C) comprises the RNA equivalent of the sequence of (SEQ ID NO: 41)
5'-AAAATCCGTAGCGTCTAAACGGTCGTGTGGGTTCAAGTCCCTCCAC
CCCCA-3';

(D) comprises a polyribonucleotide cargo; (E) comprises a 5' exon fragment comprising a second annealing region comprising from 8 to 50 ribonucleotides that can hybridize to the first annealing region; (F) comprises a 5' splice site; and (G) comprises a 5' portion of Group I catalytic intron fragment, wherein the linear polyribonucleotide does not comprise a further annealing region comprising at least 6 ribonucleotides.

2. The linear polyribonucleotide of claim 1, wherein the first annealing region comprises from 10 to 30 ribonucleotides and the second annealing region comprises from 10 to 30 ribonucleotides.

3. The linear polyribonucleotide of claim 2 wherein the first annealing region comprises 12 ribonucleotides and the second annealing region comprises 12 ribonucleotides.

4. The linear polyribonucleotide of claim 2 wherein the first annealing region comprises 17 ribonucleotides and the second annealing region comprises 17 ribonucleotides.

5. The linear polyribonucleotide of claim 2 wherein the first annealing region comprises 22 ribonucleotides and the second annealing region comprises 22 ribonucleotides.

6. The linear polyribonucleotide of claim 2, wherein the first annealing region comprises 27 ribonucleotides and the second annealing region comprises 27 ribonucleotides.

7. The linear polyribonucleotide of claim 1, wherein the first annealing region and the second annealing region comprise zero or one mismatched base pair.

8. The linear polyribonucleotide of claim 1, wherein the 3' portion of Group I catalytic intron fragment of (A) is the 5' terminus of the linear polynucleotide.

9. The linear polyribonucleotide of claim 1, wherein the 5' portion of Group I catalytic intron fragment of (G) is the 3' terminus of the linear polyribonucleotide.

10. The linear polyribonucleotide of claim 9, wherein the polyribonucleotide cargo of (D) comprises an expression sequence, a non-coding sequence, or an expression sequence and a non-coding sequence.

11. The linear polyribonucleotide of claim 10, wherein the expression sequence encodes a polypeptide.

12. The linear polyribonucleotide of claim 11, wherein the polyribonucleotide cargo of (D) comprises an IRES operably linked to the expression sequence encoding the polypeptide.

13. The linear polyribonucleotide of claim 9, wherein the linear polyribonucleotide further comprises a first spacer region between the 3' exon fragment of (C) and the polyribonucleotide cargo of (D).

14. The linear polyribonucleotide of claim 13, wherein the linear polyribonucleotide further comprises a second spacer region between the polyribonucleotide cargo of (D) and the 5' exon fragment of (E).

15. The linear polyribonucleotide of claim 14, wherein the first spacer region and the second spacer region are each from 5 to 500 ribonucleotides in length.

16. The linear polyribonucleotide of claim 9, wherein the linear polyribonucleotide is at least 1,000 ribonucleotides in length.

17. The linear polyribonucleotide of claim 16, wherein the linear polyribonucleotide is at least 3,000 ribonucleotides in length.

18. The linear polyribonucleotide of claim 9, wherein the polyribonucleotide cargo is at least 1,000 ribonucleotides in length.

19. The linear polyribonucleotide of claim 18, wherein the polyribonucleotide cargo is at least 3,000 ribonucleotides in length.

20. A circular polyribonucleotide produced from the linear polyribonucleotide of claim 9.

21. A method of expressing a polypeptide in a cell, the method comprising providing the linear polyribonucleotide of claim 9 to the cell, wherein the polyribonucleotide cargo comprises an expression sequence encoding the polypeptide.

22. A method of producing a circular polyribonucleotide, the method comprising providing the linear polyribonucleotide of claim 9 under conditions suitable for self-splicing of the linear polyribonucleotide to produce the circular polyribonucleotide.

23. The linear polyribonucleotide of claim 11, wherein the sequence of the 3' exon fragment of (C) is the RNA equivalent of (SEQ ID NO: 41)
5'-AAAATCCGTAGCGTCTAAACGGTCGTGTGGGTTCAAGTCCCTCCACCCCCA-3'.

\* \* \* \* \*

SEQUENCE LISTING

Sequence total quantity: 102

SEQ ID NO: 1           moltype =     length =
SEQUENCE: 1
000

SEQ ID NO: 2           moltype =     length =
SEQUENCE: 2
000

SEQ ID NO: 3           moltype =     length =
SEQUENCE: 3
000

SEQ ID NO: 4           moltype =     length =
SEQUENCE: 4
000

SEQ ID NO: 5           moltype = RNA  length = 12
FEATURE                Location/Qualifiers
source                 1..12
                       mol_type = other RNA
                       organism = synthetic construct
SEQUENCE: 5
tccgtagcgt ct                                                              12

SEQ ID NO: 6           moltype = RNA  length = 12
FEATURE                Location/Qualifiers
source                 1..12
                       mol_type = other RNA
                       organism = synthetic construct
SEQUENCE: 6
agacgctacg ga                                                              12

SEQ ID NO: 7           moltype =     length =
SEQUENCE: 7
000

SEQ ID NO: 8           moltype = RNA  length = 10
FEATURE                Location/Qualifiers
source                 1..10
                       mol_type = other RNA
                       organism = synthetic construct
SEQUENCE: 8
acgaccgttt                                                                 10

SEQ ID NO: 9           moltype = RNA  length = 15
FEATURE                Location/Qualifiers
source                 1..15
                       mol_type = other RNA
                       organism = synthetic construct
SEQUENCE: 9
cccacacgac cgttt                                                           15

SEQ ID NO: 10          moltype =     length =
SEQUENCE: 10
000

SEQ ID NO: 11          moltype = RNA  length = 10
FEATURE                Location/Qualifiers
source                 1..10
                       mol_type = other RNA
                       organism = synthetic construct
SEQUENCE: 11
aaacggtcgt                                                                 10

SEQ ID NO: 12          moltype = RNA  length = 15
FEATURE                Location/Qualifiers
source                 1..15
                       mol_type = other RNA
                       organism = synthetic construct
SEQUENCE: 12
aaacggtcgt gtggg                                                           15

SEQ ID NO: 13          moltype =     length =
SEQUENCE: 13
000

SEQ ID NO: 14          moltype =     length =

```
SEQUENCE: 14
000

SEQ ID NO: 15            moltype =    length =
SEQUENCE: 15
000

SEQ ID NO: 16            moltype = RNA   length = 12
FEATURE                  Location/Qualifiers
source                   1..12
                         mol_type = other RNA
                         organism = synthetic construct
SEQUENCE: 16
aaggtaaata tt                                                              12

SEQ ID NO: 17            moltype = RNA   length = 12
FEATURE                  Location/Qualifiers
source                   1..12
                         mol_type = other RNA
                         organism = synthetic construct
SEQUENCE: 17
aatatttacc tt                                                              12

SEQ ID NO: 18            moltype =    length =
SEQUENCE: 18
000

SEQ ID NO: 19            moltype =    length =
SEQUENCE: 19
000

SEQ ID NO: 20            moltype =    length =
SEQUENCE: 20
000

SEQ ID NO: 21            moltype =    length =
SEQUENCE: 21
000

SEQ ID NO: 22            moltype = RNA   length = 17
FEATURE                  Location/Qualifiers
source                   1..17
                         mol_type = other RNA
                         organism = synthetic construct
SEQUENCE: 22
tccgtagcgt ctaaacg                                                         17

SEQ ID NO: 23            moltype = RNA   length = 17
FEATURE                  Location/Qualifiers
source                   1..17
                         mol_type = other RNA
                         organism = synthetic construct
SEQUENCE: 23
cgtttagacg ctacgga                                                         17

SEQ ID NO: 24            moltype = RNA   length = 22
FEATURE                  Location/Qualifiers
source                   1..22
                         mol_type = other RNA
                         organism = synthetic construct
SEQUENCE: 24
tccgtagcgt ctaaacggtc gt                                                   22

SEQ ID NO: 25            moltype = RNA   length = 22
FEATURE                  Location/Qualifiers
source                   1..22
                         mol_type = other RNA
                         organism = synthetic construct
SEQUENCE: 25
acgaccgttt agacgctacg ga                                                   22

SEQ ID NO: 26            moltype = RNA   length = 27
FEATURE                  Location/Qualifiers
source                   1..27
                         mol_type = other RNA
                         organism = synthetic construct
SEQUENCE: 26
tccgtagcgt ctaaacggtc gtgtggg                                              27
```

```
SEQ ID NO: 27            moltype = RNA   length = 27
FEATURE                  Location/Qualifiers
source                   1..27
                         mol_type = other RNA
                         organism = synthetic construct
SEQUENCE: 27
cccacacgac cgtttagacg ctacgga                                          27

SEQ ID NO: 28            moltype = RNA   length = 131
FEATURE                  Location/Qualifiers
source                   1..131
                         mol_type = other RNA
                         organism = synthetic construct
SEQUENCE: 28
aacaacagat aacttacagc tagtcggaag gtgcagagac tcgacgggag ctaccctaac      60
gtcaagacga gggtaaagag agagtccaat tctcaaagcc aataggcagt agcgaaagct     120
gcgggagaat g                                                          131

SEQ ID NO: 29            moltype = RNA   length = 118
FEATURE                  Location/Qualifiers
source                   1..118
                         mol_type = other RNA
                         organism = synthetic construct
SEQUENCE: 29
aaataattga gccttagaga agaaattctt taagtggatg ctctcaaact cagggaaacc      60
taaatctagc tatagacaag gcaatcctga gccaagccga agtagtaatt agtaagtt       118

SEQ ID NO: 30            moltype = RNA   length = 178
FEATURE                  Location/Qualifiers
source                   1..178
                         mol_type = other RNA
                         organism = synthetic construct
SEQUENCE: 30
cttctgttga tatggatgca gttcacagac taaatgtcgg tcggggaaga tgtattcttc      60
tcataagata tagtcggacc tctccttaat gggagctagc ggatgaagtg atgcaacact     120
ggagccgctg ggaactaatt tgtatgcgaa agtatattga ttagttttgg agtactcg      178

SEQ ID NO: 31            moltype = RNA   length = 235
FEATURE                  Location/Qualifiers
source                   1..235
                         mol_type = other RNA
                         organism = synthetic construct
SEQUENCE: 31
aaatagcaat atttaccttt ggagggaaaa gttatcaggc atgcacctgg tagctagtct      60
ttaaccaat agattgcatc ggtttaaaag gcaagaccgt caaattgcgg gaaagggtc      120
aacagccgtt cagtaccaag tctcagggga aactttgaga tggccttgca aagggtatgg    180
taataagctg acgacatgg tcctaaccac gcagccaagt cctaagtcaa cagat          235

SEQ ID NO: 32            moltype = RNA   length = 167
FEATURE                  Location/Qualifiers
source                   1..167
                         mol_type = other RNA
                         organism = synthetic construct
SEQUENCE: 32
ggttctacat aaaatgcctaa cgactatccc tttggggagt agggtcaagt gactcgaaac     60
gatagacaac ttgctttaac aagttggaga tatagtctgc tctgcatggt gacatgcagc    120
tggatataat tccggggtaa gattaacgac cttatctgaa cataatg                  167

SEQ ID NO: 33            moltype = RNA   length = 93
FEATURE                  Location/Qualifiers
source                   1..93
                         mol_type = other RNA
                         organism = synthetic construct
SEQUENCE: 33
taattgaggc ctgagtataa ggtgacttat acttgtaatc tatctaaacg gggaacctct     60
ctagtagaca atcccgtgct aaattgtagg act                                  93

SEQ ID NO: 34            moltype = RNA   length = 12
FEATURE                  Location/Qualifiers
source                   1..12
                         mol_type = other RNA
                         organism = synthetic construct
SEQUENCE: 34
agaatgaaaa tc                                                          12

SEQ ID NO: 35            moltype = RNA   length = 12
FEATURE                  Location/Qualifiers
source                   1..12
                         mol_type = other RNA
```

```
                        organism = synthetic construct
SEQUENCE: 35
ggacttaaat aa                                                            12

SEQ ID NO: 36           moltype = RNA   length = 12
FEATURE                 Location/Qualifiers
source                  1..12
                        mol_type = other RNA
                        organism = synthetic construct
SEQUENCE: 36
tactcgtaag gt                                                            12

SEQ ID NO: 37           moltype = RNA   length = 12
FEATURE                 Location/Qualifiers
source                  1..12
                        mol_type = other RNA
                        organism = synthetic construct
SEQUENCE: 37
ctctctaaat ag                                                            12

SEQ ID NO: 38           moltype = RNA   length = 12
FEATURE                 Location/Qualifiers
source                  1..12
                        mol_type = other RNA
                        organism = synthetic construct
SEQUENCE: 38
ataatgctac cg                                                            12

SEQ ID NO: 39           moltype = RNA   length = 12
FEATURE                 Location/Qualifiers
source                  1..12
                        mol_type = other RNA
                        organism = synthetic construct
SEQUENCE: 39
ttgggttaat tg                                                            12

SEQ ID NO: 40           moltype = RNA   length = 51
FEATURE                 Location/Qualifiers
source                  1..51
                        mol_type = other RNA
                        organism = synthetic construct
SEQUENCE: 40
aaaatccgtt gaccttaaac ggtcgtgtgg gttcaagtcc ctccaccccc a                 51

SEQ ID NO: 41           moltype = RNA   length = 51
FEATURE                 Location/Qualifiers
source                  1..51
                        mol_type = other RNA
                        organism = synthetic construct
SEQUENCE: 41
aaaatccgta gcgtctaaac ggtcgtgtgg gttcaagtcc ctccaccccc a                 51

SEQ ID NO: 42           moltype = RNA   length = 15
FEATURE                 Location/Qualifiers
source                  1..15
                        mol_type = other RNA
                        organism = synthetic construct
SEQUENCE: 42
agacgctacg gactt                                                         15

SEQ ID NO: 43           moltype = RNA   length = 20
FEATURE                 Location/Qualifiers
source                  1..20
                        mol_type = other RNA
                        organism = synthetic construct
SEQUENCE: 43
cgtttagacg ctacggactt                                                    20

SEQ ID NO: 44           moltype = RNA   length = 25
FEATURE                 Location/Qualifiers
source                  1..25
                        mol_type = other RNA
                        organism = synthetic construct
SEQUENCE: 44
acgaccgttt agacgctacg gactt                                              25

SEQ ID NO: 45           moltype = RNA   length = 30
FEATURE                 Location/Qualifiers
source                  1..30
```

```
                        mol_type = other RNA
                        organism = synthetic construct
SEQUENCE: 45
cccacacgac cgtttagacg ctacggactt                                    30

SEQ ID NO: 46           moltype =    length =
SEQUENCE: 46
000

SEQ ID NO: 47           moltype = RNA   length = 15
FEATURE                 Location/Qualifiers
source                  1..15
                        mol_type = other RNA
                        organism = synthetic construct
SEQUENCE: 47
taaggtaaat attgc                                                    15

SEQ ID NO: 48           moltype = RNA   length = 10
FEATURE                 Location/Qualifiers
source                  1..10
                        mol_type = other RNA
                        organism = synthetic construct
SEQUENCE: 48
atgactctct                                                          10

SEQ ID NO: 49           moltype = RNA   length = 15
FEATURE                 Location/Qualifiers
source                  1..15
                        mol_type = other RNA
                        organism = synthetic construct
SEQUENCE: 49
ctaccgttta atatt                                                    15

SEQ ID NO: 50           moltype = RNA   length = 15
FEATURE                 Location/Qualifiers
source                  1..15
                        mol_type = other RNA
                        organism = synthetic construct
SEQUENCE: 50
ctcaatttta atatt                                                    15

SEQ ID NO: 51           moltype = RNA   length = 14
FEATURE                 Location/Qualifiers
source                  1..14
                        mol_type = other RNA
                        organism = synthetic construct
SEQUENCE: 51
atgttttctt gggt                                                     14

SEQ ID NO: 52           moltype = AA   length = 9
FEATURE                 Location/Qualifiers
source                  1..9
                        mol_type = protein
                        organism = synthetic construct
SEQUENCE: 52
GDVESNPGP                                                            9

SEQ ID NO: 53           moltype = AA   length = 9
FEATURE                 Location/Qualifiers
source                  1..9
                        mol_type = protein
                        organism = synthetic construct
SEQUENCE: 53
GDIEENPGP                                                            9

SEQ ID NO: 54           moltype = AA   length = 7
FEATURE                 Location/Qualifiers
source                  1..7
                        mol_type = protein
                        organism = synthetic construct
SEQUENCE: 54
VEPNPGP                                                              7

SEQ ID NO: 55           moltype = AA   length = 7
FEATURE                 Location/Qualifiers
source                  1..7
                        mol_type = protein
                        organism = synthetic construct
SEQUENCE: 55
```

```
IETNPGP                                                                                 7

SEQ ID NO: 56           moltype = AA  length = 9
FEATURE                 Location/Qualifiers
source                  1..9
                        mol_type = protein
                        organism = synthetic construct
SEQUENCE: 56
GDIESNPGP                                                                               9

SEQ ID NO: 57           moltype = AA  length = 9
FEATURE                 Location/Qualifiers
source                  1..9
                        mol_type = protein
                        organism = synthetic construct
SEQUENCE: 57
GDVELNPGP                                                                               9

SEQ ID NO: 58           moltype = AA  length = 9
FEATURE                 Location/Qualifiers
source                  1..9
                        mol_type = protein
                        organism = synthetic construct
SEQUENCE: 58
GDIETNPGP                                                                               9

SEQ ID NO: 59           moltype = AA  length = 8
FEATURE                 Location/Qualifiers
source                  1..8
                        mol_type = protein
                        organism = synthetic construct
SEQUENCE: 59
GDVENPGP                                                                                8

SEQ ID NO: 60           moltype = AA  length = 9
FEATURE                 Location/Qualifiers
source                  1..9
                        mol_type = protein
                        organism = synthetic construct
SEQUENCE: 60
GDVEENPGP                                                                               9

SEQ ID NO: 61           moltype = AA  length = 9
FEATURE                 Location/Qualifiers
source                  1..9
                        mol_type = protein
                        organism = synthetic construct
SEQUENCE: 61
GDVEQNPGP                                                                               9

SEQ ID NO: 62           moltype = AA  length = 7
FEATURE                 Location/Qualifiers
source                  1..7
                        mol_type = protein
                        organism = synthetic construct
SEQUENCE: 62
IESNPGP                                                                                 7

SEQ ID NO: 63           moltype = AA  length = 9
FEATURE                 Location/Qualifiers
source                  1..9
                        mol_type = protein
                        organism = synthetic construct
SEQUENCE: 63
GDIELNPGP                                                                               9

SEQ ID NO: 64           moltype = AA  length = 9
FEATURE                 Location/Qualifiers
source                  1..9
                        mol_type = protein
                        organism = synthetic construct
SEQUENCE: 64
HDIETNPGP                                                                               9

SEQ ID NO: 65           moltype = AA  length = 9
FEATURE                 Location/Qualifiers
source                  1..9
                        mol_type = protein
                        organism = synthetic construct
```

```
SEQUENCE: 65
HDVETNPGP                                                                                      9

SEQ ID NO: 66            moltype = AA  length = 9
FEATURE                  Location/Qualifiers
source                   1..9
                         mol_type = protein
                         organism = synthetic construct
SEQUENCE: 66
HDVEMNPGP                                                                                      9

SEQ ID NO: 67            moltype = AA  length = 9
FEATURE                  Location/Qualifiers
source                   1..9
                         mol_type = protein
                         organism = synthetic construct
SEQUENCE: 67
GDMESNPGP                                                                                      9

SEQ ID NO: 68            moltype = AA  length = 9
FEATURE                  Location/Qualifiers
source                   1..9
                         mol_type = protein
                         organism = synthetic construct
SEQUENCE: 68
GDVETNPGP                                                                                      9

SEQ ID NO: 69            moltype = AA  length = 9
FEATURE                  Location/Qualifiers
source                   1..9
                         mol_type = protein
                         organism = synthetic construct
SEQUENCE: 69
GDIEQNPGP                                                                                      9

SEQ ID NO: 70            moltype = AA  length = 8
FEATURE                  Location/Qualifiers
source                   1..8
                         mol_type = protein
                         organism = synthetic construct
SEQUENCE: 70
DSEFNPGP                                                                                       8

SEQ ID NO: 71            moltype = AA  length = 6
FEATURE                  Location/Qualifiers
source                   1..6
                         mol_type = protein
                         organism = synthetic construct
SEQUENCE: 71
CHYSEL                                                                                         6

SEQ ID NO: 72            moltype = AA  length = 9
FEATURE                  Location/Qualifiers
source                   1..9
                         mol_type = protein
                         organism = synthetic construct
VARIANT                  1
                         note = V, H, or absent
VARIANT                  2
                         note = D, G, or absent
VARIANT                  3
                         note = D, V, I, S, or M
VARIANT                  5
                         note = X is any amino acid
SEQUENCE: 72
XXXEXNPGP                                                                                      9

SEQ ID NO: 73            moltype = AA  length = 8
FEATURE                  Location/Qualifiers
source                   1..8
                         mol_type = protein
                         organism = synthetic construct
VARIANT                  2
                         note = V or I
VARIANT                  4
                         note = X is any amino acid
SEQUENCE: 73
DXEXNPGP                                                                                       8
```

| SEQ ID NO: 74 | moltype = length = |
| SEQUENCE: 74 | |
| 000 | |

| SEQ ID NO: 75 | moltype = length = |
| SEQUENCE: 75 | |
| 000 | |

| SEQ ID NO: 76 | moltype = length = |
| SEQUENCE: 76 | |
| 000 | |

| SEQ ID NO: 77 | moltype = length = |
| SEQUENCE: 77 | |
| 000 | |

| SEQ ID NO: 78 | moltype = length = |
| SEQUENCE: 78 | |
| 000 | |

| SEQ ID NO: 79 | moltype = RNA length = 10 |
| FEATURE | Location/Qualifiers |
| source | 1..10 |
| | mol_type = other RNA |
| | organism = synthetic construct |

SEQUENCE: 79
```
ccrrccatgg                                                                  10
```

| SEQ ID NO: 80 | moltype = RNA length = 182 |
| FEATURE | Location/Qualifiers |
| source | 1..182 |
| | mol_type = other RNA |
| | organism = Synechococcus elongatus |

SEQUENCE: 80
```
taaacaacta acagctttag aaggtgcaga gactagacgg gagctaccct aacggattca    60
gccgagggta aagggatagt ccaattctca acatcgcgat tgttgatggc agcgaaagtt   120
gcagagagaa tgaaaatccg ctgactgtaa aggtcgtgag ggttcgagtc cctccgcccc   180
ca                                                                  182
```

| SEQ ID NO: 81 | moltype = RNA length = 128 |
| FEATURE | Location/Qualifiers |
| source | 1..128 |
| | mol_type = other RNA |
| | organism = Synechococcus elongatus |

SEQUENCE: 81
```
acggtagacg cagcggactt agaaaactgg gcctcgatcg cgaaagggat cgagtggcag    60
ctctcaaact cagggaaacc taaaacttta aacattmaag tcatggcaat cctgagccaa   120
gctaaagc                                                            128
```

| SEQ ID NO: 82 | moltype = RNA length = 210 |
| FEATURE | Location/Qualifiers |
| source | 1..210 |
| | mol_type = other RNA |
| | organism = Anabaena azollae |

SEQUENCE: 82
```
ttaaactcaa aatttaaaat cccaaattca aaattccggg aaggtgcaga gactcgacgg    60
gagctaccct aacgtaaagc cgagggtaaa gggagagtcc aattctcaaa gcctgaagtt   120
gctgaagcaa caaggcagta gtgaaagctg cgagagaatg aaaatccgtt gactgtaaaa   180
agtcgtgggg gttcaagtcc ccccacccccc                                   210
```

| SEQ ID NO: 83 | moltype = RNA length = 151 |
| FEATURE | Location/Qualifiers |
| source | 1..151 |
| | mol_type = other RNA |
| | organism = Anabaena azollae |

SEQUENCE: 83
```
atggtagacg ctacggactt agaaaactga gccttgatag agaaatcttt taagtggaag    60
ctctcaaatt cagggaaacc taaatctgaa tacagatatg caatcctga gccaagccca   120
gaaaatttag acttgagatt tgattttgga g                                  151
```

| SEQ ID NO: 84 | moltype = RNA length = 207 |
| FEATURE | Location/Qualifiers |
| source | 1..207 |
| | mol_type = other RNA |
| | organism = Anabaena cylindrica |

SEQUENCE: 84
```
ggctttcaat ttgaaatcag aaattcaaaa ttcaggaag gtgcagagac tcgacgggag    60
ctaccctaac gtaaagcga gggtaaaggg agagtccaat tcttaaagcc tgaagttgtg   120
caagcaacaa ggcaacagtg aaagctgtgg aagaatgaaa atccgttgac cttaaacggt   180
```
cgtgggggtt caagtccccc cacccccc                                                     207

SEQ ID NO: 85          moltype = RNA   length = 147
FEATURE                Location/Qualifiers
source                 1..147
                       mol_type = other RNA
                       organism = Anabaena cylindrica
SEQUENCE: 85
atggtagacg ctacggactt agaaaactga gccttgatag agaaatcttt caagtggaag    60
ctctcaaatt cagggaaacc taaatctgaa tacagatatg gcaatcctga gccaagcccg   120
gaaattttag aatcaagatt ttatttt                                       147

SEQ ID NO: 86          moltype = RNA   length = 178
FEATURE                Location/Qualifiers
source                 1..178
                       mol_type = other RNA
                       organism = Scytonema hofmannii
SEQUENCE: 86
agaaatggag aaggtgtaga gactggaagg caggcaccct aacgttaaag gcgagggtga    60
agggacagtc cagaccacaa accagtaaat ctgggcagcg aaagctgtag atggtaagca   120
taacccgaag gtcagtggtt caaatccact tcccgccacc aaattaaaaa aacaataa     178

SEQ ID NO: 87          moltype = RNA   length = 178
FEATURE                Location/Qualifiers
source                 1..178
                       mol_type = other RNA
                       organism = Scytonema hofmannii
SEQUENCE: 87
agaaatggag aaggtgtaga gactggaagg caggcaccct aacgttaaag gcgagggtga    60
agggacagtc cagaccacaa accagtaaat ctgggcagcg aaagctgtag atggtaagca   120
taacccgaag gtcagtggtt caaatccact tcccgccacc aaattaaaaa aacaataa     178

SEQ ID NO: 88          moltype = RNA   length = 190
FEATURE                Location/Qualifiers
source                 1..190
                       mol_type = other RNA
                       organism = Anabaena sp.
SEQUENCE: 88
aacaacagat aacttactaa cttacagcta gtcggaaggt gcagagactc gacgggagct    60
accctaacgt caagacgagg gtaaagagag agtccaattc tcaaagccaa taggcagtag   120
cgaaagctgc gggagaatga aaatccgtag cgtctaaacg gtcgtgtggg ttcaagtccc   180
tccacccccca                                                         190

SEQ ID NO: 89          moltype = RNA   length = 141
FEATURE                Location/Qualifiers
source                 1..141
                       mol_type = other RNA
                       organism = Anabaena sp.
SEQUENCE: 89
agacgctacg gacttaaata attgagcctt agagaagaaa ttctttaagt ggatgctctc    60
aaactcaggg aaacctaaat ctagctatag acaaggcaat cctgagccaa gccgaagtag   120
taattagtaa gttagtaagt t                                             141

SEQ ID NO: 90          moltype = RNA   length = 186
FEATURE                Location/Qualifiers
source                 1..186
                       mol_type = other RNA
                       organism = Anabaena sp.
SEQUENCE: 90
aacaacagat aacttactag ttactagtcg gaaggtgcag agactcgacg ggagctaccc    60
taacgtcaag acgagggtaa agagagagtc caattctcaa agccaatagg cagtagcgaa   120
agctgcggga gaatgaaaat ccgtagcgtc taaacggtcg tgtgggttca agtccctcca   180
ccccca                                                              186

SEQ ID NO: 91          moltype = RNA   length = 133
FEATURE                Location/Qualifiers
source                 1..133
                       mol_type = other RNA
                       organism = Anabaena sp.
SEQUENCE: 91
agacgctacg gacttaaata attgagcctt agagaagaaa ttctttaagt ggatgctctc    60
aaactcaggg aaacctaaat ctagctatag acaaggcaat cctgagccaa gccgaagtag   120
taattagtaa gtt                                                      133

SEQ ID NO: 92          moltype = RNA   length = 17
FEATURE                Location/Qualifiers
source                 1..17
                       mol_type = other RNA
                       organism = Synechococcus elongatus -continued

```
SEQUENCE: 92
tccgctgact gtaaagg                                                   17

SEQ ID NO: 93           moltype = RNA   length = 17
FEATURE                 Location/Qualifiers
source                  1..17
                        mol_type = other RNA
                        organism = Synechococcus elongatus
SEQUENCE: 93
tccgctgcgt ctaccgt                                                   17

SEQ ID NO: 94           moltype = RNA   length = 17
FEATURE                 Location/Qualifiers
source                  1..17
                        mol_type = other RNA
                        organism = Anabaena azollae
SEQUENCE: 94
tccgttgact gtaaaaa                                                   17

SEQ ID NO: 95           moltype = RNA   length = 17
FEATURE                 Location/Qualifiers
source                  1..17
                        mol_type = other RNA
                        organism = Anabaena azollae
SEQUENCE: 95
tccgtagcgt ctaccat                                                   17

SEQ ID NO: 96           moltype = RNA   length = 17
FEATURE                 Location/Qualifiers
source                  1..17
                        mol_type = other RNA
                        organism = Anabaena cylindrica
SEQUENCE: 96
tccgttgacc ttaaacg                                                   17

SEQ ID NO: 97           moltype = RNA   length = 17
FEATURE                 Location/Qualifiers
source                  1..17
                        mol_type = other RNA
                        organism = Anabaena cylindrica
SEQUENCE: 97
tccgtagcgt ctaccat                                                   17

SEQ ID NO: 98           moltype = RNA   length = 17
FEATURE                 Location/Qualifiers
source                  1..17
                        mol_type = other RNA
                        organism = Scytonema hofmannii
SEQUENCE: 98
cccgaaggtc agtggtt                                                   17

SEQ ID NO: 99           moltype = RNA   length = 17
FEATURE                 Location/Qualifiers
source                  1..17
                        mol_type = other RNA
                        organism = Scytonema hofmannii
SEQUENCE: 99
cccgacgagc taccagg                                                   17

SEQ ID NO: 100          moltype = RNA   length = 315
FEATURE                 Location/Qualifiers
source                  1..315
                        mol_type = other RNA
                        organism = Anabaena sp.
SEQUENCE: 100
agacgctacg gacttaaata attgagcctt agagaagaaa ttctttaagt ggatgctctc    60
aaactcaggg aaacctaaat ctagctatag acaaggcaat cctgagccaa gccgaagtag   120
taattagtaa gttaacaaca gataacttac agctagtcgg aaggtgcaga gactcgacgg   180
gagctaccct aacgtcaaga cgagggtaaa gagagagtcc aattctcaaa gccaataggc   240
agtagcgaaa gctgcgggag aatgaaaatc cgttgacctt aaacggtcgt gtgggttcaa   300
gtccctccac cccca                                                   315

SEQ ID NO: 101          moltype = RNA   length = 331
FEATURE                 Location/Qualifiers
source                  1..331
                        mol_type = other RNA
                        organism = synthetic construct
SEQUENCE: 101
agacgctacg gacttaaata attgagcctt agagaagaaa ttctttaagt ggatgctctc    60
```

```
                                    -continued
aaactcaggg aaacctaaat ctagctatag acaaggcaat cctgagccaa gccgaagtag  120
taattagtaa gttagtaagt taacaacaga taacttacta acttacagct agtcggaagg  180
tgcagagact cgacgggagc taccctaacg tcaagacgag ggtaaagaga gagtccaatt  240
ctcaaagcca ataggcagta gcgaaagctg cgggagaatg aaaatccgta gcgtctaaac  300
ggtcgtgtgg gttcaagtcc ctccacccc a                                 331

SEQ ID NO: 102          moltype = RNA  length = 319
FEATURE                 Location/Qualifiers
source                  1..319
                        mol_type = other RNA
                        organism = synthetic construct
SEQUENCE: 102
agacgctacg gacttaaata attgagcctt agagaagaaa ttctttaagt ggatgctctc   60
aaactcaggg aaacctaaat ctagctatag acaaggcaat cctgagccaa gccgaagtag  120
taattagtaa gttaacaaca gataacttac tagttactag tcggaaggtg cagagactcg  180
acgggagcta ccctaacgtc aagacgaggg taaagagaga gtccaattct caaagccaat  240
aggcagtagc gaaagctgcg ggagaatgaa aatccgtagc gtctaaacgg tcgtgtgggt  300
tcaagtccct ccaccccca                                               319
```